(12) United States Patent
Crowley et al.

(10) Patent No.: US 9,840,481 B2
(45) Date of Patent: Dec. 12, 2017

(54) ALLOSTERIC MODULATORS OF NICOTINIC ACETYLCHOLINE RECEPTORS

(71) Applicant: MERCK SHARP & DOHME CORP., Rahway, NJ (US)

(72) Inventors: Brendan M. Crowley, Collegeville, PA (US); Brian T. Campbell, Bensalem, PA (US); Joseph L. Duffy, Cranford, NJ (US); Thomas J. Greshock, Collegeville, PA (US); Deodial G. Guiadeen, Chesterfield, NJ (US); Andrew John Harvey, Paddington (AU); Belinda C. Huff, Thebarton SA (AU); Kenneth J. Leavitt, Mount Laurel, NJ (US); Vanessa L. Rada, Hatfield, PA (US); John M. Sanders, Hatfield, PA (US); William D. Shipe, Chalfont, PA (US); Linda M. Suen, Philadelphia, PA (US); Ian M. Bell, Harleysville, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 15/463,336

(22) Filed: Mar. 20, 2017

(65) Prior Publication Data
US 2017/0275260 A1 Sep. 28, 2017

Related U.S. Application Data

(60) Provisional application No. 62/369,778, filed on Aug. 2, 2016, provisional application No. 62/311,888, filed on Mar. 22, 2016.

(51) Int. Cl.

| | |
|---|---|
| C07D 285/12 | (2006.01) |
| C07D 231/12 | (2006.01) |
| C07D 249/04 | (2006.01) |
| C07D 261/08 | (2006.01) |
| C07D 263/32 | (2006.01) |
| C07D 271/06 | (2006.01) |
| C07D 271/07 | (2006.01) |
| C07D 277/26 | (2006.01) |
| C07D 285/08 | (2006.01) |
| A61K 31/4245 | (2006.01) |
| A61K 31/433 | (2006.01) |
| C07D 271/107 | (2006.01) |
| A61K 31/421 | (2006.01) |
| A61K 31/42 | (2006.01) |
| A61K 31/4192 | (2006.01) |
| A61K 31/415 | (2006.01) |
| A61K 31/426 | (2006.01) |

(52) U.S. Cl.
CPC .......... *C07D 285/12* (2013.01); *A61K 31/415* (2013.01); *A61K 31/4192* (2013.01); *A61K 31/42* (2013.01); *A61K 31/421* (2013.01); *A61K 31/426* (2013.01); *A61K 31/4245* (2013.01); *A61K 31/433* (2013.01); *C07D 231/12* (2013.01); *C07D 249/04* (2013.01); *C07D 261/08* (2013.01); *C07D 263/32* (2013.01); *C07D 271/06* (2013.01); *C07D 271/107* (2013.01); *C07D 277/26* (2013.01); *C07D 285/08* (2013.01)

(58) Field of Classification Search
None
See application file for complete search history.

(56) References Cited

U.S. PATENT DOCUMENTS

| | | | |
|---|---|---|---|
| 3,487,154 A | 12/1969 | Coen | |
| 3,522,302 A | 7/1970 | Kaiser et al. | |
| 5,286,736 A | 2/1994 | Soyka et al. | |

(Continued)

FOREIGN PATENT DOCUMENTS

| | | |
|---|---|---|
| EP | 0068998 | 6/1982 |
| EP | 0633259 | 6/1994 |

(Continued)

OTHER PUBLICATIONS

Charles J. Frazier et al., Acetylcholine Activates an Alpha-Bungarotoxin-Sensitive Nicotinic Current in Rat Hippocampal Interneurons, But Not Pyramidal Cells, The Journal of Neuroscience, 1998, 1187-1195, 18(4).

(Continued)

*Primary Examiner* — Timothy R Rozof
(74) *Attorney, Agent, or Firm* — Matthew A. Leff; John C. Todaro

(57) ABSTRACT

The present disclosure relates to compounds of formula I that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia, as well as for L-DOPA induced-dyskinesia and inflammation

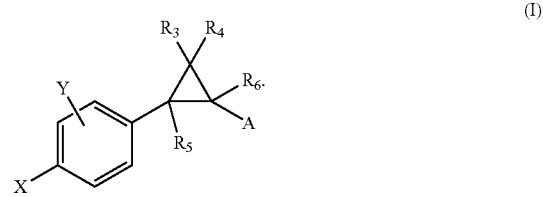

38 Claims, No Drawings

(56) References Cited

U.S. PATENT DOCUMENTS

| | | | |
|---|---|---|---|
| 6,235,791 | B1 | 5/2001 | Breliere et al. |
| 7,723,391 | B2 | 5/2010 | Du Bois et al. |
| 8,470,985 | B2 * | 6/2013 | Bhattacharjee ........ C07H 17/08 536/7.2 |
| 8,642,660 | B2 | 2/2014 | Goldfarb |
| 8,716,309 | B2 | 5/2014 | Maeng et al. |
| 8,765,790 | B2 | 7/2014 | Eskildsen et al. |
| 8,815,914 | B2 | 8/2014 | Sams et al. |
| 9,050,327 | B2 | 6/2015 | Eskildsen et al. |
| 9,062,013 | B2 | 6/2015 | Harvey et al. |
| 2002/0032199 | A1 | 3/2002 | Poss et al. |
| 2003/0073849 | A1 | 4/2003 | Mattson et al. |
| 2009/0163545 | A1 | 6/2009 | Goldfarb |
| 2010/0041763 | A1 | 2/2010 | Elworthy |

FOREIGN PATENT DOCUMENTS

| | | |
|---|---|---|
| EP | 1930001 | 6/2008 |
| WO | WO9804251 | 2/1998 |
| WO | WO9905143 | 2/1999 |
| WO | WO9941254 | 8/1999 |
| WO | WO0004021 | 1/2000 |
| WO | WO0127107 | 4/2001 |
| WO | WO0155146 | 8/2001 |
| WO | WO0185701 | 11/2001 |
| WO | WO02079152 | 10/2002 |
| WO | WO03082190 | 10/2003 |
| WO | WO2004063179 | 7/2004 |
| WO | WO2009043784 | 4/2009 |
| WO | WO2009085177 | 7/2009 |
| WO | WO2010070032 | 6/2010 |
| WO | WO2010084160 | 7/2010 |
| WO | WO2010096011 | 8/2010 |
| WO | WO2010144646 | 12/2010 |
| WO | WO2010144959 | 12/2010 |
| WO | 2011019538 A1 | 2/2011 |
| WO | WO2012012410 | 1/2012 |
| WO | WO2012047852 | 4/2012 |
| WO | WO2012051361 | 4/2012 |
| WO | WO2012083170 | 6/2012 |
| WO | WO2012103583 | 8/2012 |
| WO | WO2012114285 | 8/2012 |
| WO | 2012151361 A1 | 11/2012 |
| WO | 2013005153 | 1/2013 |
| WO | WO2013007621 | 1/2013 |
| WO | WO2013020622 | 2/2013 |
| WO | WO2014006117 | 1/2014 |
| WO | WO2014006120 | 1/2014 |
| WO | WO2014019023 | 2/2014 |
| WO | WO2014090731 | 6/2014 |
| WO | WO2014144871 | 9/2014 |
| WO | WO2014172759 | 10/2014 |
| WO | WO2014195848 A1 | 12/2014 |
| WO | WO2015095952 | 7/2015 |
| WO | WO2015095953 | 7/2015 |
| WO | WO2015187088 | 12/2015 |
| WO | WO2015187089 | 12/2015 |
| WO | WO2015191799 | 12/2015 |

OTHER PUBLICATIONS

Charles R. Breese et al., Comparison of the Regional Expression of Nicotinic Acetylcholine Receptor Alpha7 mRNA and [125I]-Alpha-Bungarotoxin Binding in Human Postmortem Brain, The Journal of Comparative Neurology, 1997, 385-398, 387.
Danhui Zhang et al., The Alpha7 Nicotinic Receptor Agonist ABT-107 Decreases L-Dopa-Induced Dyskinesias in Parkinsonian Monkeys, The Journal of Pharmacology and Experimental Therapeutics, 2014, 25-32, 351.
Daniel B. Timmermann et al., An Allosteric Modulator of the Alpha7 Nicotinic Acetylcholine Receptor Possessing Cognition-Enhancing Properties in Vivo, The Journal of Pharmacology and Experimental Therapeutics, 2007, 294-307, 323(1).

Daniel Bertrand et al., Therapeutic Potential of Alpha7 Nicotinic Acetylcholine Receptors, Pharmacological Reviews, 2015, 1025-1073, 67.
Dey, Journal of Biomolecular Structure, In Search of Allosteric Modulators of Alpha 7, 2011, 695-715, 29(6).
Dimauro et al, Structural modifications of N-arylamide oxadiazoles: Identification of N-arylpiperidine oxadiazoles as potent and selective agonists of CB2, Bioorganic & Medicinal Chemistry Letters, vol. 18, Issue 15, Aug. 1, 2008, pp. 4267-4274.
Eskildsen et al, Discovery and optimization of Lu AF58801, a novel, selective and brain penetrant . . . , Bioorganic & Medicinal Chemistry Letters, 2014, 288-293, 24.
Farkas et al., Relation Between Chemical Structure and Insecticidal Activitiy in Pyerethroid Comounds. I. An Analogue of Chrysanthemic Acid Containing Chlorine in the Side Chain, Dept. of Organic Synthesis, 1959, pp. 2230-2236, 24.
Goldfarb, CAPLUS, Abstract, 151:92849, 2009.
Gündisch D, Eibl C. Nicotinic acetylcholine receptor ligands; a patent review (2006-2011). Expert opinion on therapeutic patents. 2011;21(12):1867-1896.
Hong Wang et al., Nicotinic acetylcholine receptor Alpha7 subunit is an essential regulator of inflammation, Nature, 2003, 384-388, 421.
Hurst et al., A Novel Positive Allosteric Modulator of the 7 Neuronal, J. of Neuroscience, 2005, pp. 4396-4405, 25 (17).
International Searching Authority, International Search Report and Written Opinion, PCT/AU2013/000849, Nov. 1, 2013.
J. Nishimura et al., A Novel Synthesis of Methylcyclopropanes, Tetrahedron, 1969, 2647-2659, 25.
Martin G. Banwell et al., Synthesis, X-ray Crystal Structure, and Antimitotic Properties of 6-Chloro-2-methoxy-5-(2',3',4'-trimethoxyphenyl)cyclohepta-2,4,6-trien-1-one, a Bicyclic Analogue of Coichicine, J. Org. Chem., 1988, 4945-4952, 53(21).
Michael G. Edwards et al., gem-Dimethylcyclopropanation Using Triisopropylsulfoxonium Tetrafluoroborate: Scope and Limitations, Synthesis, 2008, 3279-3288, 20.
Moebius et al., A Randomized, Double-Blind, Placebo-Controlled, 24-Week, Phase 2b Outcomes Study of 3 Different Doses of Encenicline or Placebo in Subjects With Mild to Moderate Probable Alzheimer's Disease (P7.100), Neurology, 2015, 14 Supplement P7.100, 84.
Paul T. Francis et al., The cholinergic hypothesis of Alzheimer's disease: a review of progress, J. Neurol. Neurosurg. Psychiary, 1999, 137-147, 66.
Perollier et al., A Convenient Access to N, N-Disubstituted Amides Dervied from (1R,3S)-(–)2, 2-Dimethyl-3-Formylcyclopropane-1 Carboxylic Acid, Bull. Soc. Chim FR., 1997, pp. 517-523, 134.
Peter F. Drygala et al., A Convenient Synthesis of 2-Hydroxybenzensulfonamide, Synthetic Communications, 1984, 671-675, 24(5).
Ramin Faghih et al, Discovery of 4-(5-(4-Chlorophenyl)-2-Methyl-3-Propionyl-1h-Pyrrol-1YL) Benzenesulfonamide as a Novel Positive Allosteric Modulator of the Alpha-Nicotinic Acetylcholine Receptor, J. Med. Chem., 2009, 3377-3384, 52.
Richard Se Keefe et al., Randomized, Double-Blind, Placebo-Controlled Study of Encenicline, an Alpha7 Nicotinic Acetylcholine Receptor Agonist, as a Treatment for Cognitive Impairment in Schizophrenia, Neuropsychopharmacology, 2015, 3053-3060, 40.
Roderic Graf, Uber das Sulfamidsaurechlorid, Chemische Berichte, 1959, 509-513, 92.
Rosas-Ballina et al., Acetylcholine-Synthesizing T Cells Relay Neural Signals in a Vagus Nerve Circuit, Science, 2011, pp. 98-101, 334.
Sahdeo et al, Characterization of RO5126946, A Novel Alpha-7 Nicotinic Acetylsholine Receptor-Positive Allosteric Modulator, J. Pharmacol Exp Ther, 2014, 455-468, 350.
Saleem Ahmad et al, Arylcyclopropanecarboxyl Guanidines as Novel, Potent and Selective Inhibitors of the Sodium Hydrogen Exchanger Isoform-1, J. Med. Chem., 2001, 3302-3310, 44.
Shaw-Tao Lin et al, Preparation of Arylspiro[2,4]hept-5-enes From Aryldibromocyclopropanes Via Diallylation and Metathesis Reaction, Journal of Chemical Research, 2006, 591-592.

(56) References Cited

OTHER PUBLICATIONS

Sinkus et al., The human CHRNA7 and CHRFAM7A genes: A review of the genetics,, Neuropharmacology, 2015, pp. 274-288, 96.
Suzuki et al., 3-[(2,4-Dimethoxy)Benzylidene]-, J. of Neuroscience Research, 2013, pp. 462-471, 91.
William R. Dolbier Jr. et al., Trimethylsilyl fluorosulfonyldifluoroacetate (TFDA): a new, highly efficient difluorocarbene reagent, J. Fluorine. Chem., 2003, 459-469, 125.
WJ De Jonge et al., The alpha7 nicotinic acetylcholine receptor as a pharmacological target for inflammation, British Journal of Pharmacology, 2007, 915-929, 151.
International Search Report and Written Opinion for PCT Application No. PCT/US2017/023127, dated Jun. 6, 2017, 13 pages.

\* cited by examiner

ALLOSTERIC MODULATORS OF NICOTINIC ACETYLCHOLINE RECEPTORS

CROSS REFERENCE TO RELATED APPLICATIONS

This application is a U.S. Non-Provisional application which claims the benefit of priority of U.S. Provisional Application No. 62/369,778, filed Aug. 2, 2016 and U.S. Provisional Application No. 62/311,888, filed Mar. 22, 2016.

FIELD OF THE INVENTION

The present disclosure relates to compounds that are useful as modulators of α7 nAChR, compositions comprising such compounds, and the use of such compounds for preventing, treating, or ameliorating disease, particularly disorders of the central nervous system such as cognitive impairments in Alzheimer's disease, Parkinson's disease, and schizophrenia.

BACKGROUND OF THE INVENTION

The α7 nAChR is a fast desensitizing ligand-gated ion channel that has high permeability to $Ca^{2+}$. In human brain, α7 nAChRs are highly expressed in the cortex and hippocampus, regions associated with cognition, see for example, Breese et al. *J. Comp. Neurol.* (1997) 387:385-398. In neurons, α7 nAChRs are localized in both pre-synaptic and post-synaptic structures, where activation of the receptor can modulate neurotransmitter release, neuronal excitability, and intracellular signalling, see for example, Frazier et al. *J Neurosci.* (1998) 18:1187-1195.

Cognitive impairments are prevalent in many neurological and psychiatric diseases, including Alzheimer's disease (AD), schizophrenia, and Parkinson's disease, and dysfunction in cholinergic signalling contributes to the cognitive impairments of these diseases, see for example, Francis et al. *J. Neurol. Neurosurg. Psychiatry* (1999) 66:137-147. For example, a principal feature of the pathogenesis in AD is the loss of cholinergic neurons in the basal forebrain nuclei, whereas increasing cholinergic transmission via inhibition of acetylcholine esterase is the standard of care for the cognitive symptoms of AD. More specific to the α7 nAChR, it was recently demonstrated that encenicline, a partial agonist of the α7 nAChR, improves cognition in Alzheimer's disease, see for example, Moebius H et al., *67th Annual Meeting. Am. Acad. Neurol.* (AAN) 2015, Abst P7.100. Evidence implicating α7 nAChRs in the etiology of schizophrenia comes from studies demonstrating reduced expression of neuronal α7 nAChRs in the brain of schizophrenic patients and the observation that schizophrenics frequently smoke, which is believed to be a form of self-medication. In addition, variants in the promotor region of the gene coding for the α7 nAChR, CHRNA7, which impacts expression of the α7 nAChR protein, are associated with symptoms of schizophrenia, see for example, Sinkus et al. *Neuropharmacology* (2015) 96:274-288. Moreover, accumulating evidence from clinical trials has indicated that activating α7 nAChR with agonists may have beneficial effects on cognition, see for example, Keefe et al. *Neuropsychopharmacology* (2015) 40:3053-3060 and Bertrand et al. *Pharmacology Reviews* (2015) 67:1025-1073. Therefore, targeting the α7 nAChR represents a therapeutic strategy for the treatment of cognitive impairments associated with various cognitive disorders.

Parkinson's disease (PD) is a neurodegenerative disease characterized by progressive deficits in motor function, such as tremor, bradykinesia, rigidity and impaired postural reflex. The main pathological finding associated with the disease is degeneration of dopaminergic neurons in the substantia nigra, resulting in loss of dopaminergic tone in the striatum. L-DOPA is the current standard treatment for the motor symptoms in PD. However, chronic treatment with L-DOPA in PD patients also induces dyskinesia, a side effect of L-DOPA therapy. New lines of evidence indicate that activating α7 nAChRs acutely alleviates dyskinesia in several animal models, see for example, Zhang et al. *J. Pharmacol. Exp. Ther.* (2014) 351:25-32. In addition, accumulating evidence shows that pretreatment with α7 nAChR agonists may protect against neurodegeneration in nigrostriatal neurons, suggesting α7 activation may have disease modifying properties too, see for example, Suzuki et al. *J. Neurosci. Res.* (2013) 91:462-471. Overall, α7 nAChR is an attractive target for both ameliorating disease progression and managing dyskinesia.

In addition to its expression in the central nervous system, the α7 nAChR is widely expressed in peripheral immune cells including macrophage, monocytes, dendritic cells, and B and T cells, see for example, Rosas-Ballina et al. *Science* (2011) 334:98-101. Activation of peripheral α7 nAChRs is critical for inhibiting the release of proinflammatory cytokines via the cholinergic anti-inflammatory pathway, see for example, Wang et al. *Nature* (2003) 421:384-388. Therefore, α7 nAChR is a potential target for several inflammatory diseases such as rheumatoid arthritis, and atherosclerosis, see for example, WJ de Jonge et al. *British J. Pharmacol.* (2007) 151:915-929.

In recent years, α7-selective positive allosteric modulators (PAMs) have been proposed as a therapeutic approach to treating cognitive impairments in AD, PD, and schizophrenia, as well as L-DOPA-induced dyskinesia and inflammation. In contrast to α7 agonists that activate the channel irrespective of endogenous agonist, PAMs increase the potency of the endogenous agonist without perturbing the temporal and spatial integrity of neurotransmission. There are two class of α7 PAMs, type I and type II, which differ based on the functional properties of modulation. The type I PAMs (e.g. NS1738, see for example, Timmermann et al. *J. Pharmacol. Exp. Ther.* (2007) 323:294-307) predominantly affect the peak current with little or no effect on receptor desensitization, while the type II PAMs (e.g. PNU120596, see for example, Hurst et al. *J. Neurosci.* (2005) 25:4396-4405) markedly delay desensitization of the receptor. Additionally, α7 nAChR PAMs may have improved selectivity over related channel targets, presumably through binding to non-conserved regions of the receptor.

The present invention is directed to a new class of compounds that exhibit positive allosteric modulation of the α7 nAChR.

SUMMARY OF THE INVENTION

The present disclosure relates to novel compounds of formula I and pharmaceutically acceptable salts thereof. These compounds may be useful, either as compounds or their pharmaceutically acceptable salts (when appropriate), in the modulation of the α7 nAChR, the prevention, treatment, or amelioration of disease, particularly disorders of the central nervous system such as cognitive impairments in Alzheimer's disease, Parkinson's disease, and schizophrenia and/or as pharmaceutical composition ingredients. As pharmaceutical composition ingredients, these compounds and their salts may be the primary active therapeutic agent, and, when appropriate, may be combined with other therapeutic agents including but not limited to acetylcholinesterase inhibitors, NMDA receptor antagonists, beta-secretase inhibitors, M4 mAChR agonists or PAMs, mGluR2 antagonists or NAMs or PAMs, 5-HT6 antagonists, histamine H3 receptor antagonists, PDE4 inhibitors, PDE9 inhibitors, HDAC6 inhibitors, antipsychotics, MAO-B inhibitors, and levodopa.

In one aspect, the present invention relates to a compound of formula I:

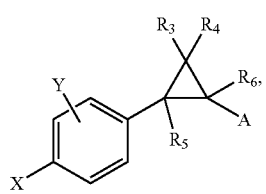

or a pharmaceutically acceptable salt thereof, wherein:
X is selected from

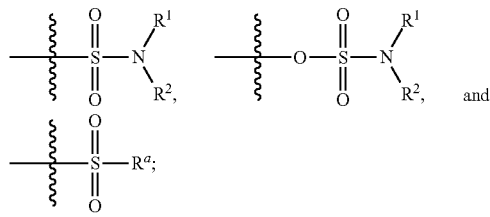

Y is selected from 1 to 4 substituents, each independently selected from H, $(C_1-C_4)$alkyl, halogen, and OH, wherein said alkyl is optionally substituted with one or more halogen or OH;

A is a 5-membered heteroaryl ring which is substituted with 1 to 3 R groups each independently selected from OH, oxo, $NR^7R^8$, CN, alkoxy, halogen, aminoalkyl, hydroxyalkyl, alkyl, cycloalkyl, aryl, heteroaryl, and heterocyclyl, wherein said alkoxy, aminoalkyl, hydroxyalkyl, alkyl, cycloalkyl, aryl, heteroaryl and heterocyclyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(C_1-C_4)$alkyl, $C=O(C_1-C_4)$alkyl, $(C=O)NR^7R^8$, $(C=O)OR^7$, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, aryl, heteroaryl and heterocyclyl are optionally independently substituted with one or more halogen, $CF_3$, OH and oxo;

$R^1$ is H or $(C_1-C_4)$alkyl;
$R^2$ is H or $(C_1-C_4)$alkyl;
$R^3$ is H, halogen or $(C_1-C_4)$alkyl, wherein said alkyl is optionally substituted with one or more halogen;
$R^4$ is H, halogen or $(C_1-C_4)$alkyl, wherein said alkyl is optionally substituted with one or more halogen;
or, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl;
$R^5$ is H or $(C_1-C_4)$alkyl;
$R^6$ is H or $(C_1-C_4)$alkyl;
$R^7$ is H or $(C_1-C_4)$alkyl;
$R^8$ is H or $(C_1-C_4)$alkyl; and
$R^a$ is H or $(C_1-C_4)$alkyl.

The present invention also includes pharmaceutical compositions containing a compound of the present invention and methods of preparing such pharmaceutical compositions. The present invention further includes methods of preventing, treating, or ameliorating the cognitive impairments associated with Alzheimer's disease, Parkinson's disease, and schizophrenia.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are positive allosteric modulators of α7 nAChR.

In a first embodiment of the invention, X is

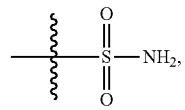 [SMILES: *S(N)(=O)=O]

and the other groups are as provided in the general formula above.

In a second embodiment of the invention, Y is H and the other groups are as provided in the general formula above, or as in the first embodiment.

In a third embodiment of the invention, A is selected from

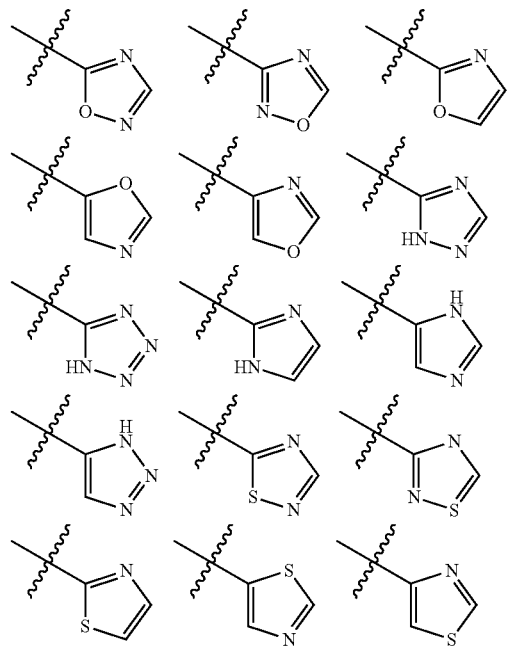

-continued

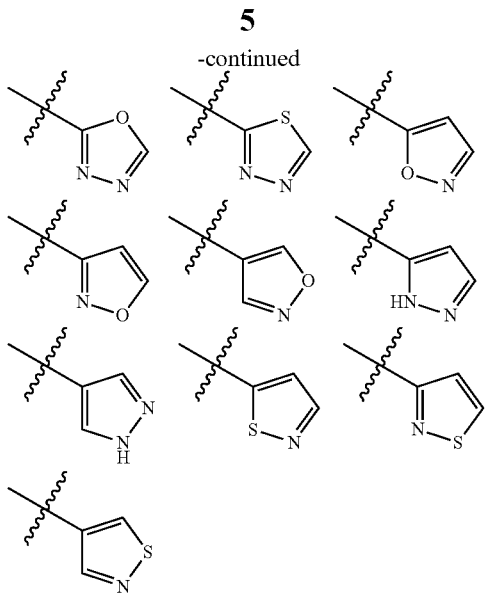

each substituted with 1 to 3 R groups independently selected from $(C_1$-$C_4)$alkyl, $(C_3$-$C_6)$cycloalkyl, aryl, heteroaryl and heterocyclyl, wherein each are optionally substituted with one or more substituents independently selected from F, Cl, Br, OH, oxo, $CF_3$, $OCF_3$, CN, $(C_1$-$C_4)$alkyl, $O(C_1$-$C_4)$alkyl, $S(C_1$-$C_4)$alkyl, $C=O(C_1$-$C_4)$alkyl, $(C_2$-$C_4)$alkynyl, $(C_3$-$C_6)$cycloalkyl, $O(C_3$-$C_6)$cycloalkyl, $C=O(C_3$-$C_6)$cycloalkyl, aryl, heteroaryl and heterocyclyl, wherein said alkyl, aryl, heteroaryl and heterocyclyl are optionally independently substituted with one or more F, Cl, $CF_3$, OH and oxo; and the other groups are as provided in the general formula above, or as in the first or second embodiment.

In a fourth embodiment of the invention, $R^5$, $R^6$, and $R^a$ are independently H or methyl, and the other groups are as provided in the general formula above, or as in the first, second, or third embodiments.

In a fifth embodiment of the invention, $R^3$ and $R^4$ are independently H, F or methyl, and the other groups are as provided in the general formula above, or as in the first through fourth embodiments.

In a sixth embodiment of the invention, the compound of the invention has the formula:

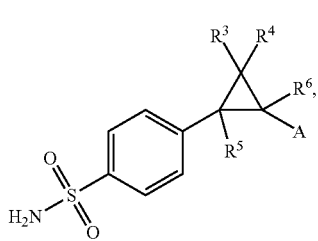

(Ia)

or a pharmaceutically acceptable salt thereof, wherein;
A is selected from

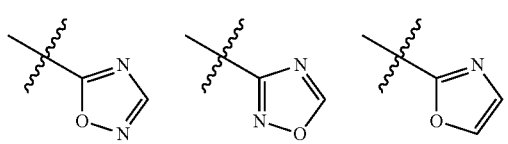

-continued

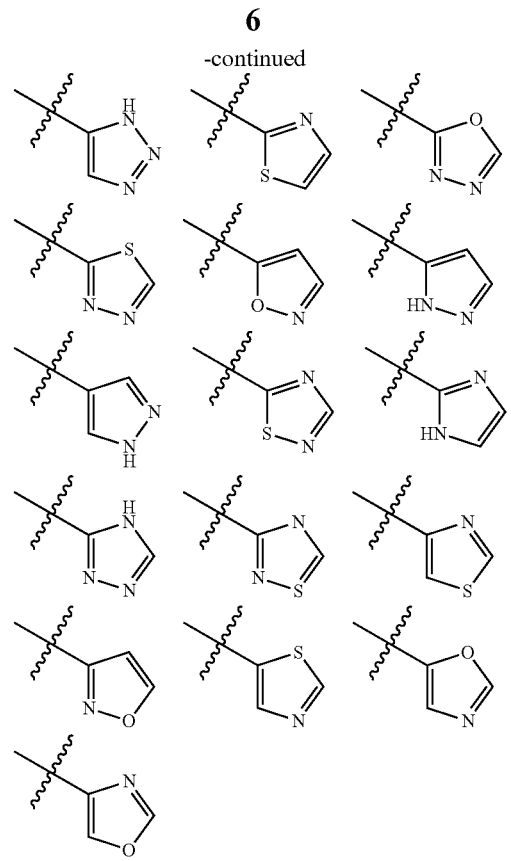

each substituted with 1 to 2 R groups independently selected from $(C_1$-$C_4)$alkyl, $(C_3$-$C_6)$cycloalkyl, aryl, heteroaryl and heterocyclyl, wherein each are optionally substituted with one or more substituents independently selected from F, Cl, Br, OH, oxo, $CF_3$, $OCF_3$, CN, $(C_1$-$C_4)$alkyl, $O(C_1$-$C_4)$alkyl, $S(C_1$-$C_4)$alkyl, $C=O(C_1$-$C_4)$alkyl, $(C_2$-$C_4)$alkynyl, $(C_3$-$C_6)$cycloalkyl, $O(C_3$-$C_6)$cycloalkyl, $C=O(C_3$-$C_6)$cycloalkyl, aryl, heteroaryl and heterocyclyl, wherein said alkyl, aryl, heteroaryl and heterocyclyl are optionally independently substituted with one or more F, Cl, $CF_3$, OH and oxo; and
$R^3$, $R^4$, $R^5$ and $R^6$ are as provided in the first through fifth embodiments.

In a seventh embodiment of the invention, the compound of the invention has the formula:

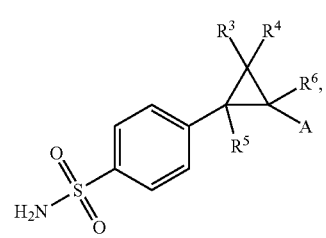

(Ia)

or a pharmaceutically acceptable salt thereof, wherein;
A is selected from

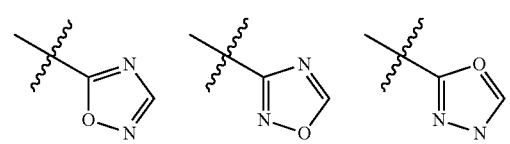

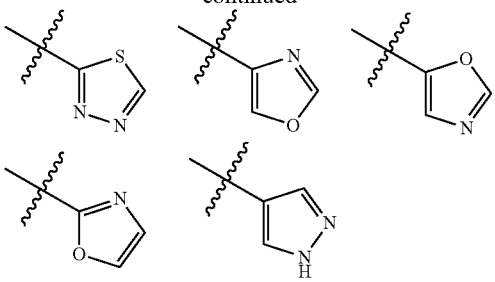

each substituted with 1 to 2 R groups independently selected from $(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, $C=O(C_3-C_6)$cycloalkyl, phenyl, O-phenyl, imidazolyl, pyrazinyl, furanyl, oxazolidinyl, pyrrolidinyl, and benzoxazolyl, wherein said alkyl, phenyl, oxazolidinyl, pyrrolidinyl, and benzoxazolyl are optionally independently substituted with one or more F, Cl, $CF_3$ and oxo;

$R^5$ and $R^6$ are independently H or methyl; and $R^3$ and $R^4$ are as provided in the first through fifth embodiments.

In an eighth embodiment of the invention, the compound of the invention has the formula:

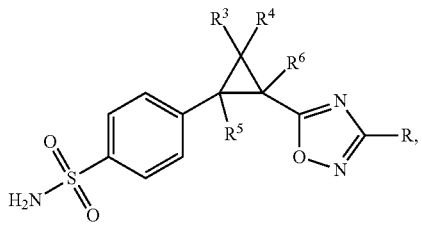

(Ib)

or a pharmaceutically acceptable salt thereof, wherein;

R is selected from $(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, $C=O(C_3-C_6)$cycloalkyl, phenyl, O-phenyl, imidazolyl, pyrazinyl, furanyl, oxazolidinyl, pyrrolidinyl, and benzoxazolyl, wherein said alkyl, phenyl, oxazolidinyl, pyrrolidinyl, and benzoxazolyl are optionally independently substituted with one or more F, Cl, $CF_3$ and oxo;

$R^3$ and $R^4$ are independently H, F or methyl; and $R^5$ and $R^6$ are independently H or methyl.

The invention is also directed to a compound, or a pharmaceutically acceptable salt thereof, selected from the following exemplified compounds:

4-((1S,3S)-3-(3-(5-Fluoro-2-methylphenyl)-1,2,4-oxadiazol-5-yl)-2,2-dimethylcyclopropyl)-benzenesulfonamide;
4-((1S,3S)-3-(5-(2-Cyclopropylethyl)-1,2,4-oxadiazol-3-yl)-2,2-dimethylcyclopropyl)benzenesulfonamide;
4-((1S,3S)-2,2-Dimethyl-3-(5-(2,3,6-trifluorophenyl)-1,2,4-oxadiazol-3-yl)cyclopropyl) benzenesulfonamide;
4-((1R,2R)-2-(3-(3-Fluorophenyl)-1,2,4-oxadiazol-5-yl)cyclopropyl)benzenesulfonamide;
4-{(1R,3R)-3-[5-(2,4-Difluorophenyl)-1,3,4-thiadiazol-2-yl]-2,2-dimethylcyclopropyl}benzenesulfonamide;
4-{((1S,3S)-3-[5-(2,4-Difluorophenyl)-1,3,4-oxadiazol-2-yl]-2,2-dimethylcyclopropyl}benzenesulfonamide;
4-{(1S,3S)-2,2-Difluoro-3-[3-(propan-2-yl)-1,2,4-oxadiazol-5-yl]cyclopropyl}benzenesulfonamide;
4-[(1R,2R)-2-(5-Phenyl-1,3-oxazol-2-yl)cyclopropyl]benzenesulfonamide;
4-[(1R,2R)-2-(4-Phenyl-1,3-oxazol-2-yl)cyclopropyl]benzenesulfonamide;
4-[(1R,3R)-2,2-Dimethyl-3-(2-phenyl-1,3-oxazol-5-yl)cyclopropyl]benzenesulfonamide;
4-[(1R,3R)-2,2-Dimethyl-3-(3-phenylisoxazol-5-yl)cyclopropyl]benzenesulfonamide;
4-[(1R,3R)-2,2-Dimethyl-3-(1-phenyl-1H-1,2,3-triazol-4-yl)cyclopropyl]benzenesulfonamide;
4-{(1R,3R)-3-[1-(3-Fluorophenyl)-1H-pyrazol-4-yl]-2,2-dimethylcyclopropyl}benzene sulfonamide;
4-{(1R,2R)-2-[4-(3-Fluorophenyl)-1,3-thiazol-2-yl]cyclopropyl}benzenesulfonamide;
4-[(1R,2R)-2-(5-Methyl-4-phenyl-1,3-thiazol-2-yl)cyclopropyl]benzenesulfonamide;
4-[(1R,2R)-2-(4-Methyl-5-phenyl-1,3-thiazol-2-yl)cyclopropyl]benzenesulfonamide;
4-[(1S,3S)-2,2-Dimethyl-3-(5-phenyl-1,3-thiazol-2-yl)cyclopropyl]benzenesulfonamide;
4-{trans-2-[3-(Propan-2-yl)-1,2,4-thiadiazol-5-yl]cyclopropyl}benzenesulfonamide;
4-{(1R,2R)-2-[3-(5-Chloro-2-methoxyphenyl)-1,2,4-oxadiazol-5-yl]cyclopropyl}benzene sulfonamide;
4-((1R,3R)-3-(3-Cyclohexyl-1,2,4-oxadiazol-5-yl)-2,2-dimethylcyclopropyl)benzene sulfonamide;
4-{(1S,3S)-2,2-Dimethyl-3-[5-(propan-2-yl)-1,3-thiazol-2-yl]cyclopropyl}benzenesulfonamide;
4-(2-Methyl-3-(3-phenyl-1,2,4-oxadiazol-5-yl)cyclopropyl) benzenesulfonamide;
4-{(1R,2R)-2-[1-(3-Fluorobenzyl)-1H-pyrazol-3-yl]cyclopropyl}benzenesulfonamide;
4-[trans-2-(2-Phenyl-1,3-oxazol-4-yl)cyclopropyl]benzenesulfonamide;
4-[(1R,2R)-2-(2-Phenyl-1,3-thiazol-4-yl)cyclopropyl]benzenesulfonamide;
4-{(1R,2R)-2-[1-(3-Fluorophenyl)-1H-1,2,3-triazol-4-yl]cyclopropyl}benzenesulfonamide;
4-[(1R,2R)-2-(2-Phenyl-1,3-thiazol-5-yl)cyclopropyl]benzenesulfonamide;
4-[(1R,2R)-2-(2-Cyclohexyl-1,3-oxazol-5-yl)cyclopropyl]benzenesulfonamide;
4-{(1R,2R)-2-[5-(Piperidin-1-yl)-1,2,4-thiadiazol-3-yl]cyclopropyl}benzenesulfonamide;
4-[trans-2,2-Dimethyl-3-(3-phenyl-1,2,4-oxadiazol-5-yl)cyclopropyl]phenyl sulfamate;
4-[(1R,3R)-3-(4,5-Dicyclopropyl-1,3-oxazol-2-yl)-2,2-dimethylcyclopropyl]benzene sulfonamide;
4-[trans-2,2-Dimethyl-3-(3-phenyl-1,2,4-oxadiazol-5-yl)cyclopropyl]-2-fluorobenzenesulfonamide;
5-{trans-2,2-Dimethyl-3-[4-(methylsulfonyl)phenyl]cyclopropyl}-3-phenyl-1,2,4-oxadiazole;

4-[trans-3-(5-Cyclopentylisoxazol-3-yl)-2,2-dimethylcyclopropyl]benzenesulfonamide;

4-{(1S,3S)-3-[2-(3-Fluorophenyl)-1-methyl-1H-imidazol-4-yl]-2,2-dimethylcyclopropyl}benzenesulfonamide;

4-{trans-2,2-Dichloro-3-[3-(3-fluorophenyl)-1,2,4-oxadiazol-5-yl]cyclopropyl}benzenesulfonamide;

4-{(1R,2R)-2-[5-(Piperidin-1-yl)-1,2,4-oxadiazol-3-yl]cyclopropyl}benzenesulfonamide 4-[trans-2,2-Dimethyl-3-(3-phenyl-1,2,4-oxadiazol-5-yl)cyclopropyl]-3-methylbenzenesulfonamide 4-{(1R,3R)-3-[3-(5-Chloro-2-methoxyphenyl)-1,2,4-oxadiazol-5-yl]-2,2-dimethylcyclopropyl}benzenesulfonamide;

4-[(1R,3R)-3-{3-[4-Fluoro-2-(trifluoromethyl)phenyl]-1,2,4-oxadiazol-5-yl}-2,2-dimethyl cyclopropyl]benzenesulfonamide;

4-[(1R,3R)-2,2-Dimethyl-3-(3-phenyl-1,2,4-oxadiazol-5-yl)cyclopropyl]benzenesulfonamide;

4-[(1R,3R)-3-{3-[5-Chloro-2-(propan-2-yloxy)phenyl]-1,2,4-oxadiazol-5-yl}-2,2-dimethyl cyclopropyl]benzenesulfonanmide;

4-[(1S,2S)-2-(3-Phenyl-1,2,4-oxadiazol-5-yl)cyclopropyl]benzenesulfonamide;

4-{(1R,3R)-3-[3-(5-Fluoro-2-methylphenyl)-1,2,4-oxadiazol-5-yl]-2,2-dimethylcyclopropyl}benzenesulfonamide;

4-{(1R,3R)-3-[3-(2,4-Difluorophenyl)-1,2,4-oxadiazol-5-yl]-2,2-dimethylcyclopropyl}benzenesulfonamide;

4-{(1S,2S)-2-[3-(2,4-Difluorophenyl)-1,2,4-oxadiazol-5-yl]cyclopropyl}benzenesulfonanmide;

4-[(1S,3S)-2,2-Difluoro-3-(3-phenyl-1,2,4-oxadiazol-5-yl)cyclopropyl]benzenesulfonamide;

4-{(1R,3R)-3-[3-(3-Fluorophenyl)-1,2,4-oxadiazol-5-yl]-2,2-dimethylcyclopropyl}benzenesulfonamide;

4-{(1R,3R)-3-[3-(2,6-Difluorophenyl)-1,2,4-oxadiazol-5-yl]-2,2-dimethylcyclopropyl}benzenesulfonamide;

4-{(1R,3R)-3-[3-(2-Fluorophenyl)-1,2,4-oxadiazol-5-yl]-2,2-dimethylcyclopropyl}benzenesulfonamide;

4-[(1R,3R)-2,2-Dimethyl-3-{3-[2-(trifluoromethyl)phenyl]-1,2,4-oxadiazol-5-yl}cyclopropyl]benzenesulfonamide;

4-{(1R,3R)-3-[3-(3-Bromophenyl)-1,2,4-oxadiazol-5-yl]-2,2-dimethylcyclopropyl}benzenesulfonamide;

4-{(1S,2S)-2-[3-(5-Chloro-2-methoxyphenyl)-1,2,4-oxadiazol-5-yl]cyclopropyl}benzenesulfonamide;

4-{(1R,3R)-2,2-Dimethyl-3-[3-(propan-2-yl)-1,2,4-oxadiazol-5-yl]cyclopropyl}benzenesulfonamide;

4-{(1R,3R)-3-[3-(5-Fluoropyridin-3-yl)-1,2,4-oxadiazol-5-yl]-2,2-dimethylcyclopropyl}benzenesulfonamide;

4-[(1R,3R)-3-(3-Cyclobutyl-1,2,4-oxadiazol-5-yl)-2,2-dimethylcyclopropyl]benzenesulfonamide;

4-[(1S,2S)-2-(3-Cyclohexyl-1,2,4-oxadiazol-5-yl)cyclopropyl]benzenesulfonamide;

4-{(1S,2S)-2-[3-(5-Fluoropyridin-3-yl)-1,2,4-oxadiazol-5-yl]cyclopropyl}benzenesulfonanmide;

4-{(1S,2S)-2-[3-(2-Methylpyridin-3-yl)-1,2,4-oxadiazol-5-yl]cyclopropyl}benzenesulfonamide;

4-[(1R,3R)-2,2-Dimethyl-3-{3-[5-(trifluoromethyl)pyridin-3-yl]-1,2,4-oxadiazol-5-yl}cyclopropyl]benzenesulfonanmide;

4-{(1R,3R)-3-[3-(3,3-Difluorocyclobutyl)-1,2,4-oxadiazol-5-yl]-2,2-dimethylcyclopropyl}benzenesulfonamide;

4-[(1R,3R)-3-(3-Cyclopentyl-1,2,4-oxadiazol-5-yl)-2,2-dimethylcyclopropyl]benzene sulfonamide;

4-{(1R,3R)-3-[3-(Cyclopropylmethyl)-1,2,4-oxadiazol-5-yl]-2,2-dimethylcyclopropyl}benzenesulfonamide;

4-{(1R,3R)-2,2-Dimethyl-3-[3-(tetrahydrofuran-3-yl)-1,2,4-oxadiazol-5-yl]cyclopropyl}benzenesulfonamide;

4-{(1R,3R)-2,2-Dimethyl-3-[3-(tetrahydrofuran-2-yl)-1,2,4-oxadiazol-5-yl]cyclopropyl}benzenesulfonamide;

4-{(1R,3R)-2,2-Dimethyl-3-[3-(1-phenylcyclopropyl)-1,2,4-oxadiazol-5-yl]cyclopropyl}benzenesulfonamide;

4-{(1R,3R)-3-[3-(5-Fluoro-2,3-dihydro-1H-inden-1-yl)-1,2,4-oxadiazol-5-yl]-2,2-dimethyl cyclopropyl}benzenesulfonanmide;

4-{(1R,3R)-2,2-Dimethyl-3-[3-(spiro[3.3]hept-2-yl)-1,2,4-oxadiazol-5-yl]cyclopropyl}benzenesulfonamide;

4-{(1R,3R)-3-[3-(1-Acetylpiperidin-4-yl)-1,2,4-oxadiazol-5-yl]-2,2-dimethylcyclopropyl}benzenesulfonamide;

4-[(1S,3S)-3-(3-tert-Butyl-1,2,4-oxadiazol-5-yl)-2,2-difluorocyclopropyl]benzenesulfonamide;

4-[(1S,3S)-2,2-Dimethyl-3-{3-[1-(trifluoromethyl)cyclopropyl]-1,2,4-oxadiazol-5-yl}cyclopropyl]benzenesulfonamide;

4-[(1S,3S)-3-(3-Cyclopentyl-1,2,4-oxadiazol-5-yl)-2,2-difluorocyclopropyl]benzenesulfonamide;

4-{(1S,3S)-3-[3-(5-Chloro-2-methoxyphenyl)-1,2,4-oxadiazol-5-yl]-2,2-dimethylcyclopropyl}benzenesulfonamide;

4-[(1S,3S)-3-{3-[4-Fluoro-2-(trifluoromethyl)phenyl]-1,2,4-oxadiazol-5-yl}-2,2-dimethyl cyclopropyl]benzenesulfonanmide;

4-[(1S,3S)-3-{3-[5-Chloro-2-(propan-2-yloxy)phenyl]-1,2,4-oxadiazol-5-yl}-2,2-dimethyl cyclopropyl]benzenesulfonanmide;

4-[(1S,3S)-2,2-Dimethyl-3-(3-phenyl-1,2,4-oxadiazol-5-yl)cyclopropyl]benzenesulfonamide;

4-[(1R,2R)-2-(3-Phenyl-1,2,4-oxadiazol-5-yl)cyclopropyl]benzenesulfonamide;

4-[(1R,2R)-2-{3-[2-(Trifluoromethyl)phenyl]-1,2,4-oxadiazol-5-yl}cyclopropyl]benzenesulfonamide;

4-[(1R,2R)-2-{3-[4-Fluoro-2-(trifluoromethyl)phenyl]-1,2,4-oxadiazol-5-yl}cyclopropyl]benzenesulfonamide;

4-[(1R,2R)-2-{3-[5-Fluoro-2-(trifluoromethyl)phenyl]-1,2,4-oxadiazol-5-yl}cyclopropyl]benzenesulfonamide;

4-{(1R,2R)-2-[3-(2,6-Difluorophenyl)-1,2,4-oxadiazol-5-yl]cyclopropyl}benzenesulfonanmide;

4-{(1R,2R)-2-[3-(3-Bromophenyl)-1,2,4-oxadiazol-5-yl]cyclopropyl}benzenesulfonamide;

4-{(1R,2R)-2-[3-(2-Fluoro-6-methylphenyl)-1,2,4-oxadiazol-5-yl]cyclopropyl}benzenesulfonamide;

4-{(1S,3S)-3-[3-(2,4-Difluorophenyl)-1,2,4-oxadiazol-5-yl]-2,2-dimethylcyclopropyl}benzenesulfonamide;

4-{(1R,2R)-2-[3-(2,4-Difluorophenyl)-1,2,4-oxadiazol-5-yl]cyclopropyl}benzenesulfonanmide;

4-{(1R,2R)-2-[3-(4-Fluorophenyl)-1,2,4-oxadiazol-5-yl]cyclopropyl}benzenesulfonamide;

4-{(1R,2R)-2-[3-(2,3-Difluorophenyl)-1,2,4-oxadiazol-5-yl]cyclopropyl}benzenesulfonamide;

4-{(1R,2R)-2-[3-(2,5-Difluorophenyl)-1,2,4-oxadiazol-5-yl]cyclopropyl}benzenesulfonanmide;

4-{(1R,2R)-2-[3-(2-Methylphenyl)-1,2,4-oxadiazol-5-yl]cyclopropyl}benzenesulfonanmide;

4-{(1R,2R)-2-[3-(3-Methylphenyl)-1,2,4-oxadiazol-5-yl]cyclopropyl}benzenesulfonamide;

4-{(1R,2R)-2-[3-(4-Methylphenyl)-1,2,4-oxadiazol-5-yl]cyclopropyl}benzenesulfonamide;

4-{(1R,2R)-2-[3-(2-Fluorophenyl)-1,2,4-oxadiazol-5-yl]cyclopropyl}benzenesulfonamide;

4-[(1R,3R)-2,2-Difluoro-3-(3-phenyl-1,2,4-oxadiazol-5-yl)cyclopropyl]benzenesulfonamide;

4-{(1R,3R)-2,2-Difluoro-3-[3-(propan-2-yl)-1,2,4-oxadiazol-5-yl]cyclopropyl}benzenesulfonamide;

4-[(1S,3S)-2,2-Dimethyl-3-{3-[4-(trifluoromethyl)pyridin-3-yl]-1,2,4-oxadiazol-5-yl}cyclopropyl]benzenesulfonamide;

4-[(1S,3S)-3-(3-Cyclohexyl-1,2,4-oxadiazol-5-yl)-2,2-dimethylcyclopropyl]benzenesulfonamide;

4-{(1S,3S)-2,2-Dimethyl-3-[3-(pyridin-2-yl)-1,2,4-oxadiazol-5-yl]cyclopropyl}benzenesulfonamide;

4-{(1S,3S)-2,2-Dimethyl-3-[3-(propan-2-yl)-1,2,4-oxadiazol-5-yl]cyclopropyl}benzenesulfonamide;

4-{(1S,3S)-3-[3-(5-Fluoropyridin-3-yl)-1,2,4-oxadiazol-5-yl]-2,2-dimethylcyclopropyl}benzenesulfonamide;

4-[(1S,3S)-3-(3-Cyclobutyl-1,2,4-oxadiazol-5-yl)-2,2-dimethylcyclopropyl]benzenesulfonamide;

4-[(1R,2R)-2-(3-Cyclohexyl-1,2,4-oxadiazol-5-yl)cyclopropyl]benzenesulfonamide;

4-[(1S,3S)-3-(3-Cyclopropyl-1,2,4-oxadiazol-5-yl)-2,2-dimethylcyclopropyl]benzene sulfonamide;

4-[(1S,3S)-3-(3-tert-Butyl-1,2,4-oxadiazol-5-yl)-2,2-dimethylcyclopropyl]benzenesulfonamide;

4-{(1R,2R)-2-[3-(Propan-2-yl)-1,2,4-oxadiazol-5-yl]cyclopropyl}benzenesulfonamide;

4-{(1R,2R)-2-[3-(5-Fluoropyridin-3-yl)-1,2,4-oxadiazol-5-yl]cyclopropyl}benzenesulfonamide;

4-[(1S,3S)-2,2-Dimethyl-3-(3-methyl-1,2,4-oxadiazol-5-yl)cyclopropyl]benzenesulfonamide;

4-{(1S,3S)-2,2-Dimethyl-3-[3-(2,2,2-trifluoroethyl)-1,2,4-oxadiazol-5-yl]cyclopropyl}benzenesulfonamide;

4-{(1S,3S)-2,2-Dimethyl-3-[3-(2-methylpyridin-3-yl)-1,2,4-oxadiazol-5-yl]cyclopropyl}benzenesulfonamide;

4-{(1R,2R)-2-[3-(2-Methylpyridin-3-yl)-1,2,4-oxadiazol-5-yl]cyclopropyl}benzenesulfonamide;

4-[(1S,3S)-2,2-Dimethyl-3-{3-[5-(trifluoromethyl)pyridin-3-yl]-1,2,4-oxadiazol-5-yl}cyclopropyl]benzenesulfonamide;

4-{(1S,3S)-3-[3-(3,3-Difluorocyclobutyl)-1,2,4-oxadiazol-5-yl]-2,2-dimethylcyclopropyl}benzenesulfonamide;

4-{(1R,2R)-2-[3-(3,3-Difluorocyclobutyl)-1,2,4-oxadiazol-5-yl]cyclopropyl}benzenesulfonamide;

4-[(1S,3S)-3-(3-Cyclopentyl-1,2,4-oxadiazol-5-yl)-2,2-dimethylcyclopropyl]benzene sulfonamide;

4-[(1R,2R)-2-(3-Cyclopentyl-1,2,4-oxadiazol-5-yl)cyclopropyl]benzenesulfonamide;

4-[(1R,2R)-2-{3-[5-(Trifluoromethyl)pyridin-3-yl]-1,2,4-oxadiazol-5-yl}cyclopropyl]benzenesulfonamide;

4-{(1R,2R)-2-[3-(1-Phenylcyclopropyl)-1,2,4-oxadiazol-5-yl]cyclopropyl}benzenesulfonamide;

4-{(1R,2R)-2-[3-(2-Cyclopropylpyridin-3-yl)-1,2,4-oxadiazol-5-yl]cyclopropyl}benzenesulfonamide;

4-[(1R,2R)-2-{3-[4-(Trifluoromethyl)pyridin-3-yl]-1,2,4-oxadiazol-5-yl}cyclopropyl]benzenesulfonamide;

4-{(1R,2R)-2-[3-(2,4-Difluorobenzyl)-1,2,4-oxadiazol-5-yl]cyclopropyl}benzenesulfonamide;

4-{(1S,3S)-3-[3-(Cyclopropylmethyl)-1,2,4-oxadiazol-5-yl]-2,2-dimethylcyclopropyl}benzenesulfonamide;

4-{(1R,2R)-2-[3-(Cyclopropylmethyl)-1,2,4-oxadiazol-5-yl]cyclopropyl}benzenesulfonamide;

4-[(1S,3S)-2,2-Dimethyl-3-{3-[6-(trifluoromethyl)pyridin-3-yl]-1,2,4-oxadiazol-5-yl}cyclopropyl]benzenesulfonamide;

4-[(1S,3S)-2,2-Dimethyl-3-{3-[2-(trifluoromethyl)pyridin-3-yl]-1,2,4-oxadiazol-5-yl}cyclopropyl]benzenesulfonamide;

4-{(1R,2R)-2-[3-(4-Methyl-1,3-oxazol-5-yl)-1,2,4-oxadiazol-5-yl]cyclopropyl}benzenesulfonamide;

4-{(1S,3S)-3-[3-(2-Hydroxycyclohexyl)-1,2,4-oxadiazol-5-yl]-2,2-dimethylcyclopropyl}benzenesulfonamide;

4-[(1S,3S)-2,2-Dimethyl-3-{3-[1-(trifluoromethyl)cyclopropyl]-1,2,4-oxadiazol-5-yl}cyclopropyl]benzenesulfonamide;

4-{(1S,3S)-2,2-Dimethyl-3-[3-(1-methylcyclohexyl)-1,2,4-oxadiazol-5-yl]cyclopropyl}benzenesulfonamide;

4-{(1R,3R)-2,2-Difluoro-3-[3-(2-fluoropropan-2-yl)-1,2,4-oxadiazol-5-yl]cyclopropyl}benzenesulfonamide;

4-{trans-2-[3-(5-Chloro-2-methoxyphenyl)-1,2,4-oxadiazol-5-yl]cyclopropyl}benzenesulfonamide;

4-{trans-3-[3-(5-Chloro-2-methoxyphenyl)-1,2,4-oxadiazol-5-yl]-2,2-difluorocyclopropyl}benzenesulfonamide;

4-{2-[3-(2,4-Difluorophenyl)-1,2,4-oxadiazol-5-yl]-2-methylcyclopropyl}benzenesulfonamide;

4-{2-[3-(2,4-Difluorophenyl)-1,2,4-oxadiazol-5-yl]-1-methylcyclopropyl}benzenesulfonamide;

4-{(1R,3R)-3-[5-(2,6-Difluorophenyl)-1,3,4-oxadiazol-2-yl]-2,2-dimethylcyclopropyl}benzenesulfonamide;

4-[(1R,3R)-3-{5-[5-Fluoro-2-(trifluoromethyl)phenyl]-1,3,4-oxadiazol-2-yl}-2,2-dimethyl cyclopropyl]benzenesulfonanmide;

4-[(1R,3R)-3-{5-[2-Fluoro-6-(trifluoromethyl)phenyl]-1,3,4-oxadiazol-2-yl}-2,2-dimethyl cyclopropyl]benzenesulfonanmide;

4-[(1R,3R)-2,2-Dimethyl-3-(5-phenyl-1,3,4-thiadiazol-2-yl)cyclopropyl]benzenesulfonamide;

4-[(1R,3R)-2,2-Dimethyl-3-(5-phenyl-1H-1,2,4-triazol-3-yl)cyclopropyl]benzenesulfonamide;

4-{(1R,3R)-3-[5-(2-Cyclopropylpyridin-3-yl)-1,3,4-oxadiazol-2-yl]-2,2-dimethylcyclopropyl}benzenesulfonamide;

4-[(1R,3R)-3-(5-Cyclohexyl-1,3,4-thiadiazol-2-yl)-2,2-dimethylcyclopropyl]benzene sulfonamide;

4-[(1S,3S)-2,2-Dimethyl-3-(5-phenyl-1,3,4-oxadiazol-2-yl)cyclopropyl]benzenesulfonamide;

4-[(1S,3S)-2,2-Dimethyl-3-{5-[3-(trifluoromethyl)phenyl]-1,3,4-oxadiazol-2-yl}cyclopropyl]benzenesulfonamide;

4-{(1S,3S)-3-[5-(3-Fluorophenyl)-1,3,4-oxadiazol-2-yl]-2,2-dimethylcyclopropyl}benzenesulfonamide;

4-[(1S,3S)-2,2-Dimethyl-3-{5-[2-(trifluoromethyl)phenyl]-1,3,4-oxadiazol-2-yl}cyclopropyl]benzenesulfonamide;

4-{(1S,3S)-3-[5-(2,6-Difluorophenyl)-1,3,4-oxadiazol-2-yl]-2,2-dimethylcyclopropyl}benzenesulfonamide;

4-[(1S,3S)-3-{5-[5-Fluoro-2-(trifluoromethyl)phenyl]-1,3,4-oxadiazol-2-yl}-2,2-dimethyl cyclopropyl]benzenesulfonamide;

4-[(1S,3S)-2,2-Dimethyl-3-(5-phenyl-1,3,4-thiadiazol-2-yl)cyclopropyl]benzenesulfonamide;

4-{(1S,3S)-3-[5-(2,4-Difluorophenyl)-1,3,4-thiadiazol-2-yl]-2,2-dimethylcyclopropyl}benzenesulfonamide;

4-{(1S,3S)-2,2-Dimethyl-3-[5-(propan-2-yl)-1,3,4-oxadiazol-2-yl]cyclopropyl}benzenesulfonamide;

4-[(1S,3S)-3-(5-Cyclopentyl-1,3,4-oxadiazol-2-yl)-2,2-dimethylcyclopropyl]benzene sulfonamide;

4-{(1S,3S)-3-[5-(Cyclopropylmethyl)-1,3,4-oxadiazol-2-yl]-2,2-dimethylcyclopropyl}benzenesulfonamide;

4-{(1S,3S)-3-[5-(2-Cyclopropylpyridin-3-yl)-1,3,4-oxadiazol-2-yl]-2,2-dimethylcyclopropyl}benzenesulfonamide;

4-[(1S,3S)-3-(5-Cyclohexyl-1,3,4-thiadiazol-2-yl)-2,2-dimethylcyclopropyl]benzenesulfonamide;

4-[(1S,3S)-3-(5-Cyclopentyl-1,3,4-thiadiazol-2-yl)-2,2-dimethylcyclopropyl]benzene sulfonamide;

4-[(1S,3S)-3-(5-Cyclopropyl-1,3,4-thiadiazol-2-yl)-2,2-dimethylcyclopropyl]benzene sulfonamide;

4-[(1R,2R)-2-(5-Cyclopentyl-1,3,4-thiadiazol-2-yl)cyclopropyl]benzenesulfonamide;

4-[(1S,3S)-3-{5-[2-Fluoro-6-(trifluoromethyl)phenyl]-1,3,4-oxadiazol-2-yl}-2,2-dimethyl cyclopropyl]benzenesulfonamide;

4-[(1S,3S)-2,2-Dimethyl-3-(5-phenyl-1,2,4-oxadiazol-3-yl)cyclopropyl]benzenesulfonamide;

4-{(1S,3S)-3-[5-(2-Chloro-4-fluorophenyl)-1,2,4-oxadiazol-3-yl]-2,2-dimethylcyclopropyl}benzenesulfonamide;

4-{(1S,3S)-2,2-Dimethyl-3-[5-(2,4,6-trifluorophenyl)-1,2,4-oxadiazol-3-yl]cyclopropyl}benzenesulfonamide;

4-[(1S,3S)-3-{5-[4-Fluoro-3-(trifluoromethoxy)phenyl]-1,2,4-oxadiazol-3-yl}-2,2-dimethyl cyclopropyl]benzenesulfonamide;

4-{(1S,3S)-3-[5-(3-Fluorophenyl)-1,2,4-oxadiazol-3-yl]-2,2-dimethylcyclopropyl}benzenesulfonamide;

4-{(1S,3S)-3-[5-(2-Fluoro-6-methylphenyl)-1,2,4-oxadiazol-3-yl]-2,2-dimethylcyclopropyl}benzenesulfonamide;

4-[(1S,3S)-3-{5-[2-Fluoro-5-(2-oxo-1,3-oxazolidin-3-yl)phenyl]-1,2,4-oxadiazol-3-yl}-2,2-dimethylcyclopropyl]benzenesulfonamide;

4-{(1S,3S)-3-[5-(2,6-Difluorophenyl)-1,2,4-oxadiazol-3-yl]-2,2-dimethylcyclopropyl}benzenesulfonamide;

4-{(1S,3S)-3-[5-(3-Cyclopropylphenyl)-1,2,4-oxadiazol-3-yl]-2,2-dimethylcyclopropyl}benzenesulfonamide;

4-{(1S,3S)-2,2-Dimethyl-3-[5-(2,3,5-tifluorophenyl)-1,2,4-oxadiazol-3-yl]cyclopropyl}benzenesulfonamide;

4-{(1S,3S)-3-[5-(4-Ethynylphenyl)-1,2,4-oxadiazol-3-yl]-2,2-dimethylcyclopropyl}benzenesulfonamide;

4-{(1S,3S)-3-[5-(4-Cyanophenyl)-1,2,4-oxadiazol-3-yl]-2,2-dimethylcyclopropyl}benzenesulfonamide;

4-[(1S,3S)-2,2-Dimethyl-3-{5-[4-(trifluoromethoxy)phenyl]-1,2,4-oxadiazol-3-yl}cyclopropyl]benzenesulfonamide;

4-[(1S,3S)-2,2-Dimethyl-3-{5-[3-(1,1,2,2-tetrafluoroethoxy)phenyl]-1,2,4-oxadiazol-3-yl}cyclopropyl]benzenesulfonamide;

4-{(1R,2R)-2-[5-(3-Fluorophenyl)-1,2,4-oxadiazol-3-yl]cyclopropyl}benzenesulfonamide;

4-{(1S,3S)-3-[5-(2,4-Difluorobenzyl)-1,2,4-oxadiazol-3-yl]-2,2-dimethylcyclopropyl}benzenesulfonamide;

4-[(1S,3S)-3-{5-[1-(3-Chlorophenoxy)ethyl]-1,2,4-oxadiazol-3-yl}-2,2-dimethylcyclopropyl]benzenesulfonamide;

4-{(1S,3S)-3-[5-(5-Fluoro-2,3-dihydro-1H-inden-1-yl)-1,2,4-oxadiazol-3-yl]-2,2-dimethyl cyclopropyl}benzenesulfonanmide;

4-[(1S,3S)-3-{5-[1-(2,5-Difluorophenyl)cyclobutyl]-1,2,4-oxadiazol-3-yl}-2,2-dimethyl cyclopropyl]benzenesulfonanmide;

4-[(1S,3S)-3-{5-[(5-Chloro-2-oxo-1,3-benzoxazol-3(2H)-yl)methyl]-1,2,4-oxadiazol-3-yl}-2,2-dimethylcyclopropyl]benzenesulfonamide;

4-{(1S,3S)-2,2-Dimethyl-3-[5-(1,3-thiazol-4-yl)-1,2,4-oxadiazol-3-yl]cyclopropyl}benzenesulfonamide;

4-{(1S,3S)-2,2-Dimethyl-3-[5-(4-methyl-1,3-oxazol-5-yl)-1,2,4-oxadiazol-3-yl]cyclopropyl}benzenesulfonamide;

4-{(1S,3S)-3-[5-(2-Cyclopropyl-1H-imidazol-4-yl)-1,2,4-oxadiazol-3-yl]-2,2-dimethyl cyclopropyl}benzenesulfonamide;

4-{(1S,3S)-3-[5-(1-Cyclopropylpiperidin-4-yl)-1,2,4-oxadiazol-3-yl]-2,2-dimethylcyclopropyl}benzenesulfonamide;

4-{(1S,3S)-2,2-Dimethyl-3-[5-(1-methyl-1H-pyrrol-3-yl)-1,2,4-oxadiazol-3-yl]cyclopropyl}benzenesulfonamide;

4-[(1S,3S)-3-{5-[1-(1H-Imidazol-1-yl)ethyl]-1,2,4-oxadiazol-3-yl}-2,2-dimethylcyclopropyl]benzenesulfonamide;

4-[(1S,3S)-2,2-Dimethyl-3-{5-[1-(pyrazin-2-yl)cyclopropyl]-1,2,4-oxadiazol-3-yl}cyclopropyl]benzenesulfonamide;

4-[(1S,3S)-2,2-Dimethyl-3-{5-[4-(trifluoromethyl)quinolin-2-yl]-1,2,4-oxadiazol-3-yl}cyclopropyl]benzenesulfonamide;

4-[(1S,3S)-3-{5-[6-(2-Fluoroethoxy)pyridin-3-yl]-1,2,4-oxadiazol-3-yl}-2,2-dimethyl cyclopropyl]benzenesulfonamide;

4-{(1S,3S)-2,2-Dimethyl-3-[5-(tetrahydrofuran-2-ylmethyl)-1,2,4-oxadiazol-3-yl]cyclopropyl}benzenesulfonamide;

4-{(1S,3S)-3-[5-(1,1-Difluoroethyl)-1,2,4-oxadiazol-3-yl]-2,2-dimethylcyclopropyl}benzenesulfonamide;

4-[(1S,3S)-3-{5-[4-(4-Fluorophenyl)-1H-imidazol-2-yl]-1,2,4-oxadiazol-3-yl}-2,2-dimethyl cyclopropyl]benzenesulfonamide;

4-[(1S,3S)-2,2-Dimethyl-3-(5-{2-[(2,2,2-trifluoroethyl)sulfanyl]-1,3-oxazol-5-yl}-1,2,4-oxadiazol-3-yl)cyclopropyl]benzenesulfonamide;

4-[(1S,3S)-2,2-Dimethyl-3-{5-[3-(trifluoromethyl)pyridin-4-yl]-1,2,4-oxadiazol-3-yl}cyclopropyl]benzenesulfonamide;

4-[(1S,3S)-2,2-Dimethyl-3-{5-[4-(trifluoromethyl)pyridin-3-yl]-1,2,4-oxadiazol-3-yl}cyclopropyl]benzenesulfonamide;

4-[(1S,3S)-2,2-Dimethyl-3-{5-[2-(trifluoromethyl)pyridin-3-yl]-1,2,4-oxadiazol-3-yl}cyclopropyl]benzenesulfonamide;

4-{(1S,3S)-2,2-Dimethyl-3-[5-(4H-thieno[3,2-b]pyrrol-5-yl)-1,2,4-oxadiazol-3-yl]cyclopropyl}benzenesulfonamide;

4-[(1S,3S)-3-{5-[1-(Cyclopropylcarbonyl)azetidin-3-yl]-1,2,4-oxadiazol-3-yl}-2,2-dimethyl cyclopropyl]benzenesulfonamide;

4-{(1S,3S)-3-[5-(2-Cyclopentyl-1-oxooctahydrocyclopenta[c]pyrrol-5-yl)-1,2,4-oxadiazol-3-yl]-2,2-dimethylcyclopropyl}benzenesulfonanmide;

4-[(1S,3S)-3-(5-Cyclopropyl-1,2,4-oxadiazol-3-yl)-2,2-dimethylcyclopropyl]benzenesulfonamide;

4-[(1S,3S)-3-(5-Cyclopentyl-1,2,4-oxadiazol-3-yl)-2,2-dimethylcyclopropyl]benzene sulfonamide;

4-{(1S,3S)-2,2-Dimethyl-3-[5-(spiro[2.5]oct-4-yl)-1,2,4-oxadiazol-3-yl]cyclopropyl}benzenesulfonamide;

4-{(1S,3S)-2,2-Dimethyl-3-[5-(2,2,2-trifluoro-1-hydroxyethyl)-1,2,4-oxadiazol-3-yl]cyclopropyl}benzenesulfonamide;

4-{(1S,3S)-3-[5-(4-Hydroxycyclohexyl)-1,2,4-oxadiazol-3-yl]-2,2-dimethylcyclopropyl}benzenesulfonamide;

4-{(1S,3S)-3-[5-(3-Hydroxycyclobutyl)-1,2,4-oxadiazol-3-yl]-2,2-dimethylcyclopropyl}benzenesulfonamide;

4-{(1S,3S)-2,2-Dimethyl-3-[5-(3-oxo-3,4-dihydro-2H-1,4-benzoxazin-8-yl)-1,2,4-oxadiazol-3-yl]cyclopropyl}benzenesulfonamide;

4-{(1S,3S)-3-[5-(2-Hydroxy-1,3-benzothiazol-6-yl)-1,2,4-oxadiazol-3-yl]-2,2-dimethyl cyclopropyl}benzenesulfonamide;

4-{(1R,3R)-3-[5-(2-Cyclopropylethyl)-1,2,4-oxadiazol-3-yl]-2,2-dimethylcyclopropyl}benzenesulfonamide;

4-[(1R,2R)-2-(5-Cyclohexyl-1,2,4-oxadiazol-3-yl)cyclopropyl]benzenesulfonamide;

4-[(1R,2R)-2-{5-[1-(Trifluoromethyl)cyclopropyl]-1,2,4-oxadiazol-3-yl}cyclopropyl]benzenesulfonamide;

4-{(1R,2R)-2-[5-(5-Fluoropyridin-3-yl)-1,2,4-oxadiazol-3-yl]cyclopropyl}benzenesulfonamide;
4-{(1R,3R)-3-[4-(2-Fluorophenyl)-1,3-oxazol-2-yl]-2,2-dimethylcyclopropyl}benzenesulfonamide;
4-{(1R,3R)-3-[4-(2,4-Difluorophenyl)-1,3-oxazol-2-yl]-2,2-dimethylcyclopropyl}benzenesulfonamide;
4-{(1R,3R)-3-[4-(2,5-Difluorophenyl)-1,3-oxazol-2-yl]-2,2-dimethylcyclopropyl}benzenesulfonamide;
4-[(1R,3R)-3-(4-tert-Butyl-1,3-oxazol-2-yl)-2,2-dimethylcyclopropyl]benzenesulfonamide;
4-[(1R,3R)-3-(4-Cyclopropyl-1,3-oxazol-2-yl)-2,2-dimethylcyclopropyl]benzenesulfonamide;
4-[(1S,2S)-2-(4-Phenyl-1,3-oxazol-2-yl)cyclopropyl]benzenesulfonamide;
4-{(1S,2S)-2-[4-(3-Fluorophenyl)-1,3-thiazol-2-yl]cyclopropyl}benzenesulfonamide;
4-[(1R,3R)-3-(4-Cyclopentyl-1,3-oxazol-2-yl)-2,2-dimethylcyclopropyl]benzenesulfonamide;
4-[(1R,3R)-3-(5-Cyclopentyl-1,3-thiazol-2-yl)-2,2-dimethylcyclopropyl]benzenesulfonamide;
4-{(1S,2S)-2-[5-(3-Fluorophenyl)-1,3-thiazol-2-yl]cyclopropyl}benzenesulfonamide;
4-[(1S,3S)-3-(5-Cyclopentyl-1,3-oxazol-2-yl)-2,2-difluorocyclopropyl]benzenesulfonamide; 4-{(1S,3S)-3-[4-(2-Fluorophenyl)-1,3-oxazol-2-yl]-2,2-dimethylcyclopropyl}benzenesulfonamide;
4-{(1S,3S)-3-[4-(2,5-Difluorophenyl)-1,3-oxazol-2-yl]-2,2-dimethylcyclopropyl}benzenesulfonamide;
4-{(1S,3S)-3-[4-(2,4-Difluorophenyl)-1,3-oxazol-2-yl]-2,2-dimethylcyclopropyl}benzenesulfonamide;
4-[(1R,2R)-2-(5-tert-Butyl-1,3-oxazol-2-yl)cyclopropyl]benzenesulfonamide;
4-[(1R,2R)-2-(5-Cyclopropyl-1,3-oxazol-2-yl)cyclopropyl]benzenesulfonamide;
4-[(1R,2R)-2-(4-Ethyl-1,3-oxazol-2-yl)cyclopropyl]benzenesulfonamide;
4-[(1S,3S)-3-(4-tert-Butyl-1,3-oxazol-2-yl)-2,2-dimethylcyclopropyl]benzenesulfonamide;
4-[(1S,3S)-3-(4-Ethyl-1,3-oxazol-2-yl)-2,2-dimethylcyclopropyl]benzenesulfonamide;
4-[(1R,2R)-2-(4-Phenyl-1,3-thiazol-2-yl)cyclopropyl]benzenesulfonamide;
4-{(1S,3S)-3-[4-(3-Fluorophenyl)-1,3-thiazol-2-yl]-2,2-dimethylcyclopropyl}benzenesulfonamide;
4-{(1S,3S)-2,2-Dimethyl-3-[4-(propan-2-yl)-1,3-thiazol-2-yl]cyclopropyl}benzenesulfonamide;
4-[(1R,2R)-2-(4-Phenyl-1H-imidazol-2-yl)cyclopropyl]benzenesulfonamide;
4-[(1R,3R)-3-(5-Cyclopentyl-1,3-oxazol-2-yl)-2,2-difluorocyclopropyl]benzenesulfonamide;
4-[(1S,3S)-3-(5-Cyclopentyl-1,3-oxazol-2-yl)-2,2-dimethylcyclopropyl]benzenesulfonamide;
4-[(1R,2R)-2-(5-Cyclopentyl-1,3-thiazol-2-yl)cyclopropyl]benzenesulfonamide;
4-[(1S,3S)-3-(5-Cyclopentyl-1,3-thiazol-2-yl)-2,2-dimethylcyclopropyl]benzenesulfonamide;
4-[(1S,3S)-3-(4-Cyclopentyl-1,3-oxazol-2-yl)-2,2-dimethylcyclopropyl]benzenesulfonamide;
4-{(1R,2R)-2-[5-(3-Fluorophenyl)-1,3-thiazol-2-yl]cyclopropyl}benzenesulfonamide;
4-[(1R,2R)-2-(4-Cyclopentyl-1,3-oxazol-2-yl)cyclopropyl]benzenesulfonamide;
4-[(1R,3S)-3-(4-Cyclohexyl-1,3-thiazol-2-yl)-2,2-difluorocyclopropyl]benzenesulfonamide;
4-[(1S,3S)-2,2-Dimethyl-3-(2-phenyl-1,3-oxazol-5-yl)cyclopropyl]benzenesulfonamide;
4-[(1S,2S)-2-(2-Phenyl-1,3-oxazol-5-yl)cyclopropyl]benzenesulfonamide;
4-[(1R,2R)-2-(2-Phenyl-1,3-oxazol-5-yl)cyclopropyl]benzenesulfonamide;
4-[(1S,3S)-2,2-Dimethyl-3-(3-phenylisoxazol-5-yl)cyclopropyl]benzenesulfonamide;
4-{(1R,3R)-3-[1-(3-Fluorophenyl)-1H-1,2,3-triazol-4-yl]-2,2-dimethylcyclopropyl}benzenesulfonamide;
4-{(1S,3S)-3-[1-(3-Fluorophenyl)-1H-1,2,3-triazol-4-yl]-2,2-dimethylcyclopropyl}benzenesulfonamide;
4-[(1S,3S)-2,2-Dimethyl-3-(1-phenyl-1H-1,2,3-triazol-4-yl)cyclopropyl]benzenesulfonamide;
4-[(1R,3R)-3-(1-Cyclopentyl-1H-pyrazol-4-yl)-2,2-dimethylcyclopropyl]benzenesulfonamide;
4-[(1R,3R)-3-(5-Ethoxy-1,2,4-thiadiazol-3-yl)-2,2-dimethylcyclopropyl]benzenesulfonamide;
4-{(1R,2R)-2-[5-(3-Fluorophenyl)-1,2,4-thiadiazol-3-yl]cyclopropyl}benzenesulfonamide;
4-[(1R,2R)-2-(5-Cyclohexyl-1,2,4-thiadiazol-3-yl)cyclopropyl]benzenesulfonamide;
4-{(1S,3S)-2,2-Difluoro-3-[5-(piperidin-1-yl)-1,2,4-thiadiazol-3-yl]cyclopropyl}benzenesulfonamide;
4-[(1S,3S)-2,2-Difluoro-3-(5-phenyl-1,2,4-thiadiazol-3-yl)cyclopropyl]benzenesulfonamide;
4-[(1R,2R)-2-(2-Cyclopentyl-1,3-thiazol-4-yl)cyclopropyl]benzenesulfonamide;
4-[(1S,3S)-3-(2-Cyclopentyl-1,3-thiazol-4-yl)-2,2-dimethylcyclopropyl]benzenesulfonamide;
4-[(1R,3R)-3-(5-Cyclohexyl-1,2,4-oxadiazol-3-yl)-2,2-dimethylcyclopropyl]benzenesulfonamide;
4-[(1R,3R)-2,2-Dimethyl-3-(5-phenyl-1,2,4-oxadiazol-3-yl)cyclopropyl]benzenesulfonamide;
4-{(1R,3R)-3-[5-(3-Fluorophenyl)-1,2,4-oxadiazol-3-yl]-2,2-dimethylcyclopropyl}benzenesulfonamide;
4-[(1R,3R)-2,2-Dimethyl-3-{5-[1-(trifluoromethyl)cyclopropyl]-1,2,4-oxadiazol-3-yl}cyclopropyl]benzenesulfonamide;
4-{(1R,3R)-2,2-Dimethyl-3-[5-(piperidin-1-yl)-1,2,4-oxadiazol-3-yl]cyclopropyl}benzenesulfonamide;
4-[(1R,2R)-2-(2-Cyclopentyl-1,3-oxazol-5-yl)cyclopropyl]benzenesulfonamide;
4-[(1S,2S)-2-(2-Phenyl-1,3-thiazol-5-yl)cyclopropyl]benzenesulfonamide;
4-[trans-2,2-Difluoro-3-(5-phenyl-1,3-oxazol-2-yl)cyclopropyl]benzenesulfonamide;
4-[2-Methyl-3-(3-phenyl-1,2,4-oxadiazol-5-yl)cyclopropyl]benzenesulfonamide;
4-[trans-2-(3-Phenyl-1,2,4-oxadiazol-5-yl)spiro[2.4]hept-1-yl]benzenesulfonamide;
4-{trans-2-[3-(3-Fluorophenyl)-1,2,4-thiadiazol-5-yl]cyclopropyl}benzenesulfonamide;
4-[trans-2,2-Dichloro-3-(3-cyclopentyl-1,2,4-oxadiazol-5-yl)cyclopropyl]benzenesulfonamide;
4-{trans-3-[5-(3-Fluorophenyl)isoxazol-3-yl]-2,2-dimethylcyclopropyl}benzenesulfonamide;
4-[trans-2,2-Dimethyl-3-(3-phenyl-1,2,4-oxadiazol-5-yl)cyclopropyl]-3-fluorobenzenesulfonamide;
4-[trans-2,2-Dimethyl-3-(3-phenyl-1,2,4-oxadiazol-5-yl)cyclopropyl]-2-methylbenzenesulfonamide; and
4-[trans-2,2-Dichloro-3-(3-phenyl-1,2,4-oxadiazol-5-yl)cyclopropyl]benzenesulfonamide.

Other embodiments of the present invention include the following:

(a) A pharmaceutical composition comprising a compound of formula I and a pharmaceutically acceptable carrier.

(b) The pharmaceutical composition of (a), further comprising a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(c) The pharmaceutical composition of (b), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(d) A pharmaceutical combination that is (i) a compound of formula I and (ii) a second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa wherein the compound of formula I and the second therapeutic agent are each employed in an amount that renders the combination effective for treating cognitive impairments associated with Alzheimer's disease, Parkinson's disease, and schizophrenia.

(e) The combination of (d), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(f) A use of a compound of formula I in the preparation of a medicament for modulating α7 nAChR activity in a subject in need thereof.

(g) A use of a compound of formula I in the preparation of a medicament for treating cognitive impairments associated with Alzheimer's disease, Parkinson's disease, and schizophrenia in a subject in need thereof.

(h) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject an effective amount of a compound of formula I.

(i) The method of (h), wherein the compound of formula I is administered in combination with an effective amount of at least one second therapeutic agent selected from the group consisting of acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

(j) The method of (i), wherein the second therapeutic agent is an antipsychotic selected from the group consisting of clozapine, olanzapine, risperidone, aripiprazole, quetiapine, haloperidol, loxapine, thioridazine, molindone, thiothixene, fluphenazine, mesoridazine, trifluoperazine, chlorpromazine, and perphenazine.

(k) A method of modulating α7 nAChR activity in a subject in need thereof, which comprises administering to the subject the pharmaceutical composition of (a), (b), or (c) or the combination of (d) or (e).

(l) A method of treating cognitive impairments associated with Alzheimer's disease, Parkinson's disease, and schizophrenia and/or reducing the likelihood or severity of symptoms of cognitive impairments associated with Alzheimer's disease, Parkinson's disease, and schizophrenia in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (l) above are understood to include all embodiments of the compounds and/or salts, including such embodiments as result from combinations of embodiments.

Additional embodiments of the invention include the pharmaceutical compositions, combinations, uses and methods set forth in (a) through (l) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) preventing or treating cognitive impairments associated with Alzheimer's disease, Parkinson's disease, schizophrenia, and L-DOPA induced-dyskinesia, or (b) treating cognitive impairments associated with Alzheimer's disease, Parkinson's disease, schizophrenia, and L-DOPA induced-dyskinesia and/or reducing the likelihood or severity of symptoms of cognitive impairments associated with Alzheimer's disease, Parkinson's disease, schizophrenia, and L-DOPA induced-dyskinesia, or (c) use in medicine. In these uses, the compounds of the present invention can optionally be employed in combination with one or more second therapeutic agents selected from acetylcholinesterase inhibitors such as donepezil, rivastigmine, and galantamine; NMDA receptor antagonists such as memantine; beta-secretase inhibitors such as verubecestat, and AZD3293; M4 mAChR agonists or PAMs; mGluR2 antagonists or NAMs or PAMs; 5-HT6 antagonists such as idalopirdine, RVT-101, AVN-101, AVN322, SUVN-502, and SYN-120; histamine H3 receptor antagonists such as S38093; PDE4 inhibitors such as HT0712; PDE9 inhibitors such as BI40936; HDAC6 inhibitors; antipsychotics; LRRK2 inhibitors; MAO-B inhibitors; and levodopa.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "administration" and variants thereof (e.g., "administering" a compound) in reference to a compound of the invention means providing the compound to the individual in need of treatment. When a compound of the invention is provided in combination with one or more other active agents (e.g., cholinesterase inhibitors such as donepezil, rivastigmine, and galantamine), "administration" and its variants are each understood to include concurrent and sequential provision of the compound or salt and other agents.

As used herein, the term "5-membered heteroaryl ring" refers to a stable unsaturated 5-membered ring that contains from 1 to 4 heteroatoms selected from the group consisting of O, N, and S. A 5-membered heteroaryl ring within the scope of this definition includes but is not limited to: furanyl, imidazolyl, isothiazolyl, isoxazolyl, oxadiazolyl, oxazolyl, pyrazolyl, pyrrolyl, tetrazolyl, thiadiazolyl, thiazolyl, thienyl, and triazolyl.

The term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from 1 to 12 carbon atoms. In different embodiments, an alkyl group contains from 1 to 6 carbon atoms [$(C_1-C_6)$alkyl] or from 1 to 4 carbon atoms [$(C_1-C_4)$alkyl] or from 1 to 3 carbon atoms [$(C_1-C_3)$alkyl]. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

The term "aryl" (or "aryl ring system") refers to any mono- and poly-carbocyclic ring systems wherein the individual carbocyclic rings in the polyring systems are fused or attached to each other via a single bond and wherein at least one ring is aromatic. Suitable aryl groups include phenyl, indanyl, naphthyl, tetrahydronaphthyl, and biphenyl. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "composition" is intended to encompass a product comprising the specified ingredients, as well as any product which results from combining the specified ingredients.

The term "compound" is intended to encompass chemical agents described by generic formula I in all forms. Such chemical agents can be present in different forms such as hydrates, solvates, and polymorphs.

The term "cycloalkyl" as used herein, refers to a non-aromatic mono- or multicyclic ring system comprising from 3 to 10 ring carbon atoms. In one embodiment, a cycloalkyl contains from 5 to 10 ring carbon atoms. In another embodiment, a cycloalkyl contains from 3 to 7 ring atoms. In another embodiment, a cycloalkyl contains from 3 to 6 ring atoms [$(C_3-C_6)$cycloalkyl]. In another embodiment, a cycloalkyl contains from 5 to 7 ring atoms. In another embodiment, a cycloalkyl contains from 5 to 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl, bicyclo[3.1.0]hexyl and adamantyl. The term "3 to 7-membered cycloalkyl" refers to a cycloalkyl group having from 3 to 7 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

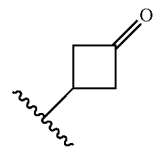 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate t7 nAChR activity and thereby elicit the response being sought (i.e., a "therapeutically effective amount"). When the active compound (i.e., active ingredient) is administered as the salt, references to the amount of active ingredient are to the free acid or free base form of the compound.

The term "halogen" (or "halo") refers to atoms of fluorine, chlorine, bromine and iodine (alternatively referred to as fluoro, chloro, bromo, and iodo).

The term "heteroaryl" as used herein, refers to any monocyclic or multicyclic ring system comprising 5 to 14 ring atoms, wherein from 1 to 4 of the ring atoms is independently O, N, or S and the remaining ring atoms are carbon atoms, and wherein at least one ring is aromatic. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group is usually joined via a ring carbon atom but may be joined via a non-carbon atom provided that this results in a stable compound, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O, and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include benzimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzoyl and the like, and all isomeric forms thereof. The term "heteroaryl" also refers to partially saturated heteroaryl moieties such as, for example, tetrahydroisoquinolyl, tetrahydroquinolyl and the like, provided that they contain at least one aromatic ring. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring.

The term "heterocycle" or "heterocyclyl" as used herein is intended to mean a 3-to 10-membered non-aromatic heterocycle containing from 1 to 4 heteroatoms selected from the group consisting of O, N, and S, and includes monocyclic or bicyclic groups (fused, bridged or spirocyclic). Further examples of "heterocyclyl" include, but are not limited to the following: oxazoline, isoxazoline, oxetanyl, tetrahydropyranyl, azetidinyl, 1,4-dioxanyl, hexahydroazepinyl, piperazinyl, piperidinyl, pyrrolidinyl, morpholinyl, thiomorpholinyl, dihydrofuranyl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydrotetrazolyl, dihydrothiadiazolyl, dihydrothiazolyl, dihydrothienyl, dihydrotriazolyl, tetrahydrofuranyl, and tetrahydrothienyl, and N-oxides thereof. Attachment of a heterocyclyl substituent can occur via a carbon atom or via a heteroatom.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms. The term "$C_1$-$C_4$ hydroxyalkyl" refers to a hydroxyalkyl group having from 1 to 4 carbon atoms. The term "$C_1$-$C_3$ hydroxyalkyl" refers to a hydroxyalkyl group having from 1 to 3 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing" as used herein with respect to Alzheimer's disease or other neurological diseases, refers to reducing the likelihood of disease progression.

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Unless expressly stated to the contrary, substitution by a named substituent is permitted on any atom provided such substitution is chemically allowed and results in a stable compound. Combinations of substituents and/or variables are permissible only if such combinations result in stable compounds. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

In another embodiment of formula I, X is

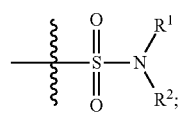

wherein $R^1$ and $R^2$ are H.

In another embodiment of formula I, Y is selected from 1 to 4 substituents, each independently selected from H, ($C_1$-$C_4$)alkyl, halogen, and OH, wherein said alkyl is optionally substituted with one or more halogen or OH.

In another embodiment of formula I, Y is selected from 1 to 4 substituents, wherein 2 substituents are H and the other substituents are independently selected from ($C_1$-$C_4$)alkyl, halogen, and OH, wherein said alkyl is optionally substituted with one or more halogen or OH.

In another embodiment of formula I, Y is selected from 1 to 4 substituents, wherein 3 substituents are H and the other substituent is ($C_1$-$C_4$)alkyl or halogen.

In another embodiment of formula I, Y is selected from 1 to 4 substituents, wherein 3 substituents are H and the other substituent is selected from methyl or fluorine.

In another embodiment of formula I, Y is H.

In another embodiment of formula I, A is a 5-membered heteroaryl ring which is substituted with 1 to 3 R groups each independently selected from alkyl, cycloalkyl, aryl, heteroaryl, and heterocyclyl, wherein said alkyl, cycloalkyl, aryl, heteroaryl and heterocyclyl are optionally substituted with one or more substituents independently selected from F, Cl, Br, OH, oxo, $CF_3$, $OCF_3$, CN, ($C_1$-$C_6$)alkyl, O($C_1$-$C_4$) alkyl, S($C_1$-$C_4$)alkyl, C=O($C_1$-$C_4$)alkyl, ($C_2$-$C_4$)alkynyl, ($C_3$-$C_6$)cycloalkyl, O($C_3$-$C_6$)cycloalkyl, C=O($C_3$-$C_6$)cycloalkyl, and phenyl, wherein said alkyl and phenyl are optionally independently substituted with one or more halogen, $CF_3$, OH and oxo.

In another embodiment of formula I, A is a 5-membered heteroaryl ring selected from

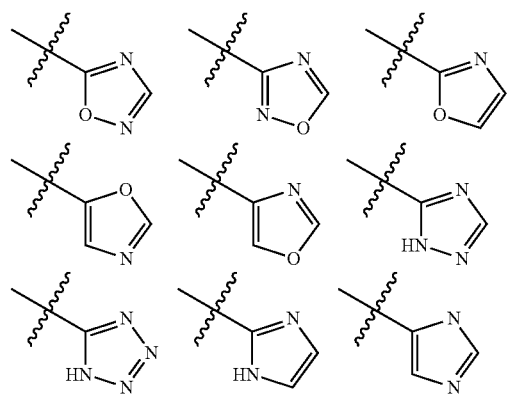

23

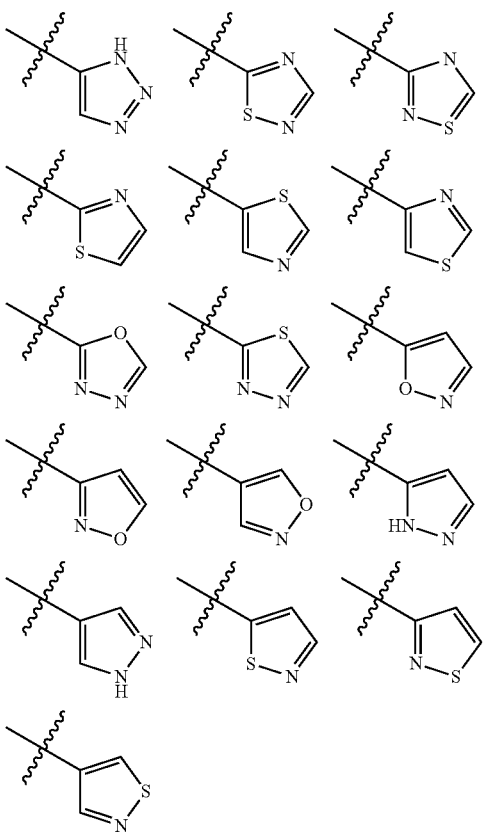

which are each substituted with 1 to 3 R groups independently selected from CN, alkoxy, halogen, aminoalkyl, hydroxyalkyl, alkyl, cycloalkyl, aryl, heteroaryl, and heterocyclyl, wherein said alkyl, cycloalkyl, aryl, heteroaryl and heterocyclyl are optionally substituted with one or more substituents independently selected from F, Cl, Br, OH, oxo, CF$_3$, OCF$_3$, CN, (C$_1$-C$_4$)alkyl, O(C$_1$-C$_4$)alkyl, S(C$_1$-C$_4$)alkyl, C=O(C$_1$-C$_4$)alkyl, (C$_2$-C$_4$)alkynyl, (C$_3$-C$_6$)cycloalkyl, O(C$_3$-C$_6$)cycloalkyl, C=O(C$_3$-C$_6$)cycloalkyl, aryl, heteroaryl and heterocyclyl, wherein said alkyl, aryl, heteroaryl and heterocyclyl are optionally independently substituted with one or more F, Cl, CF$_3$ and oxo.

In another embodiment of formula I or Ia, A is a 5-membered heteroaryl ring selected from

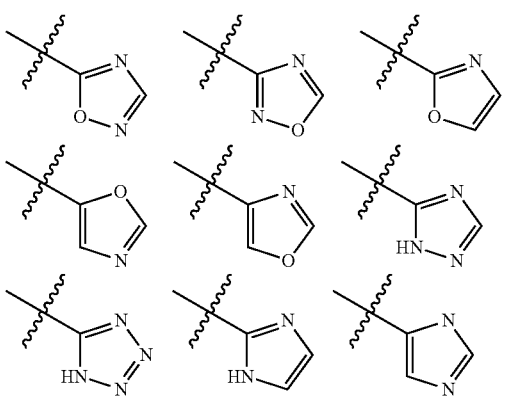

24

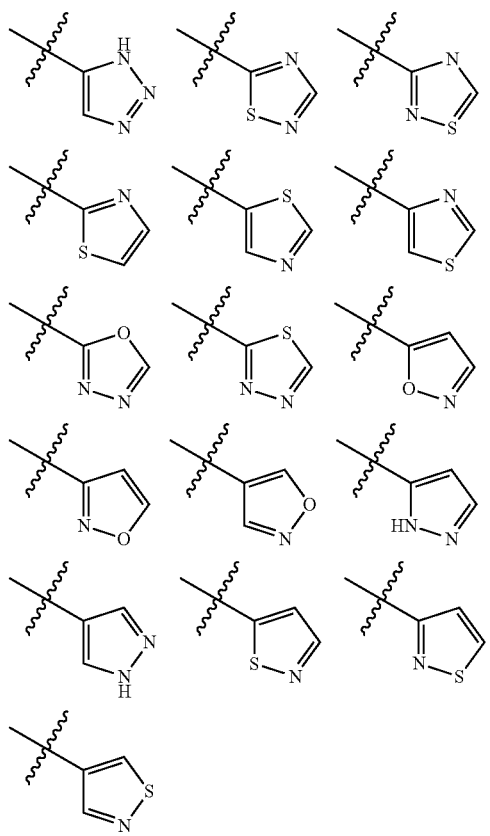

H which are each substituted with 1 to 2 R groups independently selected from cyano, alkoxy, halogen, aminoalkyl, hydroxyalkyl, alkyl, cycloalkyl, aryl, heteroaryl, and heterocyclyl, wherein said alkyl, cycloalkyl, aryl, heteroaryl, and heterocyclyl are optionally substituted with one or more substituents independently selected from F, Cl, Br, OH, oxo, CF$_3$, OCF$_3$, CN, (C$_1$-C$_4$)alkyl, O(C$_1$-C$_4$)alkyl, S(C$_1$-C$_4$)alkyl, C=O(C$_1$-C$_4$)alkyl, (C$_2$-C$_4$)alkynyl, (C$_3$-C$_6$)cycloalkyl, O(C$_3$-C$_6$)cycloalkyl, C=O(C$_3$-C$_6$)cycloalkyl, aryl, heteroaryl and heterocyclyl, wherein said alkyl, aryl, heteroaryl and heterocyclyl are optionally independently substituted with one or more F, Cl, CF$_3$ and oxo.

In another embodiment of formula I or Ia, A is a 5-membered heteroaryl ring selected from

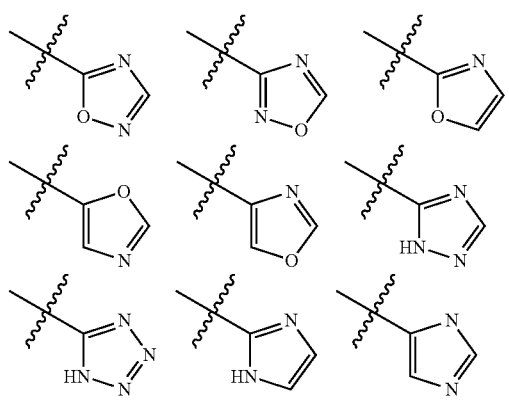

-continued

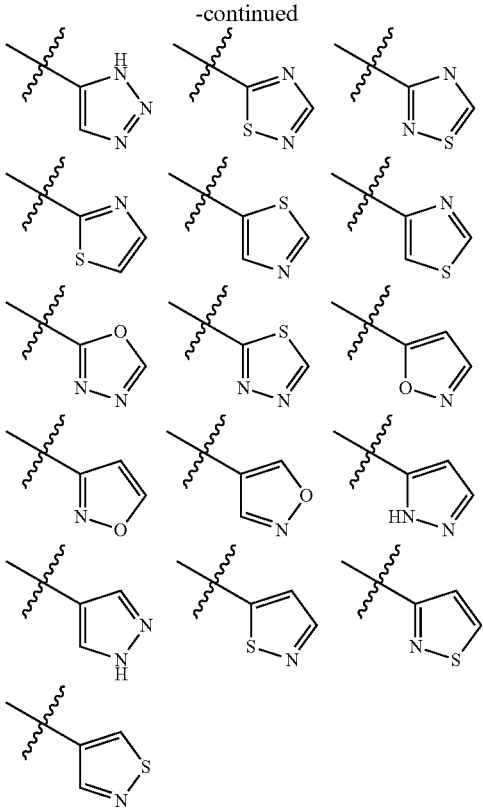

which are each substituted with 1 R group selected from CN, alkoxy, halogen, aminoalkyl, hydroxyalkyl, alkyl, cycloalkyl, aryl, heteroaryl, and heterocyclyl, wherein said alkyl, cycloalkyl, aryl, heteroaryl, and heterocyclyl are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, C=$O(C_1-C_4)$ alkyl, $(C_2-C_4)$alkynyl, $(C_3-C_6)$cycloalkyl, $O(C_3-C_6)$cycloalkyl, C=$O(C_3-C_6)$cycloalkyl, aryl, heteroaryl and heterocyclyl, wherein said alkyl, aryl, heteroaryl and heterocyclyl are optionally independently substituted with one or more F, Cl, $CF_3$ and oxo.

In another embodiment of formula I or Ia, A is a 5-membered heteroaryl ring selected from pyrazole, thiadiazole, triazole, isoxazole, oxazole, oxadiazole, and thiazole, which are each substituted with 1 to 3 R groups independently selected from CN, alkoxy, halogen, aminoalkyl, hydroxyalkyl, alkyl, cycloalkyl, aryl, heteroaryl, and heterocyclyl, wherein said alkoxy, alkyl, cycloalkyl, aryl, heteroaryl, and heterocyclyl are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, C=$O(C_1-C_4)$alkyl, $(C_2-C_4)$alkynyl, $(C_3-C_6)$cycloalkyl, $O(C_3-C_6)$cycloalkyl, C=$O(C_3-C_6)$cycloalkyl, aryl, heteroaryl and heterocyclyl, wherein said alkyl, aryl, heteroaryl and heterocyclyl are optionally independently substituted with one or more F, Cl, $CF_3$ and oxo.

In another embodiment of formula I or Ia, A is a 5-membered heteroaryl ring selected from pyrazole, thiadiazole, triazole, isoxazole, oxazole, oxadiazole, and thiazole, which are each substituted with 1 to 2 R groups independently selected from $(C_1-C_4)$alkyl, $O(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, wherein each are optionally substituted with one or more substituents independently selected from F, Cl, Br, OH, oxo, $CF_3$, $OCF_3$, CN, $(C_1-C_4)$ alkyl, $O(C_1-C_4)$alkyl, $S(C_1-C_4)$alkyl, C=$O(C_1-C_4)$alkyl, $(C_2-C_4)$alkynyl, $(C_3-C_6)$cycloalkyl, $O(C_3-C_6)$cycloalkyl, C=$O(C_3-C_6)$cycloalkyl, phenyl, O-phenyl, heteroaryl and heterocyclyl, wherein said alkyl, phenyl, heteroaryl and heterocyclyl are optionally independently substituted with one or more F, Cl, $CF_3$ and oxo.

In another embodiment of formula I or Ia, A is a 5-membered heteroaryl ring selected from pyrazole, thiadiazole, triazole, isoxazole, oxazole, oxadiazole, and thiazole, which are each substituted with 1 R group selected from $(C_1-C_4)$ alkyl, $O(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, C=$O(C_1-C_4)$alkyl, $(C_2-C_4)$alkynyl, $(C_3-C_6)$ cycloalkyl, $O(C_3-C_6)$cycloalkyl, C=$O(C_3-C_6)$cycloalkyl, phenyl, O-phenyl, heteroaryl and heterocyclyl, wherein said alkyl, phenyl, heteroaryl and heterocyclyl are optionally independently substituted with one or more F, Cl, $CF_3$ and oxo.

In another embodiment of formula I or Ia, A is a 5-membered heteroaryl ring selected from pyrazole, thiadiazole, triazole, isoxazole, oxazole, oxadiazole, and thiazole, which are each substituted with 1 to 2 R groups independently selected from $(C_1-C_4)$alkyl, $O(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, wherein each are optionally substituted with one or more substituents independently selected from F, Cl, OH, oxo, $CF_3$, $OCF_3$, CN, $(C_1-C_4)$ alkyl, $O(C_1-C_4)$alkyl, $S(C_1-C_4)$alkyl, C=$O(C_1-C_4)$alkyl, $(C_1-C_4)$alkynyl, $(C_3-C_6)$cycloalkyl, $O(C_3-C_6)$cycloalkyl, C=$O(C_3-C_6)$cycloalkyl, phenyl, and O-phenyl.

In another embodiment of formula I or Ia, A is a 5-membered heteroaryl ring selected from pyrazole, thiadiazole, triazole, isoxazole, oxazole, oxadiazole, and thiazole, which are each substituted with 1 R group selected from $(C_1-C_4)$ alkyl, $O(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, C=$O(C_1-C_4)$alkyl, $(C_2-C_4)$alkynyl, $(C_3-C_6)$ cycloalkyl, $O(C_3-C_6)$cycloalkyl, C=$O(C_3-C_6)$cycloalkyl, phenyl and O-phenyl.

In another embodiment of formula I or Ia, A is a 5-membered heteroaryl ring selected from furanyl, imidazolyl, isothiazolyl, isoxazolyl, oxadiazolyl, oxazolyl, pyrazolyl, pyrrolyl, tetrazolyl, thiadiazolyl, thiazolyl, thienyl, and triazolyl.

In another embodiment of formula I, Ia, or Ib, when the R groups are aryl, heteroaryl and heterocyclyl, said aryl, heteroaryl and heterocyclyl are independently selected from phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, each optionally substituted with one or more F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, aryl, heteroaryl and heterocyclyl are optionally independently substituted with one or more F, Cl, $CF_3$ and oxo.

In another embodiment of formula I, Ia, or Ib, when the R groups are aryl, heteroaryl and heterocyclyl, said aryl, heteroaryl and heterocyclyl are independently selected from phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, each optionally substituted with one or more F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, and $C=O(C_3-C_6)$cycloalkyl.

In another embodiment of formula I, Ia, or Ib, when the R groups are aryl, heteroaryl and heterocyclyl, said aryl, heteroaryl and heterocyclyl are independently selected from phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl, each optionally substituted with one or more F, Cl, Br, OH, oxo, $CF_3$, $OCF_3$, CN, $(C_1-C_4)$alkyl, and $O(C_1-C_4)$alkyl.

In another embodiment of formula I, Ia, or Ib, the R groups are independently selected from alkyl, cycloalkyl and phenyl, said alkyl, cycloalkyl or phenyl are optionally substituted with one or more F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, aryl, heteroaryl and heterocyclyl are optionally independently substituted with one or more F, Cl, $CF_3$ and oxo.

In another embodiment of formula I, Ia, or Ib, the R groups are independently selected from alkyl, cycloalkyl and phenyl, said alkyl, cycloalkyl or phenyl are optionally substituted with one or more F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, and $C=O(C_3-C_6)$cycloalkyl.

In another embodiment of formula I, Ia, or Ib, the R groups are independently selected from alkyl, cycloalkyl and phenyl, said alkyl, cycloalkyl or phenyl are optionally substituted with one or more F, Cl, Br, OH, oxo, $CF_3$, $OCF_3$, CN, $(C_1-C_4)$alkyl, and $O(C_1-C_4)$alkyl.

In another embodiment of formula I, Ia, or Ib, the R groups are optionally substituted with one or more F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, and $C=O(C_3-C_6)$cycloalkyl.

In another embodiment of formula I, Ia, or Ib, the R groups are optionally substituted with one or more F, Cl, Br, OH, oxo, $CF_3$, $OCF_3$, CN, $(C_1-C_4)$alkyl, and $O(C_1-C_4)$alkyl.

In another embodiment of formula I, $R^1$ is H or methyl.

In another embodiment of formula I, $R^2$ is H or methyl.

In another embodiment of formula I, Ia, or Ib, $R^3$ is H, halogen or $(C_1-C_4)$alkyl, $R^4$ is H, halogen or $(C_1-C_4)$alkyl, or $R^3$ and $R^4$ optionally can come to together to form a cyclopropyl, cyclobutyl, cyclopentyl or cyclohexyl ring.

In another embodiment of formula I, Ia, or Ib, $R^3$ is H, F or methyl.

In another embodiment of formula I, Ia, or Ib, $R^4$ is H, F or methyl.

In another embodiment of formula I, Ia, or Ib, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl.

In another embodiment of formula I, Ia, or Ib, $R^3$ and $R^4$ optionally can come to together to form a cyclopropyl, cyclobutyl, cyclopentyl or cyclohexyl ring.

In another embodiment of formula I, Ia, or Ib, $R^5$ is H or methyl.

In another embodiment of formula I, Ia, or Ib, $R^5$ is H.

In another embodiment of formula I, Ia, or Ib, $R^6$ is H or methyl.

In another embodiment of formula I, Ia, or Ib, $R^6$ is H.

In another embodiment of formula I, Ia, or Ib, $R^7$ is H or methyl.

In another embodiment of formula I, Ia, or Ib, $R^8$ is H or methyl.

In another embodiment of formula I, $R^a$ is H or methyl.

In another embodiment of formula I, $R^a$ is H.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1H$) and deuterium ($^2H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

It is understood by one skilled in the art that carbon atoms in organic molecules may often be replaced by silicon atoms to give analogous stable compounds. For example, carbon atoms in alkoxy, alkyl, cycloalkyl, heteroaryl, heterocyclyl, and hydroxyalkyl groups may often be replaced by silicon atoms to provide stable compounds. All such compounds are within the scope of the present invention.

When any variable (for example, R) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of the present invention may have utility in preventing, treating, or ameliorating Alzheimer's disease. The compounds may also be useful in preventing, treating, or ameliorating other diseases mediated by the α7 nAChR, such as schizophrenia, sleep disorders, Parkinson's disease, autism, microdeletion syndrome, inflammatory diseases, pain disorders (including acute pain, inflammatory pain and neuropathic pain) and cognitive disorders (including mild cognitive impairment). Other conditions that may be prevented, treated, or ameliorated by the compounds of the invention include pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, kidney diseases, cancer, and atherosclerosis.

In preferred embodiments, the compounds of the invention may be useful in preventing, treating, or ameliorating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

Thus, in another specific embodiment, the present invention provides a method for preventing, treating, or ameliorating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression; emotional/mood disorders; as well as sleep walking and enuresis; and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis); repetitive motion pain; dental pain; cancer pain; myofascial pain (muscular injury, fibromyalgia); perioperative pain (general surgery, gynecological); chronic pain; dysmennorhea, as well as pain associated with angina, and inflammatory pain of varied origins (e.g. osteoarthritis, rheumatoid arthritis, rheumatic disease, teno-synovitis and gout); headache; migraine and cluster headache; primary hyperalgesia; secondary hyperalgesia; primary allodynia; secondary allodynia; or other pain caused by central sensitization.

Potential conditions or disorders that have a strong inflammatory component for which the compounds of the invention may be useful include one or more of the following conditions or diseases: diabetes (systemic inflammation in diabetes marked by increases in blood cytokines e.g. IL-6 and TNFα which may lead to insulin resistance); asthma; arthritis; cystic fibrosis; sepsis; ulcerative colitis; inflammatory bowel disease; atherosclerosis; neuroinflammation associated with neurodegenerative diseases (e.g. Alzheimer's disease, Parkinson's disease, Creutzfeldt-Jacob disease, frontotemporal dementia, corticobasal degeneration, Pick's disease, progressive supranuclear palsy, traumatic brain injury, Huntington's disease, amyotrophic lateral sclerosis).

Compounds of the invention may also be used to treat or prevent or ameliorate dyskinesia and protect against neurodegeneration in nigrostriatal neurons in Parkinson's disease. Furthermore, compounds of the invention may be used to decrease tolerance and/or dependence to opioid treatment of pain, and for treatment of withdrawal syndrome of e.g., alcohol, opioids, and cocaine.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1):1-19; P. Gould, *International J. of Pharmaceutics* (1986) 33:201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, tert-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of preventing, treating, or ameliorating the cognitive impairments in Alzheimer's disease, Parkinson's disease, schizophrenia, L-DOPA induced-dyskinesia, and inflammation, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, $18^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, and the severity of the particular condition.

As noted above, the present invention also relates to a method of preventing, treating, or ameliorating the cognitive impairments in Alzheimer's disease, Parkinson's disease, schizophrenia, L-DOPA induced-dyskinesia, and inflammation with a compound of the present invention in combination with one or more therapeutic agents and a pharmaceutical composition comprising a compound of the present invention and one or more therapeutic agents selected from the group consisting of anti-Alzheimer's Disease agents, for example beta-secretase inhibitors; M1 mAChR agonist or PAMs; M4 mAChR agonists or PAMs; mGluR2 antagonists or NAMs or PAMs; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; LRRK2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; GABAA inverse agonists; GSK30 inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds of the instant invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5-HT2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the compounds of the instant invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride; COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compound of the instant invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the compounds of the instant invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compounds of the instant invention may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds of the instant invention include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SP1860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED 160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5-HT receptor agonists or antagonists; mGlu5 antagonists, such as AZD9272; alpha agonists, such as AGN XX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5-HT2 antagonists including 5-HT2A antagonists and 5-HT2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

Compounds of the instant invention are useful for the treatment of moderate to severe dementia of the Alzheimer's type alone or in combination with an NMDA receptor antagonist, such as memantine, or in combination with an acetylcholinesterase inhibitor (AChEI) such as donepezil.

Compounds of the instant invention are useful for the treatment of mild to moderate dementia of the Alzheimer's type alone or in combination with either galantamine, rivastigmine, or donepezil.

Compounds of the instant invention are useful for the treatment of dementia associated with Parkinson's disease alone or in combination with rivastigmine.

Compounds of the instant invention are useful for the treatment of motor fluctuations in patients with advanced Parkinson's disease alone or in combination with carbidopa and levodopa.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). A compound of the invention and an additional therapeutic agent may be present in fixed amounts (dosage amounts) in a single dosage unit (e.g., a capsule, a tablet and the like).

The α7 nAChR positive allosteric modulator (PAM) activity of the present compounds may be tested using assays known in the art. The α7 nAChR PAMs described herein have activities in an automated patch-clamp electrophysiology functional assay as described in the examples. The assay was performed using the IonFlux HT in a whole-cell, population patch configuration. See Golden et al. *Assay Drug Dev. Technol.* (2011) 9:608-619. The compounds were assessed for their ability to modulate the function of the human α7 nAChR stably expressed in a HEK cell line both in the presence, and in the absence of the natural α7 agonist acetylcholine. By performing a series of such measurements at different concentrations, the effective concentration of the α7 nAChR PAMs ($EC_{50}$) was determined. See Spencer et al. *Assay Drug Dev. Technol.* (2012) 10:313-324.

The present invention also includes processes for making compounds of formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

General Schemes

The compounds of the present invention can be prepared readily according to the following schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

Many compounds of the present invention may be prepared according to Scheme 1, in which acid 1.1 is reacted with CDI in 1,4-dioxane and then treated with amide oxime 1.2 in 1,4-dioxane at elevated temperature to afford product 1.3. Other coupling reagents, such as EDC and HOAt, and solvents, such as toluene, can be employed in this transformation. If 1.3 is a mixture of enantiomers or diastereomers, the mixture may be separated by chiral chromatography. Alternatively, 1.1 and 1.2 may be employed as single enantiomers or diastereomers to obtain 1.3 enriched in a single enantiomer or diastereomer. Other methods of forming the oxadiazole may also be employed, such as reacting the corresponding ester of acid 1.1 with amide oxime 1.2 in the presence of potassium carbonate (or other bases) in ethanol (or other solvents) at elevated temperature or by reacting acid 1.1 with amide oxime 1.2 in the presence of EDC and HOAt followed either by adding T3P to the reaction mixture or by treating the isolated intermediate with TBAF in tetrahydrofuran.

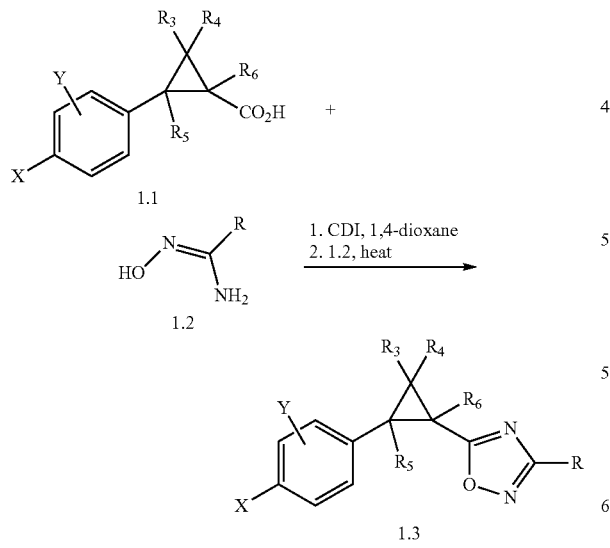

In a similar manner, additional compounds of the present invention may be prepared according to Scheme 2, in which acid 2.1 is first reacted with CDI in 1,4-dioxane and then treated with amide oxime 1.2 in 1,4-dioxane at elevated temperature to afford product 2.2. If 2.2 is a mixture of enantiomers or diastereomers, the mixture may be separated by chiral chromatography. Alternatively, 2.1 and 1.2 may be employed as single enantiomers or diastereomers to obtain 2.2 enriched in a single enantiomer or diastereomer. Oxadiazole 2.2 is then sulfonylated by treatment with neat chlorosulfonic acid (or a mixture of a halogenated solvent and chlorosulfonic acid) followed by treatment of the resultant sulfonyl chloride with a solution of ammonia in a solvent (e.g. water, 1,4-dioxane, tetrahydrofuran, methanol) to afford sulfonamide product 2.3.

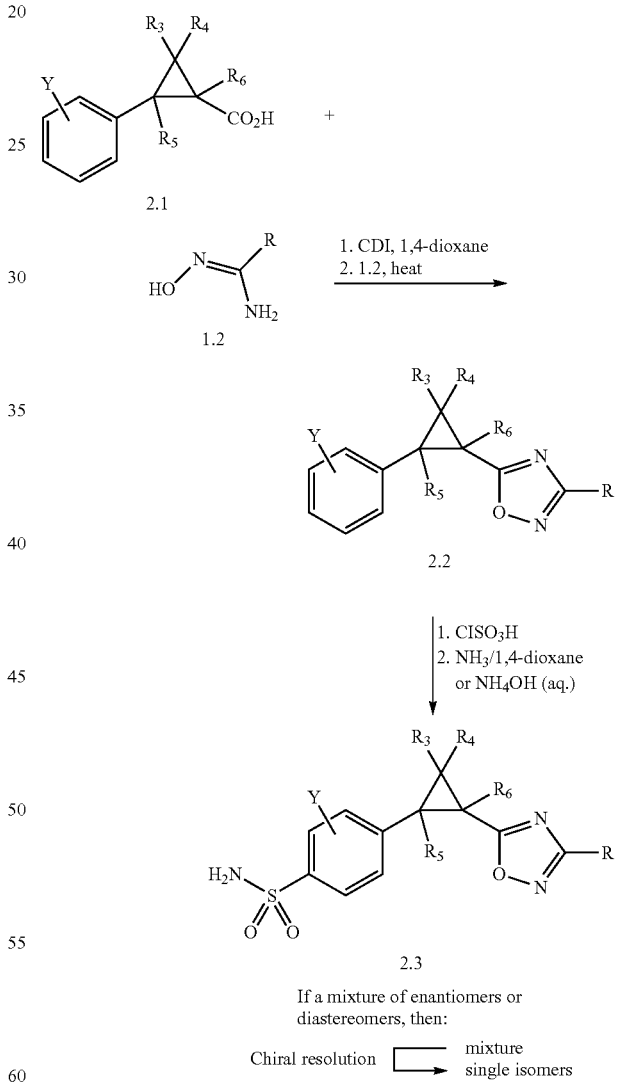

Additional compounds of the present invention may be prepared according to Scheme 3, in which the cyclopropane intermediate 3.1 is an amide oxime. Acid 3.2 is reacted with CDI in 1,4-dioxane and then treated with amide oxime 3.1 and warmed to elevated temperature to afford product 3.3.

SCHEME 3

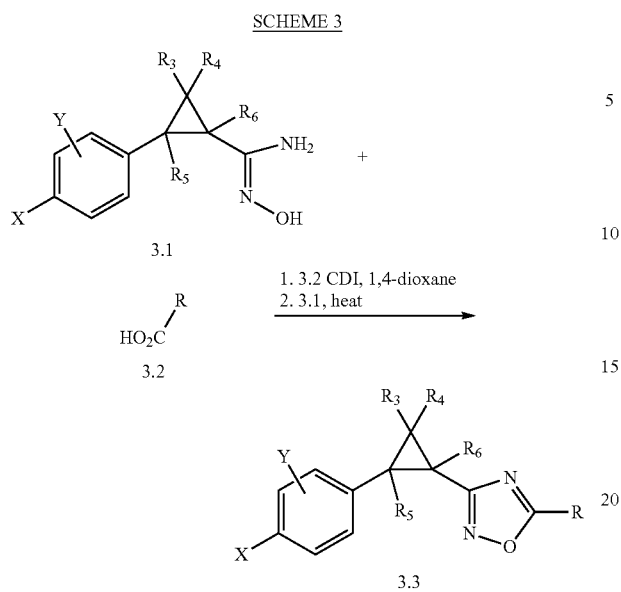

In addition, compounds of the present invention may be prepared according to Scheme 4, in which acid 1.1 is reacted with acyl hydrazine 4.1 in the presence of HATU and NMM. Other coupling reagents and conditions can be employed to effect this transformation. The resulting hydrazide is then treated with Lawesson's reagent and warmed to elevated temperature to afford thiadiazole product 4.2. Other thionating reagents, such as $P_4S_{10}$ and hexamethyldisiloxane or hexamethyldisilathiane, and solvents, such as 1,4-dioxane, can be used for this transformation. Additionally, dehydrating reagents, such as PTSA, can be employed to facilitate the formation of the heterocycle after thionation.

SCHEME 4

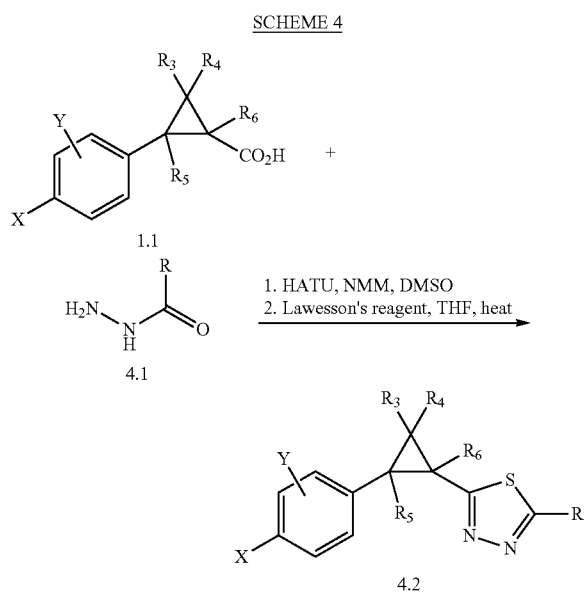

Other compounds of the present invention may be prepared according to Scheme 5, in which acid 1.1 is reacted with CDI in 1,4-dioxane and then treated with acyl hydrazine 5.1 at elevated temperature followed by dehydration of the resultant amide by treatment with phosphorous(V) oxychloride at elevated temperature to afford product 5.2. Other coupling reagents and conditions can be employed to effect this transformation. Other dehydrating reagents, such as Burgess reagent or triflic anhydride, may also be used for this transformation.

SCHEME 5

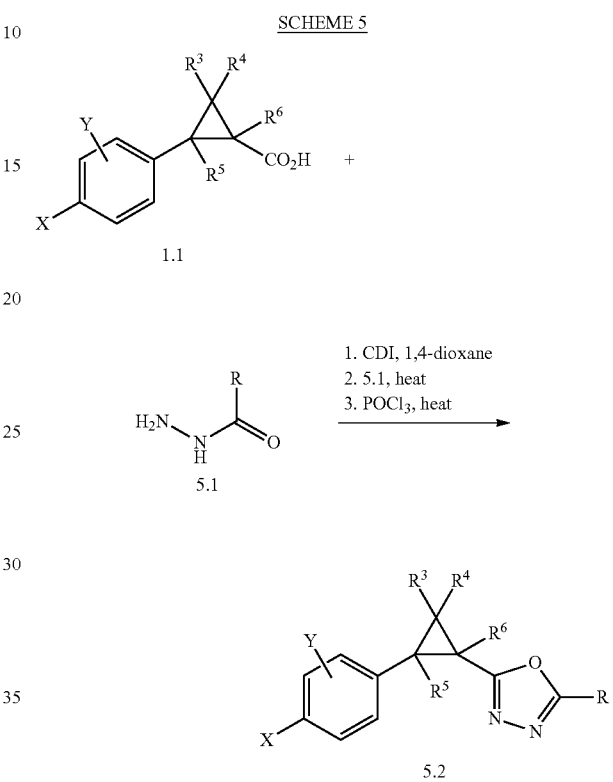

Certain oxazole-containing compounds of the present invention may be prepared according to Scheme 6, in which acid 1.1 is reacted with CDI in 1,4-dioxane and then treated with amino ketone 6.1 followed by cyclodehydration of the resultant amide by treatment with sulfuric acid to afford product 6.2. Other coupling and dehydrating reagents and conditions can be employed to effect this transformation.

SCHEME 6

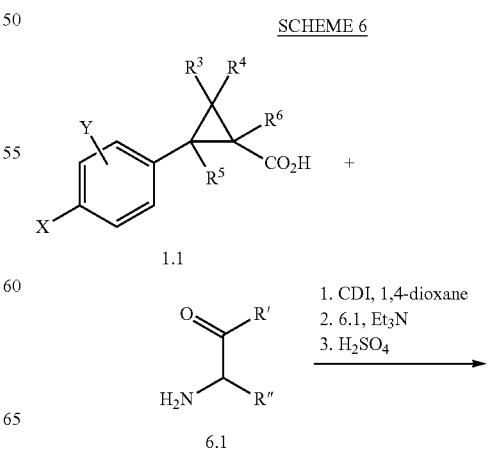

-continued

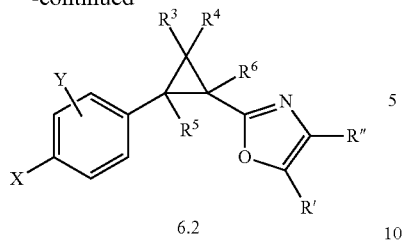

6.2

In addition, other oxazole-containing compounds of the present invention may be prepared according to Scheme 7, in which amide 7.1 is reacted with haloketone 7.2 in the presence of silver trifluoromethanesulfonate at elevated temperature to afford product 7.3. Other soft Lewis acids, such as boron trifluoride diethyl etherate, and halides, such as chloride or iodide, can be employed to effect this transformation. Additionally, dehydrating reagents can be employed to complete the formation of the oxazole after coupling of 7.1 and 7.2.

SCHEME 7

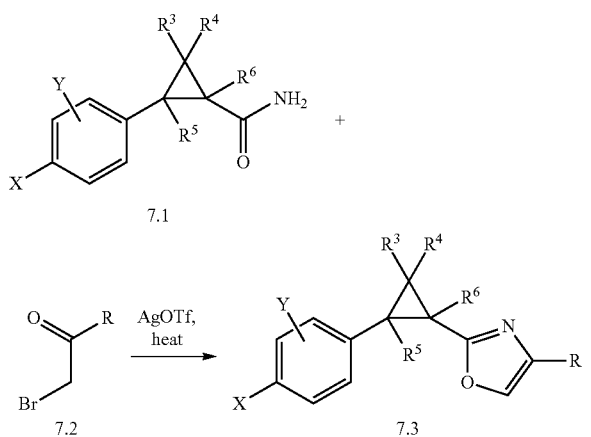

Additional oxazole-containing compounds of the present invention may be prepared according to Scheme 8, in which acid 8.1 is first treated with oxalyl chloride and DMF followed by reaction of the resulting acid chloride with isocyanide 8.2 in the presence of 2,6-lutidine at elevated temperature and the resultant oxazole treated with trifluoroacetic acid to remove the tert-butyl and tert-butyl carbamate groups protecting groups to afford product 8.3. Other bases, coupling conditions, and acids, such as HCl, can be employed to effect these transformations.

SCHEME 8

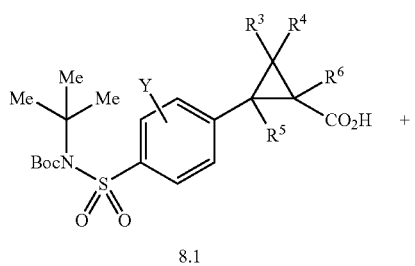

8.1

-continued
1. 8.1, COCl$_2$, DMF
2. 8.2, 2,6-lutidine, heat
3. TFA, DCM

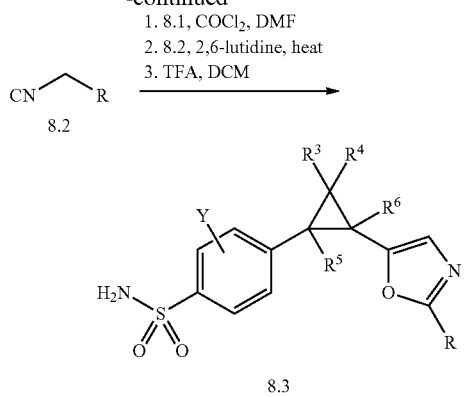

8.3

In addition, compounds of the present invention may be prepared according to Scheme 9, in which alkyne 9.1 participates in a [3+2] cycloaddition with the nitrile oxide (formed in situ by treatment of nitroalkane 9.2 with benzenesulfonyl chloride in the presence of triethylamine) to afford isoxazole 9.3. Other nitrile oxide precursors, such as oximes or chlorooximes, activating reagents for nitroalkanes, such as POCl$_3$, and bases, such as pyridine, can be employed to effect this transformation.

SCHEME 9

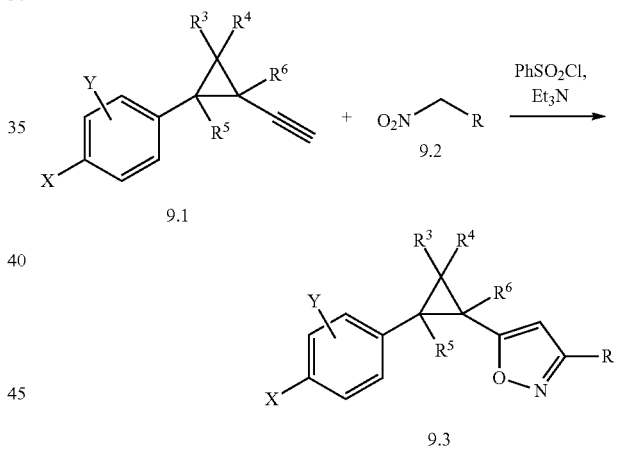

Certain triazole-containing compounds of the present invention may be prepared according to Scheme 10, in which alkyne 9.1 participates in a copper catalyzed [3+2] dipolar cycloaddition with azide 10.1 in the presence of a copper(I) source and an appropriate ligand to afford triazole 10.2.

SCHEME 10

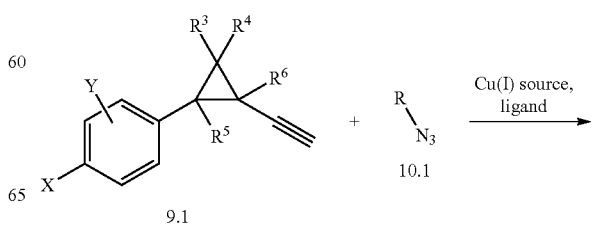

-continued

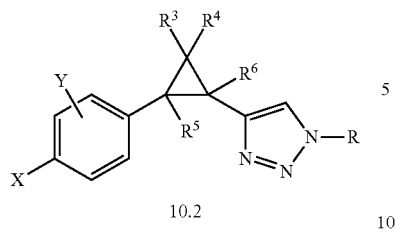

10.2

In addition, compounds of the present invention may be prepared according to Scheme 11, in which aldehyde 11.1 is reacted with hydrazine 11.2 in the presence of HCl in methanol at elevated temperature followed by removal of the formamidine protecting group by treatment with hydrazine hydrate to afford pyrazole 11.3.

SCHEME 11

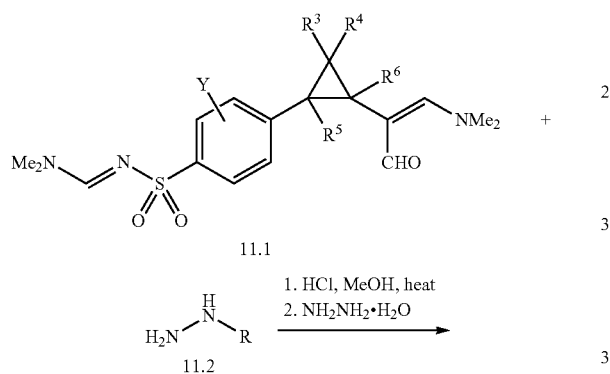

Further compounds of the present invention may be prepared according to Scheme 12, in which thioamide 12.1 is reacted with haloketone 12.2 in ethanol at elevated temperature to afford product 12.3. Similar to Scheme 7, soft Lewis acids and other halides and solvents can be employed to effect this transformation as well. Additionally, dehydrating reagents can be employed to facilitate the formation of the heterocycle after coupling of 12.1 and 12.2.

SCHEME 12

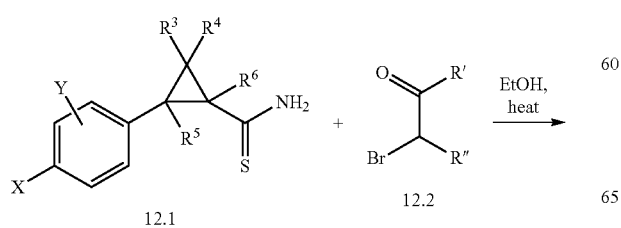

-continued

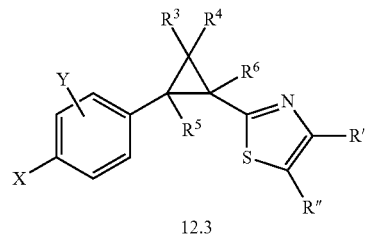

12.3

A number of compounds of the present invention may be prepared according to Scheme 13, in which boronic acid 13.1 is reacted with heteroaryl chloride 13.2 under palladium-catalyzed conditions to afford product 13.3. A variety of different catalysts (including those containing other metals such as nickel), ligands, bases, and solvents can be employed in this reaction. Boronate esters or other boronic acid derivatives may also be used as alternatives to boronic acid 13.1 as well as a variety of alternatives to the heteroaryl chloride 13.2, including bromides, iodided, triflates, or tosylates. Thiadiazole 13.3 is then sulfonylated by treatment with neat chlorosulfonic acid (or a mixture of a halogenated solvent and chlorosulfonic acid) followed by treatment of the resultant sulfonyl chloride with a solution of ammonia in a solvent (e.g. water, 1,4-dioxane, tetrahydrofuran, methanol) to afford sulfonamide product 13.4. If 13.4 is a mixture of enantiomers or diastereomers, the mixture may be separated by chiral chromatography. Alternatively, 13.1, 13.2, and 13.3 may be employed as single enantiomers or diastereomers to obtain 13.4 enriched in a single enantiomer or diastereomer.

SCHEME 13

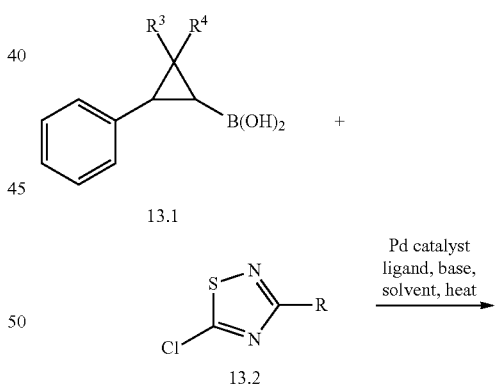

-continued

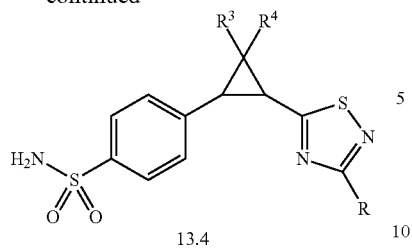

13.4

If a mixture of enantiomers or diastereomers, then:

Chiral resolution: mixture → single isomers

Other compounds of the present invention may be prepared according to Scheme 14, in which pyrazole 14.1 is treated with NaHMDS and then reacted with alkyl (or heteroalkyl or cycloalkyl or heterocyclyl) bromide 14.2 followed by treatment with hydrazine hydrate to afford product 14.3. Alternatives to bromide 14.2 may be used in this procedure, including the corresponding chloride, iodide, mesylate, tosylate, or triflate, and other bases, such as LDA, NaH, or potassium tert-butoxide, can also be employed in this transformation.

SCHEME 14

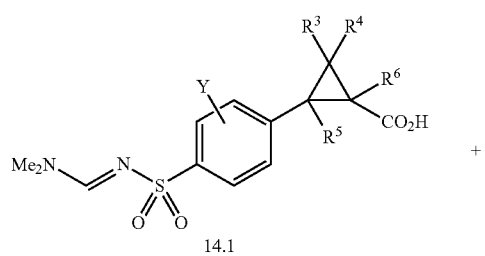

14.1

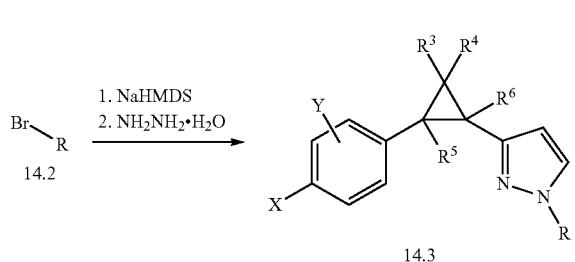

14.3

In addition, certain compounds of the present invention may be prepared according to Scheme 15, in which boronate ester 15.1 is reacted with heteroaryl bromide 15.2 under palladium-catalyzed conditions followed by treatment with hydrazine hydrate to afford product 15.3. Boronate esters or other boronic acid derivatives may also be used as alternatives to boronic acid 15.1 as well as a variety of alternatives to the heteroaryl chloride 15.2, including bromides, iodided, triflates, or tosylates. A variety of different catalysts (including other metals such as nickel), ligands, bases, and solvents can be employed in this reaction.

SCHEME 15

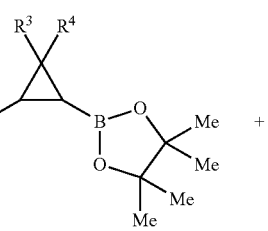

15.1

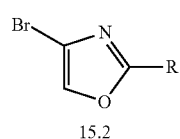

15.2

1. Pd catalyst, ligand, base, solvent, heat
2. NH$_2$NH$_2$•H$_2$O

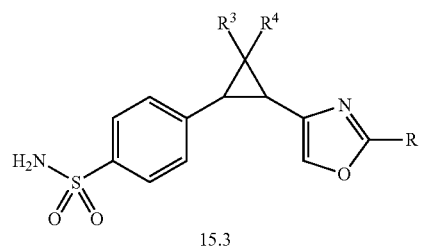

15.3

Certain thiazole-containing compounds of the present invention may be prepared according to Scheme 16, in which haloketone 16.1 is reacted with thioamide 16.2 in ethanol at elevated temperature to afford product 16.3. Similar to Schemes 7 and 12, soft Lewis acids and other halides and solvents can be employed to effect this transformation as well. Additionally, dehydrating reagents can be employed to complete the formation of the heterocycle after coupling of 16.1 and 16.2 and an amine base can be included to sequester acid formed during the reaction. The amidine variant of 16.2 could be employed to furnish the corresponding imidazole, which could then be N-alkylated by treatment with an alkyl halide in the presence of a base.

SCHEME 16

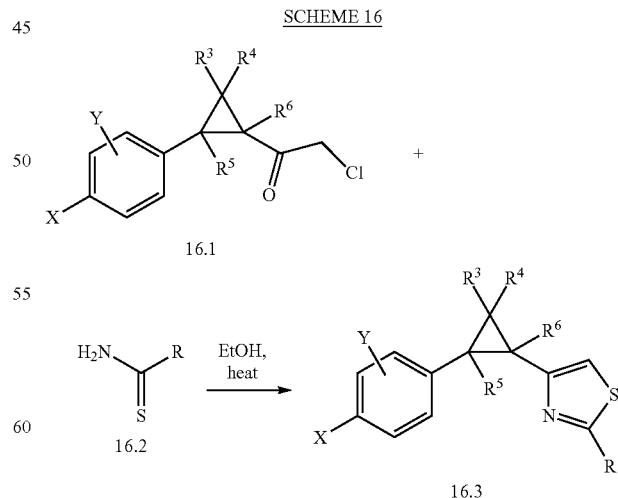

In addition, other thiazole-containing compounds of the present invention may be prepared according to Scheme 17, in which amine 17.1 is reacted with acyl chloride 17.2 in the presence of potassium carbonate and the resulting amide treated with Lawesson's reagent at elevated temperature followed by treatment with trifluoroacetic acid to afford thiazole 17.3. Other bases, thionating reagents, and acids can be employed in these transformations.

SCHEME 17

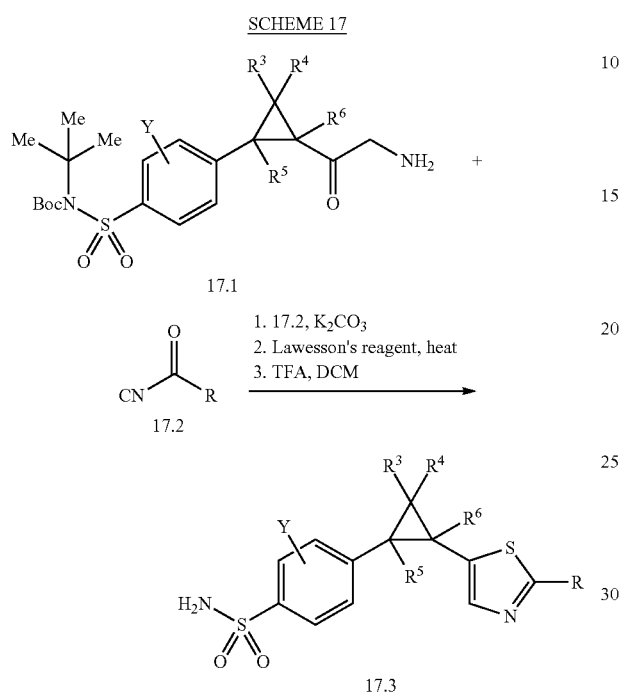

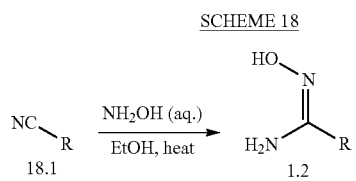

Some useful synthetic intermediates like amide oxime 1.2 may be prepared according to Scheme 18, in which nitrile 18.1 is treated with hydroxylamine at elevated temperature to afford amide oxime 1.2. Other solvents and forms of hydroxylamine (such as the hydrochloride salt; if this form is employed, than a suitable base, such as sodium carbonate, can also be included in the reaction mixture) can be employed in this transformation.

SCHEME 18

Useful synthetic intermediates like 19.3 may be prepared according to Scheme 19. The sequence begins with sulfonylation of ester 19.1 by treatment with neat chlorosulfonic acid (or a mixture of a halogenated solvent and chlorosulfonic acid) followed by treatment of the resultant sulfonyl chloride with a solution of ammonia in a solvent (e.g. water, 1,4-dioxane, tetrahydrofuran, methanol) and chiral resolution of the isomeric mixture to afford enantiopure sulfonamide 19.2. Ester 19.2 can then be saponified by treatment with sodium hydroxide to afford acid 19.3. Other bases, such as lithium hydroxide or potassium trimethylsilanolate, can be employed in this transformation.

SCHEME 19

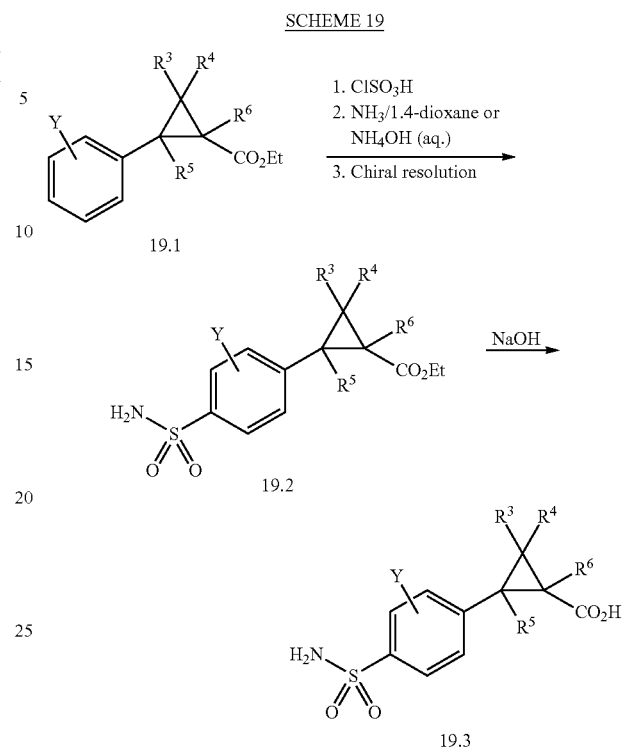

Another approach to intermediates like 19.3 is illustrated in Scheme 20. The sequence begins with chiral resolution of an isomeric mixture of acid 20.1 followed by esterification of the resulting enantiopure acid by treatment with thionyl chloride in ethanol to afford ester 20.2. Next, ester 20.2 is sulfonylated by treatment with neat chlorosulfonic acid (or a mixture of a halogenated solvent and chlorosulfonic acid) followed by treatment of the resultant sulfonyl chloride with a solution of ammonia in a solvent (e.g. water, 1,4-dioxane, tetrahydrofuran, methanol). Saponification of the resulting sulfonamide then affords acid 19.3. Other methods of esterification, such as by use of an alkyl halide and a base, and other bases for the saponification can be employed in this sequence.

SCHEME 20

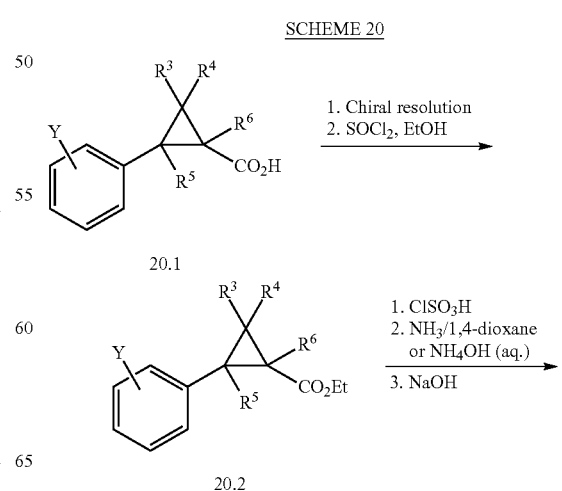

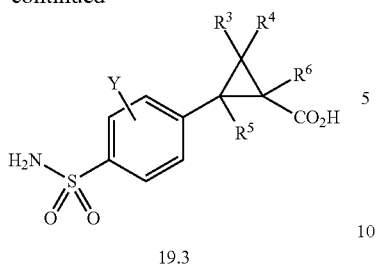

19.3

Intermediates like 8.1 may be prepared according to Scheme 21. Sulfonamide 19.2 is treated with di-tert-butyl dicarbonate in the presence of DMAP at elevated temperature followed by saponification of the resulting bis-protected sulfonamide to afford acid 8.1. Other standard saponification conditions can be employed in this sequence.

SCHEME 21

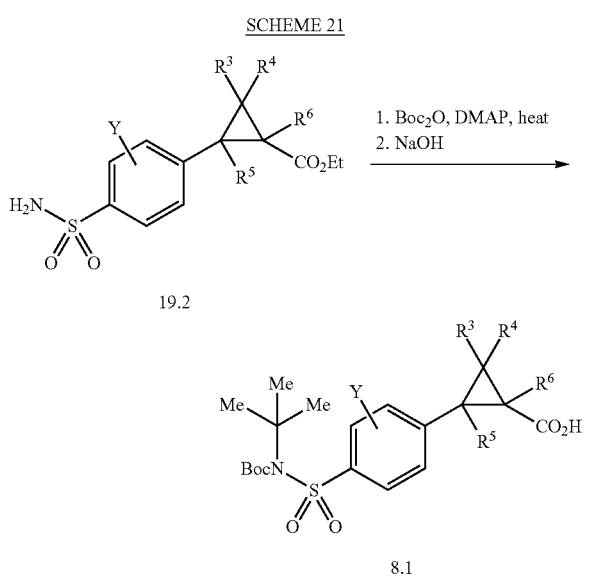

Intermediates like amide oxime 3.1 may be prepared according to Scheme 22. This sequence starts with acid 1.1, which is converted to amide 7.1 by coupling with ammonium chloride in the presence of HATU and NMM (other coupling reagents and bases can be used for this reaction as well). Amide 7.1 is then dehydrated with POCl$_3$ (other dehydrating reagents can also be employed) followed by treatment of the resulting nitrile with hydroxylamine to afford amide oxime 3.1.

SCHEME 22

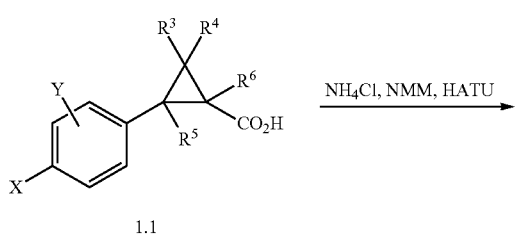

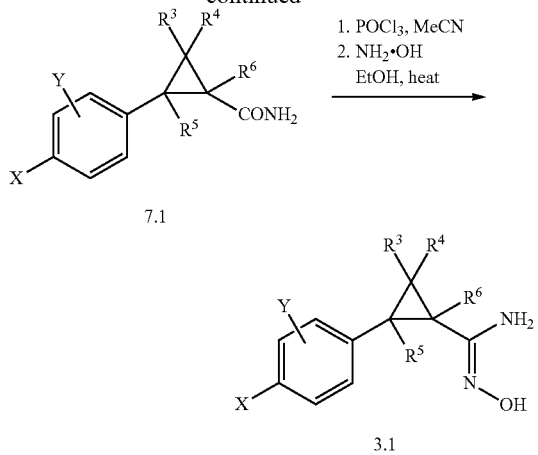

Intermediates like 12.1 in the present invention may be prepared according to Scheme 23, in which amide 7.1 is treated with Lawesson's reagent to afford thioamide 12.1. Other thionating reagents can be employed for this transformation. Thioamide 12.1 can be employed as an intermediate in schemes in the present invention that involve compounds similar to 12.1.

SCHEME 23

Intermediates like alkyne 9.1 may be prepared according to Scheme 24. Ester 24.1 is reduced by treatment with LAH and the resulting alcohol oxidized by treatment with Dess-Martin periodinane to afford aldehyde 24.2. Other reducing agents (such as DIBAL) and oxidizing reagents (such as Collin's reagent, PCC, or PDC) may be used in these transformations. Aldehyde 24.2 can then be reacted with dimethyl (1-diazo-2-oxopropyl)phosphonate in the presence of potassium carbonate to afford alkyne 9.1. Other bases can be employed in this transformation.

SCHEME 24

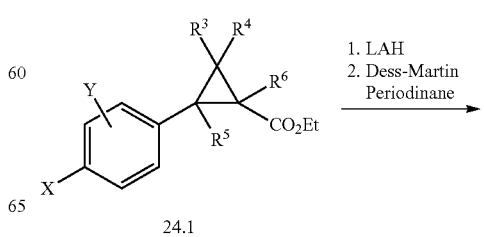

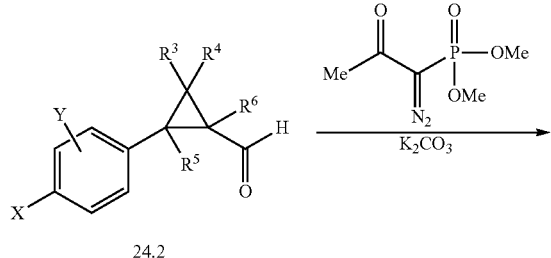

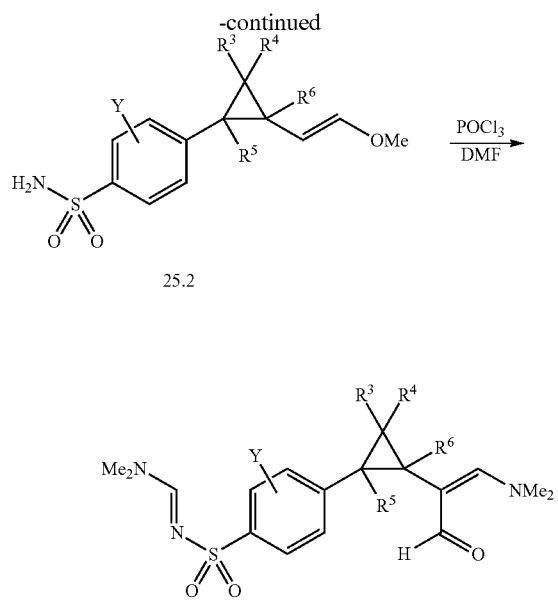

Intermediates like 11.1 may be prepared according to Scheme 25. The sequence begins with treating (methoxymethyl)triphenylphosphonium chloride with n-butyllithium at low temperature and then reacting the resultant ylide with aldehyde 25.1 to afford enol ether 25.2. Enol ether 25.2 can then be treated with $POCl_3$ in DMF to afford aldehyde 11.1.

SCHEME 25

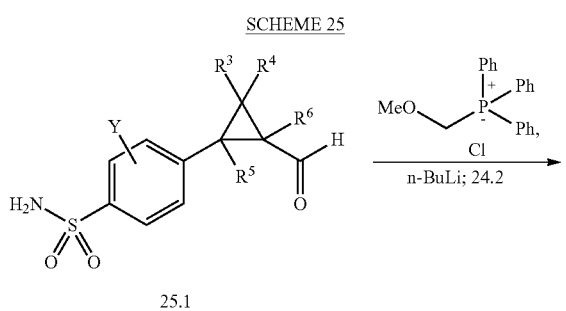

Other useful intermediates like 26.5 may be prepared according to Scheme 26. The sequence begins with treating sulfonamide 26.1 with DMF-DMA at elevated temperature to afford aryl bromide 26.2. Aryl bromide 26.2 is then reacted with alkenyl boronate 26.3 under palladium-catalyzed conditions to afford styrenyl boronate 26.4. A variety of different catalysts (including other metals such as nickel), ligands, bases, and solvents can be employed in this reaction. Styrenyl boronate 26.4 can then be treated with TMSD in the presence of palladium acetate followed by treatment of the resulting cyclopropane with triflic acid to afford cyclopropyl boronate 26.5. Other palladium (as well as copper and rhodium) catalysts can be employed in the cyclopropanation reaction.

SCHEME 26

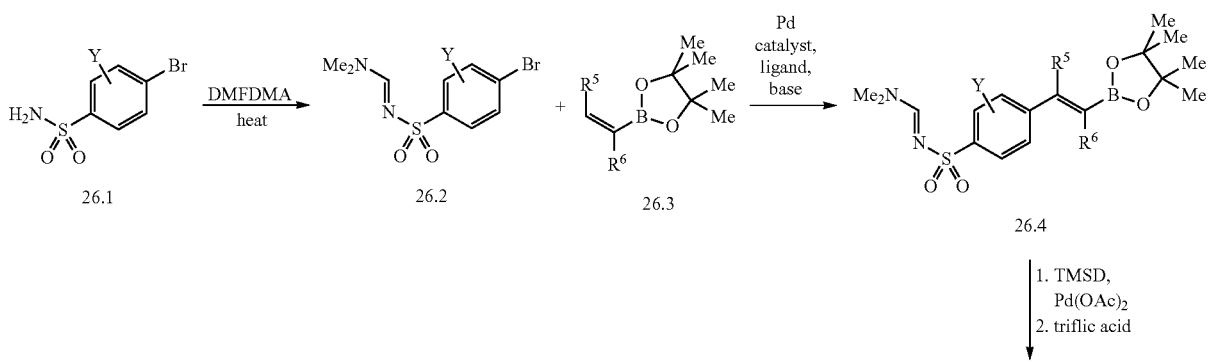

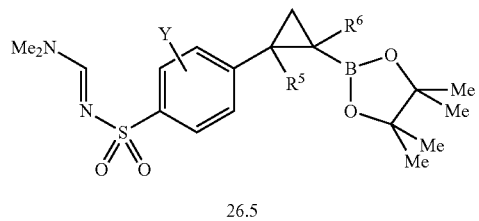

26.5

Intermediates like pyrazole 14.1 may be prepared according to Scheme 27. The sequence begins with treating acid 19.3 with N,O-dimethylhydroxylamine hydrochloride followed by reacting the resulting Weinreb amide with methylmagnesium chloride and then treating the resulting ketone with DMF-DMA to afford formamidine 27.1. Formamidine 27.1 can then be treated with hydrazine followed by treatment with DMF-DMA to afford pyrazole 14.1.

SCHEME 27

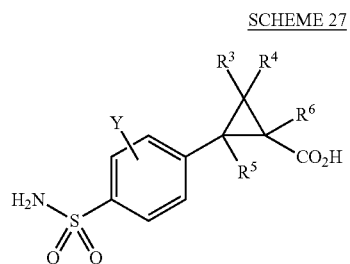

19.3

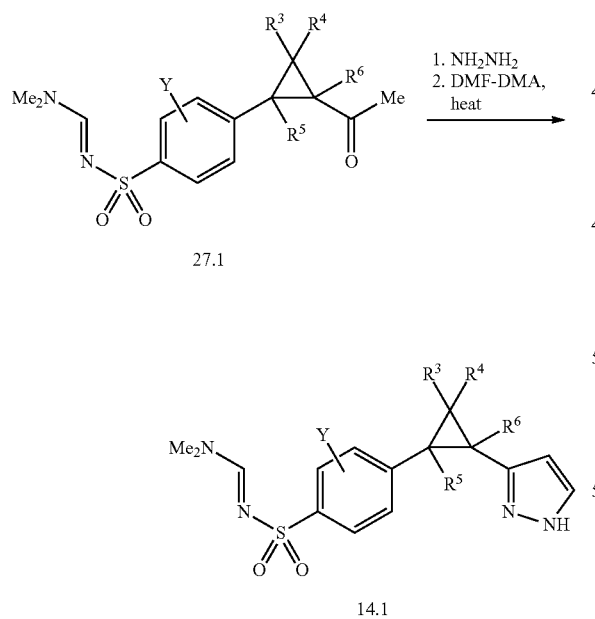

27.1

14.1

Haloketone intermediates of interest like 16.1 may be prepared according to Scheme 28, in which acid 1.1 is treated with sulfuric acid in the presence of methanol and then reacting the resultant ester with chloroiodomethane in the presence of LDA to afford haloketone 16.1. Other bases can be employed in this transformation.

SCHEME 28

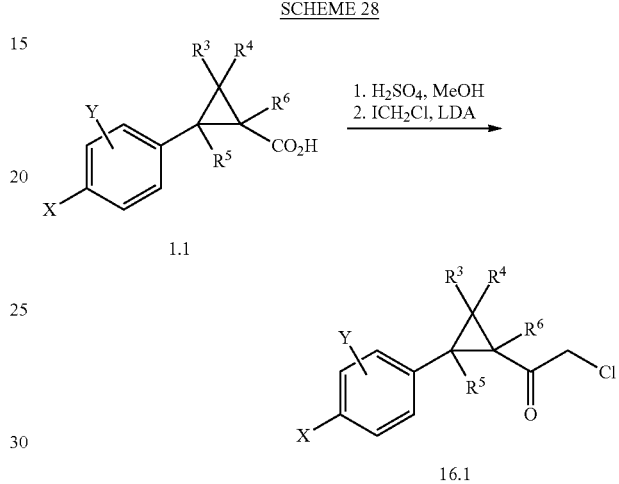

1.1

16.1

Other useful intermediates like 17.1 may be prepared according to Scheme 29. The sequence begins with reacting ester 29.1 with chloroiodomethane in the presence of LDA followed by treatment of the resultant haloketone with sodium azide to afford azide 29.2. Azide 29.2 can then be reduced by treatment with triphenylphosphine in the presence of PTSA in a mixture of water and tetrahydrofuran to afford amine 17.1. Other reducing reagents, acids, and solvents can be employed in this transformation.

SCHEME 29

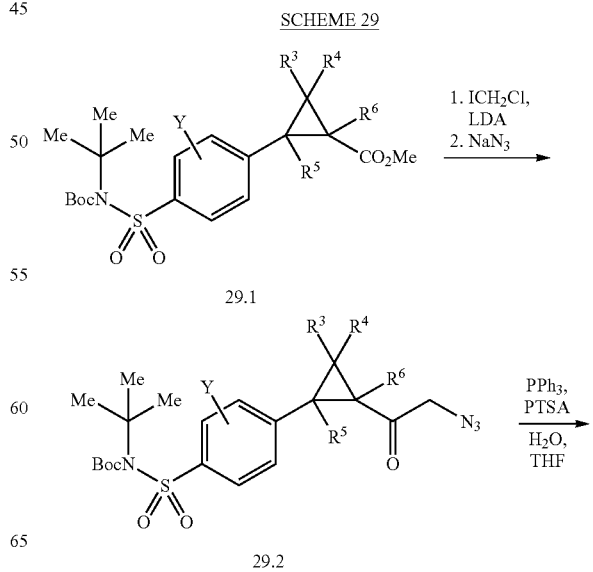

29.1

29.2

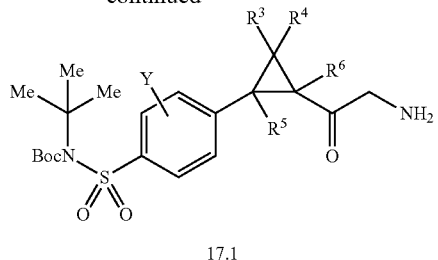

17.1

Additional compounds in the present invention may be prepared according to Scheme 30, in which amide oxime 3.1 is first reacted with 1,1'-thiocarbonyldiimidazole and then treated with boron trifluoride diethyl etherate to form the corresponding thiadiazolone, which is then treated with phosphorous oxychloride to afford chlorothiadiazole 30.1. Other Lewis acids and halogenating reagents (such as PCl$_5$, thionyl chloride, and N-chlorosuccinimde) can be employed for these transformations. Chlorothiadiazole 30.1 may be reacted with primary or secondary amine 30.2 at ambient or elevated temperature to afford amniothiadiazole 30.3. Alternatively, chlorothiadiazole 30.1 can be reacted with alcohols to form the corresponding alkoxythiadiazole.

SCHEME 30

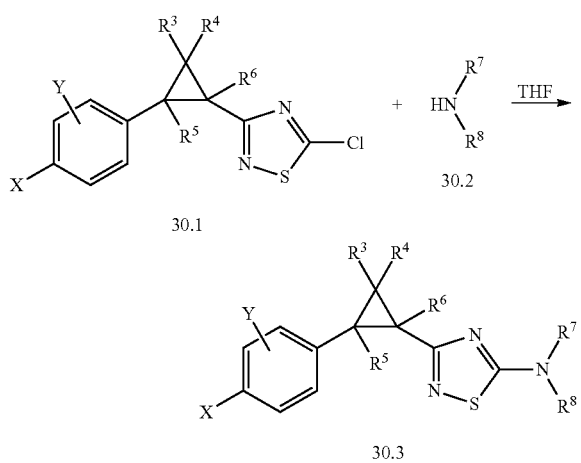

In addition, compounds in the present invention may be prepared according to Scheme 31, in which amine 17.1 is reacted with acyl chloride 17.2 in the presence of potassium carbonate and the resulting amide treated with phosphorous oxychloride at elevated temperature followed by treatment with trifluoroacetic acid to afford oxazole 31.1. Other bases, dehydrating reagents, and acids can be employed in these transformations.

SCHEME 31

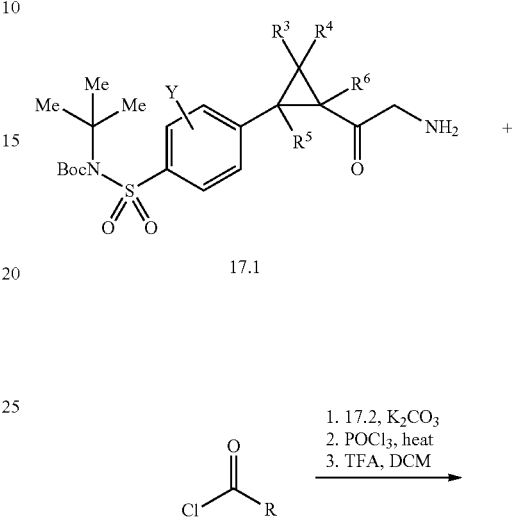

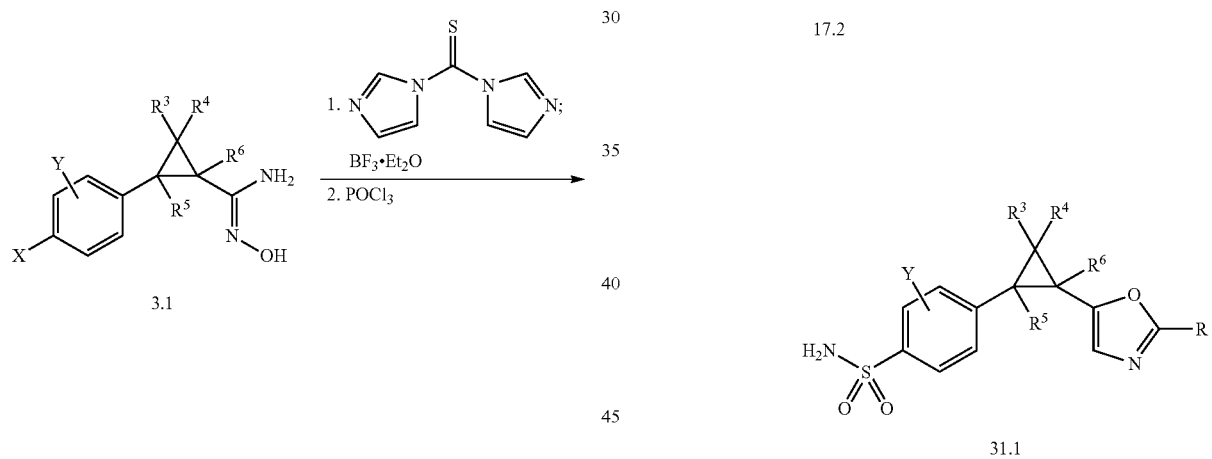

31.1

Additional compounds in the present invention may be prepared according to Scheme 32, which starts with Wittig olefination of aldehyde 32.1 by reaction with phosphorane 32.2 at elevated temperature to afford cinnamate 32.3. Cinnamate 32.3 is then reacted with ylide precursor 32.4 in the presence of n-butyllithium to afford cyclopropane 32.5. Cyclopropane 32.5 is then reacted with phenylmethanethiol in the presence of a palladium catalyst (such as tris(dibenzylideneacetone)dipalladium(0)), a ligand (such as Xantphos), and a base (such as N,N-diisopropylethylamine) to convert the aryl bromide to the corresponding thioether, which is then treated with DCDMH followed by ammonium hydroxide to afford sulfonamide 32.6. Other palladium catalysts or precatalysts, ligands, bases, and halogenating reagents (such as sulfuryl chloride) may be used in these transformations. Saponification of the methyl ester of sulfonamide 32.6 by treatment with lithium hydroxide then affords acid 32.7.

SCHEME 32

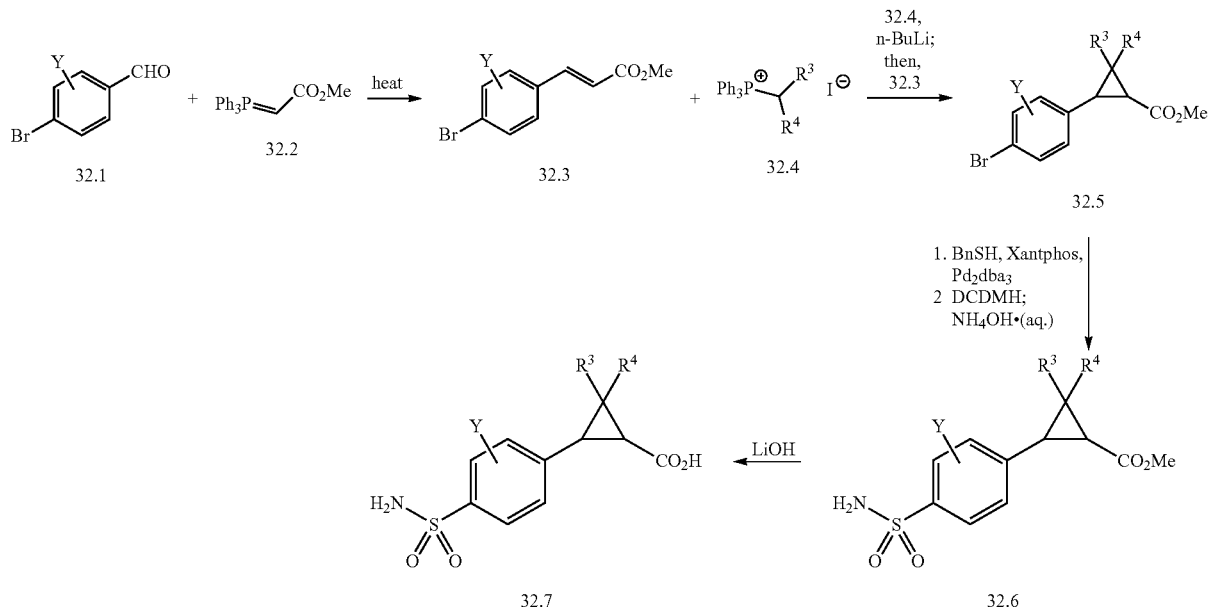

Further compounds in the present invention may be prepared according to Scheme 33, which starts with protection of aldehyde 33.1 as the acetal followed by treatment with a phase transfer catalyst (such as TBAB) in a mixture of chloroform and concentrated, aqueous strong base (such as sodium hydroxide) to afford dichlorocyclopropane 33.2. Dichlorocyclopropane 33.2 is then treated with an acid (such as HCl) to remove the acetal, the resulting aldehyde oxidized with sodium chlorite (or other suitable oxidants, such as TPAP) to the corresponding carboxylic acid, and this acid converted to methyl ester 33.4 by treatment with trimethyl-silyldiazomethane. Ester 33.4 is then treated with HCl in acetic acid to furnish acid 33.5.

SCHEME 33

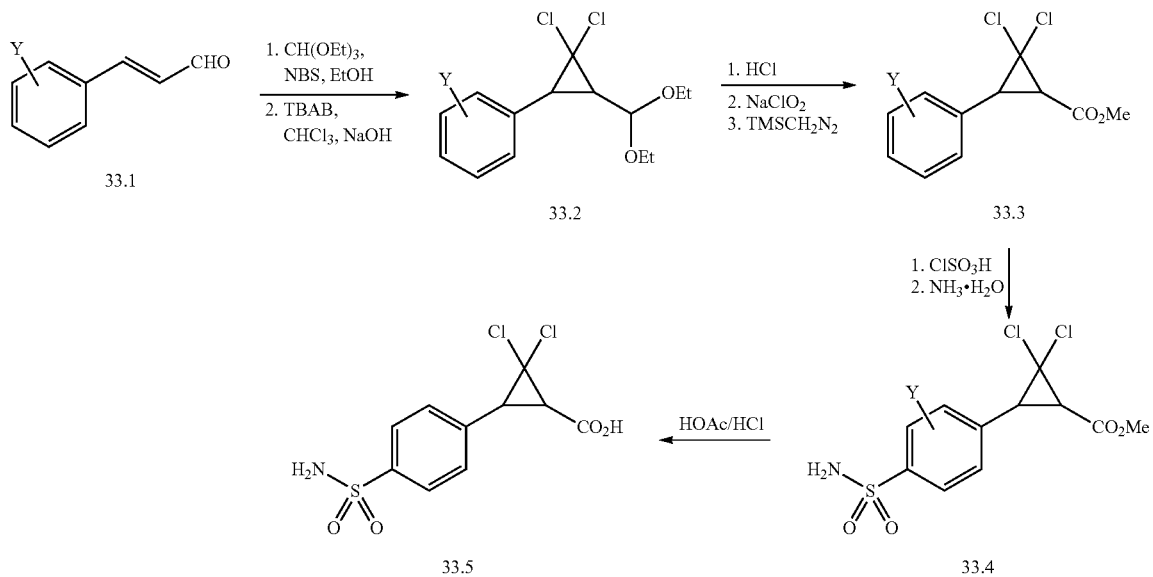

Further compounds in the present invention may be prepared according to Scheme 34, in which aldehyde 32.1 is first reacted with cyanoacetate 34.1 in the presence of piperidine and acetic acid to give styrenyl ester 34.2. Ester 34.2 is then reacted with nitroalkane 34.3 in the presence of base at elevated temperature to afford cyclopropane 34.4. Cyclopropane 34.4 can then be saponified, decarboxylated, and the embedded nitrile hydrolyzed to give methyl ester 34.5. Methyl ester 34.5 is then reacted with phenylmethanethiol in the presence of a palladium catalyst (such as tris(dibenzylideneacetone)dipalladium(0)), a ligand (such as Xantphos), and a base (such as diisopropylethylamine) to convert the aryl bromide to the corresponding thioether, which is then treated with DCDMH followed by ammonium hydroxide to afford sulfonamide 34.6. Other palladium catalysts or precatalysts, ligands, bases, and halogenating reagents (such as sulfuryl chloride) may be used in these transformations. Saponification of the methyl ester of sulfonamide 34.6 by treatment with lithium hydroxide then affords acid 34.7.

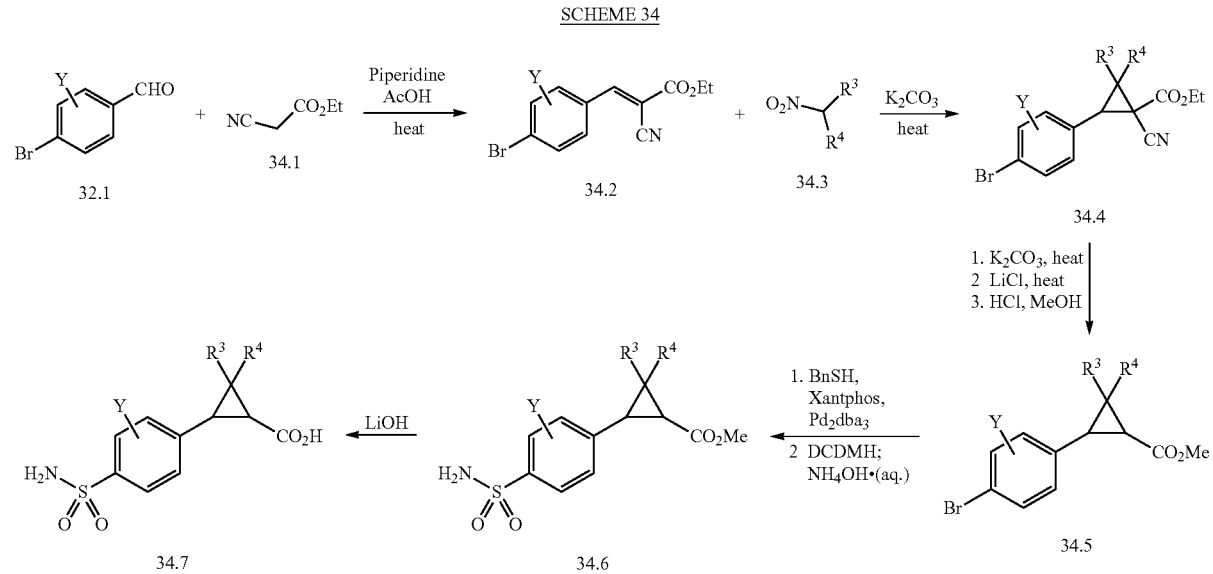

SCHEME 34

It is understood that the compounds and intermediates in the foregoing reaction schemes may be employed as synthetic intermediates in other schemes that involve similar intermediates to produce alternative compounds of the present invention.

In some cases the order of carrying out the foregoing reaction schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases the final product may be further modified, for example, by manipulation of substituents. These manipulations may include, but are not limited to, reduction, oxidation, alkylation, acylation, and hydrolysis reactions which are commonly known to those skilled in the art.

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

The following abbreviations are used throughout the text:

| | |
|---|---|
| Ac | acetyl |
| AIBN | 2,2'-azobisisobutyronitrile |
| app | apparent |
| aq | aqueous |
| Ar | aryl |
| $B_2(Pin)_2$ | bis(pinacolato)diboron |
| BINAP | 2,2'-bis(diphenylphosphino)-1,1'-binaphthalene |
| Bn | benzyl |

-continued

| | |
|---|---|
| Boc | tert-butoxycarbonyl |
| BOP | (benzotriazol-1-yloxy)tris(dimethylamino)phosphonium hexafluorophosphate |
| br | broad |
| BSA | bovine serum albumin |
| Bu | butyl |
| ca | circa (approximately) |
| CAN | ammonium cerium(IV) nitrate |
| Cbz | carboxybenzyl |
| CDI | 1,1'-carbonyldiimidazole |
| d | doublet |
| DABCO | diazabicyclo[2.2.2]octane |
| DAST | (diethylamino)sulfur trifluoride |
| dba | dibenzylideneacetone |
| DBU | 1,8-diazabicyclo[5.4.0]undec-7-ene |
| DCE | 1,2-dichloroethane |
| DCDMH | 1,3-dichloro-5,5-dimethylhydantoin |
| dd | doublet of doublets |
| DIBAL | diisobutylaluminum hydride |
| DIEA | N,N-diisopropylethylamine |
| DMA | N,N-dimethylacetamide |
| DMAP | 4-(dimethylamino)pyridine |
| DMEM | Dulbecco's modified eagle medium (high glucose) |
| DMF | N,N-dimethylformamide |
| DMF-DMA | N,N-dimethylformamide dimethylacetal |
| DMPU | N,N'-dimethylpropyleneurea |
| DMSO | dimethylsulfoxide |
| DPBF | 1,3-diphenylisobenzofuran |
| dppf | 1,1'-bis(diphenylphosphino)ferrocene |
| EDC | N-(3-dimethylaminopropyl)-N'-ethylcarbodiimide hydrochloride |
| EDTA | ethylenediaminetetraacetic acid |
| EGTA | ethylene glycol-bis(r3-aminoethyl ether)-N,N,N',N'-tetraacetic acid |

| | |
|---|---|
| eq | equivalents |
| ESI | electrospray ionization |
| Et | ethyl |
| FBS | fetal bovine serum |
| h | hours |
| HATU | O-(7-azabenzotriazol-1-yl)-N,N,N'N'-tetramethyluronium hexafluorophosphate |
| HEK | human embryonic kidney |
| HEPES | N-(2-hydroxyethyl)piperazine-N'-(2-ethanesulfonic acid) |
| HMDS | hexamethyldisilazane |
| HMTA | hexamethylenetetramine |
| HOAt | 1-hydroxy-7-azabenzotriazole |
| HOBt | 1-hydroxybenzotriazole |
| HPLC | high performance liquid chromatography |
| Hz | Hertz |
| imid | imidazole |
| i-Pr | isopropyl |
| J | coupling constant |
| LAH | lithium aluminum hydride |
| LCMS | liquid chromatography-mass spectrometry |
| LDA | lithium diisopropylamide |
| m/z | mass to charge ratio |
| m | multiplet |
| mCPBA | 3-chloroperoxybenzoic acid |
| Me | methyl |
| min | minutes |
| MP | macroporous polystyrene |
| Ms | methanesulfonyl |
| MTBE | methyl tert-butyl ether |
| MW | molecular weight |
| NBS | N-bromosuccinimide |
| NHS | N-hydroxysuccinimide |
| n-BuLi | n-butyllithium |
| n-HexLi | n-hexyllithium |
| NMM | N-methyl morpholine |
| NMP | 1-methyl-2-pyrrolidinone |
| NMR | nuclear magnetic resonance |
| OAc | acetate |
| p | pentet |
| PBPB | pyridinium bromide perbromide |
| PBS | phosphate-buffered saline |
| PCC | pyridinium chlorochromate |
| PDC | pyridinium dichromate |
| Pd/C | palladium on carbon |
| Ph | phenyl |
| PMBCl | 4-methoxybenzyl chloride |
| psi | pounds per square inch |
| p-Ts | para-toluenesulfonyl |
| PTSA | para-toluenesulfonic acid |
| Py | pyridyl |
| q | quartet |
| RIC-3 | resistance to inhibitors of cholinesterase 3 |
| rt | room temperature |
| s | singlet |
| SEM | 2-trimethylsilylethoxymethyl |
| SEMCl | 2-trimethylsilylethoxymethyl chloride |
| SFC | supercritical fluid chromatography |
| SM | starting material |
| t | triplet |
| T3P | 2,4,6-tripropyl-1,3,5,2,4,6-trioxatriphosphorinane-2,4,6-trioxide |
| TBAB | tetra-n-butylammonium bromide |
| TBAF | tetra-n-butylammonium fluoride |
| TBDPS | tert-butyldiphenylsilyl |
| TBDPSCl | tert-butyldiphenylsilyl chloride |
| t-Bu | tert-butyl |
| TCCA | trichloroisocyanuric acid |
| TEA | triethylamine |
| TFA | trifluoroacetic acid |
| Tf | trifluoromethanesulfonyl |
| TCFH | tetramethylchloroformamidinium hexafluorophosphate |
| THF | tetrahydrofuran |
| TMG | tetramethylguanidine |
| TMSD | trimethylsilyldiazomethane |
| TPAP | tetrapropylammonium perruthenate |
| Trisyl | 2,4,6-triisopropylbenzenesulfonyl |
| V/V | volume to volume |
| X-Phos | 2-dicyclohexylphosphino-2',4',6'-triisopropylbiphenyl |
| Xantphos | (9,9-dimethyl-9H-xanthene-4,5-diyl)bis(diphenylphosphane) |

Intermediate 1

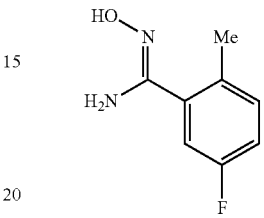

5-Fluoro-N'-hydroxy-2-methylbenzenecarboximidamide

5-Fluoro-2-methylbenzonitrile (1.01 g, 7.47 mmol) was dissolved in ethanol (15 mL) at ambient temperature. Hydroxylamine (0.550 mL, 8.97 mmol) was added and the reaction mixture warmed to 90° C. The reaction mixture was allowed to stir for 12 h at 90° C. The reaction mixture was allowed to cool and was concentrated under reduced pressure. The residue was purified by silica gel chromatography, eluting with a gradient of ethyl acetate:hexanes—0:100 to 35:65, to afford the title compound. MS: m/z=169.1 [M+H].

Intermediate 2

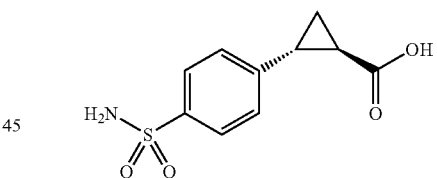

(1R,2R)-2-(4-Sulfamoylphenyl)cyclopropanecarboxylic acid

Step A: Ethyl (1R,2R)-2-(4-sulfamoylphenyl)cyclopropanecarboxlate

To a stirred solution of ethyl trans-2-phenylcyclopropanecarboxylate (700 g, 3.68 mol) in chloroform (6 L) at 0° C. was added chlorosulfonic acid (2.45 L, 36.8 mol) dropwise. The resulting mixture was allowed to warm to ambient temperature and stirring was continued for 2 h, then the reaction mixture was cooled to 0° C. and quenched by addition of water (3 L). The resulting mixture was extracted with dichloromethane (2×3 L) and the combined organic extracts were dried (sodium sulfate), filtered, and concentrated under reduced pressure. The residue was dissolved in 1,4-dioxane (15 L) and ammonium hydroxide solution (30%, 2.1 L, 18.0 mol) was added dropwise. The resulting mixture was allowed to stir for 30 min at ambient temperature and then diluted with water (10 L). The resulting mixture was extracted with ethyl acetate (3×5 L) and the combined organic extracts were washed with saturated aqueous sodium chloride (10 L), dried (sodium sulfate), filtered, and concentrated under reduced pressure to provide the racemic title compound. The enantiomers were resolved by SFC, utilizing a Chiralcel OD-H column and eluting with ethanol:carbon dioxide:diethylamine—20:80:0.2. The first major peak to elute was ethyl (1S,2S)-2-(4-sulfamoylphenyl)cyclopropanecarboxylate, and the second major peak to elute was ethyl (1R,2R)-2-(4-sulfamoylphenyl)cyclopropanecarboxylate, the title compound. MS: m/z=270.1 [M+H].

Step B: (1R,2R)-2-(4-Sulfamoylphenyl)cyclopropanecarboxylic acid

To a stirred solution of ethyl (1R,2R)-2-(4-sulfamoylphenyl)cyclopropanecarboxylate (190 g, 0.705 mol) in tetrahydrofuran (3 L) and methanol (600 mL) at ambient temperature at 0° C. was added aqueous sodium hydroxide (2.12 M, 1.00 L, 2.12 mol) dropwise. The resulting mixture was allowed to stir at ambient temperature for 2 h and then concentrated under reduced pressure to remove the organic solvents. The resulting mixture was adjusted to pH=4 by addition of aqueous hydrochloric acid (2.0 M) and extracted with ethyl acetate (2×2 L) and the combined organic extracts were washed with saturated aqueous sodium chloride (1 L), dried (sodium sulfate), filtered, and concentrated under reduced pressure. The residue was purified by recrystallization from diethyl ether to afford the title compound. MS: m/z=242.1 [M+H].

Intermediate 3

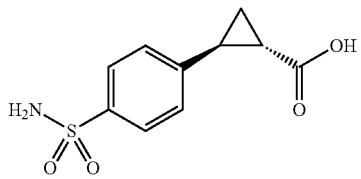 [SMILES: NS(=O)(=O)c1ccc([C@H]2C[C@@H]2C(=O)O)cc1]

(1S,2S)-2-(4-Sulfamoylphenyl)cyclopropanecarboxylic acid

Essentially following the procedures described in Intermediate 2, but using ethyl (1S,2S)-2-(4-sulfamoylphenyl)cyclopropanecarboxylate (described in Intermediate 2) in place of ethyl (1R,2R)-2-(4-sulfamoylphenyl)cyclopropanecarboxylate, the title compound was obtained. MS: m/z=242.1 [M+H].

Intermediate 4

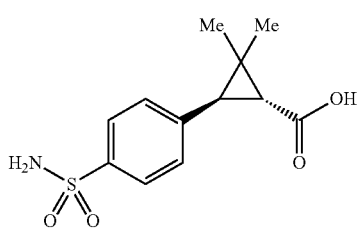 [SMILES: CC1(C)[C@H](C(=O)O)[C@H]1c1ccc(S(N)(=O)=O)cc1]

(1R,3R)-2,2-Dimethyl-3-(4-sulfamoylphenyl)cyclopropanecarboxylic acid

Step A: (1R,3R)-2,2-Dimethyl-3-phenylcyclopropanecarboxylic acid

The enantiomers of trans-2,2-dimethyl-3-phenylcyclopropanecarboxylic acid (957 g, 5.03 mol) were resolved by SFC, utilizing a Lux-5u column and eluting with methanol: carbon dioxide—30:70. The first major peak to elute was (1R,3R)-2,2-dimethyl-3-phenylcyclopropanecarboxylic acid, the title compound, and the second major peak to elute was (1S,3S)-2,2-dimethyl-3-phenylcyclopropanecarboxylic acid. MS: m/z=191.1 [M+H].

Step B: Ethyl (1R,3R)-2,2-dimethyl-3-phenylcyclopropanecarboxylate

To a stirred solution of (1R,3R)-2,2-dimethyl-3-phenylcyclopropanecarboxylic acid (267 g, 1.40 mol) in ethanol (2.7 L) was added thionyl chloride (497 g, 4.21 mol) dropwise at 0° C. The resulting solution was allowed to stir for 1 h at ambient temperature and concentrated under reduced pressure. The residue was dissolved in ethyl acetate (2 L), washed with saturated aqueous sodium bicarbonate (2×1.5 L) and saturated aqueous sodium chloride (3 L), dried (magnesium sulfate), and concentrated under reduced pressure to afford the title compound. MS: m/z=219.1 [M+H].

Step C: Ethyl (1R,3R)-2,2-dimethyl-3-(4-sulfamoylphenyl)cyclopropanecarboxylate

To a stirred solution of ethyl (1R,3R)-2,2-dimethyl-3-phenylcyclopropanecarboxylate (245 g, 1.12 mol) in chloroform (2.5 L) at 0° C. was added chlorosulfonic acid (1564 g, 13.48 mol) dropwise. The resulting solution was allowed to stir for 30 min at 0° C., warmed to ambient temperature, and allowed to stir for 2 h. The reaction mixture was cooled to 0° C., water (2 L) was added, and the resulting solution was extracted with ethyl acetate (2×3 L). The organic extracts were combined, washed with saturated aqueous sodium chloride (3 L), dried (magnesium sulfate), and concentrated under reduced pressure. The residue was dissolved in 1,4-dioxane (9 L), cooled to 5° C., and ammonium hydroxide solution (30%, 1.75 L, 13.5 mol) was added. The resulting solution was allowed to stir for 30 min at ambient temperature, diluted with water (5 L), and the resulting solution extracted with ethyl acetate (3×3 L). The combined organic extracts were washed with saturated aqueous sodium chloride (5 L), dried (magnesium sulfate), and concentrated under reduced pressure. The residue was purified by silica gel chromatography, eluting with a gradient of ethyl acetate:petroleum ether—17:83 to 33:67 to afford the title compound. MS: m/z=298.0 [M+H].

Step D: (1R,3R)-2,2-Dimethyl-3-(4-sulfamoylphenyl)cyclopropanecarboxylic acid

To a solution of (1R,3R)-ethyl 2,2-dimethyl-3-(4-sulfamoylphenyl)cyclopropanecarboxylate (15 g, 50.4 mmol) in tetrahydrofuran (400 mL) and methanol (100 mL) at ambient temperature was added sodium hydroxide (1.0 M, 150 mL, 150 mmol). The reaction mixture was warmed to 60° C. and allowed to stir for 2.5 h. The reaction mixture was cooled to 0° C., hydrochloric acid (1.00 M, 12.5 mL, 151 mmol) slowly added, and the resulting mixture concentrated under reduced pressure to remove methanol, tetrahydrofuran, and a small amount of the water. The mixture was extracted with ethyl acetate (3×200 mL) and the combined organic extracts were washed with saturated aqueous sodium chloride (150 mL), dried (sodium sulfate), filtered, and concentrated under reduced pressure to afford the title compound. MS: m/z=270.1 [M+H].

Intermediate 5

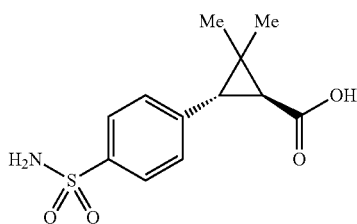 [SMILES: CC1(C)[C@@H](C(=O)O)[C@@H]1c1ccc(S(N)(=O)=O)cc1]

(1S,3S)-2,2-Dimethyl-3-(4-sulfamoylphenyl)cyclopropanecarboxylic acid

Essentially following the procedures described in Intermediate 4, but using (1S,3S)-2,2-dimethyl-3-phenylcyclopropanecarboxylic acid (described in Intermediate 4) in place of (1R,3R)-2,2-dimethyl-3-phenylcyclopropanecarboxylic acid, the title compound was obtained. MS: m/z=270.2 [M+H].

Intermediate 6

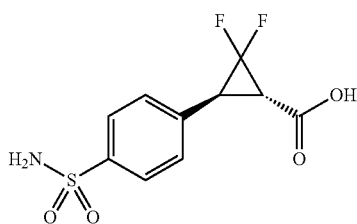 [SMILES: NS(=O)(=O)c1ccc([C@@H]2[C@@H](C(=O)O)C2(F)F)cc1]

(1S,3S)-2,2-Difluoro-3-(4-sulfamoylphenyl)cyclopropanecarboxylic acid

Step A: Ethyl (1S,3S)-2,2-difluoro-3-(4-sulfamoylphenyl)cyclopropanecarboxlate

To chlorosulfonic acid (35.5 mL, 530 mmol) at 0° C. was added ethyl trans-2,2-difluoro-3-phenylcyclopropanecarboxylate (10.0 g, 44.2 mmol) (Dolbier et al. *J. Fluorine Chem.* (2004) 125:459-469) dropwise. The reaction mixture was allowed to stir at 0° C. for 30 min, warmed to ambient temperature, and allowed to stir for 2 h. The reaction mixture was slowly added to slowly stirred ice/water (500 mL) over the course of 5 min. The resulting suspension was then diluted with ethyl acetate (400 mL) and allowed to stir for 5 min. The layers were separated and the aqueous layer extracted with ethyl acetate (2×400 mL). The combined organic extracts were washed with water (400 mL), dried (magnesium sulfate), and concentrated under reduced pressure. The residue was dissolved in 1,4-dioxane (400 mL) and ammonium hydroxide (30%, 92 mL, 1.36 mol) was added. The reaction mixture was allowed to stir at ambient temperature for 2.5 h and then concentrated under reduced pressure. The residue was purified by silica gel chromatography, eluting with a gradient of ethyl acetate:hexanes—0:100 to 40:60 to afford the racemic title compound. The racemate was resolved by SFC, utilizing a ChiralPak AD-H column, eluting with isopropanol:carbon dioxide:diethylamine—20:80:0.1. The first major peak to elute was ethyl (1R,3R)-2,2-difluoro-3-(4-sulfamoylphenyl)cyclopropanecarboxylate and the second major peak to elute was ethyl (1S,3S)-2,2-difluoro-3-(4-sulfamoylphenyl)cyclopropanecarboxylate, the title compound. MS: m/z=306.2 [M+H].

Step B: (1S,3S)-2,2-Difluoro-3-(4-sulfamoylphenyl)cyclopropanecarboxylic acid

To a solution of ethyl (1S,3S)-2,2-difluoro-3-(4-sulfamoylphenyl)cyclopropane carboxylate, (500 mg, 1.64 mmol) in acetonitrile (8.2 mL) was added aqueous lithium hydroxide (1.0 M, 4.9 mL, 4.9 mmol) and the reaction mixture allowed to stir at ambient temperature for 18 h. The reaction mixture was concentrated under reduced pressure and the aqueous layer acidified with aqueous HCl (1 M). The mixture was then extracted with ethyl acetate (3×20 mL) and the combined organic extracts washed with saturated aqueous sodium chloride (20 mL), dried (magnesium sulfate) and concentrated under reduced pressure to afford the title compound. MS: m/z=278.1 [M+H].

Intermediate 7

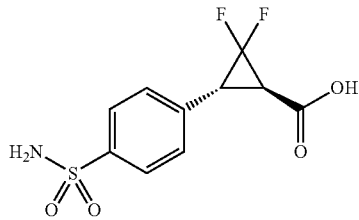 [SMILES: NS(=O)(=O)c1ccc([C@H]2[C@H](C(=O)O)C2(F)F)cc1]

(1R,3R)-2,2-Difluoro-3-(4-sulfamoylphenyl)cyclopropanecarboxylic acid

Essentially following the procedures described in Intermediate 6, but using ethyl (1R,3R)-2,2-difluoro-3-(4-sulfamoylphenyl)cyclopropanecarboxylate (described in Intermediate 6) in place of ethyl (1S,3S)-2,2-difluoro-3-(4-sulfamoylphenyl)cyclopropanecarboxylate, the title compound was obtained. MS: m/z=278.1 [M+H].

Intermediate 8

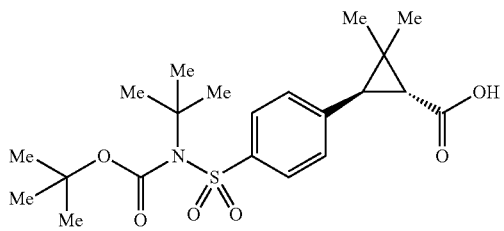 [SMILES: CC(C)(C)OC(=O)N(C(C)(C)C)S(=O)(=O)c1ccc([C@@H]2[C@@H](C(=O)O)C2(C)C)cc1]

(1R,3R)-3-{4-[(tert-Butoxycarbonyl)(tert-butyl)sulfamoyl]phenyl}-2,2-dimethylcyclopropanecarboxylic acid Step A: Ethyl (1R,3R)-3-{4-[(tert-butoxycarbonyl)(tert-butyl)sulfamoyl]phenyl}-2,2-dimethylcyclopropanecarboxylate To a stirred solution of ethyl (1R,3R)-2,2-dimethyl-3-(4-sulfamoylphenyl)cyclopropanecarboxylate (described in Intermediate 4) (2.00 g, 6.73 mmol) in tetrahydrofuran (24 mL) at ambient temperature were added di-tert-butyl dicarbonate (7.34 g, 33.6 mmol) and DMAP (82 mg, 0.67 mmol). The resulting mixture was allowed to stir at ambient temperature for 18 h, then at 50° C. for 7 h, then allowed to cool to ambient temperature. Di-tert-butyl dicarbonate (1.50 g, 6.87 mmol) was added and the reaction mixture was allowed to stir at 50° C. for 3 h, then allowed to cool to ambient temperature. Di-tert-butyl dicarbonate (3.00 g, 13.7 mmol) and DMAP (82 mg, 0.67 mmol) were added and the reaction mixture was allowed to stir at 50° C. for 3 h, then allowed to cool to ambient temperature. The resulting mixture was concentrated under reduced pressure and the residue was purified by silica gel chromatography, eluting with a gradient of ethyl acetate:hexanes—0:100 to 30:70 to afford the title compound. MS: m/z=517.3 [M+CH$_3$CN+Na].

Step B: (1R,3R)-3-{4-[(tert-Butoxycarbonyl)(tert-butyl)sulfamoyl]phenyl}-2,2-dimethylcyclopropanecarboxylic acid To a stirred solution of ethyl (1R,3R)-3-{4-[(tert-butoxycarbonyl)(tert-butyl)sulfamoyl]phenyl}-2,2-dimethylcyclopropanecarboxylate (2.36 g, 5.19 mmol) in tetrahydrofuran (15 mL) and methanol (15 mL) at ambient temperature was added aqueous sodium hydroxide (2.0 M, 9.47 mL, 18.9 mmol) dropwise. The resulting mixture was allowed to stir at ambient temperature for 18 h and then poured into water (50 mL). The resulting mixture was adjusted to pH=4 by addition of aqueous hydrochloric acid (1.0 M) and extracted with ethyl acetate (2×100 mL). The combined organic extracts were washed with saturated aqueous sodium chloride (40 mL), dried (sodium sulfate), filtered, and concentrated under reduced pressure to provide the title compound, which was used without further purification. MS: m/z=489.2 [M+CH$_3$CN+Na].

Intermediate 9

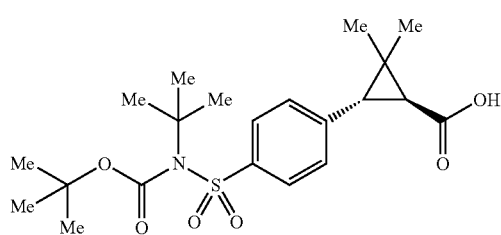 [SMILES: CC(C)(C)OC(=O)N(C(C)(C)C)S(=O)(=O)c1ccc([C@H]2[C@H](C(=O)O)C2(C)C)cc1]

(1S,3S)-3-{4-[(tert-Butoxycarbonyl)(tert-butyl)sulfamoyl]phenyl}-2,2-dimethylcyclopropanecarboxylic acid Essentially following the procedures described in Intermediate 8, but using ethyl (1S,3S)-2,2-dimethyl-3-(4-sulfamoylphenyl)cyclopropanecarboxylate (described in Intermediate 5) in place of ethyl (1R,3R)-2,2-dimethyl-3-(4-sulfamoylphenyl)cyclopropanecarboxylate, the title compound was obtained. MS: m/z=489.4 [M+CH$_3$CN+Na].

Intermediate 10

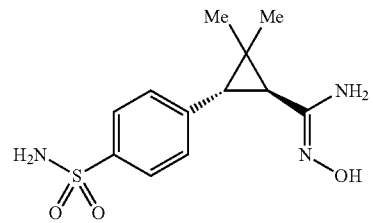 [SMILES: CC1(C)[C@@H](/C(N)=N/O)[C@@H]1c1ccc(S(N)(=O)=O)cc1]

(1S,3S)—N'-Hydroxy-2,2-dimethyl-3-(4-sulfamoylphenyl)cyclopropanecarboximidamide Step A: (1S3S)-2,2-Dimethyl-3-(4-sulfamoylphenyl)cyclopropanecarboxamide (1S,3S)-2,2-Dimethyl-3-(4-sulfamoylphenyl)cyclopropanecarboxylic acid (Intermediate 5) (4.0 g, 14.85 mmol) was dissolved in dichloromethane (34 mL) and dimethyl sulfoxide (3.8 mL) at ambient temperature. N-Methylmorpholine (3.3 mL, 30.0 mmol), HATU (5.85 g, 15.39 mmol), and ammonium chloride (1.59 g, 29.7 mmol) were added sequentially. The reaction mixture was allowed to stir for 14 h at ambient temperature. The reaction mixture was concentrated under reduced pressure. The residue was purified by preparative HPLC, eluting with a gradient of acetonitrile:water:trifluoroacetic acid—5:95:0.1 to 55:45:0.1 to afford the title compound. MS: m/z=269.1 [M+H].

Step B: 4-[(1S,3S)-3-Cyano-2,2-dimethylcyclopropyl]benzenesulfonamide (1S,3S)-2,2-Dimethyl-3-(4-sulfamoylphenyl)cyclopropanecarboxamide (3.23 g, 12.04 mmol) was dissolved in acetonitrile (60 mL) at ambient temperature. Phosphorous oxychloride (2.24 mL, 24.07 mmol) was added and the reaction mixture was warmed to 80° C. and allowed to stir for 45 min. The reaction mixture was allowed to cool and saturated aqueous sodium bicarbonate (20 mL) was added slowly. The resulting mixture was adjusted to pH 8 by addition of saturated aqueous sodium carbonate (10 mL) and extracted with ethyl acetate (3×30 mL). The combined organic extracts were washed with saturated aqueous sodium bicarbonate (15 mL) and saturated aqueous sodium chloride (15 mL), dried (sodium sulfate), filtered, and concentrated under reduced pressure. The residue was purified by silica gel chromatography, eluting with a gradient of ethyl acetate:ethanol:hexanes—3:1:96 to 21:7:72 to afford the title compound. MS: m/z=251.1 [M+H].

Step C: (1S,3S)—N'-Hydroxy-2,2-dimethyl-3-(4-sulfamoylphenyl)cyclopropanecarboximidamide To a stirred solution of 4-[(1S,3S)-3-cyano-2,2-dimethylcyclopropyl]benzenesulfonamide (2.63 g, 10.51 mmol) in ethanol (52 mL) was added hydroxylamine (6.44 mL, 105 mmol). The reaction mixture was warmed to 60° C. and allowed to stir for 13 h. The reaction mixture was allowed to cool and was concentrated under reduced pressure. The residue was co-evaporated with methanol (2×) and acetonitrile (4×) to afford the title compound in sufficient purity for use in the next step. MS: m/z=284.1 [M+H].

Intermediate 11

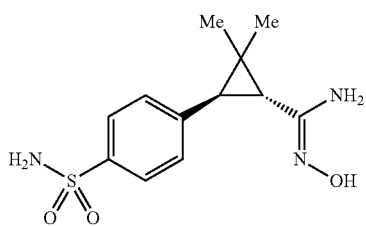 [SMILES: CC1(C)[C@H](/C(N)=N/O)[C@H]1c1ccc(S(N)(=O)=O)cc1]

(1R,3R)—N'-Hydroxy-2,2-dimethyl-3-(4-sulfamoylphenyl)cyclopropanecarboximidamide Essentially following the procedures described in Intermediate 10, but using (1R,3R)-2,2-dimethyl-3-(4-sulfamoylphenyl)cyclopropanecarboxylic acid (described in Intermediate 4) in place of (1S,3S)-2,2-dimethyl-3-(4-sulfamoylphenyl)cyclopropanecarboxylic acid, the title compound was obtained. MS: m/z=284.1 [M+H].

Intermediate 12

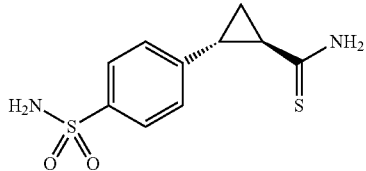 [SMILES: NC(=S)[C@@H]1C[C@H]1c1ccc(S(N)(=O)=O)cc1]

(1R,2R)-2-(4-Sulfamoylphenyl)cyclopropanecarbothioamide

Step A: (1R,2R)-2-(4-Sulfamoylphenyl)cyclopropanecarboxamide

To a solution of (1R,2R)-2-(4-sulfamoylphenyl)cyclopropanecarboxylic acid (Intermediate 2) (3.00 g, 12.4 mmol) in dichloromethane (37 mL) and dimethyl sulfoxide (4.1 mL) at ambient temperature were added HATU (5.20 g, 13.7 mmol), N-methylmorpholine (5.5 ml, 49.7 mmol), and ammonium chloride (2.00 g, 37.3 mmol) sequentially and the reaction mixture allowed to stir for 15 h. The reaction mixture was concentrated under reduced pressure and the residue purified by silica gel column chromatography, eluting with a gradient of ethyl acetate:ethanol:hexanes—0:0:100 to 67:33:0. The product-containing fractions were combined and concentrated under reduced pressure. Further purification was achieved by washing the solid residue with dichloromethane to afford the title compound. MS: m/z=241.1 [M+H].

Step B: (1R,2R)-2-(4-Sulfamoylphenyl)cyclopropanecarbothioamide

To a suspension of (1R,2R)-2-(4-sulfamoylphenyl)cyclopropanecarboxamide (1.15 g, 4.79 mmol) in tetrahydrofuran (19 mL) at ambient temperature was added Lawesson's reagent (1.94 g, 4.79 mmol) and the reaction mixture allowed to stir for 5 h. The reaction mixture was concentrated under reduced pressure and purified by silica gel column chromatography, eluting with a gradient of ethyl acetate:ethanol:hexanes—0:0:100 to 67:33:0. The product-containing fractions were combined and concentrated under reduced pressure. Further purification was achieved by washing the solid residue with dichloromethane to afford the titled compound. MS: m/z=257.2 [M+H].

Intermediate 13

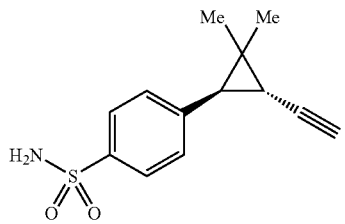 [SMILES: C#C[C@@H]1[C@@H](c2ccc(S(N)(=O)=O)cc2)C1(C)C]

4-[(1R,3S)-3-Ethynyl-2,2-dimethylcyclopropyl]benzenesulfonamide

Step A: 4-[(1R,3R)-3-(Hydroxymethyl)-2,2-dimethylcyclopropyl]benzenesulfonamide

To a solution of ethyl (1R,3R)-2,2-dimethyl-3-(4-sulfamoylphenyl)cyclopropanecarboxylate (described in Intermediate 4) (3.0 g, 10.1 mmol) in tetrahydrofuran (30 mL) at 0° C. was added a 1.0 M solution of diisobutylaluminum hydride (1.0 M in hexane, 60.5 mL, 60.5 mmol). The reaction mixture was allowed to stir for 1 h and then water (3 mL) was added. The resulting mixture was filtered through a pad of Celite, washed with methanol (3×50 mL), and concentrated under reduced pressure to afford the title compound. MS: m/z=278.1 [M+Na].

Step B: 4-[(1R,3R)-3-Formyl-2,2-dimethylcyclopropyl]benzenesulfonamide

To a solution of 4-[(1R,3R)-3-(hydroxymethyl)-2,2-dimethylcyclopropyl]benzenesulfonamide (100 mg, 0.39 mmol) in dichloromethane (3.9 mL) at 0° C. was added Dess-Martin periodinane (199 mg, 0.47 mmol) and the reaction mixture allowed to stir for 30 min. The reaction mixture was allowed to warm to ambient temperature and allowed to stir for 6 h. The reaction mixture was quenched with saturated aqueous sodium bicarbonate (2 mL) and saturated aqueous sodium thiosulfate (2 mL). The phases were separated and the aqueous phase was extracted with dichloromethane (2×5 mL). The combined organic extracts were dried (magnesium sulfate), filtered, and concentrated under reduced pressure. The residue was purified by silica gel chromatography, eluting with a gradient of ethyl acetate:hexanes—0:100 to 50:50, to afford the title compound. MS: m/z=254.1 [M+H].

Step C: 4-[(1R,3S)-3-Ethynyl-2,2-dimethylcyclopropyl]benzenesulfonamide

Dimethyl (1-diazo-2-oxopropyl)phosphonate (53.7 mg, 0.279 mmol) were added to a solution of 4-[(1R,3R)-3-formyl-2,2-dimethylcyclopropyl]benzenesulfonamide and potassium carbonate (64.4 mg, 0.466 mmol) in methanol (0.35 mL) and the solution was allowed to stir for 18 h at ambient temperature. The reaction mixture was then diluted with diethyl ether (4 mL), washed with saturated aqueous sodium bicarbonate (4 mL), dried (magnesium sulfate), filtered, and concentrated under reduced pressure. The residue was purified by silica gel chromatography, eluting with a gradient of ethyl acetate:hexanes—0:100 to 50:50, to afford the title compound. MS: m/z=250.1 [M+H].

Intermediate 14

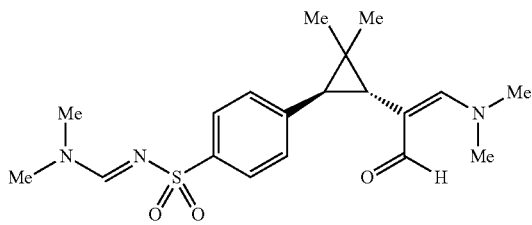 [SMILES: CN(C)/C=C(\C=O)[C@@H]1[C@@H](c2ccc(S(=O)(=O)/N=C/N(C)C)cc2)C1(C)C]

N-[(Dimethylamino)methylidene]-4-{(1R,3R)-3-[1-(dimethylamino)-3-oxoprop-1-en-2-yl]-2,2-dimethylcyclopropyl}benzenesulfonamide To a solution of (methoxymethyl)triphenylphophonium chloride (5.68 g, 16.6 mmol) in tetrahydrofuran (25 mL) at −78° C. was added n-butyllithium (2.5 M in tetrahydrofuran, 6.63 mL, 16.6 mmol). The reaction mixture was warmed to 0° C. and allowed to stir for 30 min and then cooled to −78° C. 4-((1R,3R)-3-Formyl-2,2-dimethylcyclopropyl)benzenesulfonamide (described in Intermediate 13) (1.40 g, 5.53 mmol) was added to this solution and the reaction mixture warmed to ambient temperature and allowed to stir for 30 min. The reaction mixture was diluted with water (50 mL) and ethyl acetate (50 mL). The phases were separated and the aqueous phase extracted with ethyl acetate (2×50 mL). The combined organic extracts were washed with saturated aqueous sodium chloride (25 mL), dried (magnesium sulfate), filtered, and concentrated under reduced pressure. The residue was purified by silica gel chromatography, eluting with ethyl acetate:hexanes—25:75. The product-containing fractions were combined and concentrated under reduced pressure. The resulting solid was added to a flask containing a solution [prepared by treating a solution of N,N-dimethylformamide (0.550 mL, 7.11 mmol) in chloroform (5 mL) at 0° C. with phosphorous oxychloride (0.663 mL, 7.11 mmol) followed by warming the resultant mixture to 40° C. then cooling it back to 0° C.] at 0° C. and the reaction mixture warmed to 55° C. and allowed to stir for 30 min. The reaction mixture was cooled to 0° C. and potassium carbonate (1.97 g, 14.2 mmol) in water (10 mL) was added. The reaction mixture was diluted with water (20 mL) and dichloromethane (30 mL). The phases were separated and the aqueous phase extracted with dichloromethane (2×30 mL). The combined organic extracts were washed with saturated aqueous sodium chloride (25 mL), dried (magnesium sulfate), filtered, and concentrated under reduced pressure to afford the title compound. MS: m/z=378.2 [M+H].

Intermediate 15

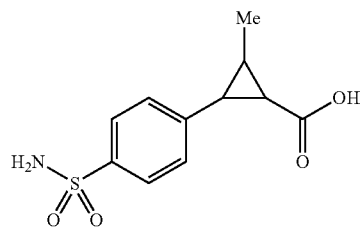 [SMILES: CC1C(C(=O)O)C1c1ccc(S(N)(=O)=O)cc1]

2-Methyl-3-(4-sulfamoylphenyl)cyclopropanecarboxylic acid, diastereomer 4

Step A: Methyl 2-methyl-3-(4-sulfamoylphenyl)cyclopropanecarboxylate, diastereomer 4

To a solution of 2-methyl-3-phenylcyclopropanecaboxylic acid (2.64 g, 15.0 mmol) in dichloromethane (30 mL) and methanol (7.5 mL) was slowly added a solution of TMS-diazomethane in ether (2 M, 9.00 mL, 18.0 mmol). After gas evolution ceased, the reaction mixture was allowed to stir for 10 minutes, concentrated under reduced pressure, and the resulting residue purified by silica gel chromatography, eluting with a gradient of ethyl acetate:hexanes—0:100 to 20:80. The residue was added dropwise to chlorosulfonic acid (12.0 mL, 179 mmol) at 0° C. and the reaction mixture allowed to stir for 30 min. The reaction mixture was allowed to warm to ambient temperature and allowed to stir for 30 min. The reaction mixture was then poured over ice, diluted with water (15 mL), stirred vigorously, and the aqueous phase decanted. The remaining residue was dissolved in 1,4-dioxane (12 mL), ammonium hydroxide was added (6.00 mL, 43.1 mmol), and the reaction mixture allowed to stir for 30 min. The reaction mixture was filtered (washing with ethyl acetate) and the filtrate concentrated under reduced pressure. The residue was purified by silica gel chromatography, eluting with a gradient of ethyl acetate:hexanes—5:95 to 50:50 and then chirally resolved by SFC, first utilizing an AS-H column, eluting with isopropanol:carbon dioxide:diethylamine—12:88:0.1 and then utilizing an OD-H column, eluting with methanol:carbon dioxide:diethylamine—30:70:0.1. The fourth major peak to elute, diastereomer 4, (as determined by analytical SFC, utilizing an AS-H column eluting with isopropanol:carbon dioxide:diethylamine—20:80:0.1) was the title compound. MS: m/z=270.2 [M+H].

Step B: 2-Methyl-3-(4-sulfamoylphenyl)cyclopropanecarboxylic acid, diastereomer 4

To a solution of methyl 2-methyl-3-(4-sulfamoylphenyl)cyclopropanecaboxlate, diastereomer 4, (121 mg, 0.449 mmol) in tetrahydrofuran (2.80 mL) was added aqueous sodium hydroxide (1 M, 1.40 mL, 1.40 mmol) and the reaction mixture allowed to stir at ambient temperature for 4 h. The reaction mixture was then acidified to pH 1 with aqueous HCl (1 N, 3.0 mL, 3.0 mmol), extracted with ethyl acetate (2×10 mL), and the combined organic extracts washed with saturated aqueous sodium chloride and concentrated under reduced pressure to afford the title compound. MS: m/z=256.1 [M+H].

Intermediate 16

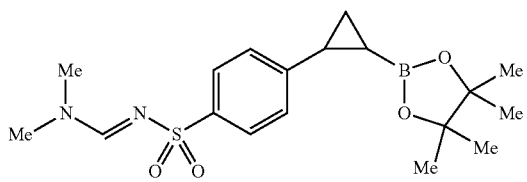 [SMILES: CN(C)/C=N/S(=O)(=O)c1ccc(C2CC2B2OC(C)(C)C(C)(C)O2)cc1]

N-[(Dimethylamino)methylidene]-4-[trans-2-(4,4,5,5-tetramethyl-1,3,2-dioxaborolan-2-yl)cyclopropyl]benzenesulfonamide Step A: 4-Bromo-N-[(dimethylamino)methylidene]benzenesulfonamide A stirred solution of 4-bromobenzenesulfonamide (5.00 g, 21.2 mmol) in N,N-dimethylformamide dimethyl acetal (113 mL) was heated at 110° C. for 18 h, then allowed to cool to ambient temperature. The resulting mixture was concentrated under reduced pressure to give the title compound in sufficient purity for use in the next step. MS: m/z=291.0 [M+H].

Step B: N-[(Dimethylamino)methylidene]-4-[(E)-2-(4,4,5,5-tetramethyl-1,3,2-dioxaborolan-2-yl)ethenyl]benzenesulfonamide To a stirred solution of 4-bromo-N-[(dimethylamino)methylidene]benzenesulfonamide (6.10 g, 21.0 mmol) in toluene (70 mL) at ambient temperature were added vinylboronic acid pinacol ester (7.11 mL, 41.9 mmol), bis(tri-tert-butylphosphine)palladium(0) (535 mg, 1.05 mmol), and triethylamine (6.42 mL, 46.1 mmol). The resulting mixture was heated at 80° C. for 18 h, then poured into water (100 mL) and extracted with ethyl acetate (2×200 mL). The combined organic extracts were washed with saturated aqueous sodium chloride (100 mL), dried (sodium sulfate), filtered, and concentrated under reduced pressure. The residue was purified by silica gel chromatography, eluting with a gradient of ethyl acetate:hexanes—0:100 to 30:70 to afford the title compound. MS: m/z=365.3 [M+H].

Step C: N-[(Dimethylamino)methylidene]-4-[trans-2-(445,55-tetramethyl-1,32-dioxaborolan-2-yl)-3-(trimethylsilyl)cyclopropyl]benzenesulfonamide To a stirred solution of N-[(dimethylamino)methylidene]-4-[(E)-2-(4,4,5,5-tetramethyl-1,3,2-dioxaborolan-2-yl)ethenyl]benzenesulfonamide (6.00 g, 16.5 mmol) in tetrahydrofuran (82 mL) at ambient temperature were added palladium(II) acetate (924 mg, 4.12 mmol) and (trimethylsilyl)diazomethane (2.0 M in diethyl ether, 24.7 mL, 49.4 mmol), sequentially. The reaction mixture was allowed to stir at ambient temperature for 18 h, then acetic acid (12 mL) was added and the resulting mixture was poured into water (200 mL) and extracted with dichloromethane (3×200 mL). The combined organic extracts were dried (sodium sulfate), filtered, and concentrated under reduced pressure. The residue was purified by silica gel chromatography, eluting with a gradient of ethyl acetate:hexanes—10:90 to 60:40 to afford the title compound. MS: m/z=451.3 [M+H].

Step D: N-[(Dimethylamino)methylidene]-4-[trans-2-(4,4,5,5-tetramethyl-1,3,2-dioxaborolan-2-yl)cyclopropyl]benzenesulfonamide To a stirred solution of N-[(dimethylamino)methylidene]-4-[trans-2-(4,4,5,5-tetramethyl-1,3,2-dioxaborolan-2-yl)-3-(trimethylsilyl)cyclopropyl]benzenesulfonamide (1.25 g, 2.77 mmol) in dichloromethane (22 mL) at 0° C. was added trifluoromethanesulfonic acid (0.801 mL, 9.02 mmol). The reaction mixture was allowed to warm to ambient temperature and allowed to stir for 2 h, then poured into saturated aqueous sodium bicarbonate (50 mL), and extracted with dichloromethane (2×100 mL). The combined organic extracts were dried (sodium sulfate), filtered, and concentrated under reduced pressure. The residue was purified by silica gel chromatography, eluting with a gradient of methanol:dichloromethane—0:100 to 4:96 to afford the title compound. MS: m/z=379.3 [M+H].

Intermediate 17

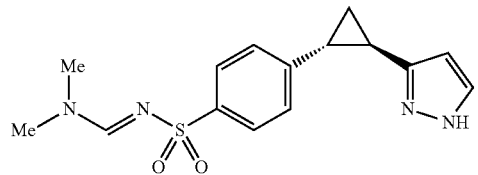 [SMILES: CN(C)/C=N/S(=O)(=O)c1ccc([C@@H]2C[C@H]2c2cc[nH]n2)cc1]

N-[(Dimethylamino)methylidene]-4-[(1R,2R)-2-(1H-pyrazol-3-yl)cyclopropyl]benzenesulfonamide Step A: (1R,2R)—N-Methoxy-N-methyl-2-(4-sulfamoylphenyl)cyclopropanecarboxamide To a suspension of (1R,2R)-2-(4-sulfamoylphenyl)cyclopropanecarboxylic acid (Intermediate 2) (1.9 g, 7.9 mmol) in dichloromethane (16 mL) were added triethylamine (3.29 mL, 23.6 mmol) and HATU (3.59 g, 9.45 mmol) sequentially. The reaction mixture was allowed to stir for 5 min and then N,O-dimethylhydroxylamine hydrochloride (0.922 g, 9.45 mmol) was added. The reaction mixture was allowed to stir for 18 h and then diluted with ethyl acetate and washed with saturated aqueous sodium bicarbonate (2×20 mL). The organic phase was concentrated under reduced pressure and the residue suspended in dichloromethane and filtered. The resulting solid was washed with water to afford the title compound. MS: m/z=285.1 [M+H].

Step B: 4-[(1R,2R)-2-Acetylcyclopropyl]benzenesulfonamide

To a solution of (1R,2R)—N-methoxy-N-methyl-2-(4-sulfamoylphenyl)cyclopropanecarboxamide in tetrahydrofuran (28 mL) at −15° C. was added a solution of methylmagnesium chloride (3.0 M, 22.7 mL, 67.9 mmol) in tetrahydrofuran. The reaction mixture was allowed to warm to ambient temperature and allowed to stir for 18 h. The reaction mixture was cooled to 0° C. and saturated aqueous ammonium chloride (50 mL) added slowly. The resulting mixture was extracted with ethyl acetate (3×40 mL) and the combined organic extracts washed with saturated aqueous sodium chloride (2 mL), dried (sodium sulfate), and concentrated under reduced pressure. The residue was purified by silica gel chromatography, eluting with a gradient of ethyl acetate:ethanol:hexanes—0:0:100 to 60:20:20 to afford the title compound. MS: m/z=240.1 [M+H].

Step C: N-[(Dimethylamino)methylidene]-4-{(1R, 2R)-2-[3-(dimethylamino)prop-2-enoyl]cyclopropyl}benzenesulfonamide 4-[(1R,2R)-2-acetylcyclopropyl]benzenesulfonamide (0.825 g, 3.45 mmol) was suspended in N,N-dimethylformamide dimethylacetal (9.23 ml, 69.0 mmol) in a sealable vial. The vial was sealed and the reaction mixture warmed to 110° C. and allowed to stir for 18 h. The reaction mixture was cooled to ambient temperature and diluted with dichloromethane. The organic phase was washed with water (3×10 mL), dried (sodium sulfate), and concentrated under reduced pressure to afford the title compound. MS: m/z=350.2 [M+H].

Step D: 4-[(1R,2R)-2-(1H-Pyrazol-3-yl)cyclopropyl]benzenesulfonamide

To a solution of N-[(dimethylamino)methylidene]-4-{(1R,2R)-2-[3-(dimethylamino)prop-2-enoyl]cyclopropyl}benzenesulfonamide (1.21 g, 3.45 mmol) in methanol (17 mL) at ambient temperature was added hydrazine (2.17 mL, 69.0 mmol) and the reaction mixture allowed to stir for 18 h. The reaction mixture was concentrated under reduced pressure. The resulting residue was taken up in ethyl acetate (30 mL) and the organic phase washed with saturated aqueous sodium bicarbonate (2×20 mL), dried (sodium sulfate), and concentrated under reduced pressure to afford the title compound. MS: m/z=264.1 [M+H].

Step E: N-[(Dimethylamino)methylidene]-4-[(1R, 2R)-2-(1H-pyrazol-3-yl)cyclopropyl]benzenesulfonamide 4-[(1R,2R)-2-(1H-pyrazol-3-yl)cyclopropyl]benzenesulfonamide (749 mg, 2.84 mmol) was suspended in DMF-DMA (7.62 ml, 56.9 mmol) in a sealable vial. The vial was sealed and the reaction mixture warmed to 110° C. and allowed to stir for 18 h. The reaction mixture was cooled to ambient temperature and diluted with ethyl acetate. The organic phase was washed with water (3×50 mL), dried (sodium sulfate), and concentrated under reduced pressure. The residue was purified by silica gel chromatography, eluting with a gradient of ethyl acetate:ethanol:hexanes—0:0:100 to 67:33:0 to afford the title compound. MS: m/z=319.2 [M+H].

Intermediate 18

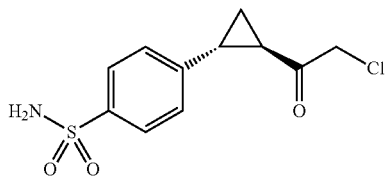 [SMILES: NS(=O)(=O)c1ccc([C@@H]2C[C@H]2C(=O)CCl)cc1]

4-[(1R,2R)-2-(2-Chloroacetyl)cyclopropyl]benzenesulfonamide

Step A: Methyl (1R,2R)-2-(4-sulfamoylphenyl)cyclopropanecarboxylate

To a solution of (1R,2R)-2-(4-sulfamoylphenyl)cyclopropanecarboxylic acid (Intermediate 2) (2.0 g, 8.29 mmol) in methanol (20 mL) was added concentrated sulfuric acid (0.044 mL, 0.83 mmol) and the reaction mixture warmed to 60° C. and allowed to stir for 14 h. The reaction mixture was concentrated under reduced pressure and dichloromethane (20 mL) was added. The mixture was washed with saturated aqueous sodium bicarbonate (20 mL), dried (sodium sulfate), and concentrated under reduced pressure to afford the title compound. MS: m/z=255.8 [M+H].

Step B: 4-[(1R,2R)-2-(2-Chloroacetyl)cyclopropyl]benzenesulfonamide

To a solution of methyl (1R,2R)-2-(4-sulfamoylphenyl)cyclopropanecarboxylate (600 mg, 2.35 mmol) in tetrahydrofuran (8 mL) at −70° C. were added chloroiodomethane (2.07 g, 11.8 mmol) and a solution of lithium diisopropylamide (2.0 M in tetrahydrofuran/heptane/ethylbenzene, 8.23 mL, 16.5 mmol), sequentially, and the reaction mixture allowed to stir for 1 h. Acetic acid (1.5 mL) was added and the reaction mixture was allowed to warm to ambient temperature and stir for 1 h. The reaction mixture was poured into water (5 mL) and the aqueous phase was extracted with ethyl acetate (2×5 mL). The combined organic extracts were dried (sodium sulfate) and concentrated under reduced pressure. The residue was purified by preparative silica gel thin layer chromatography, eluting with ethyl acetate:petroleum ether—33:67 to afford the title compound. $^1$H NMR (400 MHz, CDCl$_3$): δ 7.86 (d, J=8.4 Hz, 2H); 7.24 (d, J=8.4 Hz, 2H); 4.83 (s, 1H); 4.82 (s, 1H); 3.74 (s, 2H); 2.59 (m, 1H); 1.98 (m, 1H); 1.71 (m, 1H); 1.38 (m, 1H).

Intermediate 19

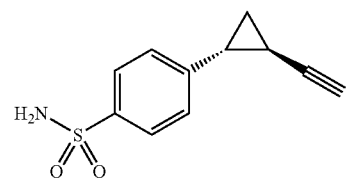

4-[(1R,2R)-2-Ethynylcyclopropyl]benzenesulfonamide

Step A: 4-[(1R,2R)-2-(Hydroxymethyl)cyclopropyl]benzenesulfonamide

To a solution of (1R,2R)-2-(4-sulfamoylphenyl)cyclopropanecarboxylic acid (Intermediate 2) (3.0 g, 12 mmol) in tetrahydrofuran (50 mL) at 0° C. was added a solution of borane (1.0 M in tetrahydrofuran, 24.9 mL, 24.9 mmol). The reaction mixture was allowed to warm to ambient temperature and stir for 3 h. The reaction mixture was poured into water (50 mL) and the mixture extracted with ethyl acetate (3×50 mL). The combined organic extracts were dried (sodium sulfate) and concentrated under reduced pressure to afford the title compound. ¹H NMR (400 MHz, CD₃OD): δ 7.76 (d, J=8.0 Hz, 2H); 7.24 (d, J=8.0 Hz, 2 H); 3.62 (dd, J=11.2, 6.0 Hz, 1H); 3.49 (dd, J=11.2, 6.8 Hz, 1H); 1.92 (m, 1H); 1.45 (m, 1 H); 1.02 (m, 2H).

Step B:
4-[(1R,2R)-2-Ethynylcyclopropyl]benzenesulfonamide

To a solution of 4-[(1R,2R)-2-(hydroxymethyl)cyclopropyl]benzenesulfonamide (1.00 g, 4.40 mmol) in tetrahydrofuran (20 mL) was added pyridinium chlorochromate (1.90 g, 8.80 mmol) at 0° C. The reaction mixture was allowed to warm to ambient temperature and stir for 5 h. The reaction mixture was diluted with water (50 mL) and ethyl acetate (50 mL). The organic layer was separated, dried (sodium sulfate), and concentrated under reduced pressure. The residue was taken up in methanol (30 mL) and treated with potassium carbonate (2.76 g, 20.0 mmol) and dimethyl (1-diazo-2-oxopropyl)phosphonate (921 mg, 4.79 mmol), sequentially. The reaction mixture was allowed to stir for 1 h, then warmed to 60° C. and allowed to stir for 2 h. The reaction mixture was concentrated under reduced pressure, water (30 mL) was added, and the mixture was extracted with ethyl acetate (3×30 mL). The combined organic extracts were dried (sodium sulfate) and concentrated under reduced pressure. The residue was purified by silica gel chromatography, eluting with ethyl acetate:petroleum ether—50:50 to afford the title compound. ¹H NMR (400 MHz, CD₃OD): δ 7.79 (d, J=8.0 Hz, 2H); 7.26 (d, J=8.0 Hz, 2 H); 2.30 (m, 1H); 2.25 (s, 1H); 1.61 (m, 1H); 1.34 (m, 2H).

Intermediate 20

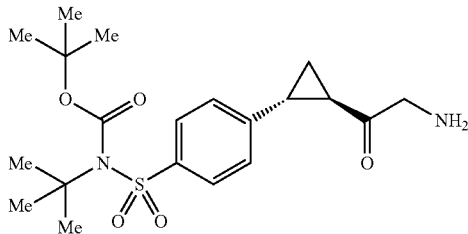 [SMILES: CC(C)(C)OC(=O)N(C(C)(C)C)S(=O)(=O)c1ccc([C@@H]2C[C@H]2C(=O)CN)cc1]

tert-Butyl tert-butyl[(4-{(1R,2R)-2-[(R)-glycyl]cyclopropyl}phenyl)sulfonyl]carbamate Step A: Methyl (1R,2R)-2-{4-[(tert-butoxycarbonyl)(tert-butyl)sulfamoyl]phenyl}cyclopropanecarboxylate To a solution of methyl (1R,2R)-2-(4-sulfamoylphenyl)cyclopropanecarboxylate (described in Intermediate 18) (1.1 g, 4.3 mmol) in tetrahydrofuran (10 mL) at ambient temperature were added 4-dimethylaminopyridine (0.158 g, 1.29 mmol) and di-tert-butyl dicarbonate (10.0 mL, 43.1 mmol). The reaction mixture was warmed to 70° C. and allowed to stir for 10 h. The reaction mixture was concentrated under reduced pressure and the resulting residue was purified by silica gel chromatography, eluting with ethyl acetate:petroleum ether—25:75 to afford the title compound. ¹H NMR (400 MHz, CDCl₃): δ 7.92 (d, J=8.4 Hz, 2H); 7.16 (d, J=8.4 Hz, 2H); 3.71 (s, 3H); 2.55 (m, 1H); 1.94 (m, 1H); 1.55 (s, 1H); 1.49 (s, 9 H); 1.43 (s, 9H); 1.35 (m, 1H).

Step B: tert-Butyl tert-butyl({4-[(1R,2R)-2-(chloroacetyl)cyclopropyl]phenyl}sulfonyl)carbamate To a solution of methyl (1R,2R)-2-{4-[(tert-butoxycarbonyl)(tert-butyl)sulfamoyl]phenyl}cyclopropanecarboxylate (200 mg, 0.49 mmol) in tetrahydrofuran (5 mL) at −78° C. were added chloroiodomethane (300 mg, 1.70 mmol) and lithium diisopropylamide (2.0 M in tetrahydrofuran/heptane/ethylbenzene, 0.97 mL, 1.9 mmol) sequentially. The reaction mixture was allowed to stir for 20 min and then warmed to −40° C. and allowed to stir for 10 min. To the reaction mixture was added an aqueous solution of HCl (1 M, 10 mL, 10 mmol). The reaction mixture was concentrated under reduced pressure and the resulting residue purified by silica gel chromatography, eluting with ethyl acetate:petroleum ether—25:75 to afford the title compound. ¹H NMR (400 MHz, CDCl₃): δ 7.89 (d, J=8.4 Hz, 2 H); 7.14 (d, J=8.4 Hz, 2H); 4.19 (s, 2H); 2.59 (m, 1H); 2.44 (m, 1H); 1.76 (m, 1H); 1.45 (s, 9H); 1.39 (s, 9H); 1.20 (m, 1H).

Step C: tert-Butyl tert-butyl[(4-{(1R,2R)-2-[(R)-glycyl]cyclopropyl}phenyl)sulfonyl]carbamate To a solution of tert-butyl tert-butyl({4-[(1R,2R)-2-(chloroacetyl)cyclopropyl]phenyl}sulfonyl)carbamate (1.2 g, 2.8 mmol) in tetrahydrofuran (10 mL) and water (0.5 mL) at ambient temperature was added sodium azide (0.36 g, 5.6 mmol). The reaction mixture was allowed to stir for 10 h and then diluted with water (50 mL) and extracted with ethyl acetate (3×50 mL). The combined organic extracts were washed with saturated aqueous sodium chloride (25 mL), dried (sodium sulfate), and concentrated under reduced pressure. The residue was purified by silica gel chromatography, eluting with ethyl acetate:petroleum ether—20:80. The product-containing fractions were combined and concentrated under reduced pressure. The residue was taken up in tetrahydrofuran (5 mL) and water (0.5 mL) at ambient temperature and treated with triphenylphosphine (264 mg, 1.01 mmol) and p-toluenesulfonic acid (192 mg, 1.01 mmol) sequentially. The reaction mixture was allowed to stir for 1 h. The reaction mixture was concentrated under reduced pressure to afford the title compound. MS: m/z=821.4 [2M+H].

Intermediate 21

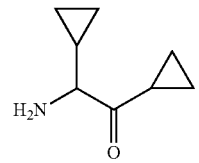

2-Amino-1,2-dicyclopropylethanone

Step A: 2-Bromo-1, 2-dicyclopropylethanone

To a solution of 1,2-dicyclopropylethanone (400 mg, 3.22 mmol) in methanol (3 mL) at 0° C. was added bromine (0.199 mL, 3.87 mmol) dropwise. The mixture was warmed to ambient temperature and allowed to stir for 1 h. Saturated aqueous sodium sulfite (10 mL) was added and the resulting mixture extracted with ethyl acetate (30 mL). The organic layer was separated, dried (magnesium sulfate), and concentrated under reduced pressure to afford the title compound in sufficient purity for use in the next step. $^1$H NMR (400 MHz, CDCl$_3$): δ 3.73 (d, J=10.4 Hz, 1H), 2.24 (m, 1H), 1.55 (m, 1H), 1.13 (m, 2H), 1.02 (m, 2H), 0.86 (m, 2H), 0.48 (m, 2H).

Step B:
N-(1,2-Dicyclopropyl-2-oxoethyl)formamide

To a stirred solution of 2-bromo-1,2-dicyclopropylethan-1-one (50 mg, 0.25 mmol) in acetonitrile (2 mL) at ambient temperature were added sodium N-formylformamide (47 mg, 0.49 mmol) and potassium carbonate (68 mg, 0.49 mmol). The reaction mixture was warmed to 80° C. and allowed to stir for 2 h. The reaction mixture was diluted with water (5 mL) and dichloromethane (10 mL). The organic layer was separated, dried (magnesium sulfate) and concentrated under reduced pressure to afford the title compound in sufficient purity for use in the next step. MS: m/z=168.0 [M+H].

Step C: 2-Amino-1, 2-dicyclopropylethanone

To a stirred solution of N-(1,2-dicyclopropyl-2-oxoethyl)formamide (48 mg, 0.29 mmol) in methanol (3 mL) at ambient temperature was added an aqueous solution of HCl (12 N, 0.3 mL, 3.60 mmol). The reaction mixture was warmed to 30° C. and allowed to stir for 12 h. The reaction mixture was concentrated under reduced pressure to afford the title compound. MS: m/z=140.0 [M+H].

Intermediate 22

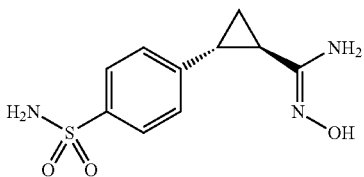 [SMILES: N/C(=N\O)[C@@H]1C[C@H]1c1ccc(S(N)(=O)=O)cc1]

(1R,2R)—N'-Hydroxy-2-(4-sulfamoylphenyl)cyclopropanecarboximidamide

Step A:
4-[(1R,2R)-2-Cyanocyclopropyl]benzenesulfonamide (1R,2R)-2-(4-Sulfamoylphenyl)cyclopropanecarboxamide (described in Intermediate 12) (1.72 g, 7.16 mmol) was dissolved in acetonitrile (36 mL) at ambient temperature. Phosphorous oxychloride (1.33 mL, 14.3 mmol) was added, the reaction mixture warmed to 80° C. and allowed to stir for 30 min. The reaction mixture was slowly added to cold, saturated aqueous sodium bicarbonate (50 mL) and the aqueous phase extracted with ethyl acetate (3×50 mL). The combined organic phases were washed with saturated aqueous sodium chloride (15 mL), dried (magnesium sulfate), filtered, and concentrated under reduced pressure. The residue was purified by silica gel chromatography, eluting with a gradient of ethyl acetate:hexanes—0:100 to 60:40 to afford the title compound. MS: m/z=223.1 [M+H].

Step B: (1R,2R)—N'-Hydroxy-2-(4-sulfamoylphenyl)cyclopropanecarboximidamide

To a stirred solution of 4-[(1R,2R)-2-cyanocyclopropyl]benzenesulfonamide (960 mg, 4.32 mmol) in ethanol (22 mL) was added hydroxylamine (2.65 mL, 43.2 mmol). The reaction mixture was warmed to 60° C. and allowed to stir for 1 h. The reaction mixture was allowed to cool and was concentrated under reduced pressure. The residue was co-evaporated with methanol (2×) and acetonitrile (4×) to afford the title compound in sufficient purity for use in the next step. MS: m/z=256.1 [M+H].

Intermediate 23

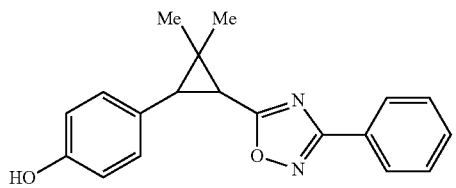 [SMILES: CC1(C)C(c2ccc(O)cc2)C1c1nc(-c2ccccc2)no1]

4-[trans-2,2-Dimethyl-3-(3-phenyl-1,2,4-oxadiazol-5-yl)cyclopropyl]phenol

Step A: 5-[trans-3-(4-Bromophenyl)-2,2-dimethylcyclopropyl]-3-phenyl-1,2,4-oxadiazole To a solution of isopropyltriphenylphosphonium iodide (15.3 g, 35.3 mmol) in tetrahydrofuran (30 mL) at −50° C. was added a solution of n-butyllithium in hexane (2.5 M, 12.9 mL, 32.3 mmol). The reaction mixture was allowed to stir for 30 min and then warmed to ambient temperature and allowed to stir for 2 h. The reaction mixture was cooled to −50° C. and ethyl (2E)-3-(4-bromophenyl)prop-2-enoate (3.00 g, 11.8 mmol) was added. The reaction mixture was warmed to ambient temperature and allowed to stir for 12 h. Water (50 mL) was added and the aqueous layer was extracted with ethyl acetate (2×20 mL). The combined organic extracts were dried (sodium sulfate), filtered, and concentrated under reduced pressure. The residue was dissolved in ethanol (20 mL) and water (4 mL) and lithium hydroxide (1.21 g, 50.5 mmol) was added. The reaction mixture was warmed to 50° C. and allowed to stir for 4 h. The reaction mixture was then extracted with ethyl acetate (2×5 mL). The aqueous layer was adjusted to pH 1 by the addition of aqueous HCl (3 M, ca 20 mL) and extracted with ethyl acetate (2×5 mL). The combined organic extracts were dried (sodium sulfate), filtered, and concentrated under reduced pressure. The residue was dissolved in N,N-dimethylformamide (5 mL) and HATU (2.68 g, 7.06 mmol), diisopropylethylamine (3.70 mL, 21.2 mmol), and N-hydroxybenzenecarboximidamide (1.92 g, 14.1 mmol) were added. The reaction mixture was allowed to stir at ambient temperature for 30 min and then warmed to 100° C. and allowed to stir for 5 h. The reaction mixture was diluted with water (50 mL) and the aqueous layer extracted with ethyl acetate (2×10 mL). The combined organic extracts were dried (sodium sulfate), filtered, and concentrated under reduced pressure. The filtrate was concentrated under reduced pressure. The residue was purified by silica gel chromatography, eluting with ethyl acetate:petroleum ether—9:91 to afford the title compound. MS: m/z=371.5 [M+H].

Step B: 5-{trans-2,2-Dimethyl-3-[4-(4,4,5,5-tetramethyl-1,3,2-dioxaborolan-2-yl)phenyl]cyclopropyl}-3-phenyl-1, 2,4-oxadiazole To a solution of 5-[trans-3-(4-bromophenyl)-2,2-dimethylcyclopropyl]-3-phenyl-1,2,4-oxadiazole (50 mg, 0.14 mmol) in 1,4-dioxane (2 mL) at ambient temperature were added 4,4,4',4',5,5,5',5'-octamethyl-2,2'-bi-1,3,2-dioxaborolane (51.6 mg, 0.203 mmol), potassium acetate (39.9 mg, 0.406 mmol), and PdCl$_2$(dppf) (9.9 mg, 0.014 mmol). The reaction mixture was warmed to 90° C. and allowed to stir for 12 h. The reaction mixture was filtered and concentrated under reduced pressure. The residue was purified by silica gel chromatography, eluting with ethyl acetate:petroleum ether—9:91 to afford the title compound. $^1$H NMR (400 MHz, CDCl$_3$): δ 8.08 (dd, J=3.0, 4.6 Hz, 2H), 7.77 (d, J=7.6 Hz, 2H), 7.45-7.48 (m, 3H), 7.25 (d, J=8.0 Hz, 2H), 3.05 (d, J=6.0 Hz, 1H), 2.60 (d, J=6.0 Hz, 1H), 1.41 (s, 3H), 1.34 (s, 12H), 1.03 (s, 3H).

Step C: 4-[trans-2,2-Dimethyl-3-(3-phenyl-1,2,4-oxadiazol-5-yl)cyclopropyl]phenol To a solution of 5-{trans-2,2-dimethyl-3-[4-(4,4,5,5-tetramethyl-1,3,2-dioxaborolan-2-yl)phenyl]cyclopropyl}-3-phenyl-1,2,4-oxadiazole (45 mg, 0.11 mmol) in tetrahydrofuran (5 mL) at 0° C. was added sodium hydroxide (25.9 mg, 0.649 mmol) followed by dropwise addition of an aqueous solution of hydrogen peroxide (30%, 0.066 mL, 0.65 mmol). The reaction mixture was allowed to stir for 1 h. A saturated aqueous solution of sodium sulfite (10 mL) was added and the mixture extracted with ethyl acetate (2×5 mL). The combined organic extracts were dried (sodium sulfate), filtered, and concentrated under reduced pressure to afford the title compound. MS: m/z=307.1 [M+H].

Intermediate 24

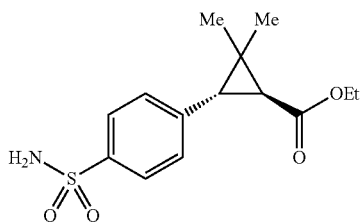 [SMILES: CCOC(=O)[C@H]1[C@H](c2ccc(S(N)(=O)=O)cc2)C1(C)C]

Ethyl (1S,3S)-2,2-dimethyl-3-(4-sulfamoylphenyl)cyclopropanecarboxylate

Essentially following the procedures described in Intermediate 4, but using (1S,3S)-2,2-dimethyl-3-phenylcyclopropanecarboxylic acid in place of (1R,3R)-2,2-dimethyl-3-phenylcyclopropanecarboxylic acid, the title compound was obtained. MS: m/z=298.0 [M+H].

Intermediate 25

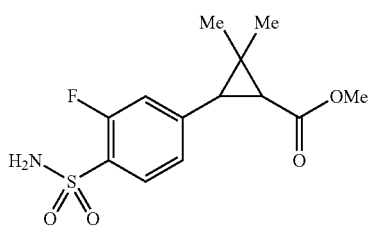 [SMILES: COC(=O)C1C(c2ccc(S(N)(=O)=O)c(F)c2)C1(C)C]

Methyl trans-3-(2-fluoro-4-sulfamoylphenyl)-2,2-dimethylcyclopropanecarboxylate

Step A: Methyl (2E)-3-(4-bromo-3-fluorophenyl)prop-2-enoate

To a stirred solution of 4-bromo-3-fluorobenzaldehyde (1.00 g, 4.93 mmol) in toluene (20 mL) was added methyl (2E)-(tritylphosphanylidene)ethanoate (2.47 g, 7.39 mmol). The reaction mixture was warmed to 80° C. and allowed to stir for 16 h. The reaction mixture was concentrated under reduced pressure and water (50 mL) was added. The aqueous layer was extracted with ethyl acetate (3×80 mL). The combined organic extracts were washed with saturated aqueous sodium chloride (150 mL), dried (sodium sulfate), filtered, and concentrated under reduced pressure. The residue was purified by silica gel chromatography, eluting with a gradient of ethyl acetate:petroleum ether—0:100 to 10:90, to afford the title compound. $^1$H NMR (400 MHz, CDCl$_3$): δ 7.53-7.59 (m, 2H), 7.24 (d, J=9.2 Hz, 1H), 7.16 (d, J=8.4 Hz, 1 H), 6.41 (d, J=16.0 Hz, 1H), 3.79 (s, 3H).

Step B: N-({[trans-3-(3-Fluoro-4-sulfamoylphenyl)-2,2-dimethylcyclopropyl]carbonyl}oxy)benzenecarboximidamide To a stirred suspension of isopropyltriphenylphosphonium iodide (3.50 g, 8.11 mmol) in tetrahydrofuran (20 mL) at −50° C. was added a solution of n-butyllithium in hexane (2.5 M, 2.97 mL, 7.43 mmol) dropwise. The reaction mixture was allowed to stir for 30 min then warmed to 15° C. and allowed to stir for 4 h. The reaction mixture was then cooled to −50° C. and methyl (2E)-3-(4-bromo-3-fluorophenyl)prop-2-enoate (700 mg, 2.70 mmol) was added. The reaction mixture was warmed to 15° C. and allowed to stir for 2 h. The reaction mixture was diluted with diethyl ether (50 mL), an aqueous solution of hydrogen peroxide (10%, 30 mL) was added, and the layers separated. The organic layer was washed with water (50 mL), saturated aqueous sodium sulfite solution (50 mL), and saturated aqueous sodium chloride (50 mL), dried (sodium sulfate), filtered, and concentrated under reduced pressure. The residue was purified by silica gel chromatography, eluting with a gradient of ethyl acetate:petroleum ether—0:100 to 5:95, to give the title compound. $^1$H NMR (400 MHz, CDCl$_3$): δ 7.42-7.48 (m, 1H), 6.94 (dd, J=9.54, 1.76 Hz, 1H), 6.85 (d, J=8.28 Hz, 1H), 3.74 (s, 3H), 2.64 (d, J=5.77 Hz, 1H), 1.93 (d, J=5.77 Hz, 1H), 1.37 (s, 3H), 0.94 (s, 3H).

Step C: Methyl trans-3-[4-(benzylsulfanyl)-3-fluorophenyl]-2,2-dimethylcyclopropanecarboxylate To a stirred solution of N-({[trans-3-(3-fluoro-4-sulfamoylphenyl)-2,2-dimethylcyclopropyl]carbonyl}oxy)benzenecarboximidamide (150 mg, 0.498 mmol) in 1,4-dioxane (3 mL) were added phenylmethanethiol (0.088 mL, 0.75 mmol), diisopropylethylamine (0.174 mL, 0.996 mmol), Pd$_2$(dba)$_3$ (45.6 mg, 0.0498 mmol) and Xantphos (86 mg, 0.15 mmol). The reaction mixture was deoxygenated with nitrogen, warmed to 100° C., and allowed to stir for 16 h. The reaction mixture was cooled, diluted with water (30 mL), and extracted with ethyl acetate (3×30 mL). The combined organic extracts were washed with saturated aqueous sodium chloride (50 mL), dried (sodium sulfate), filtered, and concentrated under reduced pressure. The residue was purified by silica gel chromatography, eluting with ethyl acetate:petroleum ether—5:95, to give the title compound.

$^1$H NMR (400 MHz, CDCl$_3$): δ 7.11-7.28 (m, 6H), 6.77-6.90 (m, 2H), 4.05 (s, 2H), 3.73 (s, 3H), 2.63 (d, J=5.95 Hz, 1H), 1.92 (d, J=5.95 Hz, 1H), 1.36 (s, 3H), 0.91 (s, 3H).

Step D: Methyl trans-3-(2-fluoro-4-sulfamoylphenyl)-2,2-dimethylcyclopropanecarboxylate To a stirred solution of methyl trans-3-[4-(benzylsulfanyl)-3-fluorophenyl]-2,2-dimethylcyclopropanecarboxylate (190 mg, 0.552 mmol) in acetonitrile (2 mL) at 0° C. were added acetic acid (0.05 mL), water (0.04 mL), and 1,3-dichloro-5,5-dimethylimidazolidine-2,4-dione (326 mg, 1.66 mmol). The reaction mixture was allowed to stir for 90 min and then aqueous ammonium hydroxide (14.8 M, 0.373 mL, 5.52 mmol) was added. The reaction mixture was allowed to warm to ambient temperature and stirring was continued for 1 h. The reaction mixture was concentrated under reduced pressure, diluted with water (20 mL), and the aqueous layer extracted with ethyl acetate (3×20 mL). The combined organic extracts were washed with saturated aqueous sodium chloride (50 mL), dried (sodium sulfate), filtered, and concentrated under reduced pressure. The residue was purified by silica gel chromatography, eluting with ethyl acetate:petroleum ether—50:50, to provide the title compound. MS: m/z=301.7 [M+H]. $^1$H NMR (400 MHz, CD$_3$OD): δ 7.75-7.81 (m, 1H); 7.15-7.18 (m, 2H); 3.72 (s, 3H); 2.69 (d, J=5.87 Hz, 1H); 2.20 (d, J=5.87 Hz, 1H); 1.35 (s, 3H); 0.93 (s, 3H).

Intermediate 26

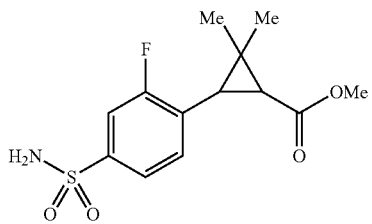 [SMILES: COC(=O)C1C(c2ccc(S(N)(=O)=O)cc2F)C1(C)C]

Methyl trans-3-(2-fluoro-4-sulfamoylphenyl)-2,2-dimethylcyclopropanecarboxylate

Essentially following the procedures described in Intermediate 25, but using 4-bromo-2-fluorobenzaldehyde in place of 4-bromo-3-fluorobenzaldehyde, the title compound was obtained. MS: m/z=343.1 [M+H+CH$_3$CN].

Intermediate 27

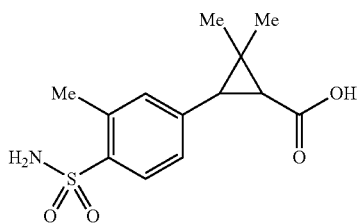 [SMILES: Cc1cc(C2C(C(=O)O)C2(C)C)ccc1S(N)(=O)=O]

trans-2,2-Dimethyl-3-(3-methyl-4-sulfamoylphenyl)cyclopropanecarboxylic acid

Essentially following the procedures described in Intermediate 25, but using 4-bromo-3-methylbenzaldehyde in place of 4-bromo-3-fluorobenzaldehyde, the title compound was obtained. MS: m/z=325.1 [M+H+CH$_3$CN].

Intermediate 28

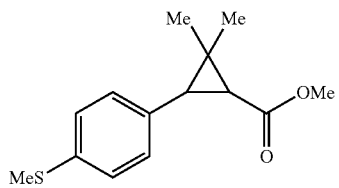 [SMILES: COC(=O)C1C(c2ccc(SC)cc2)C1(C)C]

Methyl trans-2,2-dimethyl-3-(4-(methylthio)phenyl)cyclopropanecarboxylate

Step A: Methyl 3-(4-(methylthio)phenyl)acrylate

To a stirred solution of 4-(methylthio)benzaldehyde (3.00 g, 19.7 mmol) in tetrahydrofuran (30 mL) at ambient temperature was added methyl 2-(triphenylphosphoranylidene)acetate (9.88 g, 29.6 mmol). The reaction mixture was warmed to 70° C. and allowed to stir for 12 h. The reaction mixture was cooled to ambient temperature, water (50 mL) was added, and the aqueous layer was extracted with ethyl acetate (3×50 mL). The combined organic extracts was dried (sodium sulfate), filtered, and the filtrate concentrated under reduced pressure. The residue was purified by silica gel chromatography, eluting with ethyl acetate:petroleum ether—20:80, to afford the title compound. MS: m/z=209.0 [M+H].

Step B: Methyl trans-2,2-dimethyl-3-(4-(methylthio)phenyl)cyclopropanecarboxylate To a stirred suspension of isopropyltriphenylphosphonium iodide (9.34 g, 21.6 mmol) in tetrahydrofuran (50 mL) at −50° C. was added n-butyllithium in hexane (2.5 M, 7.92 mL, 19.8 mmol) dropwise. The reaction mixture was allowed to stir for 30 min then allowed to warm to ambient temperature and stir for 4 h. The reaction mixture was cooled to −50° C., methyl 3-(4-(methylthio)phenyl)acrylate (1.5 g, 7.2 mmol) was added, and the reaction mixture allowed to warm to ambient temperature and stir for 2 h. Water (20 mL) was added and the reaction mixture was extracted with ethyl acetate (3×20 mL). The combined organic extracts were dried (sodium sulfate), filtered, and the filtrate concentrated under reduced pressure. The residue was purified by preparative HPLC, eluting with a gradient of acetonitrile:water:trifluoroacetic acid—60:40:0.1 to 90:10:0.1, to afford the title compound. $^1$H NMR (400 MHz, CDCl$_3$): δ 7.17 (d, J=7.6 Hz, 2H); 7.08 (d, J=8.2 Hz, 2H); 3.72 (s, 3H); 2.64 (d, J=5.7 Hz, 1H); 2.46 (s, 3H); 1.91 (d, J=6.0 Hz, 1H); 1.36 (s, 3H); 0.91 (s, 3H).

Intermediate 29

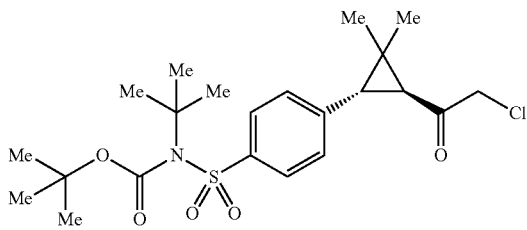 [SMILES: CC(C)(C)OC(=O)N(C(C)(C)C)S(=O)(=O)c1ccc([C@H]2[C@H](C(=O)CCl)C2(C)C)cc1]

tert-Butyl tert-butyl((4-((1S,3S)-3-(2-chloroacetyl)-2,2-dimethylcyclopropyl) phenyl)sulfonyl)carbamate

Step A: Ethyl (1S,3S)-3-(4-(N-(tert-butoxycarbonyl)-N-(tert-butyl)sulfamoyl)phenyl)-2,2-dimethylcyclopropanecarboxylate To a stirred solution of ethyl (1S,3S)-2,2-dimethyl-3-(4-sulfamoylphenyl)cyclopropanecarboxylate (Intermediate 24) (2.00 g, 6.73 mmol) in tetrahydrofuran (20 mL) at ambient temperature were added di-tert-butyl dicarbonate (14.68 g, 67.3 mmol) and 4-(dimethylamino)pyridine (0.25 g, 2.0 mmol). The reaction mixture was warmed to 70° C. and allowed to stir for 12 h. The reaction mixture was cooled to ambient temperature, concentrated under reduced pressure, and the residue purified by silica gel column chromatography, eluting with ethyl acetate:petroleum ether—17:83, to give the title compound. MS: m/z=476.3 [M+Na].

Step B: tert-Butyl tert-butyl((4-((1S,3S)-3-(2-chloroacetyl)-2,2-dimethylcyclopropyl) phenyl)sulfonyl) carbamate To a stirred solution of ethyl (1S,3S)-3-(4-(N-(tert-butoxycarbonyl)-N-(tert-butyl)sulfamoyl)phenyl)-2,2-dimethylcyclopropanecarboxylate (2.5 g, 5.5 mmol) in tetrahydrofuran (10 mL) at −78° C. were added chloroiodomethane (2.92 g, 16.5 mmol) and a solution of LDA in tetrahydrofuran/heptane/ethylbenzene (2.0 M, 11 L, 22 mmol). The reaction mixture was allowed to stir for 30 min and then warmed to −40° C. and allowed to stir for 20 min. An aqueous solution of HCl (1 M, 22 mL, 22 mmol) was added and the mixture extracted with ethyl acetate (3×30 mL). The combined organic extracts were dried (sodium sulfate), filtered, and concentrated under reduced pressure. The residue was purified by silica gel chromatography, eluting with a gradient of ethyl acetate:petroleum ether—5:95 to 9:91, to afford the title compound. $^1$H NMR (400 MHz, CDCl$_3$, 1:1 rotamer ratio, asterisks denote rotamer peaks): δ 7.96 (d, J=8.40 Hz, 2H); 7.26-7.29 (m, 2H); 4.20 (d, J=3.60 Hz, 1H); 3.88-3.99 (m, 1H); 2.97* (d, J=6.0 Hz, 0.5H); 2.93* (d, J=6.0 Hz, 0.5H); 2.59* (d, J=6.0 Hz, 0.5H); 2.46* (d, J=6.0 Hz, 0.5H); 1.51 (s, 9H), 1.47 (s, 9H); 1.30* (s, 1.5H); 1.26* (s, 1.5H); 1.01* (s, 1.5H); 0.98* (s, 1.5H).

Intermediate 30

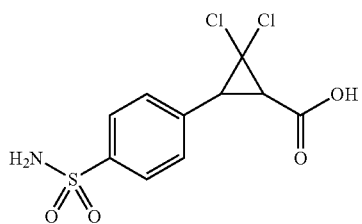 [SMILES: NS(=O)(=O)c1ccc(C2C(C(=O)O)C2(Cl)Cl)cc1]

trans-2,2-Dichloro-3-(4-sulfamoylphenyl)cyclopropanecarboxylic acid

Step A: (3,3-Diethoxyprop-1-en-1-yl)benzene

To a stirred solution of cinnamaldehyde (1.00 g, 7.57 mmol) and triethylorthoformate (1.68 g, 11.4 mmol) in ethanol (12 mL) at ambient temperature was added NBS (0.013 g, 0.076 mmol) and the reaction mixture allowed to stir for 30 min. The reaction mixture was concentrated under reduced pressure and the residue purified by silica gel chromatography, eluting with ethyl acetate:petroleum ether—1:50, to give the title compound. $^1$H NMR (400 MHz, CD$_3$OD): δ 7.39-7.43 (m, 2H); 7.29-7.31 (m, 2H); 7.22-7.27 (m, 1H); 6.68 (d, J=16.0 Hz, 1H); 6.16 (dd, J=16.0, 5.2 Hz, 1H); 5.03 (d, J=5.2 Hz, 1H); 3.67 (q, J=7.2 Hz, 2H); 3.53 (q, J=7.2 Hz, 2H); 1.14-1.22 (m, 6H).

Step B: (trans-2,2-Dichloro-3-(diethoxymethyl)cyclopropyl)benzene

To a stirred solution of (3,3-diethoxyprop-1-en-1-yl)benzene (17 g, 82 mmol) in chloroform (120 mL) at ambient temperature were added an aqueous solution of sodium hydroxide (50%, 100 mL, 1.9 mol) and N-benzyl-N,N-diethylethanaminium chloride (2.44 g, 10.7 mmol) and the reaction mixture allowed to stir for 16 h. The reaction mixture was filtered and the filtrate was extracted with dichloromethane (2×100 mL). The combined organic extracts were dried (sodium sulfate), filtered, and the filtrate concentrated under reduced pressure. The residue was purified by silica gel chromatography, eluting with ethyl acetate: petroleum ether—1:10, to give the title compound. $^1$H NMR (400 MHz, CD$_3$OD): δ 7.25-7.33 (m, 5H); 4.57 (d, J=7.6 Hz, 1H); 3.67-3.79 (m, 4H); 2.92 (d, J=8.8 Hz, 1H); 2.35 (dd, J=8.8, 7.2 Hz, 1H); 1.26 (t, J=7.2 Hz, 3H); 1.15 (J=7.2 Hz, 3H).

Step C: trans-2,2-Dichloro-3-phenylcyclopropanecarbaldehyde

To a stirred solution of (trans-2,2-dichloro-3-(diethoxymethyl)cyclopropyl)benzene (9.00 g, 31.1 mmol) in acetone (100 mL) at ambient temperature was added an aqueous solution of hydrogen chloride (3 M, 10 mL, 30 mmol) and the reaction mixture allowed to stir for 16 h. The aqueous layer was extracted with ethyl acetate (2×100 mL) and the combined organic extracts were dried (sodium sulfate), filtered, and the filtrate concentrated under reduced pressure. The residue was purified by silica gel chromatography, eluting with a gradient of ethyl acetate:petroleum ether—10:90 to 20:80, to give the title compound. $^1$H NMR (400

MHz, CD₃OD): δ 9.48 (d, J=4.4 Hz, 1H); 7.24-7.47 (m, 5H); 3.55 (d, J=8.0 Hz, 1H); 2.91 (d, J=8.4 Hz, 1H).

Step D: Methyl trans-2,2-dichloro-3-phenylcyclopropanecarboxylate

To a stirred solution of trans-2,2-dichloro-3-phenylcyclopropanecarbaldehyde (4.50 g, 20.9 mmol) in n-butanol (5.00 mL) at 0° C. were added 2-methylpent-2-ene (8.80 g, 105 mmol) and a solution of sodium chlorite (5.68 g, 62.8 mmol) and sodium dihydrogenphosphate (10.04 g, 84 mmol) in water (5 mL). The reaction mixture was allowed to warm to ambient temperature and stir for 1 h. The reaction mixture was adjusted to pH 4 and the aqueous layer extracted with ethyl acetate (2×5 mL). The combined organic extracts were dried (sodium sulfate), filtered, and the filtrate concentrated under reduced pressure. The residue was dissolved in methanol (3 mL) at ambient temperature, thionyl chloride (1.61 mL, 22.1 mmol) was added, and the reaction mixture allowed to stir for 30 min. The reaction mixture was concentrated under reduced pressure and the residue purified by silica gel chromatography, eluting with ethyl acetate: petroleum ether—10:90, to give the title compound. ¹H NMR (400 MHz, CD₃OD): δ 7.23-7.37 (m, 5H); 3.83 (s, 3H); 3.46 (d, J=8.4 Hz, 1H); 2.84 (d, J=8.4 Hz, 1H).

Step E: Methyl trans-2,2-dichloro-3-(4-sulfamoylphenyl)cyclopropanecarboxylate

To a stirred solution of methyl trans-2,2-dichloro-3-phenylcyclopropanecarboxylate (1.0 g, 4.1 mmol) in chloroform (15 mL) at 0° C. was added chlorosulfonic acid (5.37 mL, 82 mmol) and the reaction mixture allowed to stir for 2 h. The reaction mixture was poured into water (30 mL) and the aqueous phase extracted with dichloromethane (2×30 mL). The combined organic extracts were dried (sodium sulfate), filtered, and the filtrate was concentrated under reduced pressure. The residue (1.2 g, 3.5 mmol) was dissolved in 1,4-dioxane (20 mL) and ammonia (0.24 g, 14.0 mmol) was added. The reaction mixture was allowed to warm to ambient temperature and allowed to stir for 30 min. The reaction mixture was poured into water (15 mL) and the aqueous phase was extracted with ethyl acetate (2×20 mL). The combined organic extracts were dried (sodium sulfate), filtered, and the filtrate was concentrated under reduced pressure. The residue was purified by silica gel chromatography, eluting with a gradient of ethyl acetate:petroleum ether—10:90 to 50:50, to give the title compound. ¹H NMR (400 MHz, CDCl₃): δ 7.92 (d, J=8.4 Hz, 2H); 7.40 (d, J=8.4 Hz, 2H); 4.90 (s, 2H); 3.85 (s, 3H); 3.51 (d, J=8.0 Hz, 1H); 2.90 (d, J=8.4 Hz, 1H).

Step F: trans-2,2-Dichloro-3-(4-sulfamoylphenyl)cyclopropanecarboxylic acid

To a stirred solution of methyl trans-2,2-dichloro-3-(4-sulfamoylphenyl)cyclopropanecarboxylate (200 mg, 0.62 mmol) in acetic acid (2 mL) was added an aqueous solution of HCl (3M, 1 mL, 3 mmol) and the reaction mixture was warmed to 100° C. and allowed to stir for 2 h. The reaction mixture was cooled, poured into water (5 mL), and the aqueous phase extracted with ethyl acetate (2×5 mL). The combined organic extracts were dried (sodium sulfate), filtered, and the filtrate was concentrated under reduced pressure to afford the title compound in sufficient purity for use in the next step. ¹H NMR (400 MHz, CD₃OD): δ 7.84 (d, J=8.4 Hz, 2H); 7.35 (d, J=8.4 Hz, 2H); 3.40 (d, J=8.4 Hz, 1H); 2.86 (d, J=8.4 Hz, 1H).

Intermediate 31

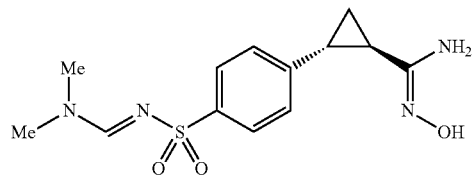 [SMILES: CN(C)/C=N/S(=O)(=O)c1ccc([C@@H]2C[C@H]2/C(N)=N/O)cc1]

(1R,2R)-2-(4-{[(Dimethylamino)methylidene]sulfamoyl}phenyl)-N'-hydroxycyclopropanecarboximidamide Step A: (1R,2R)-2-(4-Sulfamoylphenyl)cyclopropanecarboxamide To a stirred solution of (1R,2R)-2-(4-sulfamoylphenyl)cyclopropanecarboxylic acid (Intermediate 2) (1.00 g, 4.14 mmol) in tetrahydrofuran (20 mL) at ambient temperature was added 1,1'-carbonyldiimidazole (0.806 g, 4.97 mmol). The reaction mixture was warmed to 35° C. and allowed to stir for 1 h. The reaction mixture was allowed to cool to ambient temperature, then aqueous ammonium hydroxide (14.8 M, 5.6 mL, 83 mmol) was added and the mixture was allowed to stir for 12 h. The reaction mixture was concentrated under reduced pressure and the resulting mixture was adjusted to pH 3 by addition of an aqueous solution of HCl (1 M). The resulting precipitate was isolated by filtration, washing with water, and dried to afford the title compound. MS: m/z=241.2 [M+H].

Step B: 4-[(1R,2R)-2-Cyanocyclopropyl]-N-[(dimethylamino)methylidene]benzenesulfonamide To a stirred solution of (1R,2R)-2-(4-sulfamoylphenyl)cyclopropanecarboxamide (1.0 g, 4.2 mmol) in N,N-dimethylformamide (8 mL) was added thionyl chloride (3.3 g, 27 mmol) dropwise at 0° C. The resulting solution was allowed to stir for 1 h at 15° C. and then diluted with water (10 mL) and extracted with ethyl acetate (3×10 mL). The combined organic extracts were washed with saturated aqueous sodium chloride (25 mL), dried (sodium sulfate), and concentrated under reduced pressure to afford the title compound. MS: m/z=278.1 [M+H].

Step C: (1R,2R)-2-(4-{[(Dimethylamino)methylidene]sulfamoyl}phenyl)-N-hydroxycyclopropanecarboximidamide To a stirred solution of 4-[(1R,2R)-2-cyanocyclopropyl]-N-[(dimethylamino)methylidene]benzenesulfonamide (950 mg, 3.43 mmol) in ethanol (7 mL) were added hydroxylamine hydrochloride (476 mg, 6.85 mmol) and triethylamine (1.39 g, 13.7 mmol). The reaction mixture was heated at reflux for 15 h. The reaction mixture was allowed to cool and concentrated under reduced pressure. The residue was purified by silica gel chromatography, eluting with a gradient of ethyl acetate:petroleum ether—0:100 to 25:75, to afford the title compound. MS: m/z=310.9 [M+H].

Intermediate 32

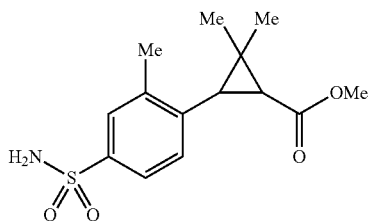 [SMILES: COC(=O)C1C(c2ccc(S(N)(=O)=O)cc2C)C1(C)C]

Methyl trans-2,2-dimethyl-3-(2-methyl-4-sulfamoyl-phenyl)cyclopropanecarboxlate

Step A: Ethyl 3-(4-bromo-2-methylphenyl)-2-cyanoprop-2-enoate

To a stirred solution of 4-bromo-2-methylbenzaldehyde (500 mg, 2.51 mmol) and ethyl 2-cyanoacetate (284 mg, 2.51 mmol) in toluene (20 mL) were added piperidine (42.8 mg, 0.502 mmol) and acetic acid (151 mg, 2.51 mmol). The reaction mixture was warmed to 130° C. and allowed to stir for 18 h with continuous removal of water. The reaction mixture was cooled to ambient temperature and concentrated under reduced pressure. The residue was purified by silica gel chromatography, eluting with a gradient of ethyl acetate:petroleum ether—0:100 to 10:90, to afford the title compound. $^1$H NMR (400 MHz, CDCl$_3$): δ 8.47 (s, 1H), 7.97-8.07 (m, 1 H), 7.48 (br, 2H), 4.40 (q, J=7.04 Hz, 2H), 2.44 (s, 3H), 1.41 (t, J=7.04 Hz, 3H).

Step B: Ethyl trans-3-(4-bromo-2-methylphenyl)-1-cyano-2,2-dimethylcyclopropanecarboxylate To a stirred solution of ethyl trans-3-(4-bromo-2-methylphenyl)-2-cyanoprop-2-enoate (100 mg, 0.340 mmol) in ethanol (5 mL) were added 2-nitropropane (36.3 mg, 0.408 mmol) and potassium carbonate (56.4 mg, 0.408 mmol). The reaction mixture was warmed to 90° C. and allowed to stir for 6 h. The reaction mixture was concentrated under reduced pressure and purified by silica gel chromatography, eluting with ethyl acetate:petroleum ether—17:83, to give the title compound. $^1$H NMR (400 MHz, CD$_3$OD) δ 7.39 (s, 1H), 7.33 (d, J=8.38 Hz, 1H), 7.21 (d, J=8.16 Hz, 1H), 4.34 (q, J=7.20 Hz, 2H), 3.07 (s, 1H), 2.27 (s, 3H), 1.50 (s, 3H), 1.39 (t, J=7.06 Hz, 3H), 1.33 (s, 3H).

Step C: trans-3-(4-Bromo-2-methylphenyl)-1-cyano-2,2-dimethylcyclopropanecarboxylic acid To a stirred solution of potassium carbonate (147 mg, 1.06 mmol) in water (1 mL) was added a solution of ethyl trans-3-(4-bromo-2-methylphenyl)-1-cyano-2,2-dimethyl-cyclopropanecarboxylate (235 mg, 0.699 mmol) in methanol (2 mL) and tetrahydrofuran (2 mL). The reaction mixture was warmed to reflux and allowed to stir for 1 h and then warmed to 85° C. and allowed to stir for 14 h. The reaction mixture was cooled to ambient temperature, concentrated under reduced pressure, and the residue was diluted with water (50 mL) and washed with ethyl acetate (2×30 mL). The layers were separated and the aqueous layer was adjusted to pH ≈ 3 by addition of an aqueous solution of HCl (3 M) and then extracted with ethyl ether (3×50 mL). The organic extracts were dried (sodium sulfate), filtered, and concentrated under reduced pressure to give the title compound. $^1$H NMR (400 MHz, CDCl$_3$): δ 7.39 (s, 1H), 7.32 (d, J=7.94 Hz, 1H), 7.20 (d, J=8.16 Hz, 1H), 3.10 (s, 1H), 2.27 (s, 3H), 1.57 (s, 3H), 1.34 (s, 3H).

Step D: trans-3-(4-Bromo-2-methylphenyl)-2,2-dimethylcyclopropanecarbonitrile

To a stirred solution of trans-3-(4-bromo-2-methylphenyl)-1-cyano-2,2-dimethylcyclopropanecarboxylic acid (210 mg, 0.68 mmol) in DMSO (3 mL) at ambient temperature were added lithium chloride (165 mg, 3.90 mmol), sodium bicarbonate (82 mg, 0.98 mmol), and water (0.070 mL, 3.9 mmol). The reaction mixture was allowed to stir for 30 min and then warmed to 175° C. and allowed to stir for 5 h. The reaction mixture was cooled, diluted with water (30 mL), and extracted with ethyl acetate (3×50 mL). The combined organic extracts were washed with water (3×50 mL) and saturated aqueous sodium chloride (50 mL), dried (sodium sulfate), filtered, and the solvent concentrated under reduced pressure to give the title compound. $^1$H NMR (400 MHz, CD$_3$OD): δ 7.37 (d, J=1.2 Hz, 1H), 7.30 (d, J=1.6 Hz, 1 H), 7.01 (d, J=8.2 Hz, 1H), 2.41 (d, J=5.9 Hz, 1H), 2.30 (s, 3H), 1.95-1.99 (m, 1H), 1.51 (s, 3H), 0.83 (s, 3H).

Step E: Methyl trans-3-(4-bromo-2-methylphenyl)-2,2-dimethylcyclopropanecarboxylate To a flask containing trans-3-(4-bromo-2-methylphenyl)-2,2-dimethylcyclopropanecarbonitrile (300 mg, 1.14 mmol) was added a solution of HCl in methanol (4 M, 10 mL, 40.0 mmol) and the reaction mixture warmed to 80° C. and allowed to stir for 24 h. The reaction mixture was concentrated under reduced pressure and the residue diluted with water (10 mL). The aqueous layer was adjusted to pH ≈ 8 by addition of a saturated aqueous solution of sodium bicarbonate and then extracted with ethyl acetate (3×30 mL). The combined organic extracts were washed with saturated aqueous sodium chloride (30 mL), dried (sodium sulfate), filtered, and concentrated under reduced pressure. The residue was purified by silica gel chromatography, eluting with ethyl acetate:petroleum ether—9:91, to give the title compound. $^1$H NMR (400 MHz, CDCl$_3$) δ 7.32 (s, 1H), 7.25 (d, J=8.22 Hz, 1H), 6.91 (d, J=8.22 Hz, 1 H), 3.75 (s, 3H), 2.51 (d, J=5.48 Hz, 1H), 2.29 (s, 3H), 1.94 (d, J=5.87 Hz, 1H), 1.43 (s, 3 H), 0.85 (s, 3H).

Step F: Methyl trans-3-[4-(benzylsulfanyl)-2-methylphenyl]-trans-2,2-dimethylcyclopropanecarboxylate To a stirred solution of methyl trans-3-(4-bromo-2-methylphenyl)-2,2-dimethylcyclopropanecarboxylate (130 mg, 0.437 mmol) in 1,4-dioxane (3 mL) were added phenylmethanethiol (0.077 mL, 0.66 mmol), DIEA (0.153 mL, 0.875 mmol), Pd$_2$(dba)$_3$ (80 mg, 0.087 mmol), and Xantphos (152 mg, 0.262 mmol). The reaction mixture was warmed to 110° C. and allowed to stir for 16 h. The reaction mixture was cooled, diluted with water (30 mL), and extracted with ethyl acetate (3×30 mL). The combined organic extracts were washed with saturated aqueous sodium chloride (50 mL), dried (sodium sulfate), filtered, and the filtrate concentrated under reduced pressure. The residue was purified by silica gel chromatography, eluting with ethyl acetate: petroleum ether—5:95, to give the title compound. ¹H NMR (400 MHz, CD₃OD): δ 7.09-7.21 (m, 7H); 6.90-7.04 (m, 1H); 4.06 (s, 2H); 3.70 (s, 3H); 2.46 (d, J=5.2 Hz, 1H); 2.21 (s, 3H); 1.98 (d, J=6.0 Hz, 1H); 1.37 (s, 3H); 0.80 (s, 3H).

Step G: Methyl trans-2,2-dimethyl-3-(2-methyl-4-sulfamoylphenyl)cyclopropanecarboxylate To a stirred solution of methyl trans-3-(4-(benzylthio)-2-methylphenyl)-2,2-dimethylcyclopropanecarboxylate (122 mg, 0.358 mmol) in acetonitrile (4 mL) at 0° C. were added acetic acid (0.1 mL), water (0.08 mL) and 1,3-dichloro-5,5-dimethylimidazolidine-2,4-dione (212 mg, 1.08 mmol) and the reaction mixture allowed to stir for 90 min. Ammonium hydroxide (14.8 M, 0.243 mL, 3.60 mmol) was added and the reaction mixture allowed to warm to ambient temperature and allowed to stir for 1 h. The reaction mixture was concentrated under reduced pressure, diluted with water (20 mL), and extracted with ethyl acetate (3×20 mL). The combined organic extracts were washed with saturated aqueous sodium chloride (50 mL), dried (sodium sulfate), filtered, and the filtrate concentrated under reduced pressure. The residue was purified by silica gel chromatography, eluting with ethyl acetate:petroleum ether—50:50, to give the title compound. ¹H NMR (400 MHz, CDCl₃): δ 7.74 (s, 1H), 7.69 (dd, J=8.16, 1.88 Hz, 1 H), 7.19 (d, J=8.03 Hz, 1H), 4.75 (s, 2H), 3.77 (s, 3H), 2.61 (d, J=6.02 Hz, 1H), 2.39 (s, 3 H), 2.05 (s, 1H), 1.46 (s, 3H), 0.85 (s, 3H).

Intermediate 33

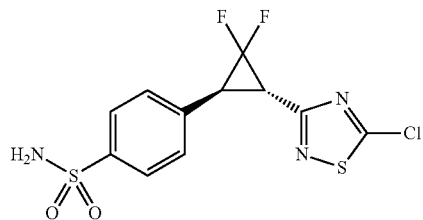 [SMILES: NS(=O)(=O)c1ccc([C@@H]2[C@@H](c3nsc(Cl)n3)C2(F)F)cc1]

4-[(1S,3S)-3-(5-Chloro-1,2,4-thiadiazol-3-yl)-2,2-difluorocyclopropyl]benzenesulfonamide Essentially following the procedures described in Example 29, but using (1S,3S)-2,2-difluoro-N-hydroxy-3-(4-sulfamoylphenyl)cyclopropanecarboximidamide (Intermediate 36) in place of (1R,2R)—N-hydroxy-2-(4-sulfamoylphenyl)cyclopropanecarboximidamide, the title compound was obtained. MS: m/z=352.0 [M+H].

Intermediate 34

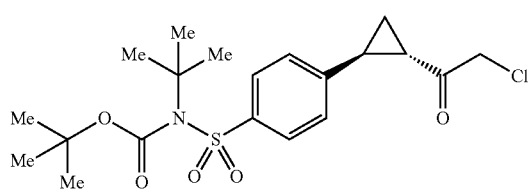 [SMILES: CC(C)(C)OC(=O)N(C(C)(C)C)S(=O)(=O)c1ccc([C@H]2C[C@@H]2C(=O)CCl)cc1]

4-[(1S,2S)-2-(Chloroacetyl)cyclopropyl]benzenesulfonamide

Essentially following the procedures described in Intermediate 29, but using ethyl (1S,2S)-2-(4-sulfamoylphenyl)cyclopropanecarboxylate (described in Intermediate 2) in place of ethyl (1S,3S)-2,2-dimethyl-3-(4-sulfamoylphenyl)cyclopropanecarboxylate, the title compound was obtained. ¹H NMR (400 MHz, CDCl₃): δ 7.96 (d, J=8.6 Hz, 2H); 7.20 (d, J=8.6 Hz, 2 H); 4.24 (s, 2H); 2.59-2.73 (m, 1H); 2.47-2.55 (m, 1H); 1.78-1.88 (m, 1H); 1.50-1.53 (m, 9 H); 1.45-1.48 (m, 10H).

Intermediate 35

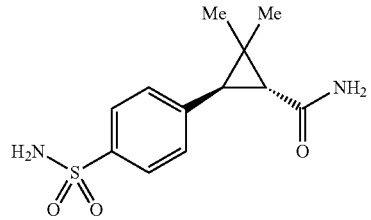 [SMILES: CC1(C)[C@H](C(N)=O)[C@H]1c1ccc(S(N)(=O)=O)cc1]

(1R,3R)-2,2-Dimethyl-3-(4-sulfamoylphenyl)cyclopropanecarboxamide

Essentially following the procedures described in Intermediate 10, but using (1R,3R)-2,2-dimethyl-3-(4-sulfamoylphenyl)cyclopropanecarboxylic acid (Intermediate 4) in place of (1S,3S)-2,2-dimethyl-3-(4-sulfamoylphenyl)cyclopropanecarboxylic acid, the title compound was obtained. MS: m/z=269.1 [M+H].

Intermediate 36

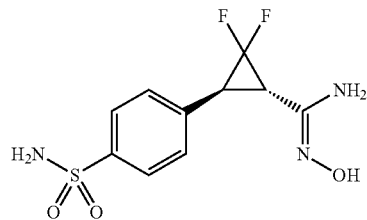 [SMILES: N/C(=N\O)[C@@H]1[C@@H](c2ccc(S(N)(=O)=O)cc2)C1(F)F]

(1S,3S)-2,2-difluoro-N'-hydroxy-3-(4-sulfamoylphenyl)cyclopropanecarboximidamide Essentially following the procedures described in Intermediate 10, but using (1S,3S)-2,2-difluoro-3-(4-sulfamoylphenyl)cyclopropanecarboxylic acid (Intermediate 4) in place of (1S,3S)-2,2-dimethyl-3-(4-sulfamoylphenyl)cyclopropanecarboxylic acid, the title compound was obtained. MS: m/z=292.0 [M+H].

Intermediate 37

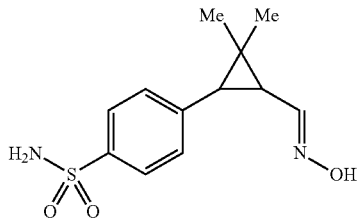 [SMILES: CC1(C)C(/C=N/O)C1c1ccc(S(N)(=O)=O)cc1]

4-(trans-3-((Hydroxyimino)methyl)-trans-2,2-dimethylcyclopropyl)benzenesulfonamide Step A: Ethyl trans-2,2-dimethyl-3-(4-sulfamoylphenyl)cyclopropanecarboxylate Essentially following the procedures described in Intermediate 4, but using trans-2,2-dimethyl-3-phenylcyclopropanecarboxylic acid in place of (1R,3R)-2,2-dimethyl-3-phenylcyclopropanecarboxylic acid, the title compound was obtained. MS: m/z=298.0 [M+H].

Step B: 4-(trans-3-(Hydroxymethyl)-2,2-dimethylcyclopropyl)benzenesulfonamide

Essentially following the procedures described in Intermediate 13, but using ethyl trans-2,2-dimethyl-3-(4-sulfamoylphenyl)cyclopropanecarboxylate in place of ethyl (1R,3R)-2,2-dimethyl-3-(4-sulfamoylphenyl)cyclopropanecarboxylate, the title compound was obtained. MS: m/z=278.1 [M+Na].

Step C: 4-(trans-3-Formyl-2,2-dimethylcyclopropyl)benzenesulfonamide

Essentially following the procedures described in Intermediate 13, but using 4-(trans-3-(hydroxymethyl)-2,2-dimethylcyclopropyl)benzenesulfonamide in place of 4-[(1R,3R)-3-(hydroxymethyl)-2,2-dimethylcyclopropyl]benzenesulfonamide, the title compound was obtained. MS: m/z=254.1 [M+H].

Step D: 4-(trans-3-((Hydroxyimino)methyl)-2,2-dimethylcyclopropyl)benzenesulfonamide To a stirred solution of 4-(trans-3-formyl-2,2-dimethylcyclopropyl)benzenesulfonamide (300 mg, 1.18 mmol) in ethanol (10 mL) at ambient temperature were added sodium carbonate (377 mg, 3.55 mmol) and hydroxylamine hydrochloride (254 mg, 3.55 mmol) and the reaction mixture allowed to stir for 16 h. The reaction mixture was concentrated under reduced pressure, water (30 mL) was added, and the mixture was extracted with ethyl acetate (3×50 mL). The combined organic extracts were washed with saturated aqueous sodium chloride (60 mL), dried (sodium sulfate), filtered, and the filtrate concentrated under reduced pressure to afford the title compound in sufficient purity for use in the next step. MS: m/z=269 [M+H].

The intermediates appearing in the following tables were prepared by analogy to the above intermediates, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE INT-A

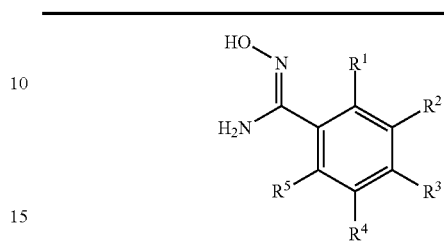

| Intermediate | R¹  | R² | R³ | R⁴ | R⁵ | MS [M + H] |
|---|---|---|---|---|---|---|
| A1 | OMe | H | H | Cl | H | 201.3 |
| A2 | CF₃ | H | F | H | H | 223.1 |
| A3 | CF₃ | H | H | F | H | 223.1 |

TABLE INT-B

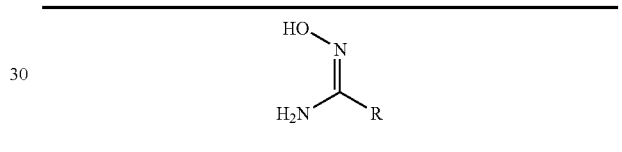

| Intermediate | R | MS (M + H) |
|---|---|---|
| B1 | 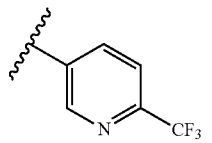 | 131.4 |
| B2 | 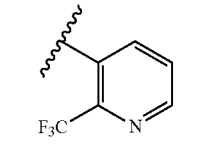 | 206.1 |
| B3 | 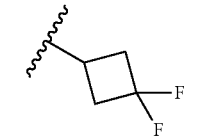 [SMILES: *C1CC(F)(F)C1] | 206.1 |
| B4 | 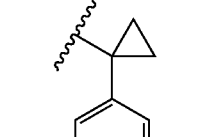 | 192.1 (M + CH₃CN + H) |
| B5 | 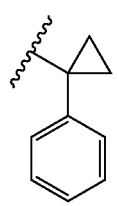 [SMILES: *C1(c2ccccc2)CC1] | 177.2 |

TABLE INT-B-continued

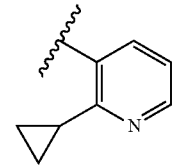 [SMILES: *c1cccnc1C1CC1]

| Intermediate | R | MS (M + H) |
|---|---|---|
| B6 | 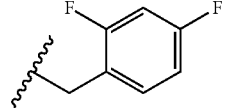 [SMILES: *Cc1ccc(F)cc1F] | 178.2 |
| B7 | 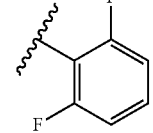 | 187.1 |
| B8 | 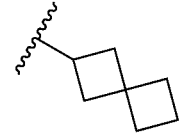 [SMILES: *C1CC2(CCC2)C1] | 173.1 |
| B9 | 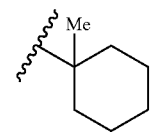 [SMILES: *C1(C)CCCCC1] | 155.1 |
| B10 | 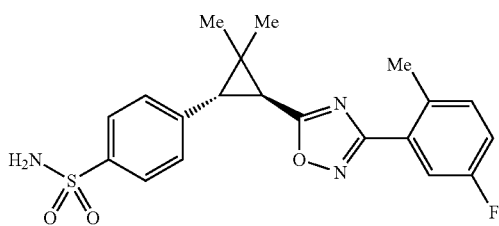 | 156.2 |

Example 1

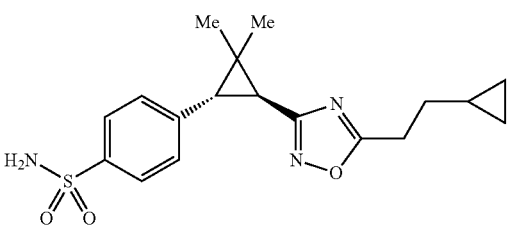 [SMILES: CC1(C)[C@@H](c2ccc(S(N)(=O)=O)cc2)[C@@H]1c1noc(CCC2CC2)n1]

4-((1S,3S)-3-(3-(5-Fluoro-2-methylphenyl)-1,2,4-oxadiazol-5-yl)-2,2-dimethylcyclopropyl)-benzenesulfonamide To a solution of (1S,3S)-2,2-dimethyl-3-(4-sulfamoylphenyl)cyclopropanecarboxylic acid (Intermediate 5) (150 mg, 0.558 mmol) in 1,4-dioxane (2.8 mL) was added 1,1'-carbonyldiimidazole (101 mg, 0.624 mmol). The reaction mixture was warmed to 45° C. and allowed to stir for 2 h. The reaction mixture was cooled to 10 ambient temperature and 5-fluoro-N'-hydroxy-2-methylbenzimidamide (Intermediate 1) (104 mg, 0.617 mmol) in 1,4-dioxane (1.5 mL) was added. The reaction mixture was warmed to 110° C., allowed to stir for 5 h, then allowed to cool, and was concentrated under reduced pressure. The residue was purified by silica gel chromatography, eluting with a gradient of ethyl acetate:hexanes—0:100 to 40:60 to afford the title compound. MS: m/z=402.2 [M+H]. $^1$H NMR (500 MHz, CDCl$_3$): δ 7.91 (d, J=7.9 Hz, 2H); 7.73 (d, J=9.6 Hz, 1H); 7.41 (d, J=8.0 Hz, 2H); 7.07-7.10 (m, 1H); 4.94 (s, 2H); 3.07 (d, J=6.0 Hz, 1H); 2.64 (d, J=6.0 Hz, 1 H); 2.60 (s, 3H); 1.06 (s, 3H).

Example 2

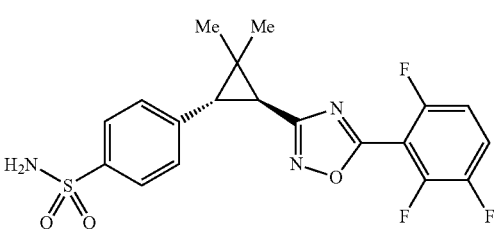 [SMILES: CC1(C)[C@@H](c2ccc(S(N)(=O)=O)cc2)[C@@H]1c1noc(-c2c(F)ccc(F)c2F)n1]

4-((1S,3S)-3-(5-(2-Cyclopropylethyl)-1,2,4-oxadiazol-3-yl)-2,2-dimethylcyclopropyl)benzenesulfonamide To a solution of 3-cyclopropylpropanoic acid (59.8 mg, 0.524 mmol) in 1,4-dioxane (2.40 mL) was added 1,1'-carbonyldiimidazole (85 mg, 0.52 mmol). The reaction mixture was warmed to 85° C. and allowed to stir for 20 min. The reaction mixture was cooled to ambient temperature and (1S,3S)—N'-hydroxy-2,2-dimethyl-3-(4-sulfamoylphenyl)cyclopropane-carboximidamide (Intermediate 10) (135 mg, 0.476 mmol) was added. The reaction mixture was warmed to 130° C., allowed to stir for 1 h, and then allowed to cool and was concentrated under reduced pressure. The residue was purified by preparative HPLC, eluting with a gradient of acetonitrile:water:trifluoroacetic acid—10:90:0.1 to 95:5:0.1. The product-containing fractions were concentrated under reduced pressure to remove acetonitrile. The remaining solution was made basic with saturated aqueous sodium bicarbonate (5 mL) and extracted with ethyl acetate (2×15 mL). The combined organic extracts were washed with saturated aqueous sodium chloride (10 mL), dried (magnesium sulfate), and concentrated under reduced pressure to give the title compound. MS: m/z=362.2 [M+H]. $^1$H NMR (500 MHz, DMSO-d$_6$): δ 7.75 (d, J=8.0 Hz, 2H); 7.50 (d, J=8.0 Hz, 2H); 7.31 (s, 2 H); 2.98 (t, J=7.3 Hz, 2H); 2.71 (m, 2H); 1.64 (q, J=7.2 Hz, 2H); 1.21 (s, 3H); 0.93 (s, 3 H); 0.74 (d, J=8.5 Hz, 1H); 0.35-0.38 (m, 2H); 0.04 (d, J=5.0 Hz, 2H).

Example 3

4-((1S,3S)-2,2-Dimethyl-3-(5-(2,3,6-trifluorophenyl)-1,2,4-oxadiazol-3-yl)cyclopropyl) benzenesulfonamide To a solution of 2,3,6-trifluorobenzoic acid (73.2 mg, 0.416 mmol) in 1,4-dioxane (1.80 mL) at ambient temperature was added 1,1'-carbonyldiimidazole (75 mg, 0.46 mmol). The reaction mixture was warmed to 85° C. and allowed to stir for 20 min. The reaction mixture was cooled to ambient temperature and (1S,3S)—N'-hydroxy-2,2-dimethyl-3-(4-sulfamoylphenyl)cyclopropanecarboximidamide (Intermediate 10) (105.1 mg, 0.371 mmol) in 1,4-dioxane (1.5 mL) was added. The reaction mixture was warmed to 130° C., allowed to stir for 1.5 h, and then allowed to cool and concentrated under reduced pressure. The residue was purified by preparative HPLC, eluting with a gradient of acetonitrile:water:trifluoroacetic acid—15:85:0.1 to 90:10:0.1. The product-containing fractions were concentrated under reduced pressure. The residue was taken up in methanol (5 mL) and treated with MP-carbonate. The mixture was allowed to stir for 20 min. The mixture was filtered and concentrated under reduced pressure to afford the title compound. MS: m/z=424.2 [M+H]. $^1$H NMR (500 MHz, DMSO-$d_6$): δ 7.92 (qd, J=9.4, 4.8 Hz, 1H); 7.77 (d, J=8.1 Hz, 2H); 7.55 (d, J=8.1 Hz, 2H); 7.48 (t, J=9.6 Hz, 1H); 7.32 (s, 2H); 2.84-2.89 (m, 2H); 1.28 (s, 3H); 0.99 (s, 3H).

Example 4

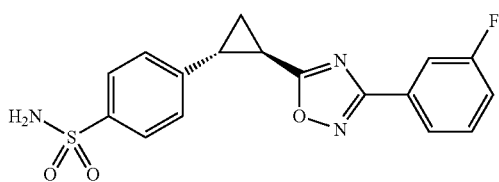

4-((1R,2R)-2-(3-(3-Fluorophenyl)-1,2,4-oxadiazol-5-yl)cyclopropyl)benzenesulfonamide To a solution of (1R,2R)-2-(4-sulfamoylphenyl)cyclopropanecarboxylic acid (Intermediate 2) (1.40 g, 5.80 mmol) in 1,4-dioxane (29 ml) at ambient temperature was added 1,1'-carbonyldiimidazole (1.04 g, 6.41 mmol). The reaction mixture was warmed to 85° C. and allowed to stir for 20 min. The reaction mixture was cooled to ambient temperature and 3-fluoro-N'-hydroxybenzimidamide (1.08 g, 7.01 mmol) was added. The reaction mixture was warmed to 135° C. and allowed to stir for 1.5 h. The reaction mixture was concentrated under reduced pressure. The residue was purified by preparative HPLC, eluting with a gradient of acetonitrile:water:trifluoroacetic acid—10:90:0.1 to 90:10:0.1. The product-containing fractions were made basic with saturated aqueous sodium bicarbonate (5 mL) and extracted with ethyl acetate (2×15 mL). The combined organic extracts were washed with saturated aqueous sodium chloride (10 mL), dried (magnesium sulfate), and concentrated under reduced pressure to afford the title compound. MS: m/z=360.2. $^1$H NMR (500 MHz, DMSO-$d_6$): δ 7.85 (d, J=7.7 Hz, 1H); 7.75 (m, 3H); 7.63 (q, J=7.2 Hz, 1H); 7.48 (d, J=7.7 Hz, 2H); 7.44-7.46 (m, 1 H); 7.33 (s, 2H); 2.85-2.92 (m, 2H); 1.86-1.94 (m, 2H).

Example 5

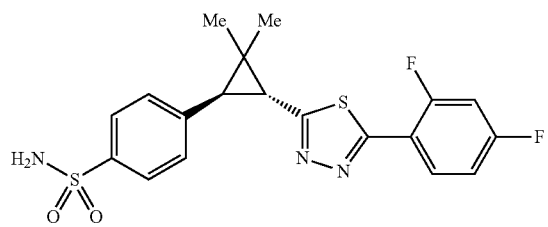 [SMILES: CC1(C)[C@H](c2ccc(S(N)(=O)=O)cc2)[C@H]1c1nnc(-c2ccc(F)cc2F)s1]

4-{(1R,3R)-3-[5-(2,4-Difluorophenyl)-1,3,4-thiadiazol-2-yl]-2,2-dimethylcyclopropyl}benzenesulfonamide To a solution of (1R,3R)-2,2-dimethyl-3-(4-sulfamoylphenyl)cyclopropanecarboxylic acid (Intermediate 4) (103 mg, 0.383 mmol) in dimethyl sulfoxide (1.90 mL) at ambient temperature were added N-methylmorpholine (0.084 mL, 0.77 mmol), HATU (165 mg, 0.433 mmol), and 2,4-difluorobenzohydrazide (82.4 mg, 0.479 mmol) sequentially. The reaction mixture was allowed to stir for 10 min, then poured into saturated aqueous ammonium chloride (10 mL), and the mixture extracted with ethyl acetate (3×15 mL). The combined organic extracts were washed with saturated aqueous ammonium chloride (2×15 mL) and saturated aqueous sodium chloride (15 mL), dried (sodium sulfate), and concentrated under reduced pressure. The residue was taken up in tetrahydrofuran (1.9 mL) and then treated with Lawesson's reagent (557 mg, 1.38 mmol). The reaction mixture was warmed to 65° C., allowed to stir for 1 h, and then concentrated under reduced pressure. The residue was purified by preparative HPLC, eluting with a gradient of acetonitrile:water:trifluoroacetic acid—15:85:0.1 to 95:5:0.1. The product-containing fractions were made basic with saturated aqueous sodium bicarbonate (5 mL) and extracted with ethyl acetate (2×15 mL). The combined organic extracts were washed with saturated aqueous sodium chloride (10 mL), dried (magnesium sulfate), and concentrated under reduced pressure to afford the title compound. MS: m/z=422.3. $^1$H NMR (500 MHz, DMSO-$d_6$): δ 8.37-8.42 (m, 1 H); 7.90 (d, J=8.0 Hz, 2H); 7.42 (d, J=8.0 Hz, 3H); 7.05-7.08 (m, 1H); 6.97-7.01 (m, 1H); 4.83 (s, 2H); 3.13 (d, J=6.1 Hz, 1H); 2.76 (d, J=6.1 Hz, 1H); 1.57 (s, 3H); 1.30 (s, 3H); 1.05 (s, 3H).

Example 6

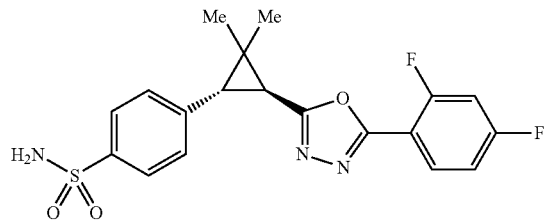 [SMILES: CC1(C)[C@@H](c2ccc(S(N)(=O)=O)cc2)[C@@H]1c1nnc(-c2ccc(F)cc2F)o1]

4-{(1S,3S)-3-[5-(2,4-Difluorophenyl)-1,3,4-oxadiazol-2-yl]-2,2-dimethylcyclopropyl}benzenesulfonamide To a solution of (1S,3S)-2,2-dimethyl-3-(4-sulfamoylphenyl)cyclopropanecarboxylic acid (Intermediate 5) (152 mg, 0.342 mmol) in 1,4-dioxane (1.70 mL) at ambient temperature was added 1,1-carbonyldiimidazole (63.7 mg, 0.393 mmol). The reaction mixture was warmed to 75° C. and allowed to stir for 20 min. The reaction mixture was then cooled to ambient temperature, 2,4-difluorobenzohydrazide (71.8 mg, 0.417 mmol) was added, and the reaction mixture warmed to 130° C. The reaction mixture was allowed to stir for 3 h. The reaction mixture was cooled to ambient temperature, phosphorous oxychloride (0.318 mL, 3.42 mmol) was added, and the reaction mixture was warmed to 70° C. and allowed to stir for 18 h. The reaction mixture was cooled to ambient temperature, poured slowly into cold, saturated aqueous sodium bicarbonate (15 mL), and the mixture extracted with ethyl acetate (3×15 mL). The combined organic extracts were washed with saturated aqueous sodium chloride (15 mL), dried (sodium sulfate), and concentrated under reduced pressure. The residue was purified by silica gel chromatography, eluting with a gradient of ethyl acetate:hexanes—0:100 to 45:55 to afford the title compound. MS: m/z=406.3. $^1$H NMR (500 MHz, DMSO-d$_6$): δ 8.06-8.11 (m, 1H); 7.90 (d, J=8.1 Hz, 2H); 7.41 (d, J=8.0 Hz, 2H); 6.99-7.07 (m, 2H); 4.80 (s, 2H); 3.01 (d, J=6.1 Hz, 1H); 2.58 (d, J=6.1 Hz, 1H); 1.39 (s, 3H); 1.05 (s, 3H).

Example 7

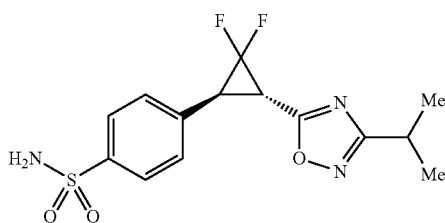 [SMILES: CC(C)c1noc([C@@H]2[C@@H](c3ccc(S(N)(=O)=O)cc3)C2(F)F)n1]

4-{(1S,3S)-2,2-Difluoro-3-[3-(propan-2-yl)-1,2,4-oxadiazol-5-yl]cyclopropyl}benzenesulfonamide To a solution of (1S,3S)-2,2-difluoro-3-(4-sulfamoylphenyl)cyclopropane carboxylic acid (Intermediate 6) (50 mg, 0.18 mmol) in 1,4-dioxane (0.90 mL) was added 1,1'-carbonyldiimidazole (35.1 mg, 0.216 mmol) and the mixture was allowed to stir at ambient temperature for 2 h. IV-Hydroxyisobutyrimidamide (23.3 mg, 0.216 mmol) was added in one portion and the mixture was allowed to stir for 30 min, then warmed to 90° C., and allowed to stir for 2 h. The reaction mixture was concentrated under reduced pressure and the residue diluted with ethyl acetate (15 mL), washed with saturated aqueous sodium chloride (2×10 mL), dried (magnesium sulfate), and concentrated under reduced pressure. The residue was purified by silica gel chromatography, eluting with a gradient of ethyl acetate:ethanol:hexanes—3:1:96 to 30:10:60 to afford the title compound. MS: m/z=344.2 [M+H]. $^1$H NMR (500 MHz, DMSO-d$_6$): δ 7.83 (d, J=8.4 Hz, 2H); 7.67 (d, J=8.3 Hz, 2H); 7.40 (s, 2H); 4.34 (dd, J=12.1, 8.25 Hz, 1H); 4.05 (dd, J=13.4, 8.06 Hz, 1H); 3.10 (m, 1H); 1.28 (d, J=6.98 Hz, 6H).

Example 8

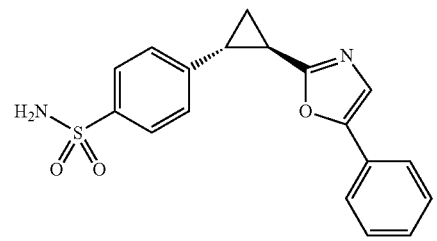 [SMILES: NS(=O)(=O)c1ccc([C@@H]2C[C@H]2c2ncc(-c3ccccc3)o2)cc1]

4-[(1R,2R)-2-(5-Phenyl-1,3-oxazol-2-yl)cyclopropyl]benzenesulfonamide

Step A: (1R,2R)—N-(2-Oxo-2-phenylethyl)-2-(4-sulfamoylphenyl)cyclopropanecarboxamide To a suspension of (1R,2R)-2-(4-sulfamoylphenyl)cyclopropanecarboxylic acid (Intermediate 2) (233 mg, 0.967 mmol) in tetrahydrofuran (4.0 mL) was added 1,1'-carbonyldiimidazole (188 mg, 1.16 mmol) and the reaction mixture allowed to stir at ambient temperature for 2 h. The resulting suspension was then added to a stirred solution of 2-amino-1-phenylethanone hydrobromide (230 mg, 1.06 mmol) and triethylamine (0.148 mL, 1.06 mmol) in tetrahydrofuran (0.8 mL) and the reaction mixture allowed to stir at ambient temperature for 18 h. The reaction mixture was concentrated under reduced pressure and the residue washed with dichloromethane and water and the resulting solid dried under reduced pressure to afford the title compound. MS: m/z=359.2 [M+H].

Step B: 4-[(1R,2R)-2-(5-Phenyl-1,3-oxazol-2-yl)cyclopropyl]benzenesulfonamide

To a flask containing (1R,2R)—N-(2-oxo-2-phenylethyl)-2-(4-sulfamoylphenyl) cyclopropanecarboxamide (100 mg, 0.279 mmol) was added sulfuric acid (concentrated, 0.297 mL, 5.58 mmol) and the resulting mixture allowed to stir at ambient temperature for 4 h. The reaction mixture was diluted with water (15 mL) and extracted with ethyl acetate (3×20 mL). The combined organic extracts were washed with aqueous sodium bicarbonate (10%, 15 mL), dried (magnesium sulfate), and concentrated under reduced pressure. The resulting solid was recrystallized from acetone. MS: m/z=341.2 [M+H]. $^1$H NMR (500 MHz, DMSO-d$_6$): δ 7.75 (d, J=7.9 Hz, 2H); 7.71 (d, J=8.0 Hz, 2H); 7.58 (s, 1H), 7.43-7.47 (m, 4H), 7.36 (t, J=7.25 Hz, 1H), 7.32 (br s, 2H), 2.70 (m, 1H), 2.60 (m, 1H), 1.80 (m, 1H), 1.67 (m, 1H).

Example 9

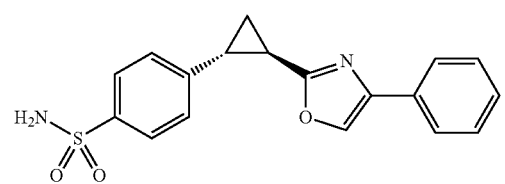 [SMILES: NS(=O)(=O)c1ccc([C@@H]2C[C@H]2c2nc(-c3ccccc3)co2)cc1]

4-[(1R,2R)-2-(4-Phenyl-1,3-oxazol-2-yl)cyclopropyl]benzenesulfonamide

To a suspension of (1R,2R)-2-(4-sulfamoylphenyl)cyclopropanecarboxamide (described in Intermediate 12) (100 mg, 0.416 mmol) in ethyl acetate (4.2 mL) were added 2-bromo-1-phenylethanone (83 mg, 0.42 mmol) and silver trifluoromethanesulfonate (107 mg, 0.416 mmol) and the reaction mixture warmed to 50° C. and allowed to stir for 16 h. The reaction mixture was diluted with ethyl acetate (10 mL) and filtered. To the filtrate was added saturated aqueous sodium chloride (15 mL) and the mixture allowed to stir for 2 h. The mixture was filtered and the phases separated. The organic phase was dried (magnesium sulfate) and concentrated under reduced pressure. The residue was purified by silica gel chromatography, eluting with a gradient of ethyl acetate:ethanol:hexanes—3:1:96 to 45:15:40 to afford the title compound. MS: m/z=341.2 [M+H]. $^1$H NMR (500 MHz, DMSO-$d_6$): δ 8.49 (s, 1H), 7.73-7.76 (m, 4H); 7.41-7.45 (m, 4H), 7.29-7.34 (m, 3H), 2.66-2.70 (m, 1H), 2.58-2.62 (m, 1H), 1.75-1.79 (m, 1H), 1.64-1.68 (m, 1H).

Example 10

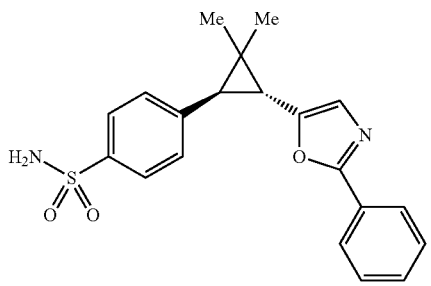 [SMILES: CC1(C)[C@H](c2ccc(S(N)(=O)=O)cc2)[C@H]1c1cnc(-c2ccccc2)o1]

4-[(1R,3R)-2,2-Dimethyl-3-(2-phenyl-1,3-oxazol-5-yl)cyclopropyl]benzenesulfonamide Step A: tert-Butyl tert-butyl({4-[(1R,3R)-2,2-dimethyl-3-(2-phenyl-1,3-oxazol-5-yl)cyclopropyl]phenyl}sulfonyl)carbamate To a suspension of (1R,3R)-3-{4-[(tert-butoxycarbonyl)(tert-butyl)sulfamoyl]phenyl}-2,2-dimethylcyclopropanecarboxylic acid (Intermediate 8) (150 mg, 0.352 mmol) in dichloromethane (1.76 mL) at 0° C. was added N,N-dimethylformamide (0.0328 mL, 0.423 mmol) followed by oxalyl chloride (0.705 mL, 1.41 mmol). The reaction mixture was allowed to stir at 0° C. for 5 min and then warmed to ambient temperature and allowed to stir for 4 h. The reaction mixture was concentrated under reduced pressure and co-evaporated with toluene (2×). The resulting residue was diluted with toluene (3.2 mL) and to the mixture were added (isocyanomethyl)benzene (0.0383 mL, 0.352 mmol) and 2,6-lutidine (0.0411 mL, 0.352 mmol). The reaction mixture was warmed to 80° C. and allowed to stir for 2.5 h. The reaction mixture was cooled to ambient temperature and diluted with water (10 mL) and extracted with ethyl acetate (2×15 mL). The combined organic extracts were washed with saturated aqueous ammonium chloride (3×10 mL), dried (magnesium sulfate) and concentrated under reduced pressure. The residue was purified by silica gel chromatography, eluting with a gradient of ethyl acetate:hexanes—0:100 to 20:80, to afford the title compound. MS: m/z=525.5 [M+H].

Step B: 4-[(1R,3R)-2,2-Dimethyl-3-(2-phenyl-1,3-oxazol-5-yl)cyclopropyl]benzenesulfonamide To a solution of tert-butyl tert-butyl({4-[(1R,3R)-2,2-dimethyl-3-(2-phenyl-1,3-oxazol-5-yl)cyclopropyl]phenyl}sulfonyl)carbamate (125 mg, 0.238 mmol) in dichloromethane (1.65 mL) was added trifluoroacetic acid (0.551 mL, 7.15 mmol) and the mixture allowed to stir at ambient temperature for 4 h. The reaction mixture was concentrated under reduced pressure. The residue was purified by silica gel chromatography, eluting with a gradient of ethyl acetate:hexanes—0:100 to 40:60, to afford the title compound. MS: m/z=369.3 [M+H]. $^1$H NMR (500 MHz, CDCl$_3$): δ 8.02 (d, J=7.8 Hz, 2H), 7.84 (d, J=8.2 Hz, 2H), 7.44-7.48 (m, 3 H), 7.41 (d, J=7.72 Hz, 2H), 6.96 (s, 1H), 4.78 (s, 2H), 2.52 (d, J=5.9 Hz, 1H) 2.37 (d, J=6.02 Hz, 1H), 1.24 (s, 3H), 1.00 (s, 3H).

Example 11

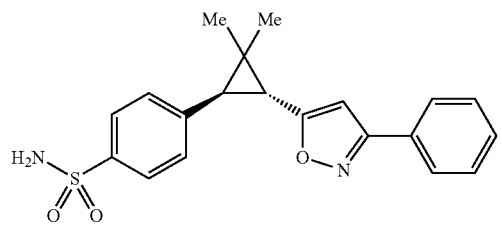 [SMILES: CC1(C)[C@H](c2ccc(S(N)(=O)=O)cc2)[C@H]1c1cc(-c2ccccc2)no1]

4-[(1R,3R)-2,2-Dimethyl-3-(3-phenylisoxazol-5-yl)cyclopropyl]benzenesulfonamide

To a stirred solution of 4-[(1R,3S)-3-ethynyl-2,2-dimethylcyclopropyl]benzenesulfonamide (Intermediate 13) (9.8 mg, 0.039 mmol), (nitromethyl)benzene (5.4 mg, 0.039 mmol), and benzenesulfonyl chloride (13.9 mg, 0.079 mmol) was added triethylamine (11.0 L, 0.079 mmol) at −10° C. The reaction mixture was allowed to warm to ambient temperature and allowed to stir for 16 h. The reaction mixture was concentrated under a stream of nitrogen gas. The residue was purified by silica gel chromatography, eluting with a gradient of ethyl acetate:hexanes—0:100 to 25:75. The product-containing fractions were combined and concentrated under reduced pressure. The residue was purified by silica gel chromatography, eluting with a gradient of methanol:dichloromethane—0:100 to 10:90 to afford the title compound. MS: m/z=369.3 [M+H]. $^1$H NMR (500 MHz, DMSO-$d_6$): δ 7.85 (d, J=7.0 Hz, 2H); 7.78 (d, J=8.0 Hz, 2H); 7.52 (m, 5H); 7.32 (s, 2H); 6.95 (s, 1H); 2.78 (d, J=6.0 Hz, 1H); 2.76 (d, J=6.0 Hz, 1H); 1.20 (s, 3H); 0.96 (s, 3H).

Example 12

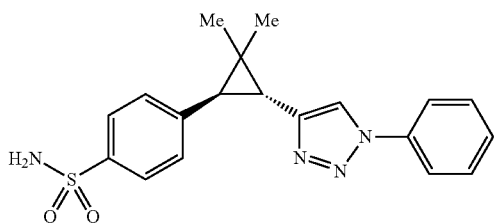 [SMILES: CC1(C)[C@H](c2ccc(S(N)(=O)=O)cc2)[C@H]1c1cn(-c2ccccc2)nn1]

4-[(1R,3R)-2,2-Dimethyl-3-(1-phenyl-1H-1,2,3-triazol-4-yl)cyclopropyl]benzenesulfonamide To a solution of 4-[(1R,3S)-3-ethynyl-2,2-dimethylcyclopropyl]benzenesulfonamide (Intermediate 13) (30 mg, 0.120 mmol), cupric sulfate (3.84 mg, 0.024 mmol) and sodium 2-(1,2-dihydroxyethyl)-4-hydroxy-5-oxo-2,5-dihydrofuran-3-olate (4.8 mg, 0.024 mmol) in methanol (1.0 mL) at ambient temperature was added a solution of azidobenzene (0.5 M in tert-butyl methyl ether, 0.722 mL, 0.361 mmol). The reaction mixture was allowed to stir at ambient temperature for 1 h and warmed to 50° C. and allowed to stir for 1 h. The reaction mixture was diluted with water (30 mL) and ethyl acetate (30 mL). The phases were separated and the aqueous phase extracted with ethyl acetate (2×30 mL). The combined organic extracts were washed with saturated aqueous sodium chloride (15 mL), dried (magnesium sulfate) and concentrated under reduced pressure. The residue was purified by preparative HPLC, eluting with a gradient of acetonitrile:water:trifluoroacetic acid—35:65:0.1 to 65:35:0.1 to afford the title compound. MS: m/z=369.1 [M+H]. $^1$H NMR (400 MHz, CD$_3$OD): δ 8.45 (s, 1H); 7.86 (m, 4H); 7.58 (m, 2H); 7.48 (m, 3H); 2.72 (d, J=6.0 Hz, 1 H); 2.57 (d, J=6.0 Hz, 1H); 1.17 (s, 3H); 1.00 (s, 3H).

Example 13

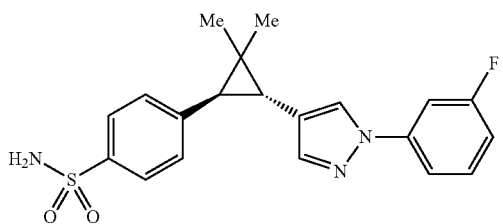 [SMILES: CC1(C)[C@H](c2ccc(S(N)(=O)=O)cc2)[C@H]1c1cnn(-c2cccc(F)c2)c1]

4-{(1R,3R)-3-[1-(3-Fluorophenyl)-1H-pyrazol-4-yl]-2,2-dimethylcyclopropyl}benzenesulfonamide Step A: N-[(Dimethylamino)methylidene]-4-{(1R,3R)-3-[1-(3-fluorophenyl)-1H-pyrazol-4-yl]-2,2-dimethylcyclopropyl}benzenesulfonamide To solution of N-[(dimethylamino)methylidene]-4-{(1R,3R)-3-[1-(dimethylamino)-3-oxoprop-1-en-2-yl]-2,2-dimethylcyclopropyl}benzenesulfonamide (Intermediate 14) (200 mg, 0.530 mmol) and (3-fluorophenyl)hydrazine (100 mg, 0.795 mmol) in methanol (3 mL) was added aqueous HCl (3 M, 0.530 mL, 1.59 mmol) at ambient temperature. The reaction mixture was warmed to 60° C. and allowed to stir for 30 min. The reaction mixture was adjusted to pH 8 with saturated aqueous sodium bicarbonate and diluted with water (20 mL) and dichloromethane (20 mL). The phases were separated and the aqueous phase extracted with dichloromethane (2×20 mL). The combined organic extracts were washed with saturated aqueous sodium chloride (15 mL), dried (magnesium sulfate) and concentrated under reduced pressure to afford the title compound. MS: m/z=441.2 [M+H].

Step B: 4-{(1R,3R)-3-[1-(3-Fluorophenyl)-1H-pyrazol-4-yl]-2,2-dimethylcyclopropyl}benzenesulfonamide To a solution of N-[(dimethylamino)methylidene]-4-{(1R,3R)-3-[1-(3-fluorophenyl)-1H-pyrazol-4-yl]-2,2-dimethylcyclopropyl}benzenesulfonamide (200 mg, 0.454 mmol) in methanol (1 mL) at ambient temperature was added hydrazine hydrate (114 mg, 2.27 mmol) and the reaction mixture allowed to stir for 1 h. The reaction mixture was directly purified by preparative HPLC, eluting with a gradient of acetonitrile:water:trifluoroacetic acid—40:60:0.1 to 60:40:0.1 to give the title compound. MS: m/z=386.1 [M+H]. $^1$H NMR (400 MHz, CD$_3$OD): δ 8.18 (s, 1H); 7.84 (d, J=8.0 Hz, 2H); 7.66 (s, 1H); 7.55 (t, J=8.0 Hz, 2 H); 7.46 (m, 3H); 7.02 (t, J=8.0 Hz, 1H); 2.41 (d, J=6.0 Hz, 1H); 2.34 (d, J=6.0 Hz, 1H); 1.13 (s, 3H); 0.94 (s, 3H).

Example 14

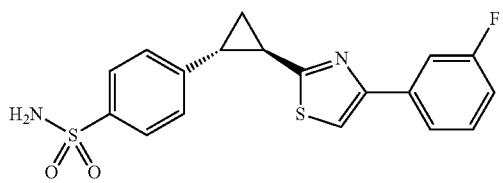 [SMILES: NS(=O)(=O)c1ccc([C@@H]2C[C@H]2c2nc(-c3cccc(F)c3)cs2)cc1]

4-{(1R,2R)-2-[4-(3-Fluorophenyl)-1,3-thiazol-2-yl]cyclopropyl}benzenesulfonamide To a solution of (1R,2R)-2-(4-sulfamoylphenyl)cyclopropanecarbothioamide (Intermediate 12) (100 mg, 0.39 mmol) in ethanol (3.9 mL) was added 2-bromo-1-(3-fluorophenyl)ethanone (85 mg, 0.39 mmol) and the reaction mixture warmed to 75° C. and allowed to stir for 2 h. The reaction mixture was cooled to ambient temperature, saturated aqueous sodium bicarbonate (5 mL) was added, and the resulting mixture extracted with ethyl acetate (3×10 mL). The combined organic extracts were dried (sodium sulfate) and concentrated under reduced pressure. The residue was purified by preparative HPLC, eluting with a gradient of acetonitrile:water:trifluoroacetic acid—15:85:0.1 to 95:5:0.1 to afford the title compound. MS: m/z=375.2 [M+H]. $^1$H NMR (500 MHz, DMSO-d$_6$): δ 8.04 (s, 1H); 7.80 (d, J=7.9 Hz, 1H); 7.73-7.76 (m, 4H); 7.46-7.50 (m, 1H); 7.43 (d, J=8.0 Hz, 2H); 7.30 (s, 2H); 7.15-7.19 (m, 1H); 2.88-2.92 (m, 1H); 2.70-2.73 (m, 1H); 1.84-1.88 (m, 1H); 1.73-1.76 (m, 1 H).

Example 15

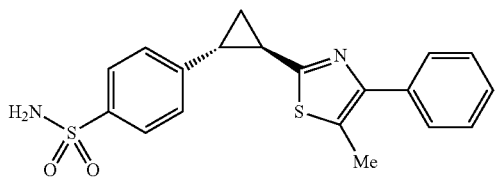 [SMILES: Cc1sc([C@@H]2C[C@H]2c2ccc(S(N)(=O)=O)cc2)nc1-c1ccccc1]

4-[(1R,2R)-2-(5-Methyl-4-phenyl-1,3-thiazol-2-yl)cyclopropyl]benzenesulfonamide

To a solution of (1R,2R)-2-(4-sulfamoylphenyl)cyclopropanecarbothioamide (Intermediate 12) (50 mg, 0.20 mmol) in ethanol (2.0 mL) was added 2-bromo-1-phenylpropan-1-one (30 µL, 0.20 mmol) and the reaction mixture warmed to 75° C. and allowed to stir for 15 h. The reaction mixture was cooled to ambient temperature, saturated aqueous sodium bicarbonate (5 mL) was added, and the resulting mixture extracted with ethyl acetate (3×5 mL). The combined organic extracts were dried (sodium sulfate) and concentrated under reduced pressure. The residue was purified by preparative HPLC, eluting with a gradient of acetonitrile:water:trifluoroacetic acid—15:85:0.1 to 95:5:0.1. The product-containing fractions were combined and concentrated under reduced pressure. Further purification was achieved by washing the solid residue with dichloromethane to afford the title compound. MS: m/z=371.2 [M+H]. $^1$H NMR (500 MHz, DMSO-$d_6$): δ 7.73 (d, J=8.0 Hz, 2H); 7.65 (d, J=7.7 Hz, 2H); 7.46 (t, J=7.6 Hz, 2H); 7.41 (d, J=8.1 Hz, 2H); 7.34-7.37 (m, 1H); 7.30 (s, 1H); 2.75-2.78 (m, 1H); 2.60-2.64 (m, 1H); 1.75-1.79 (m, 1H); 1.67-1.70 (m, 1H).

Example 16

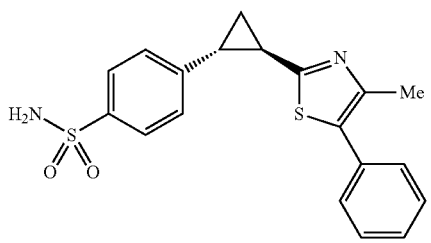 [SMILES: Cc1nc([C@@H]2C[C@H]2c2ccc(S(N)(=O)=O)cc2)sc1-c1ccccc1]

4-[(1R,2R)-2-(4-Methyl-5-phenyl-1,3-thiazol-2-yl)cyclopropyl]benzenesulfonamide

To a solution of (1R,2R)-2-(4-sulfamoylphenyl)cyclopropanecarbothioamide (Intermediate 12) (50 mg, 0.20 mmol) in ethanol (2.0 mL) was added 1-bromo-1-phenylpropan-2-one (37.4 mg, 0.176 mmol) and the reaction mixture warmed to 75° C. and allowed to stir for 22 h. The reaction mixture was cooled to ambient temperature, saturated aqueous sodium bicarbonate (5 mL) was added, and the resulting mixture extracted with ethyl acetate (3×5 mL). The combined organic extracts were dried (sodium sulfate) and concentrated under reduced pressure. The residue was purified by preparative HPLC, eluting with a gradient of acetonitrile:water:trifluoroacetic acid—15:85:0.1 to 95:5:0.1 to afford the title compound. MS: m/z=371.2 [M+H]. $^1$H NMR (500 MHz, DMSO-$d_6$): δ 7.73 (d, J=8.0 Hz, 2H); 7.45-7.46 (m, 4 H); 7.41 (d, J=8.2 Hz, 3H); 7.38 (s, 1H); 7.29 (s, 2H); 2.76-2.80 (m, 1H); 2.61-2.64 (m, 1H); 2.38 (s, 3H); 1.76-1.80 (m, 1H); 1.68-1.72 (m, 1H).

Example 17

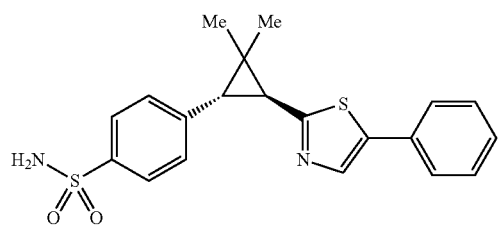 [SMILES: CC1(C)[C@@H](c2ccc(S(N)(=O)=O)cc2)[C@@H]1c1ncc(-c2ccccc2)s1]

4-[(1S,3S)-2,2-Dimethyl-3-(5-phenyl-1,3-thiazol-2-yl)cyclopropyl]benzenesulfonamide Step A: (1S,2S)-2,2-Dimethyl-N-(2-oxo-2-phenylethyl)-3-(4-sulfamoylphenyl) cyclopropanecarboxamide To a solution of (1S,3S)-2,2-dimethyl-3-(4-sulfamoylphenyl)cyclopropanecarboxylic acid (Intermediate 5) (100 mg, 0.371 mmol) in dichloromethane (1.1 mL) and dimethyl sulfoxide (0.12 mL) at ambient temperature were added HATU (155 mg, 0.408 mmol), 2-amino-1-phenylethanone hydrogen chloride (67 mg, 0.39 mmol), and N-methylmorpholine (0.12 mL, 1.1 mmol) sequentially and the reaction mixture allowed to stir for 2 h. Saturated aqueous sodium bicarbonate (5 mL) was added and the resulting mixture extracted with ethyl acetate (3×5 mL). The combined organic extracts were dried (sodium sulfate), filtered, and concentrated under reduced pressure. The residue was purified by silica gel chromatography, eluting with a gradient of ethyl acetate:hexanes—0:100 to 75:25 to afford the title compound. MS: m/z=387.3 [M+H].

Step B: 4-[(1S,3S)-2,2-Dimethyl-3-(5-phenyl-1,3-thiazol-2-yl)cyclopropyl]benzenesulfonamide To a solution of (1S,3S)-2,2-dimethyl-N-(2-oxo-2-phenylethyl)-3-(4-sulfamoylphenyl)cyclopropanecarboxamide (90 mg, 0.23 mmol) in toluene (1.9 mL) and tetrahydrofuran (0.47 mL) was added Lawesson's reagent (99 mg, 0.25 mmol) and the reaction mixture was warmed to 100° C. and allowed to stir for 3.5 h. Water (2 mL) was added and the resulting mixture extracted with ethyl acetate (3×5 mL). The combined organic extracts were dried (sodium sulfate) and concentrated under reduced pressure. The residue was purified first by silica gel chromatography, eluting with a gradient of ethyl acetate:hexanes—0:100 to 75:25 and then by preparative HPLC, eluting with a gradient of acetonitrile:water:trifluoroacetic acid—15:85:0.1 to 95:5:0.1 to afford the title compound. MS: m/z=385.3 [M+H]. $^1$H NMR (500 MHz, DMSO-$d_6$): δ 8.10 (s, 1H); 7.77 (d, J=8.0 Hz, 2H); 7.64 (d, J=7.6 Hz, 2H); 7.53 (d, J=8.0 Hz, 2H); 7.44 (t, J=7.6 Hz, 2H); 7.35 (t, J=7.6 Hz, 1H); 7.32 (s, 2H); 3.06 (d, J=6.1 Hz, 1 H); 2.92 (d, J=6.1 Hz, 1H); 1.22 (s, 3H); 0.97 (s, 3H).

Example 18

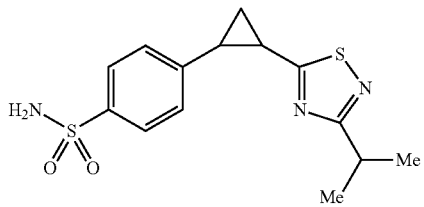 [SMILES: CC(C)c1nsc(C2CC2c2ccc(S(N)(=O)=O)cc2)n1]

4-{trans-2-[3-(Propan-2-yl)-1,2,4-thiadiazol-5-yl]
cyclopropyl}benzenesulfonamide, enantiomer B Step A: 5-(2-Phenylcyclopropyl)-3-(propan-2-yl)-1,
2,4-thiadiazole To a solution of 5-chloro-3-isopropyl-1,2,4-thiadiazole (1.00 g, 6.15 mmol) in 1,4-dioxane (22 mL) were added (2-phenylcyclopropyl)boronic acid (1.49 g, 9.22 mmol) and cesium carbonate (4.01 g, 12.3 mmol). The mixture was deoxygenated with nitrogen and $PdCl_2$(dppf)-$CH_2Cl_2$ adduct (753 mg, 0.922 mmol) was added. The reaction mixture was warmed to 100° C. and allowed to stir for 3.5 h. The reaction mixture was cooled to ambient temperature and filtered through a plug of Celite, rinsing with ethyl acetate. The filtrate was concentrated under reduced pressure and the resulting residue purified by silica gel chromatography, eluting with a gradient of ethyl acetate:hexanes—0:100 to 90:10 to afford the title compound. MS: m/z=245.1 [M+H].

Step B: 4-{trans-2-[3-(Propan-2-yl)-1,2,4-thiadiazol-5-yl]cyclopropyl}benzenesulfonamide, enantiomer B To a solution of 5-(2-phenylcyclopropyl)-3-(propan-2-yl)-1,2,4-thiadiazole (1.01 g, 4.13 mmol) in methylene chloride (8.0 mL) at 0° C. was added chlorosulfonic acid (4.0 mL, 60 mmol) and the mixture allowed to slowly warm to ambient temperature and stir for 1.5 h. The reaction mixture was added dropwise into ice water and the organic layer separated and concentrated under reduced pressure. The residue was dissolved in 1,4-dioxane (8.0 mL) and cooled to 0° C. Ammonium hydroxide (2.9 mL, 20.7 mmol) was added slowly and the reaction mixture allowed to stir at ambient temperature for 30 min. Water (10 mL) was added and the resulting mixture extracted with ethyl acetate (3×10 mL). The combined organic extracts were dried (sodium sulfate) and the concentrated under reduced pressure. The residue was purified by silica gel chromatography, eluting with a gradient of ethyl acetate:hexanes—0:100 to 100:10 to afford the title compound. The racemate was resolved by SFC, utilizing a ChiralPak AD-H column, eluting with ethanol:carbon dioxide:isopropylamine—55:45:0.3. The first major peak to elute was 4-{trans-2-[3-(propan-2-yl)-1, 2,4-thiadiazol-5-yl]cyclopropyl}benzenesulfonamide, enantiomer A, and the second compound to elute was 4-{trans-2-[3-(propan-2-yl)-1,2,4-thiadiazol-5-yl] cyclopropyl}benzenesulfonamide, enantiomer B, the title compound. MS: m/z=324.1 [M+H]. $^1$H NMR (500 MHz, DMSO-$d_6$): δ 7.74 (d, J=8.0 Hz, 2H); 7.42 (d, J=8.0 Hz, 2 H); 7.31 (s, 2H); 3.16-3.22 (m, 1H); 3.09-3.14 (m, 1H); 2.71-2.75 (m, 1H); 1.80-1.85 (m, 2 H); 1.30 (d, J=6.9 Hz, 6H).

Example 19

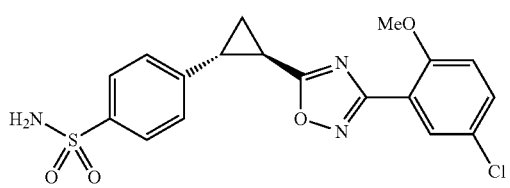 [SMILES: COc1ccc(Cl)cc1-c1noc([C@@H]2C[C@H]2c2ccc(S(N)(=O)=O)cc2)n1]

4-{(1R,2R)-2-[3-(5-Chloro-2-methoxyphenyl)-1,
2,4-oxadiazol-5-yl]cyclopropyl}benzenesulfonamide Step A: 3-(5-Chloro-2-methoxyphenyl)-5-(trans-2-phenylcyclopropyl)-1,2,4-oxadiazole To a solution of trans-2-phenylcyclopropanecarboxylic acid (487 mg, 3.00 mmol) in 1,4-dioxane (10 mL) was added 1,1'-carbonyldiimidazole (535 mg, 3.30 mmol). The reaction mixture was warmed to 45° C. and allowed to stir for 2 h. 5-Chloro-N'-hydroxy-2-methoxybenzimidamide (Intermediate A1) (602 mg, 3.00 mmol) was then added and the reaction mixture warmed to 100° C. and allowed to stir for 18 h. The reaction mixture was allowed to cool and then concentrated under reduced pressure. The residue was purified by silica gel chromatography, eluting with a gradient of ethyl acetate:hexanes—0:100 to 50:50 to afford the title compound. MS: m/z=327.4 [M+H].

Step B: 4-{(1R,2R)-2-[3-(5-Chloro-2-methoxyphenyl)-1,2,4-oxadiazol-5-yl]
cyclopropyl}benzenesulfonamide To a flask containing 3-(5-chloro-2-methoxyphenyl)-5-(trans-2-phenylcyclopropyl)-1,2,4-oxadiazole (732 mg, 2.24 mmol) at 0° C. was added cold chlorosulfonic acid (3.00 mL, 44.8 mmol). The reaction mixture was allowed to warm to ambient temperature and stir for 1 h. The reaction mixture was poured over ice water (20 mL) and extracted with ethyl acetate (3×20 mL). The combined organic extracts were concentrated under reduced pressure, the residue dissolved in 1,4-dioxane (20 mL), and ammonium hydroxide (30%, 7.00 mL, 50.3 mmol) was added. The reaction mixture was allowed to stir for 2 h and then concentrated under reduced pressure. The residue was taken up in ethyl acetate (30 mL), washed with water (20 mL), dried (magnesium sulfate), and concentrated under reduced pressure. The residue was purified by silica gel chromatography, eluting with a gradient of ethyl acetate:hexanes—5:95 to 100:0 to afford the title compound. MS: m/z=406.2 [M+H]. The racemate was resolved by SFC, utilizing a ChiralPak AD-H column, eluting with methanol:carbon dioxide—50:50. The first major peak to elute was 4-{(1S,2S)-2-[3-(5-chloro-2-methoxyphenyl)-1,2,4-oxadiazol-5-yl] cyclopropyl}benzenesulfonamide and the second major peak to elute was 4-{(1R,2R)-2-[3-(5-chloro-2-methoxyphenyl)-1,2,4-oxadiazol-5-yl] cyclopropyl}benzenesulfonamide, the title compound. MS: m/z=406.2 [M+H]. $^1$H NMR (500 MHz, DMSO-$d_6$): δ 7.82 (d, J=2.7 Hz, 1H); 7.75 (d, J=8.5 Hz, 2H); 7.61 (dd, J=2.7, 9.0 Hz, 1H); 7.48 (d, J=8.5 Hz, 2H); 7.33 (s, 2H); 7.27 (d, J=9.0 Hz, 1H); 3.89 (s, 3H), 2.91-2.83 (m, 2H); 1.91-1.84 (m, 2H).

Example 20

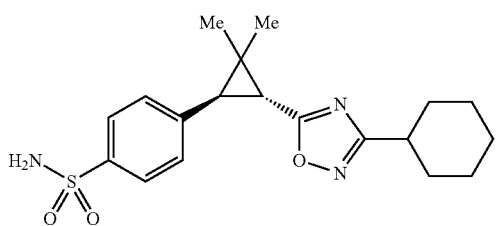 [SMILES: CC1(C)[C@H](c2ccc(S(N)(=O)=O)cc2)[C@H]1c1nc(C2CCCCC2)no1]

4-((1R,3R)-3-(3-Cyclohexyl-1,2,4-oxadiazol-5-yl)-2, 2-dimethylcyclopropyl)benzenesulfonamide To a solution of (1R,3R)-2,2-dimethyl-3-(4-sulfamoylphenyl)cyclopropanecarboxylic acid (Intermediate 4) (162 mg, 0.602 mmol) in 1,4-dioxane (3 mL) was added 1,1'-carbonyldiimidazole (107 mg, 0.660 mmol). The reaction mixture was warmed to 45° C. and allowed to stir for 2 h. N'-Hydroxycyclohexanecarboximidamide (85 mg, 0.600 mmol) was then added and the reaction mixture warmed to 105° C. and allowed to stir for 4 h. The reaction mixture was cooled to ambient temperature and purified directly by silica gel chromatography, eluting with a gradient of ethyl acetate: ethanol:hexanes—3:1:96 to 36:13:51 to afford the title compound. MS: m/z=376.3 [M+H]. $^1$H NMR (500 MHz, DMSO-$d_6$): δ 7.78 (d, J=8.3 Hz, 2H); 7.53 (d, J=8.3 Hz, 2 H); 7.34 (s, 2H); 2.95 (d, J=6.1 Hz, 1H); 2.90 (d, J=6.1 Hz, 1H); 2.80-2.74 (m, 1H); 1.93 (br d, J=12 Hz, 2H); 1.73 (br d, J=13 Hz, 2H); 1.65 (br d, J=9.0 Hz, 1H); 1.49 (br q, J=12 Hz, 2H); 1.37 (br q, J=12 Hz, 2H); 1.28-1.22 (m, 1H); 1.26 (s, 3H); 0.96 (s, 3H).

Example 21

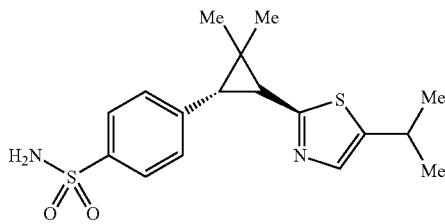

4-{(1S,3S)-2,2-Dimethyl-3-[5-(propan-2-yl)-1,3-thiazol-2-yl]cyclopropyl}benzenesulfonamide Step A: (1S,3S)-2,2-Dimethyl-N-(3-methyl-2-oxobutyl)-3-(4-sulfamoylphenyl) cyclopropanecarboxamide To a solution of (1S,3S)-2,2-dimethyl-3-(4-sulfamoylphenyl)cyclopropanecarboxylic acid (Intermediate 5) (100 mg, 0.371 mmol) in dichloromethane (1.14 mL) and dimethyl sulfoxide (124 μL) were added HATU (155 mg, 0.408 mmol), 1-amino-3-methylbutan-2-one hydrochloride (53.6 mg, 0.390 mmol), and N-methylmorpholine (122 μL, 1.11 mmol). The reaction mixture was allowed to stir at ambient temperature for 2 h. The reaction mixture was concentrated under reduced pressure and the resulting residue purified by preparative HPLC, eluting with a gradient of acetonitrile: water:trifluoroacetic acid—15:85:0.1 to 95:5:0.1 to afford the title compound. MS: m/z=353.3 [M+H].

Step B: 4-{(1S,3S)-2,2-Dimethyl-3-[5-(propan-2-yl)-1, 3-thiazol-2-yl] cyclopropyl}benzenesulfonamide To a solution of (1S,3S)-2,2-dimethyl-N-(3-methyl-2-oxobutyl)-3-(4-sulfamoylphenyl)cyclopropanecarboxamide (95 mg, 0.27 mmol) in toluene (2.2 mL) and tetrahydrofuran (0.54 mL) was added Lawesson's reagent (114 mg, 0.283 mmol). The reaction mixture was warmed to 100° C. and allowed to stir for 2 h. The reaction mixture was cooled, water added (10 mL), and the resulting mixture extracted with ethyl acetate (3×15 mL). The combined organic extracts were dried (sodium sulfate) and concentrated under reduced pressure. The residue was purified by preparative HPLC, eluting with a gradient of acetonitrile:water:trifluoroacetic acid—15:85:0.1 to 95:5:0.1 and the product containing fractions were concentrated under reduced pressure. The residue was taken up in methanol (5 mL) and treated with MP-carbonate. The mixture was allowed to stir for 20 min. The mixture was filtered and concentrated under reduced pressure to afford the title compound. MS: m/z= [M+H]. $^1$H NMR (500 MHz, DMSO-$d_6$): δ 7.75 (d, J=8.0 Hz, 2H); 7.49 (d, J=8.0 Hz, 2H); 7.41 (s, 1H); 7.30 (s, 2H); 3.18 (m, 1H); 2.93 (d, J=6.1 Hz, 1H); 2.81 (d, J=6.1 Hz, 1H); 1.27 (d, J=6.8 Hz, 6H); 1.16 (s, 3H); 0.92 (s, 3H).

Example 22

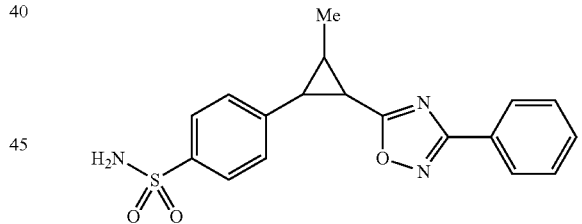

4-(2-Methyl-3-(3-phenyl-1, 2,4-oxadiazol-5-yl)cyclopropyl)benzenesulfonamide, diastereomer 4

To a solution of 2-methyl-3-(4-sulfamoylphenyl)cyclopropanecarboxylic acid, diastereomer 4 (Intermediate 15) (25 mg, 0.098 mmol) in 1,4-dioxane (0.5 mL) was added 1,1'-carbonyldiimidazole (19.1 mg, 0.118 mmol) and the reaction mixture warmed to 50° C. and allowed to stir for 2 h. N'-hydroxybenzimidamide (14.7 mg, 0.108 mmol) was then added and the reaction mixture warmed to 120° C. and allowed to stir for 4 h. The reaction mixture was then cooled to ambient temperature, concentrated under reduced pressure, and the resulting residue purified by silica gel chromatography, eluting with a gradient of ethyl acetate: hexanes—5:95 to 50:50 to afford the title compound. MS: m/z=356.2 [M+H]. $^1$H NMR (500 MHz, $d_6$-DMSO): δ 7.99 (d, J=6.4 Hz, 2H); 7.79 (d, J=8.2 Hz, 2H); 7.63-7.55 (m, 5H); 7.35 (s, 2 H); 3.11 (dd, J=9.8, 5.2 Hz, 1H); 3.01 (t, J=5.0 Hz, 1H); 2.12-2.07 (m, 1H); 1.00 (d, J=6.1 Hz, 3H).

Example 23

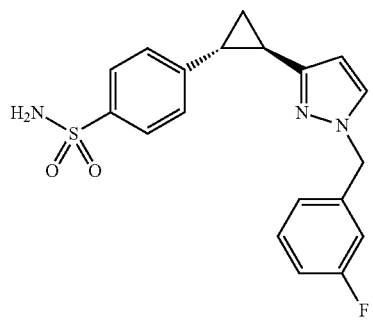 [SMILES: NS(=O)(=O)c1ccc([C@@H]2C[C@H]2c2ccn(Cc3cccc(F)c3)n2)cc1]

4-{(1R,2R)-2-[1-(3-Fluorobenzyl)-1H-pyrazol-3-yl]cyclopropyl}benzenesulfonamide

To a solution of N-[(dimethylamino)methylidene]-4-[(1R,2R)-2-(1H-pyrazol-3-yl)cyclopropyl]benzenesulfonamide (Intermediate 17) (25 mg, 0.079 mmol) in N,N-dimethylformamide (0.785 mL) at ambient temperature were added a solution of NaHMDS (1.0 M in tetrahydrofuran, 0.079 mL, 0.079 mmol) in toluene and 3-fluorobenzyl chloride (14 mg, 0.094 mmol) sequentially. The reaction mixture was allowed to stir for 18 h. The reaction mixture was concentrated under reduced pressure and the resulting residue treated with a solution of hydrazine hydrate (28% in ethanol/water, 1.0 mL, 8.8 mmol) and allowed to stir for 1.5 h. The reaction mixture was concentrated under reduced pressure and the resulting residue purified by preparative HPLC, eluting with a gradient of acetonitrile:water:trifluoroacetic acid—5:95:0.1 to 55:45:0.1 to give the title compound. MS: m/z=372.5 [M+H]. $^1$H NMR (500 MHz, DMSO-$d_6$): δ 7.74 (s, 1H); 7.69 (d, J=8.1 Hz, 2H); 7.38 (m, 1H); 7.31 (d, J=7.9 Hz, 2H); 7.26 (s, 2H); 7.11 (m, 1H); 7.03 (m, 2H); 6.12 (s, 1H); 5.27 (s, 2H); 2.25 (m, 2H); 1.45 (m, 2H).

Example 24

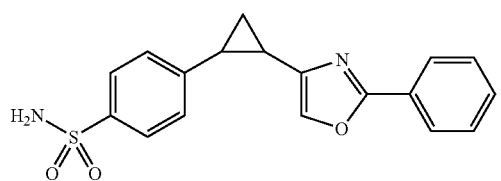 [SMILES: NS(=O)(=O)c1ccc(C2CC2c2coc(-c3ccccc3)n2)cc1]

4-[trans-2-(2-Phenyl-1,3-oxazol-4-yl)cyclopropyl]benzenesulfonamide

To a solution of N-[(dimethylamino)methylidene]-4-[trans-2-(4,4,5,5-tetramethyl-1,3,2-dioxaborolan-2-yl)cyclopropyl]benzenesulfonamide (Intermediate 16) (30 mg, 0.079 mmol) in toluene (0.79 mL) were added 4-bromo-2-phenyloxazole (31 mg, 0.12 mmol), chloro[(di(1-adamantyl)-N-butylphosphine)-2-(2-aminobiphenyl)]palladium(II) (5.3 mg, 0.0079 mmol) and an aqueous solution of tribasic potassium phosphate (1 M, 0.238 mL, 0.238 mmol) sequentially. The reaction mixture was warmed to 100° C. and allowed to stir for 18 h. The reaction mixture was diluted with ethyl acetate (3 mL), filtered through an SPE cartridge containing celite, and the filtrate concentrated under reduced pressure. The residue was treated with a solution of hydrazine hydrate (37% in water/ethanol, 1.5 mL, 17.6 mmol) and allowed to stir for 1.5 h. The reaction mixture was concentrated under reduced pressure and the resulting residue was purified by preparative HPLC, eluting with a gradient of acetonitrile:water:trifluoroacetic acid—20:80:0.1 to 60:40:0.1 to give the title compound. MS: m/z=341.1 [M+H]. $^1$H NMR (500 MHz, DMSO-$d_6$): δ 8.07 (s, 1H); 7.95 (s, 2H); 7.23 (d, J=7.9 Hz, 2H); 7.53 (m, 3H); 7.37 (d, J=8.3 Hz, 2H); 7.28 (s, 2H); 6.12 (s, 1H); 5.27 (s, 2 H); 2.54 (m, 2H); 1.45 (m, 2H); 2.42 (m, 1H); 2.32 (m, 1H); 1.60 (m, 1H), 1.50 (m, 1H).

Example 25

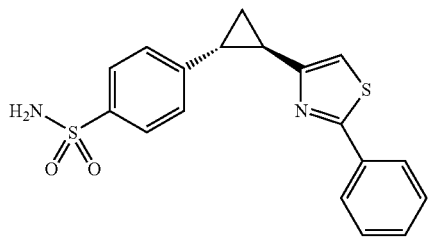 [SMILES: NS(=O)(=O)c1ccc([C@@H]2C[C@H]2c2csc(-c3ccccc3)n2)cc1]

4-[(1R,2R)-2-(2-Phenyl-1,3-thiazol-4-yl)cyclopropyl]benzenesulfonamide

To a solution of 4-[(1R,2R)-2-(2-chloroacetyl)cyclopropyl]benzenesulfonamide (Intermediate 18) (100 mg, 0.37 mmol) in ethanol (5 mL) was added benzenecarbothioamide (60 mg, 0.44 mmol) and the reaction mixture warmed to 60° C. and allowed to stir 30 min. The reaction mixture was concentrated under reduced pressure and the resulting residue purified by preparative HPLC, eluting with a gradient of acetonitrile:water:ammonium hydroxide—10:90:0.05 to 90:10:0.05 to afford the title compound. MS: m/z=357.1 [M+H]. $^1$H NMR (400 MHz, CD$_3$OD): δ 7.90-7.92 (m, 2H), 7.79 (d, J=7.60 Hz, 2H), 7.43-7.45 (m, 3H), 7.33 (d, J=8.8 Hz, 2H), 7.19 (s, 1H), 2.40-2.51 (m, 2H), 1.66-1.72 (m, 1H), 1.56-1.62 (m, 1H).

Example 26

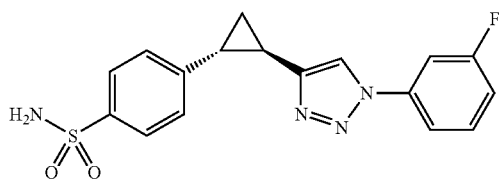 [SMILES: NS(=O)(=O)c1ccc([C@@H]2C[C@H]2c2cn(-c3cccc(F)c3)nn2)cc1]

4-{(1R,2R)-2-[1-(3-Fluorophenyl)-1H-1,2,3-triazol-4-yl]cyclopropyl}benzenesulfonamide To a solution of 4-[(1R,2R)-2-ethynylcyclopropyl]benzenesulfonamide (Intermediate 19) (50 mg, 0.226 mmol) in methanol (2 mL) at ambient temperature was added copper (II) sulfate (7.2 mg, 0.045 mmol), sodium 2-(1,2-dihydroxyethyl)-4-hydroxy-5-oxo-2,5-dihydro-furan-3-olate (9.0 mg, 0.045 mmol), and 1-azido-3-fluorobenzene (31 mg, 0.23 mmol) sequentially. The reaction mixture was allowed to stir for 1 h. The reaction mixture was filtered, and the filtrate was concentrated under reduced pressure and the resulting residue purified by preparative HPLC, eluting with a gradient of acetonitrile:water:ammonium hydroxide—26:74:0.05 to 56:44:0.05 to afford the title compound. MS: m/z=359.1 [M+H]. $^1$H NMR (400 MHz, CD$_3$OD): δ 8.34 (s, 1H); 7.83 (m, 4H); 7.32 (m, 4H); 2.47 (m, 1H); 2.42 (m, 1 H); 1.69 (m, 1H); 1.59 (m, 1H).

Example 27

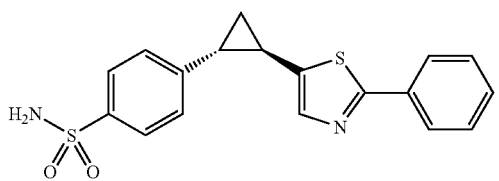 [SMILES: NS(=O)(=O)c1ccc([C@@H]2C[C@H]2c2cnc(-c3ccccc3)s2)cc1]

4-[(1R,2R)-2-(2-Phenyl-1,3-thiazol-5-yl)cyclopropyl]benzenesulfonamide

Step A: tert-Butyl tert-butyl[(4-{(1R,2R)-2-[(2-oxo-2-phenylethyl)carbamoyl]cyclopropyl}phenyl)sulfonyl]carbamate To a stirred mixture of tert-butyl tert-butyl[(4-{(1R,2R)-2-[(R)-glycyl]cyclopropyl}phenyl)sulfonyl]carbamate (Intermediate 20) (125 mg, 0.304 mmol) and potassium carbonate (842 mg, 6.09 mmol) in ethyl acetate (5 mL) and water (5 mL) at ambient temperature was added benzoyl chloride (856 mg, 6.09 mmol) dropwise. The reaction mixture was allowed to stir for 10 min and then diluted by water (50 mL) and ethyl acetate (50 mL). The organic layer was separated and concentrated under reduced pressure. The residue was purified by preparative silica gel thin layer chromatography, eluting with ethyl acetate:petroleum ether—50:50 to afford the title compound to afford the title compound. MS: m/z=537.1 [M+Na].

Step B: tert-Butyl tert-butyl({4-[(1R,2R)-2-(2-phenyl-1,3-thiazol-5-yl)cyclopropyl]phenyl}sulfonyl)carbamate To a stirred solution of tert-butyl tert-butyl[(4-{(1R,2R)-2-[(R)—N-(phenylcarbonyl)glycyl]cyclopropyl}phenyl)sulfonyl]carbamate (92 mg, 0.18 mmol) in toluene (3 mL) at ambient temperature was added Lawesson's reagent (72.3 mg, 0.179 mmol). The reaction mixture was warmed to 70° C. and allowed to stir for 1 h. The solvent was removed under reduced pressure to afford the title compound in sufficient purity for use in the next step. MS: m/z=513.2 [M+H].

Step C: 4-[(1R,2R)-2-(2-Phenyl-1,3-thiazol-5-yl)cyclopropyl]benzenesulfonamide

To a solution of tert-butyl tert-butyl({4-[(1R,2R)-2-(2-phenyl-1,3-thiazol-5-yl)cyclopropyl]phenyl}sulfonyl)car-
bamate (92 mg, 0.18 mmol) in dichloromethane (1 mL) at ambient temperature was added trifluoroacetic acid (2.00 mL, 26.0 mmol) dropwise. The reaction mixture was allowed to stir for 1 h. The reaction mixture was concentrated under reduced pressure and saturated aqueous sodium bicarbonate (10 mL) and dichloromethane (5 mL) were added. The combined organic extracts were washed with saturated aqueous sodium chloride (15 mL), dried (magnesium sulfate), and concentrated under reduced pressure. The residue was purified by preparative HPLC, eluting with a gradient of acetonitrile:water:ammonium hydroxide—10:90:0.05 to 90:10:0.05 to afford the title compound. MS: m/z=357.1 [M+H]. $^1$H NMR (CD$_3$OD, 400 MHz): δ 7.83 (m, 4H); 7.61 (s, 1H); 7.44 (m, 3H); 7.33 (d, J=8.4 Hz, 2H); 2.52 (m, 1H); 2.39 (m, 1H); 1.67 (m, 1H); 1.61 (m, 1H).

Example 28

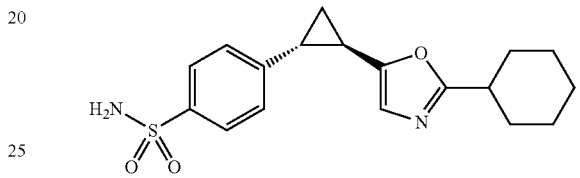

4-[(1R,2R)-2-(2-Cyclohexyl-1,3-oxazol-5-yl)cyclopropyl]benzenesulfonamide

Step A: tert-Butyl tert-butyl[(4-{(1R,2R)-2-[(R)—N-(cyclohexylcarbonyl)glycyl]cyclopropyl}phenyl)sulfonyl]carbamate To a stirred mixture of tert-butyl tert-butyl[(4-{(1R,2R)-2-[(R)-glycyl]cyclopropyl}phenyl)sulfonyl]carbamate (Intermediate 20) (300 mg, 0.73 mmol) and potassium carbonate (2.02 g, 14.6 mmol) in ethyl acetate (5 mL) and water (5 mL) at ambient temperature was added cyclohexanecarbonyl chloride (2.14 g, 14.6 mmol) dropwise. The mixture was allowed to stir for 10 min, then diluted with water (50 mL) and ethyl acetate (50 mL). The organic layer was separated, dried (magnesium sulfate), and concentrated under reduced pressure. The residue was purified by silica gel chromatography, eluting with ethyl acetate:petroleum ether—50:50 to afford the title compound. MS: m/z=543.0 [M+Na].

Step B: N-tert-Butyl-4-[(1R,2R)-2-(2-cyclohexyl-1,3-oxazol-5-yl)cyclopropyl]benzenesulfonamide To a stirred solution of tert-butyl tert-butyl[(4-{(1R,2R)-2-[(R)—N-(cyclohexylcarbonyl)glycyl]cyclopropyl}phenyl)sulfonyl]carbamate (120 mg, 0.23 mmol) in tetrahydrofuran (1 mL) at ambient temperature was added phosphyorl chloride (0.64 mL, 6.9 mmol) dropwise. The mixture was warmed to 70° C. and allowed to stir for 1 h. Saturated aqueous sodium bicarbonate (10 mL) was added and the resulting mixture extracted with ethyl acetate (5 mL). The organic layer was separated, dried (magnesium sulfate), and concentrated under reduced pressure to afford the title compound in sufficient purity for use in the next step. MS: m/z=543.0 [M+H].

Step C: 4-[(1R,2R)-2-(2-Cyclohexyl-1,3-oxazol-5-yl)cyclopropyl]benzenesulfonamide To a stirred solution of N-tert-butyl-4-[(1R,2R)-2-(2-cyclohexyl-1,3-oxazol-5-yl)cyclopropyl]benzenesulfonamide (90 mg, 0.22 mmol) in dichloromethane (1 mL) at ambient temperature was added trifluoroacetic acid (2.0 mL, 26.0 mmol) dropwise. The mixture was warmed to 30° C. and allowed to stir for 1 h. The reaction mixture was concentrated under reduced pressure and the residue diluted with saturated aqueous sodium bicarbonate (10 mL) and dichloromethane (5 mL). The organic layer was separated, dried (magnesium sulfate), and concentrated under reduced pressure. The residue was purified by preparative HPLC, eluting with a gradient of acetonitrile:water:ammonium hydroxide—10:90:0.05 to 90:10:0.05 to afford the title compound MS: m/z=347.2 [M+H]. $^1$H NMR (400 MHz, CD$_3$OD): δ 7.81 (d, J=8.4 Hz, 2H), 7.33 (d, J=8.4 Hz, 2H), 6.77 (s, 1H), 2.76-2.78 (m, 1H), 2.33-2.39 (m, 2H), 2.01-2.03 (m, 2H), 1.80-1.83 (m, 2H), 1.71-1.74 (m, 1H), 1.49-1.58 (m, 4H), 1.26-1.47 (m, 3H).

Example 29

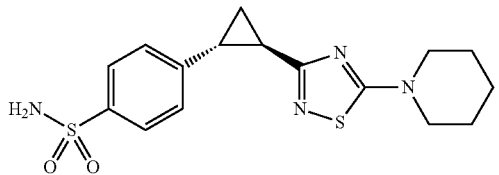 [SMILES: NS(=O)(=O)c1ccc([C@@H]2C[C@H]2c2nsc(N3CCCCC3)n2)cc1]

4-{(1R,2R)-2-[5-(Piperidin-1-yl)-1,2,4-thiadiazol-3-yl]cyclopropyl}benzenesulfonamide Step A: 4-[(R,2R)-2-(5-Oxo-4,5-dihydro-1,2,4-thiadiazol-3-yl)cyclopropyl]benzenesulfonamide To a stirred mixture of (1R,2R)—N'-hydroxy-2-(4-sulfamoylphenyl)cyclopropanecarboximidamide (Intermediate 22) (0.83 g, 3.25 mmol) in tetrahydrofuran (33 mL) at ambient temperature was added di-1H-imidazol-1-ylmethanethione (0.869 g, 4.88 mmol). The reaction mixture was allowed to stir for 30 min. Water (25 mL) was added and the resulting mixture extracted with ethyl acetate (3×30 mL). The combined organic extracts were dried (sodium sulfate) and concentrated under reduced pressure. The residue was dissolved in tetrahydrofuran (33 mL) and boron trifluoride diethyl etherate (3.29 mL, 25.9 mmol) was added dropwise. The reaction mixture was allowed to stir for 6 h. Water (25 mL) was added and the resulting mixture extracted with ethyl acetate (3×30 mL). The combined organic extracts were washed with saturated aqueous sodium chloride (15 mL), dried (sodium sulfate), and concentrated under reduced pressure. The residue was purified by preparative HPLC, eluting with a gradient of acetonitrile:water:trifluoroacetic acid—5:95:0.1 to 95:5:0.1 to give the title compound. MS: m/z=298.0 [M+H].

Step B: 4-[(1R,2R)-2-(5-Chloro-1, 2,4-thiadiazol-3-yl)cyclopropyl]benzenesulfonamide To a stirred mixture of 4-[(1R,2R)-2-(5-oxo-4,5-dihydro-1,2,4-thiadiazol-3-yl)cyclopropyl]benzenesulfonamide (157 mg, 0.528 mmol) in acetonitrile (4.64 mL) at ambient temperature was added phosphorous oxychloride (2.00 mL, 21.5 mmol). The reaction mixture was warmed to 100° C. and allowed to stir for 2 h. The reaction mixture was cooled and added dropwise to a cold, saturated aqueous solution of sodium bicarbonate (30 mL). The resulting mixture was extracted with ethyl acetate (5×20 mL). The combined organic extracts were washed with saturated aqueous sodium bicarbonate (30 mL) and saturated aqueous sodium chloride (30 mL), dried (sodium sulfate), and concentrated under reduced pressure. The residue was purified by silica gel chromatography, eluting with a gradient of ethyl acetate:hexanes—0:100 to 100:0 to afford the title compound. MS: m/z=316.0 [M+H].

Step C: 4-{(1R,2R)-2-[5-(Piperidin-1-yl)-1,2,4-thiadiazol-3-yl]cyclopropyl}benzenesulfonamide To a solution of 4-[(1R,2R)-2-(5-chloro-1,2,4-thiadiazol-3-yl)cyclopropyl]benzenesulfonamide (20 mg, 0.063 mmol) in tetrahydrofuran (0.2 mL) at ambient temperature was added piperidine (31 μl, 0.32 mmol). The reaction mixture was allowed to stir for 1 h. The reaction mixture was purified directly by silica gel chromatography, eluting with a gradient of ethyl acetate:hexanes—0:100 to 70:30 to afford the title compound. MS: m/z=365.2 [M+H]. $^1$H NMR (600 MHz, CD$_3$OD): δ 7.80 (d, J=8.1 Hz, 2H), 7.31 (d, J=8.2 Hz, 2H), 3.50 (d, J=5.5 Hz, 4H), 3.32 (br s, 1H), 2.56-2.59 (m, 1H), 2.31-2.34 (m, 1H), 1.74-1.78 (m, 1H), 1.68-1.70 (m, 5H), 1.48-1.51 (m, 1H).

Example 30

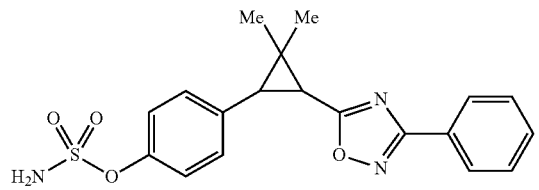 [SMILES: CC1(C)C(c2ccc(OS(N)(=O)=O)cc2)C1c1nc(-c2ccccc2)no1]

4-[trans-2,2-Dimethyl-3-(3-phenyl-1,2,4-oxadiazol-5-yl)cyclopropyl]phenyl sulfamate Step A: tert-Butyl ({4-[trans-2,2-dimethyl-3-(3-phenyl-1,2,4-oxadiazol-5-yl)cyclopropyl]phenoxy}sulfonyl)carbamate To a solution of 4-[trans-2,2-dimethyl-3-(3-phenyl-1,2,4-oxadiazol-5-yl)cyclopropyl]phenol (Intermediate 23) (30 mg, 0.098 mmol) in dichloromethane (3 mL) at ambient temperature was added triethylamine (0.14 mL, 0.98 mmol) and tert-butyl (chlorosulfonyl)carbamate (106 mg, 0.492 mmol). The reaction mixture was allowed to stir for 30 min. Water (10 mL) was added, and the mixture was extracted with ethyl acetate (2×5 mL). The combined organic extracts were dried (sodium sulfate), filtered, and concentrated under reduced pressure to afford the title compound. MS: m/z=386.1 [M+H-CO$_2$C(CH$_3$)$_3$].

Step B: 4-[trans-2,2-Dimethyl-3-(3-phenyl-1,2,4-oxadiazol-5-yl)cyclopropyl]phenyl sulfamate To a solution of tert-butyl ({4-[trans-2,2-dimethyl-3-(3-phenyl-1,2,4-oxadiazol-5-yl)cyclopropyl]phenoxy}sulfonyl)carbamate (30 mg, 0.062 mmol) in dichloromethane (2 mL) at ambient temperature was added trifluoroacetic acid (2.00 mL, 26.0 mmol). The reaction mixture was allowed to stir for 3 h. A saturated aqueous solution of sodium bicarbonate (10 mL) was added and the aqueous layer extracted with dichloromethane (3×10 mL). The combined organic extracts were dried (sodium sulfate), filtered, and concentrated under reduced pressure. The residue was purified by preparative HPLC, eluting with a gradient of acetonitrile:water:ammonium hydroxide—50: 50:0.05 to 80:20:0.05 to afford the title compound. MS: m/z=386.0 [M+H]. $^1$H NMR (400 MHz, CDCl$_3$): δ 8.06- 8.08 (m, 2H), 7.47-7.50 (m, 3 H), 7.28-7.29 (m, 4H), 5.03 (br s, 2H), 3.01 (d, J=6.0 Hz, 1H), 2.53 (d, J=6.4 Hz, 1H), 1.41 (s, 3H), 1.05 (s, 3H).

Example 31

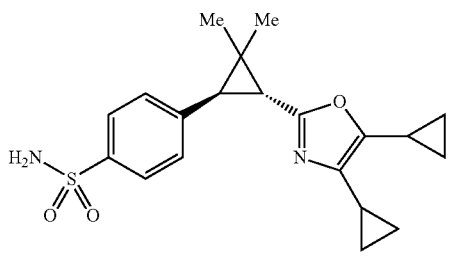 [SMILES: CC1(C)[C@H](c2ccc(S(N)(=O)=O)cc2)[C@H]1c1nc(C2CC2)c(C2CC2)o1]

4-[(1R,3R)-3-(4,5-Dicyclopropyl-1,3-oxazol-2-yl)-2, 2-dimethylcyclopropyl]benzenesulfonamide Step A: tert-Butyl tert-butyl[(4-{(1R,3R)-3-[(1,2-dicyclopropyl-2-oxoethyl)carbamoyl]-2,2-dimethylcyclopropyl}phenyl)sulfonyl]carbamate To a stirred solution of (1R,3R)-3-{4-[(tert-butoxycarbonyl)(tert-butyl)sulfamoyl]phenyl}-2,2-dimethylcyclopropanecarboxylic acid (Intermediate 8) (50 mg, 0.117 mmol) in dichloromethane (2 mL) at ambient temperature was added HATU (89 mg, 0.24 mmol) and triethylamine (0.049 mL, 0.35 mmol). 2-Amino-1,2-dicyclopropylethanone (49 mg, 0.14 mmol) was added and the reaction mixture was warmed to 30° C. and allowed to stir for 30 min. The reaction mixture was concentrated under reduced pressure and the residue purified by silica gel chromatography, eluting with ethyl acetate:petroleum ether—33:67 to afford the title compound. MS: m/z=547.1 [M+H].

Step B: tert-Butyl tert-butyl({4-[(1R,3R)-3-(4,5-dicyclopropyl-1,3-oxazol-2-yl)-2,2-dimethylcyclopropyl]phenyl}sulfonyl)carbamate To a solution of tert-butyl tert-butyl[(4-{(1R,3R)-3-[(1,2-dicyclopropyl-2-oxoethyl)carbamoyl]-2,2-dimethylcyclopropyl}phenyl)sulfonyl]carbamate (40 mg, 0.073 mmol) in tetrahydrofuran (2 mL) at ambient temperature was added phosphorous oxychloride (0.068 mL, 0.73 mmol). The reaction mixture was warmed to 70° C. and allowed to stir for 2 h. The reaction mixture was concentrated under reduced pressure to afford the title compound in sufficient purity for use in the next step. MS: m/z=529.3 [M+H].

Step C: 4-[(1R,3R)-3-(4,5-Dicyclopropyl-1,3-oxazol-2-yl)-2,2-dimethylcyclopropyl]benzenesulfonamide To a solution of tert-butyl tert-butyl((4-((1R,3R)-3-(4,5-dicyclopropyloxazol-2-yl)-2,2-dimethylcyclopropyl)phenyl)sulfonyl)carbamate (40 mg, 0.076 mmol) in dichloromethane (2 mL) at ambient temperature was added trifluoroacetic acid (2 mL, 26.0 mmol). The reaction mixture was warmed to 30° C. and allowed to stir for 3 h. The reaction mixture was concentrated under reduced pressure and the residue was purified by preparative HPLC, eluting with a gradient of acetonitrile:water:ammonium hydroxide—10:90:0.05 to 90:10:0.05 to afford the title compound. MS: m/z=373.2 [M+H]. $^1$H NMR (400 MHz, CD$_3$OD): δ 7.83 (d, J=8.4 Hz, 2H), 7.41 (d, J=8.4 Hz, 2H), 2.76 (d, J=6.4 Hz, 1H), 2.42 (d, J=6.0 Hz, 1H), 1.95-1.97 (m, 1H), 1.81- 1.83 (m, 1H), 1.17 (s, 3H), 0.94-0.96 (m, 2H), 0.92 (s, 3H), 0.81-0.86 (m, 4H), 0.74-0.76 (m, 2H).

Example 32

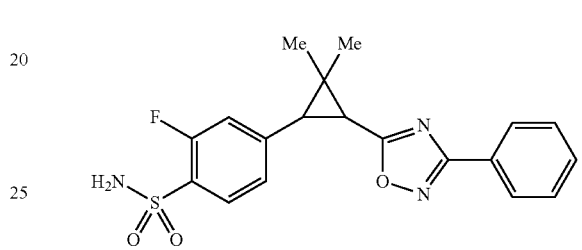

4-[trans-2,2-Dimethyl-3-(3-phenyl-1,2,4-oxadiazol-5-yl)cyclopropyl]-2-fluorobenzenesulfonamide, enantiomer A Step A: N-({[trans-3-(3-Fluoro-4-sulfamoylphenyl)-2,2-dimethylcyclopropyl]carbonyl}oxy)benzenecarboximidamide To a stirred solution of methyl trans-3-(2-fluoro-4-sulfamoylphenyl)-2,2-dimethylcyclopropanecarboxylate (Intermediate 25) (130 mg, 0.431 mmol) in methanol (2 mL), tetrahydrofuran (2 mL), and water (1 mL) was added lithium hydroxide (181 mg, 4.31 mmol) and the reaction mixture allowed to stir for 16 h. The reaction mixture was concentrated under reduced pressure and water (30 mL) was added. The resulting mixture was adjusted to pH 5 by addition of an aqueous solution of HCl (1 M) and extracted with ethyl acetate (3×30 mL). The combined organic extracts were washed with saturated aqueous sodium chloride (50 mL), dried (sodium sulfate), filtered, and concentrated under reduced pressure. The residue was dissolved in N,N-dimethylformamide (3 mL), HATU (160 mg, 0.421 mmol), and diisopropylethylamine (0.201 mL, 1.15 mmol) were added, and the reaction mixture was allowed to stir for 10 min. N-Hydroxybenzimidamide (104 mg, 0.766 mmol) was added and the reaction mixture was allowed to stir for 2 h. The reaction mixture was concentrated under reduced pressure to afford the title compound in sufficient purity for use in the next step. MS: m/z=406.2 [M+H].

Step B: 4-[trans-2,2-Dimethyl-3-(3-phenyl-1,2,4-oxadiazol-5-yl)cyclopropyl]-2-fluorobenzenesulfonamide, enantiomer A A solution of N-({[trans-3-(3-fluoro-4-sulfamoylphenyl)-2,2-dimethylcyclopropyl]carbonyl}oxy)benzenecarboximidamide (125 mg, 0.308 mmol) in N,N-dimethylformamide (3 mL) was warmed to 100° C. and allowed to stir for 5 h.

The reaction mixture was concentrated under reduced pressure. The residue was purified by preparative HPLC, eluting with a gradient of acetonitrile:water:ammonium hydroxide—40:60:0.05 to 70:30:0.05, to afford the title compound. The racemate was resolved by SFC, utilizing a ChiralPak AD-H column, eluting with a gradient of ethanol:CO$_2$:ammonium hydroxide—40:60:0.1 to 100:0:0.1. The first major peak to elute was 4-[2,2-dimethyl-3-(3-phenyl-1,2,4-oxadiazol-5-yl)cyclopropyl]-2-fluorobenzenesulfonamide, enantiomer A, the title compound. MS: m/z=388.0 [M+H]. $^1$H NMR (400 MHz, CD$_3$OD): δ 8.04-8.06 (m, 2H), 7.86 (app t, J=4.2 Hz, 1H), 7.51-7.54 (m, 3H), 7.28-7.33 (m, 2H), 3.10 (d, J=5.6 Hz, 1H), 2.89 (d, J=6.4 Hz, 1H), 1.40 (s, 3H), 1.08 (s, 3H).

Example 33

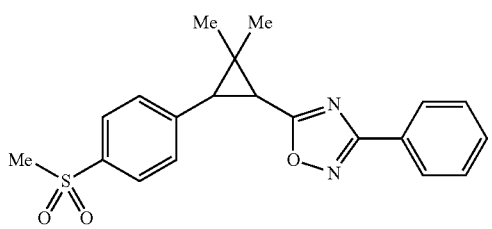 [SMILES: CC1(C)C(c2ccc(S(C)(=O)=O)cc2)C1c1nc(-c2ccccc2)no1]

5-(trans-2,2-Dimethyl-3-(4-(methylsulfonyl)phenyl-cyclopropyl)-3-phenyl-1,2,4-oxadiazole Step A: 5-(trans-2,2-Dimethyl-3-(4-(methylthio)phenyl)cyclopropyl)-3-phenyl-1,2,4-oxadiazole To a stirred solution of methyl trans-2,2-dimethyl-3-(4-(methylthio)phenyl)cyclopropanecarboxylate (Intermediate 28) (750 mg, 3.00 mmol) in methanol (9 mL) and water (3 mL) at ambient temperature was added sodium hydroxide (240 mg, 5.99 mmol). The reaction mixture was warmed to 50° C. and allowed to stir for 5 h. The reaction mixture was cooled, concentrated under reduced pressure, and the mixture was adjusted to pH z 3 by addition of an aqueous solution of HCl (3 M). The aqueous layer was extracted with ethyl acetate (3×15 mL) and the combined organic extracts were dried (sodium sulfate), filtered, and the filtrate concentrated under reduced pressure. The residue was dissolved in N,N-dimethylformamide (3 mL) at ambient temperature and triethylamine (0.35 mL, 2.54 mmol), HATU (354 mg, 0.93 mmol) and N-hydroxybenzimidamide (173 mg, 1.27 mmol) were added. The reaction mixture was allowed to stir for 20 min, warmed to 100° C., and allowed to stir for 3 h. The reaction mixture was cooled to ambient temperature, water (10 mL) was added, and the aqueous layer was extracted with ethyl acetate (3×10 mL). The combined organic extracts were dried (sodium sulfate), filtered, and the filtrate concentrated under reduced pressure. The residue was purified by silica gel chromatography, eluting with ethyl acetate:petroleum ether—10:90, to afford the title compound. MS: m/z=337.1 [M+H].

Step B: 5-(trans-2,2-Dimethyl-3-(4-(methylsulfonyl)phenyl)cyclopropyl)-3-phenyl-1,2,4-oxadiazole To a stirred solution of 5-(trans-2,2-Dimethyl-3-(4-(methylthio)phenyl)cyclopropyl)-3-phenyl-1,2,4-oxadiazole (50 mg, 0.15 mmol) in dichloromethane (1 mL) at ambient temperature was added m-CPBA (80%, 51.3 mg, 0.30 mmol) and the reaction mixture allowed to stir for 1 h. A saturated aqueous solution of sodium sulfite (1 mL) and a saturated aqueous solution of potassium carbonate (1 mL) were added and the aqueous layer was extracted with dichloromethane (3×5 mL). The combined organic extracts were dried (sodium sulfate), filtered, and the filtrate concentrated under reduced pressure. The residue was purified by preparative HPLC, eluting with a gradient of acetonitrile:water:ammonium hydroxide—45:55:0.05 to 75:25:0.05, to give the title compound. MS: m/z=369.0 [M+H]. $^1$H NMR (400 MHz, CD$_3$OD): δ 8.03-8.08 (m, 2H); 7.93 (d, J=8.4 Hz, 2H); 7.60 (d, J=8.2 Hz, 2H); 7.48-7.56 (m, 3H); 3.11-3.15 (m, 4H); 2.90 (d, J=6.2 Hz, 1H); 1.42 (s, 3H); 1.06 (s, 3H).

Example 34

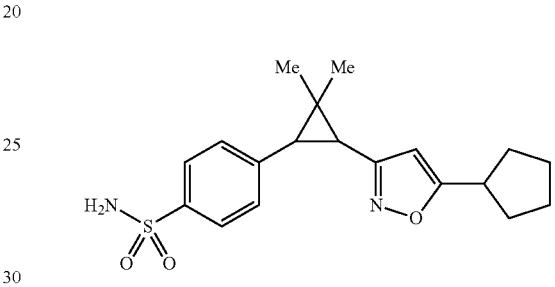

4-(trans-3-(5-Cyclopentylisoxazol-3-yl)-2,2-dimethylcyclopropyl)benzenesulfonamide To a stirred solution of 4-(trans-3-((hydroxyimino)methyl)-trans-2,2-dimethylcyclopropyl)benzenesulfonamide (Intermediate 37) (75 mg, 0.28 mmol) and ethynylcyclopentane (52.6 mg, 0.559 mmol) in methanol (2.4 mL) and water (0.6 mL) at ambient temperature was added [bis(trifluoroacetoxy)iodo]benzene (240 mg, 0.56 mmol) and the reaction mixture allowed to stir for 16 h. The reaction mixture was concentrated under reduced pressure and the residue purified by preparative HPLC, eluting with a gradient of acetonitrile:water:trifluoroacetic acid—47:53:0.1 to 67:33:0.1, to give the title compound. MS: m/z=361.1 [M+H]. $^1$H NMR (400 MHz, CD$_3$OD): δ 7.85 (d, J=8.0 Hz, 2H); 7.44 (d, J=8.0 Hz, 2H); 6.16 (s, 1H); 3.19-3.28 (m, 1H); 2.66 (d, J=6.0 Hz, 1H); 2.42 (d, J=6.4 Hz, 1H); 2.10 (d, J=6.0 Hz, 2H); 1.67-1.84 (m, 6H); 1.17 (s, 3H); 0.96 (s, 3H).

Example 35

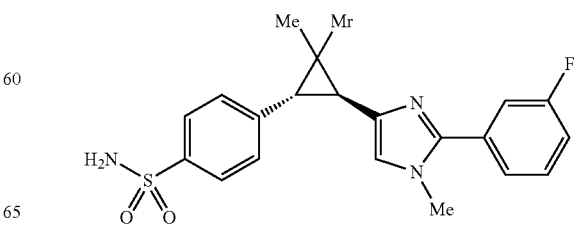

4-{(1S,3S)-3-[2-(3-Fluorophenyl)-1-methyl-1H-imidazol-4-yl]-2,2-dimethylcyclopropyl}benzenesulfonamide Step A: tert-Butyl tert-butyl((4-((1S,3S)-3-(2-(3-fluorophenyl)-1H-imidazol-5-yl)-2,2-dimethylcyclopropyl)phenyl)sulfonyl)carbamate To a stirred solution of tert-butyl tert-butyl((4-((1S,3S)-3-(2-chloroacetyl)-2,2-dimethylcyclopropyl)phenyl)sulfonyl)carbamate (Intermediate 29) (100 mg, 0.22 mmol) in N,N-dimethylformamide (3 mL) were added 3-fluorobenzimidamide (39.2 mg, 0.28 mmol) and DIEA (0.11 mL, 0.66 mmol). The reaction mixture was warmed to 80° C. and allowed to stir for 20 min. The reaction mixture was cooled to ambient temperature, diluted with water (20 mL), and extracted with ethyl acetate (2×20 mL). The combined organic extracts were washed with saturated aqueous sodium chloride (10 mL), dried (sodium sulfate), filtered, and the filtrate was concentrated under reduced pressure to afford the title compound in sufficient purity for use in the next step. MS: m/z=542.7 [M+H].

Step B: 4-((1S,3S)-3-(2-(3-Fluorophenyl)-1H-imidazol-5-yl)-2,2-dimethylcyclopropyl)benzenesulfonamide To a stirred solution of tert-butyl tert-butyl((4-((1S,3S)-3-(2-(3-fluorophenyl)-1H-imidazol-5-yl)-2,2-dimethylcyclopropyl)phenyl)sulfonyl)carbamate (30 mg, 0.055 mmol) in dichloromethane (2 mL) at ambient temperature was added trifluoroacetic acid (2 mL, 0.055 mmol) and the reaction mixture allowed to stir for 2 h. The reaction mixture was concentrated under reduced pressure and the residue purified by preparative HPLC, eluting with a gradient of acetonitrile:water:ammonium hydroxide—40:60:0.05 to 70:30:0.05, to give the title compound. MS: m/z=386.0 [M+H]. $^1$H NMR (400 MHz, CD$_3$OD): δ 7.85 (d, J=8.2 Hz, 2H); 7.67-7.69 (m, 1H); 7.60-7.63 (m, 1H); 7.42-7.49 (m, 3H); 7.07-7.12 (m, 1H); 6.96 (s, 1H); 2.50 (d, J=6.3 Hz, 1H); 2.41 (d, J=6.3 Hz, 1H); 1.13 (s, 3H); 0.97 (s, 3H).

Step C: tert-Butyl tert-butyl[(4-{(1S,3S)-3-[2-(3-fluorophenyl)-1-methyl-1H-imidazol-5-yl]-2,2-dimethylcyclopropyl}phenyl)sulfonyl]carbamate and tert-butyl tert-butyl[(4-{(1S,3S)-3-[2-(3-fluorophenyl)-1-methyl-1H-imidazol-4-yl]-2,2-dimethylcyclopropyl}phenyl)sulfonyl]carbamate To a stirred solution of tert-butyl tert-butyl((4-((1S,3S)-3-(2-(3-fluorophenyl)-1H-imidazol-5-yl)-2,2-dimethylcyclopropyl)phenyl)sulfonyl)carbamate (30 mg, 0.055 mmol) in N,N-dimethylformamide (2 mL) at ambient temperature were added potassium carbonate (15.3 mg, 0.11 mmol) and iodomethane (11.8 mg, 0.083 mmol) and the reaction mixture was allowed to stir for 1 h. The reaction mixture was diluted with water (20 mL) and extracted with ethyl acetate (2×10 mL). The combined organic extracts were washed with saturated aqueous sodium chloride (10 mL), dried (sodium sulfate), filtered, and the filtrate concentrated under reduced pressure to afford the title compounds in sufficient purity for use in the next step. MS: m/z=556.7 [M+H].

Step D: 4-{(1S,3S)-3-[2-(3-Fluorophenyl)-1-methyl-1H-imidazol-4-yl]-2,2-dimethylcyclopropyl}benzenesulfonamide To a stirred solution of tert-butyl tert-butyl[(4-{(1S,3S)-3-[2-(3-fluorophenyl)-1-methyl-1H-imidazol-5-yl]-2,2-dimethylcyclopropyl}phenyl)sulfonyl]carbamate and tert-butyl tert-butyl[(4-{(1S,3S)-3-[2-(3-fluorophenyl)-1-methyl-1H-imidazol-4-yl]-2,2-dimethylcyclopropyl}phenyl)sulfonyl]carbamate (30 mg, 0.054 mmol) in dichloromethane (2 mL) at ambient temperature was added trifluoroacetic acid (2 mL, 0.055 mmol) and the reaction mixture allowed to stir for 2 h. The reaction mixture was concentrated under reduced pressure and the residue was purified by silica gel chromatography, eluting with methanol:dichloromethane—9:91, and then by preparative HPLC, eluting with a gradient of acetonitrile:water:ammonium hydroxide—30:70:0.05 to 60:40:0.05, to give the title compound. MS: m/z=400.0 [M+H]. $^1$H NMR (400 MHz, CD$_3$OD): δ 7.85 (d, J=8.2 Hz, 2H); 7.50-7.58 (m, 1H); 7.43-7.49 (m, 3H); 7.39-7.42 (m, 1H); 7.18-7.26 (m, 1H); 7.04 (s, 1H); 3.75 (s, 3H); 2.47 (d, J=6.3 Hz, 1H); 2.38 (d, J=6.7 Hz, 1H); 1.15 (s, 3H); 0.96 (s, 3H).

Example 36

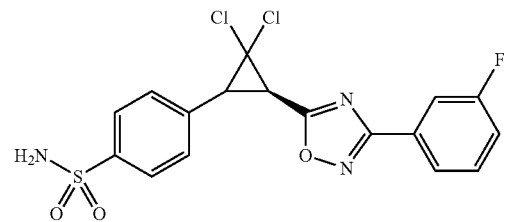 [SMILES: NS(=O)(=O)c1ccc(C2[C@H](c3nc(-c4cccc(F)c4)no3)C2(Cl)Cl)cc1]

4-{trans-2,2-Dichloro-3-[3-(3-fluorophenyl)-1,2,4-oxadiazol-5-yl]cyclopropyl}benzenesulfonamide To a stirred solution of trans-2,2-dichloro-3-(4-sulfamoylphenyl)cyclopropanecarboxylic acid (Intermediate 30) (20 mg, 0.064 mmol) in dichloromethane (1 mL) at ambient temperature was added oxalyl dichloride (16.37 mg, 0.13 mmol) and N,N-dimethylformamide (0.00050 mL, 0.00645 mmol) and the reaction mixture allowed to stir for 30 min. The reaction mixture was concentrated under reduced pressure. The residue was dissolved in dichloromethane (2 mL) at ambient temperature, triethylamine (0.018 mL, 0.13 mmol) and 3-fluoro-N-hydroxybenzimidamide (19.89 mg, 0.13 mmol) were added, and the reaction mixture was allowed to stir for 10 min. Water (5 mL) was added and the aqeuous layer was extracted with ethyl acetate (2×5 mL). The combined organic extracts were dried (sodium sulfate), filtered, and the filtrate concentrated under reduced pressure. The residue was dissolved in N,N-dimethylformamide (1 mL), warmed to 100° C., and allowed to stir for 10 h. The reaction mixture was cooled to ambient temperature and purified by preparative HPLC, eluting with a gradient of acetonitrile:water:trifluoroacetic acid—43:57:0.1 to 73:27:0.1, to give the title compound. MS: m/z=427.8 [M+H]. $^1$H NMR (400 MHz, CDCl$_3$): δ 7.95-7.97 (m, 2H); 7.81-7.83 (m, 1H); 7.79-7.80 (m, 1H); 7.42-7.51 (m, 3H); 7.15-7.20 (m, 1H); 4.90 (s, 2H); 3.89 (d, J=8.4 Hz, 1H); 3.48 (d, J=8.4 Hz, 1H).

Example 37

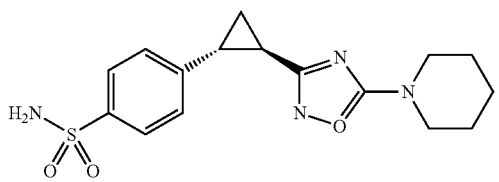

4-{(1R,2R)-2-[5-(Piperidin-1-yl)-1,2,4-oxadiazol-3-yl]cyclopropyl}benzenesulfonamide Step A: N-[(Dimethylamino)methylidene]-4-{(1R,2R)-2-[5-(piperidin-1-yl)-1,2,4-oxadiazol-3-yl]cyclopropyl}benzenesulfonamide A mixture of (1R,2R)-2-(4-{[(dimethylamino)methylidene]sulfamoyl}phenyl)-N-hydroxycyclopropanecarboximidamide (Intermediate 31) (50 mg, 0.161 mmol), 1-piperidinecarbonitrile (11.9 mg, 0.108 mmol), and zinc(II) chloride (22.0 mg, 0.161 mmol) in N,N-dimethylformamide (5 mL) was warmed to 80° C. and allowed to stir for 2 h. To the resulting mixture was added 4-toluenesulfonic acid monohydrate (30.6 mg, 0.161 mmol) and the reaction mixture was warmed to 85° C. and allowed to stir for 1 h. The reaction mixture was cooled and then diluted with water (20 mL) and extracted with ethyl acetate (2×30 mL). The combined organic extracts were washed with saturated aqueous sodium chloride (20 mL), dried (sodium sulfate), and concentrated under reduced pressure to afford the title compound. MS: m/z=404.1 [M+H].

Step B: 4-{(1R,2R)-2-[5-(Piperidin-1-yl)-1,2,4-oxadiazol-3-yl]cyclopropyl}benzenesulfonamide To a stirred solution of N-[(dimethylamino)methylidene]-4-{(1R,2R)-2-[5-(piperidin-1-yl)-1,2,4-oxadiazol-3-yl]cyclopropyl}benzenesulfonamide (20 mg, 0.050 mmol) in tetrahydrofuran (2 mL) at ambient temperature was added hydrazine hydrate (2.5 mg, 0.050 mmol). The reaction mixture was allowed to stir for 30 min then water (5 mL) was added and the resulting mixture extracted with ethyl acetate (3×5 mL). The combined organic extracts were dried (sodium sulfate) and concentrated under reduced pressure. The residue was purified by preparative HPLC, eluting with a gradient of acetonitrile:water:trifluoroacetic acid—15:85:0.1 to 95:5:0.1, and the product containing fractions were concentrated under reduced pressure to afford the title compound. MS: m/z=349.1 [M+H]. $^1$H NMR (400 MHz, CD$_3$OD): δ 7.81 (d, J=8.4 Hz, 2H); 7.33 (d, J=8.4 Hz, 2H); 3.55-3.58 (m, 4H); 2.53 (m, 1H); 2.19 (m, 1H); 1.63-1.68 (m, 7H); 1.54 (m, 1H).

Example 38

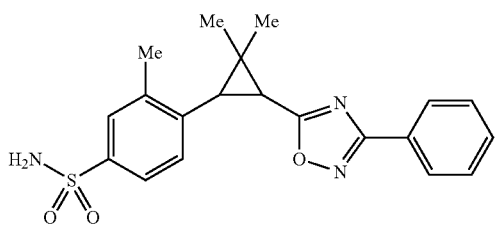 [SMILES: Cc1cc(S(N)(=O)=O)ccc1C1C(c2nc(-c3ccccc3)no2)C1(C)C]

4-[trans-2,2-Dimethyl-3-(3-phenyl-1,2,4-oxadiazol-5-yl)cyclopropyl]-3-methylbenzenesulfonamide, enantiomer A Step A: trans-2,2-Dimethyl-3-(2-methyl-4-sulfamoylphenyl)cyclopropanecarboxylic acid To a stirred solution of methyl trans-2,2-dimethyl-3-(2-methyl-4-sulfamoylphenyl)cyclopropane carboxylate (Intermediate 32) (110 mg, 0.370 mmol) in methanol (2 mL), tetrahydrofuran (2 mL), and water (1 mL) at ambient temperature was added lithium hydroxide (155 mg, 4.31 mmol) and the reaction mixture allowed to stir for 16 h. The reaction mixture was concentrated under reduced pressure, water (30 mL) was added, and the aqueous layer adjusted to pH z 5 by addition of an aqueous solution of HCl (1 M). The mixture was extracted with ethyl acetate (3×30 mL), the combined organic extracts washed with saturated aqueous sodium chloride (50 mL), dried (sodium sulfate), filtered, and the filtrate was concentrated under reduced pressure to give the title compound in sufficient purity for use in the next step.

Step B: 4-[trans-2,2-Dimethyl-3-(3-phenyl-1,2,4-oxadiazol-5-yl)cyclopropyl]-3-methylbenzenesulfonamide, enantiomer A To a stirred solution of trans-2,2-dimethyl-3-(2-methyl-4-sulfamoylphenyl)cyclopropanecarboxylic acid (103 mg, 0.364 mmol) in N,N-dimethylformamide (3 mL) at ambient temperature was added HATU (138 mg, 0.364 mmol) and DIEA (0.190 mL, 1.091 mmol) and the reaction mixture was allowed to stir for 10 min. N-Hydroxybenzimidamide (99 mg, 0.73 mmol) was added and the reaction mixture was allowed to stir for 2 h. The reaction mixture was then warmed to 100° C. and allowed to stir for 5 h. The reaction mixture was cooled to ambient temperature and purified by preparative HPLC, eluting with a gradient of acetonitrile:water:ammonia hydroxide—30:70:0.05 to 60:40:0.05 to give the racemic title compound. The racemate was resolved by SFC, utilizing an IC column, eluting with ethanol:CO$_2$:ammonium hydroxide—45:55:0.1 to 100:0:0.1. The first major peak to elute was 4-[trans-2,2-dimethyl-3-(3-phenyl-1,2,4-oxadiazol-5-yl)cyclopropyl]-3-methylbenzenesulfonamide, enantiomer A, the title compound. MS: m/z=384.0 [M+H]. $^1$H NMR (400 MHz, CD$_3$OD): δ 8.04-8.09 (m, 2H), 7.78 (s, 1H), 7.72 (d, J=8.02 Hz, 1H), 7.50-7.56 (m, 3H), 7.39 (d, J=8.22 Hz, 1H), 3.00 (d, J=6.06 Hz, 1H), 2.85 (d, J=6.26 Hz, 1H), 2.48 (s, 3H), 1.47 (s, 3H), 0.99 (s, 3H).

The examples appearing in the following tables were prepared by analogy to the above examples, as described or prepared as a result of similar transformations with modifications known to those skilled in the art. The requisite starting materials were described herein, commercially available, known in the literature, or readily synthesized by one skilled in the art. Straightforward protecting group strategies were applied in some routes.

TABLE EX-A

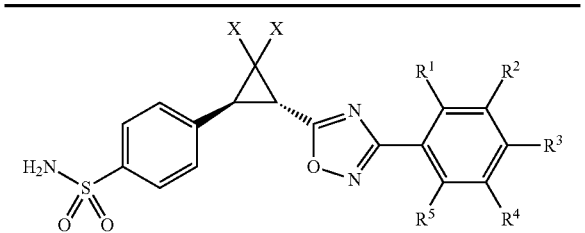

| Example | X | R¹ | R² | R³ | R⁴ | R⁵ | MS [M + H] |
|---|---|---|---|---|---|---|---|
| A1 | Me | OMe | H | H | Cl | H | 434.2 |
| A2 | Me | CF₃ | H | F | H | H | 456.2 |
| A3 | Me | H | H | H | H | H | 370.2 |
| A4 | Me | OiPr | H | H | Cl | H | 462.1 |
| A5 | H | H | H | H | H | H | 342.2 |
| A6 | Me | Me | H | H | F | H | 402.2 |
| A7 | Me | F | H | F | H | H | 406.2 |
| A8 | H | F | H | F | H | H | 378.1 |
| A9 | F | H | H | H | H | H | 378.2 |
| A10 | Me | H | F | H | H | H | 388.3 |
| A11 | Me | F | H | H | H | F | 406.3 |
| A12 | Me | F | H | H | H | H | 388.2 |
| A13 | Me | CF₃ | H | H | H | H | 438.3 |
| A14 | Me | H | Br | H | H | H | 448.2 |
| A15 | H | OMe | H | H | Cl | H | 406.2 |

TABLE EX-B

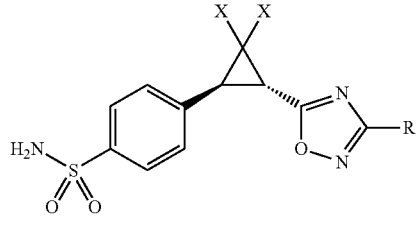

| Example | X | R | MS [M + H] |
|---|---|---|---|
| B1 | Me | CH(Me)₂ (isopropyl) | 336.2 |
| B2 | Me | 5-fluoropyridin-3-yl | 389.1 |
| B3 | Me | cyclobutyl | 348.2 |
| B4 | H | cyclohexyl | 348.2 |
| B5 | H | 5-fluoropyridin-3-yl | 361.2 |
| B6 | H | 2-methylpyridin-3-yl | 357.3 |
| B7 | Me | 5-(trifluoromethyl)pyridin-3-yl | 439.3 |
| B8 | Me | 3,3-difluorocyclobutyl | 384.3 |
| B9 | Me | cyclopentyl | 362.3 |
| B10 | Me | cyclopropylmethyl | 348.2 |
| B11 | Me | tetrahydrofuran-3-yl | 364.3 |
| B12 | Me | tetrahydrofuran-2-yl | 364.3 |
| B13 | Me | 1-phenylcyclopropyl | 410.3 |

TABLE EX-B-continued

Structure: 4-sulfamoylphenyl-cyclopropane(X,X)-1,2,4-oxadiazole-R

| Example | X | R | MS [M + H] |
|---|---|---|---|
| B14 | Me | 1-fluoroindanyl | 428.1 |
| B15 | Me | spiro[3.3]heptyl | 388.2 |
| B16 | Me | 1-acetylpiperidin-4-yl | 419.2 |
| B17 | F | tert-butyl (C(Me)₃) | 358.2 |
| B18 | F | cyclobutyl | 356.2 |
| B19 | F | cyclopentyl | 370.2 |

TABLE EX-C

Structure: 4-sulfamoylphenyl-cyclopropane(X,X)-1,2,4-oxadiazole-phenyl(R¹,R²,R³,R⁴,R⁵)

| Example | X | R¹ | R² | R³ | R⁴ | R⁵ | MS [M + H] |
|---|---|---|---|---|---|---|---|
| C1 | Me | OMe | H | H | Cl | H | 434.2 |
| C2 | Me | CF₃ | H | F | H | H | 456.2 |
| C3 | Me | OiPr | H | H | Cl | H | 462.1 |
| C4 | Me | H | H | H | H | H | 370.1 |
| C5 | H | H | H | H | H | H | 342.2 |
| C6 | H | CF₃ | H | H | H | H | 410.3 |
| C7 | H | CF₃ | H | F | H | H | 428.2 |

TABLE EX-C-continued

| Example | X | R¹ | R² | R³ | R⁴ | R⁵ | MS [M + H] |
|---|---|---|---|---|---|---|---|
| C8 | H | CF₃ | H | H | F | H | 428.2 |
| C9 | H | F | H | H | H | F | 378.2 |
| C10 | H | H | Br | H | H | H | 421.2 |
| C11 | H | Me | H | H | F | H | 374.2 |
| C12 | Me | F | H | F | H | H | 406.2 |
| C13 | H | F | H | F | H | H | 378.2 |
| C14 | H | H | H | F | H | H | 360.2 |
| C15 | H | F | F | H | H | H | 378.1 |
| C16 | H | F | H | H | F | H | 378.1 |
| C17 | H | Me | H | H | H | H | 356.2 |
| C18 | H | H | Me | H | H | H | 356.2 |
| C19 | H | H | H | Me | H | H | 356.2 |
| C20 | H | F | H | H | H | H | 360.2 |
| C21 | F | H | H | H | H | H | 378.2 |

TABLE EX-D

Structure: 4-sulfamoylphenyl-cyclopropane(X,X)-1,2,4-oxadiazole-R

| Example | X | R | MS [M + H] |
|---|---|---|---|
| D1 | F | isopropyl (CH(Me)₂) | 344.2 |
| D2 | Me | 4-(CF₃)pyridin-3-yl | 439.3 |
| D3 | Me | cyclohexyl | 376.1 |
| D4 | Me | pyridin-2-yl | 371.0 |
| D5 | Me | isopropyl (CH(Me)₂) | 336.1 |

TABLE EX-D-continued

| Example | X | R | MS [M + H] |
|---|---|---|---|
| D6 | Me | 5-fluoropyridin-3-yl | 389.1 |
| D7 | Me | cyclobutyl | 348.2 |
| D8 | H | cyclohexyl | 348.2 |
| D9 | Me | cyclopropyl | 334.2 |
| D10 | Me | tert-butyl | 350.2 |
| D11 | H | isopropyl | 308.2 |
| D12 | H | 5-fluoropyridin-3-yl | 361.2 |
| D13 | Me | Me | 308.2 |
| D14 | Me | CH2CF3 | 376.2 |
| D15 | Me | 2-methylpyridin-3-yl | 385.3 |
| D16 | H | 2-methylpyridin-3-yl | 357.3 |
| D17 | Me | 5-(trifluoromethyl)pyridin-3-yl | 439.3 |
| D18 | Me | 3,3-difluorocyclobutyl | 384.3 |
| D19 | H | 3,3-difluorocyclobutyl | 356.2 |
| D20 | Me | cyclopentyl | 362.4 |
| D21 | H | cyclopentyl | 334.2 |
| D22 | H | 3-(trifluoromethyl)pyridin-3-yl | 411.2 |
| D23 | H | 1-phenylcyclopropyl | 382.3 |
| D24 | H | 2-cyclopropylpyridin-3-yl | 383.3 |

TABLE EX-D-continued

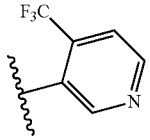 [SMILES: *c1cnccc1C(F)(F)F]

| Example | X | R | MS [M + H] |
|---|---|---|---|
| D25 | H | 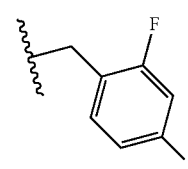 (4-CF3-pyridin-3-yl) | 411.2 |
| D26 | H | 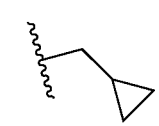 [SMILES: *CC1CC1] (2,4-difluorobenzyl) | 392.2 |
| D27 | Me | 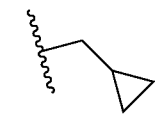 [SMILES: *CC1CC1] (cyclopropylmethyl) | 348.3 |
| D28 | H | 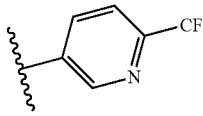 (cyclopropylmethyl) | 320.2 |
| D29 | Me | 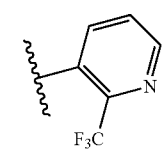 (6-CF3-pyridin-3-yl) | 439.3 |
| D30 | Me | 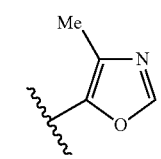 [SMILES: *c1ocnc1C] (2-CF3-pyridin-3-yl) | 439.3 |
| D31 | H | 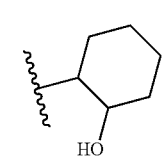 [SMILES: *C1CCCCC1O] (4-Me-oxazol-5-yl) | 347.2 |
| D32 | Me | 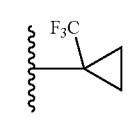 (2-hydroxycyclohexyl) | 392.0 |
| D33 | Me | 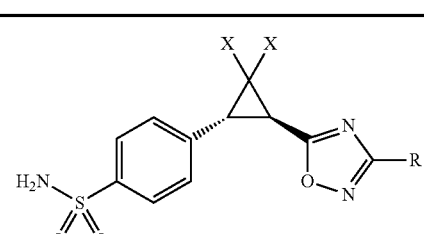 (1-CF3-cyclopropyl) | 402.0 |

TABLE EX-D-continued

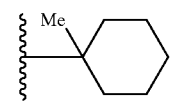

| Example | X | R | MS [M + H] |
|---|---|---|---|
| D34 | Me | 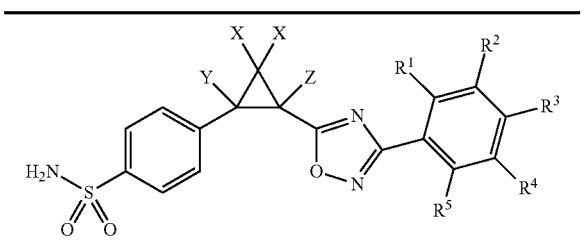 (1-methylcyclohexyl) | 389.5 |
| D35 | F | (2-fluoro-2-methylpropyl-like) | 362.1 |

TABLE EX-E

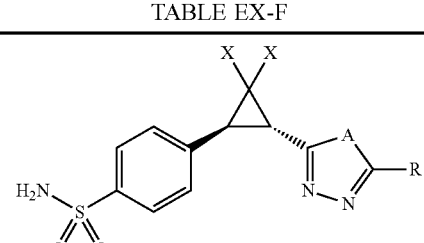

trans, racemic

| Example | X | Y | Z | R¹ | R² | R³ | R⁴ | R⁵ | MS [M + H] |
|---|---|---|---|---|---|---|---|---|---|
| E1 | H | H | H | OMe | H | H | Cl | H | 406.2 |
| E2 | F | H | H | OMe | H | H | Cl | H | 442.2 |
| E3 | H | H | Me | F | H | F | H | H | 392.3 |
| E4 | H | Me | H | F | H | F | H | H | 392.2 |

TABLE EX-F

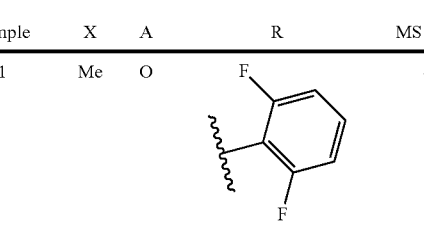

| Example | X | A | R | MS [M + H] |
|---|---|---|---|---|
| F1 | Me | O | (2,6-difluorophenyl) | 406.1 |

TABLE EX-F-continued
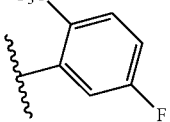
| Example | X | A | R | MS [M + H] |
|---|---|---|---|---|
| F2 | Me | O | 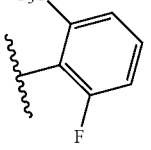 | 456.1 |
| F3 | Me | O | 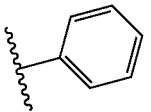 [SMILES: *c1ccccc1] | 456.1 |
| F4 | Me | S | 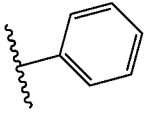 [SMILES: *c1ccccc1] | 386.2 |
| F5 | Me | NH | 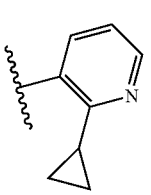 [SMILES: *c1cccnc1C1CC1] | 369.2 |
| F6 | Me | O | 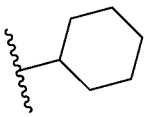 [SMILES: *C1CCCCC1] | 411.1 |
| F7 | Me | S | 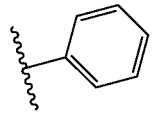 [SMILES: *c1ccccc1] | 392.3 |
TABLE EX-G
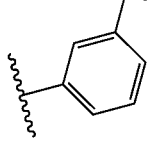
| Example | X | A | R | MS [M + H] |
|---|---|---|---|---|
| G1 | Me | O | 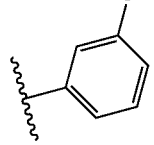 | 370.3 |
| G2 | Me | O | 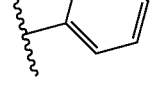 | 438.1 |
| G3 | Me | O | 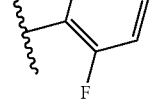 | 388.1 |
| G4 | Me | O | 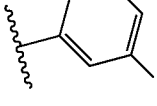 | 438.1 |
| G5 | Me | O | 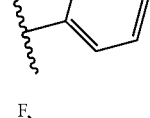 | 406.0 |
| G6 | Me | O | 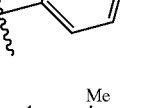 | 456.0 |
| G7 | Me | S | | 386.2 |
| G8 | Me | S | | 422.3 |
| G9 | Me | O | 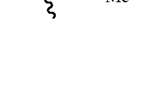 | 336.3 |

TABLE EX-G-continued

| Example | X | A | R | MS [M + H] |
|---------|---|---|---|------------|
| G10 | Me | O | cyclopentyl | 362.1 |
| G11 | Me | O | cyclopropylmethyl | 348.1 |
| G12 | Me | O | 2-cyclopropylpyridin-3-yl | 411.1 |
| G13 | Me | S | cyclohexyl | 392.3 |
| G14 | Me | S | cyclopentyl | 378.25 |
| G15 | Me | S | cyclopropyl | 350.22 |
| G16 | H | S | cyclopentyl | 350.21 |
| G17 | Me | O | 2-F₃C-6-F-phenyl | 456.0 |

TABLE EX-H

| Example | X | R¹ | R² | R³ | R⁴ | R⁵ | MS [M + H] |
|---------|---|----|----|-----|-----|-----|------------|
| H1 | Me | H | H | H | H | H | 370.3 |
| H2 | Me | Cl | H | F | H | H | 422.0 |
| H3 | Me | F | H | F | H | F | 424.2 |
| H4 | Me | H | OCF₃ | F | H | H | 472.0 |
| H5 | Me | H | F | H | H | H | 388.0 |
| H6 | Me | Me | H | H | H | F | 402.2 |
| H7 | Me | H | (2-oxo-1,3-oxazolidin-3-yl) | H | H | F | 473.3 |
| H8 | Me | F | H | H | H | F | 406.3 |
| H9 | Me | H | cPr | H | H | H | 410.2 |
| H10 | Me | F | F | H | F | H | 424.1 |
| H11 | Me | H | H | C≡CH | H | H | 394.1 |
| H12 | Me | H | H | CN | H | H | 395.1 |
| H13 | Me | H | H | OCF₃ | H | H | 454.3 |
| H14 | Me | H | OCF₂CHF₂ | H | H | H | 507.8 (M + Na) |
| H15 | H | H | F | H | H | H | 359.9 |

TABLE EX-I

| Example | X | R | MS [M + H] |
|---------|---|---|------------|
| I1 | Me | 2,4-difluorobenzyl | 420.0 |
| I2 | Me | 1-(3-chlorophenoxy)ethyl | 470.3 |

TABLE EX-I-continued

| Example | X | R | MS [M + H] |
|---|---|---|---|
| I3 | Me | 1-(6-fluoroindan-1-yl) | 428.0 |
| I4 | Me | 1-(2,5-difluorophenyl)cyclobutyl | 460.3 |
| I5 | Me | (5-chloro-2-oxo-benzoxazol-3-yl)methyl | 475.0 |
| I6 | Me | thiazol-4-yl | 377.1 |
| I7 | Me | 4-methyloxazol-5-yl | 375.0 |
| I8 | Me | 2-cyclopropyl-1H-imidazol-4-yl | 400.2 |
| I9 | Me | 1-cyclopropylpiperidin-4-yl | 417.3 |
| I10 | Me | 1-methylpyrrol-3-yl | 373.2 |
| I11 | Me | 1-(1H-imidazol-1-yl)ethyl | 388.2 |
| I12 | Me | 1-(pyrazin-2-yl)cyclopropyl | 412.2 |
| I13 | Me | 4-(trifluoromethyl)quinolin-2-yl | 489.2 |
| I14 | Me | 6-(2-fluoroethoxy)pyridin-3-yl | 433.2 |
| I15 | Me | (tetrahydrofuran-2-yl)methyl | 378.2 |
| I16 | Me | 1,1-difluoroethyl | 358.3 |
| I17 | Me | 5-(4-fluorophenyl)-1H-imidazol-2-yl | 454.2 |
| I18 | Me | 2-(2,2,2-trifluoroethylthio)oxazol-5-yl | 475.1 |

TABLE EX-I-continued

| Example | X | R | MS [M + H] |
|---|---|---|---|
| I19 | Me | 3-(trifluoromethyl)pyridin-4-yl | 439.1 |
| I20 | Me | 4-(trifluoromethyl)pyridin-3-yl | 439.1 |
| I21 | Me | 2-(trifluoromethyl)pyridin-3-yl | 439.1 |
| I22 | Me | 4H-thieno[3,2-b]pyrrol-5-yl | 415.2 |
| I23 | Me | 1-(cyclopropanecarbonyl)azetidin-3-yl | 417.2 |
| I24 | Me | 2-cyclopentyl-octahydrocyclopenta[c]pyrrol-1-on-5-yl | 507.3 (M + Na) |
| I25 | Me | cyclopropyl | 334.2 |
| I26 | Me | cyclopentyl | 384.2 (M + Na) |
| I27 | Me | spiro[2.5]octan-4-yl | 402.3 |
| I28 | Me | 1,1,1-trifluoro-2-hydroxypropan-2-yl | 392.1 |
| I29 | Me | 4-hydroxycyclohexyl | 392.2 |
| I30 | Me | 3-hydroxycyclobutyl | 364.2 |
| I31 | Me | 3-oxo-3,4-dihydro-2H-benzo[b][1,4]oxazin-8-yl | 441.2 |
| I32 | Me | 2-hydroxybenzo[d]thiazol-6-yl | 443.1 |
| I33 | Me | 2-cyclopropylethyl | 362.2 |
| I34 | H | cyclohexyl | 348.1 |
| I35 | H | 1-(trifluoromethyl)cyclopropyl | 374.1 |
| I36 | H | 5-fluoropyridin-3-yl | 360.9 |

TABLE EX-J

![Structure: 4-sulfamoylphenyl-cyclopropyl(X,X)-thiazole/oxazole with R1, R2]

| Example | X | A | R¹ | R² | MS [M + H] |
|---|---|---|---|---|---|
| J1 | Me | O | H | 2-fluorophenyl | 387.1 |
| J2 | Me | O | H | 2,4-difluorophenyl | 405.1 |
| J3 | Me | O | H | 2,5-difluorophenyl | 405.1 |
| J4 | Me | O | H | tert-butyl (C(Me)₃) | 349.1 |
| J5 | Me | O | H | cyclopropyl | 333.1 |
| J6 | H | O | H | phenyl | 341.2 |
| J7 | H | S | H | 3-fluorophenyl | 375.2 |
| J8 | Me | O | H | cyclopentyl | 361.0 |
| J9 | Me | S | cyclopentyl | H | 377.0 |
| J10 | H | S | 3-fluorophenyl | H | 375.0 |
| J11 | F | O | cyclopentyl | H | 369.1 |

TABLE EX-K

| Example | X | A | R¹ | R² | MS [M + H] |
|---|---|---|---|---|---|
| K1 | Me | O | H | 2-fluorophenyl | 387.1 |
| K2 | Me | O | H | 2,5-difluorophenyl | 405.1 |
| K3 | Me | O | H | 2,4-difluorophenyl | 405.1 |
| K4 | H | O | tert-butyl (C(Me)₃) | H | 321.2 |

TABLE EX-K-continued
| Example | X | A | R¹ | R² | MS [M + H] |
|---|---|---|---|---|---|
| K5 | H | O | 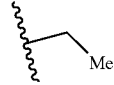 | H | 305.2 |
| K6 | H | O | H | 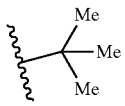 | 293.2 |
| K7 | Me | O | H |  | 349.1 |
| K8 | Me | O | H | 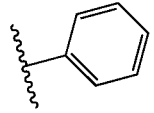 [SMILES: *c1ccccc1] | 321.1 |
| K9 | H | S | H | 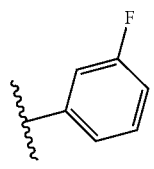 [SMILES: *c1cccc(F)c1] | 357.25 |
| K10 | Me | S | H | 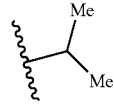 | 403.27 |
| K11 | Me | S | H | 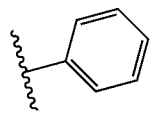 [SMILES: *c1ccccc1] | 351.26 |
| K12 | H | NH | H | 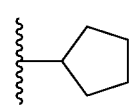 | 340.2 |
| K13 | F | O | 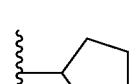 | H | 369.1 |
| K14 | Me | O |  | H | 361.0 |
| K15 | H | S | 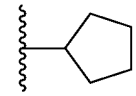 [SMILES: *C1CCCC1] | H | 349.1 |
TABLE EX-K-continued
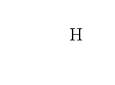
| Example | X | A | R¹ | R² | MS [M + H] |
|---|---|---|---|---|---|
| K16 | Me | S | 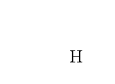 | H | 377.0 |
| K17 | Me | O | H | 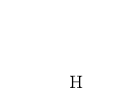 | 361.0 |
| K18 | H | O | H | 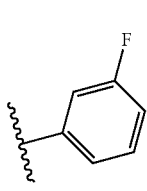 [SMILES: *c1cccc(F)c1] | 333.0 |
| K19 | F | S | H | 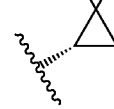 | 399.1 |
| K20 | H | S | F | H | 374.9 |
TABLE EX-L
| Example | R | MS [M + H] |
|---|---|---|
| L1 | | 369.3 |

TABLE EX-L-continued
| Example | R | MS [M + H] |
|---|---|---|
| L2 | 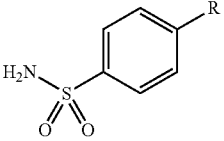 | 341.2 |
| L3 | 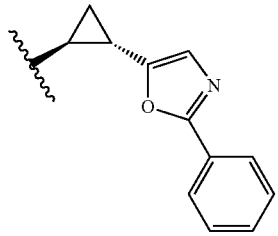 | 341.2 |
| L4 | 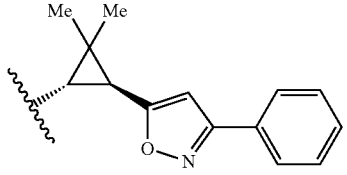 [SMILES: *[C@H]1[C@H](c2cc(-c3ccccc3)no2)C1(C)C] | 369.3 |
| L5 | 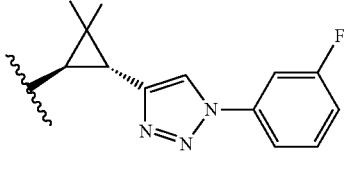 | 387.1 |
| L6 | 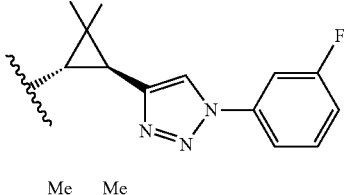 | 387.0 |
| L7 | 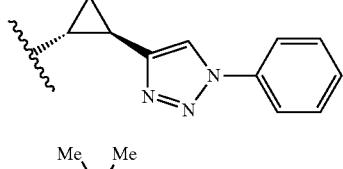 | 369.1 |
| L8 | 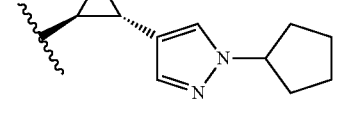 | 360.1 |
| L9 | 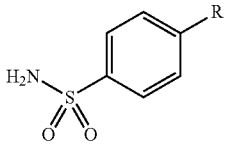 | 354.1 |
| L10 | 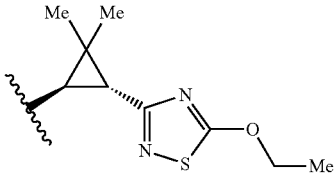 [SMILES: *[C@@H]1[C@@H](c2nsc(OCC)n2)C1(C)C] | 376.1 |
| L11 | 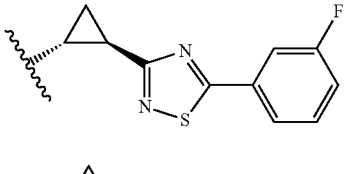 | 364.1 |
| L12 | 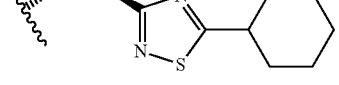 | 401.1 |
| L13 | 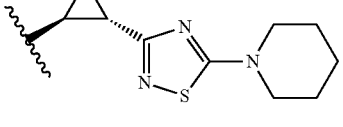 | 394.1 |
| L14 | 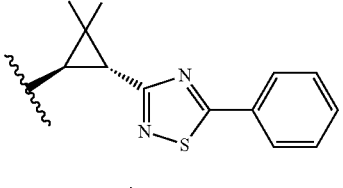 | 349.0 |
| L15 | 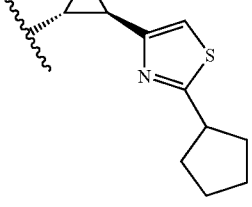 | 377.5 |

TABLE EX-L-continued

| Example | R | MS [M + H] |
|---|---|---|
| L16 | 2,2-dimethyl-cyclopropyl-[1,2,4-oxadiazol-5-yl]-cyclohexyl | 376.0 |
| L17 | 2,2-dimethyl-cyclopropyl-[1,2,4-oxadiazol-5-yl]-phenyl | 370.0 |
| L18 | 2,2-dimethyl-cyclopropyl-[1,2,4-oxadiazol-5-yl]-(3-fluorophenyl) | 388.0 |
| L19 | 2,2-dimethyl-cyclopropyl-[1,2,4-oxadiazol-5-yl]-(1-trifluoromethylcyclopropyl) | 402.0 |
| L20 | 2,2-dimethyl-cyclopropyl-[1,2,4-oxadiazol-5-yl]-piperidinyl | 377.0 |
| L21 | cyclopropyl-oxazol-5-yl-cyclopentyl | 333.0 |
| L22 | cyclopropyl-thiazol-5-yl-phenyl | 356.9 |

TABLE EX-M

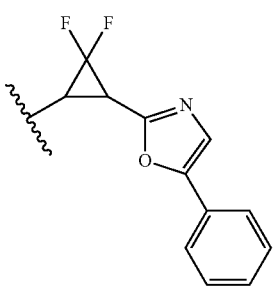 [SMILES: *C1C(c2ncc(-c3ccccc3)o2)C1(F)F]

| Example | R | X | Y | Stereochemistry Comment | MS [M + H] |
|---|---|---|---|---|---|
| M1 | 2,2-difluorocyclopropyl-oxazol-2-yl-(5-phenyl) | H | H | trans, racemic | 377.2 |

TABLE EX-M-continued

| Example | R | X | Y | Stereochemistry Comment | MS [M + H] |
|---|---|---|---|---|---|
| M2 | Me-cyclopropyl-(3-phenyl-1,2,4-oxadiazol-5-yl) | H | H | Single isomer | 356.2 |
| M3 | spiro[2.4]heptyl-(3-phenyl-1,2,4-oxadiazol-5-yl) | H | H | Single trans enantiomer | 396.0 |
| M4 | cyclopropyl-(3-(3-fluorophenyl)-1,2,4-thiadiazol-5-yl) | F | H | Single trans enantiomer | 376.1 |
| M5 | 2,2-dichlorocyclopropyl-(3-cyclopentyl-1,2,4-oxadiazol-5-yl) | H | H | trans, racemic | 402.0 |
| M6 | 2,2-dimethylcyclopropyl-(5-(3-fluorophenyl)isoxazol-3-yl) | H | H | trans, racemic | 387.1 |
| M7 | 2,2-dimethylcyclopropyl-(3-phenyl-1,2,4-oxadiazol-5-yl) | H | F | Single trans enantiomer | 388.0 |
| M8 | 2,2-dimethylcyclopropyl-(5-phenyl-1,2,4-oxadiazol-3-yl) | Me | H | Single trans enantiomer | 384.0 |

TABLE EX-M-continued

| Example | R | X | Y | Stereochemistry Comment | MS [M + H] |
|---|---|---|---|---|---|
| M9 | (dichlorocyclopropyl-oxadiazole-phenyl group) | H | H | trans, racemic | 410.0 |

The utility of the compounds in accordance with the present invention as positive allosteric modulators of α7 nicotinic acetylcholine receptor activity may be demonstrated by methodology known in the art. Direct activation of α7 (agonism), and potentiation of 5 acetylcholine-evoked α7 currents was determined as follows:

Automated Patch-Clamp Electrophysiology Functional Assay (Assay A)

Automated patch-clamp electrophysiology was performed using the IonFlux HT (Fluxion Biosciences Inc., San Francisco, Calif.) in the whole-cell, population patch configuration. Test compounds were assessed for their ability to modulate the function of the α7 nicotinic acetylcholine receptor both in the presence, and in the absence of the natural α7 agonist acetylcholine. A HEK cell line stably expressing both human RIC-3 and human α7 (PrecisION hnAChR α7/RIC-3, Eurofins Pharma, St. Charles, Mo.) was cultured in 175 cm² triple-layer tissue culture flasks to no more than 90% confluency in DMEM/F-12 growth media supplemented with 10% heat-inactivated fetal bovine serum, 1% non-essential amino acids, 0.625 μg/mL Puromycin, and 400 μg/mL Geneticin. Immediately prior to assay, cells were detached by first aspirating growth media, rinsing with Dulbecco's phosphate buffered saline, and then adding 10 mL of Accutase (Innovative Cell Technologies, San Diego, Calif.) to the flask and then incubating at 37° C. for 5 minutes. Detached cells were then recovered by the addition of 40 mL of CHO-serum-free media supplemented with 25 mM HEPES, and rocked gently in a 50 mL conical tube for 20 minutes prior to patch-clamp assay. After recovery, cells were pelleted by centrifugation at 1,000 RPM for 1 minute in a compact bench top centrifuge; recovery media was aspirated and cells were resuspended in external recording solution (150 mM NaCl, 5 mM KCl, 2 mM CaCl$_2$, 1 mM MgCl$_2$, 10 mM HEPES, 12 mM dextrose) to a density of 5.0×10⁶ cells/mL. The cell suspension was added to the cell inlet wells on an IonFlux HT population patch plate which had previously been rinsed and primed with deionized H$_2$O. Test compounds were serially diluted in DMSO and then resuspended to the final test concentration in external recording solution, with, or without 40 M acetylcholine added to the external recording solution; test compounds were then transferred to the IonFlux HT population patch plate. Internal recording solution (110 mM TrisPO$_4$, 28 mM TrisBase, 0.1 mM CaCl$_2$, 2 mM MgCl$_2$, 11 mM EGTA, 4 mM MgATP) was added to the internal recording solution inlet wells on the IonFlux HT patch plate previously loaded with cells and test compounds, and the plate loaded into the IonFlux HT instrument. A protocol was executed on the IonFlux HT to trap the cells, break into the cells, and establish the whole-cell recording configuration; cells were voltage-clamped at a holding potential of −60 mV for the duration of the experiment, all experiments were conducted at room temperature, and the IonFlux HT injection pressure was 8 psi for solution applications. Upon establishing the whole-cell configuration, external recording solution was perfused into the recording chambers for 120 seconds and then 40 μM acetylcholine was applied for 1 second and immediately washed off with external recording solution for 60 seconds. The 40 μM acetylcholine-evoked α7 current served as the current response to which subsequent test compound effects, in the presence, or in the absence of 40 μM acetylcholine would be quantified relative to. Next, test compounds were evaluated at multiple concentrations for their ability to induce, or modulate α7 current responses; three concentrations of test compound were evaluated in ascending dose fashion per recording. To assess test compound agonist activity, test compound diluted in external recording solution was applied starting from the lowest concentration of test compound being tested in the concentration series, for 58 seconds; the first 20 seconds of the 58 second compound application period coincided with a data collection sweep which was 20 seconds in duration, and collected at a rate of 5,000 samples/second. To assess test compound positive allosteric modulator activity, immediately following the 58 second test compound only application period, the same concentration of test compound, diluted in external recording solution containing 40 M acetylcholine was applied for 1 second; in this way, the test compound and the natural receptor agonist acetylcholine were co-applied, and potentiating effects of test compounds observed. The 1 second application of test compound diluted in external solution containing 40 M acetylcholine coincided with a data collection sweep which was 20 seconds in duration, and collected at a rate of 5,000 samples/second, after which, external recording solution only was applied for 42 seconds. Following this 42 second wash with external recording solution only, the next highest concentration of the test compound in the concentration series was applied in the absence and then in the presence of acetylcholine as previously described, and data collected as previously described. After test compound agonist, and positive allosteric modulator activity were assessed at three ascending concentrations, the experiment was terminated and leak subtraction performed using the IonFlux HT data analysis software. Peak current amplitudes and the area under the curve (AUC) were both quantified for each current sweep using proprietary software and test compound effects where quantified as follows.

Test compound agonist activity was calculated as:

% Agonism=($Y/X$)×100

Test compound potentiator activity was calculated as:

% Potentiation=[($Z/X$)×100]−100

X=Peak current amplitude (or AUC) evoked by 40 M acetylcholine
Y=Peak current amplitude (or AUC) evoked by test compound diluted in external recording solution
Z=Peak current amplitude (or AUC) evoked by test compound diluted in external recording solution containing 40 M acetylcholine As such, test compounds which evoked the same current amplitude as 40 μM acetylcholine alone would exhibit a calculated % Agonism of 100%. Test compounds co-applied with 40 μM acetylcholine which evoked a current amplitude 2× the current evoked from 40 μM acetylcholine alone would exhibit a calculated % Potentiation of 100%, whereas test compounds co-applied with 40 μM acetylcholine which evoked the same current amplitude as 40 μM acetylcholine alone would be characterized as exhibiting no potentiation.

Agonist and potentiation data, derived by peak current amplitude or area under the curve (AUC) were graphed and fit using a 4-parameter logistic fit based on the Levenberg-Marquardt algorithm where $y = A + ((B-A)/(1+((C/x)^D)))$ where:
A=Minimum
B=Maximum
C=$EC_{50}$
D=Slope
x=test compound concentration
y=% Agonism or % Potentiation Potency data for selected compounds of the present invention in the automated patch-clamp electrophysiology functional assay (Assay A) are represented in the table below:

| Example | α7 nAChR Potency |
|---------|------------------|
| 1 | C |
| 2 | B |
| 3 | A |
| 4 | B |
| 5 | B |
| 6 | C |
| 7 | C |
| 8 | B |
| 9 | B |
| 10 | C |
| 11 | B |
| 12 | C |
| 13 | B |
| 14 | B |
| 15 | A |
| 16 | A |
| 17 | C |
| 18 | B |
| 19 | C |
| 20 | C |
| 21 | B |
| 22 | B |
| 23 | B |
| 24 | C |
| 25 | C |
| 26 | C |
| 27 | C |
| 28 | B |
| 29 | B |
| 30 | C |
| 31 | C |
| 32 | C |
| 33 | C |
| 34 | B |
| 35 | C |
| 36 | B |
| 37 | B |
| 38 | C |
| A1 | C |
| A2 | C |
| A3 | C |
| A4 | C |
| A5 | D |
| A6 | C |
| A7 | C |
| A8 | D |
| A9 | C |
| A10 | C |
| A11 | C |
| A12 | C |
| A13 | C |
| A14 | C |
| A15 | D |
| B1 | C |
| B2 | C |
| B3 | D |
| B4 | C |
| B5 | D |
| B6 | D |
| B7 | C |
| B8 | C |
| B9 | C |
| B10 | C |
| B11 | D |
| B12 | D |
| B13 | C |
| B14 | C |
| B15 | C |
| B16 | C |
| B17 | C |
| B18 | C |
| B19 | B |
| C1 | D |
| C2 | C |
| C3 | D |
| C4 | B |
| C5 | B |
| C6 | C |
| C7 | C |
| C8 | B |
| C9 | C |
| C10 | C |
| C11 | B |
| C12 | C |
| C13 | B |
| C14 | A |
| C15 | B |
| C16 | B |
| C17 | B |
| C18 | B |
| C19 | C |
| C20 | B |
| C21 | A |
| D1 | B |
| D2 | C |
| D3 | B |
| D4 | D |
| D5 | B |
| D6 | C |

| Example | α7 nAChR Potency |
|---|---|
| D7 | B |
| D8 | B |
| D9 | B |
| D10 | B |
| D11 | B |
| D12 | C |
| D13 | D |
| D14 | C |
| D15 | C |
| D16 | C |
| D17 | C |
| D18 | A |
| D19 | C |
| D20 | A |
| D21 | B |
| D22 | C |
| D23 | C |
| D24 | B |
| D25 | C |
| D26 | C |
| D27 | B |
| D28 | C |
| D29 | C |
| D30 | C |
| D31 | C |
| D32 | C |
| D33 | B |
| D34 | B |
| D35 | B |
| E1 | C |
| E2 | C |
| E3 | D |
| E4 | C |
| F1 | C |
| F2 | C |
| F3 | C |
| F4 | B |
| F5 | C |
| F6 | C |
| F7 | C |
| G1 | C |
| G2 | C |
| G3 | C |
| G4 | C |
| G5 | C |
| G6 | C |
| G7 | C |
| G8 | C |
| G9 | C |
| G10 | C |
| G11 | C |
| G12 | C |
| G13 | C |
| G14 | C |
| G15 | C |
| G16 | C |
| G17 | C |
| H1 | B |
| H2 | C |
| H3 | B |
| H4 | C |
| H5 | C |
| H6 | B |
| H7 | C |
| H8 | B |
| H9 | C |
| H10 | B |
| H11 | C |
| H12 | C |
| H13 | C |
| H14 | B |
| H15 | B |
| I1 | B |
| I2 | A |
| I3 | A |
| I4 | B |
| I5 | C |
| I6 | C |
| I7 | C |
| I8 | C |
| I9 | C |
| I10 | C |
| I11 | D |
| I12 | C |
| I13 | C |
| I14 | C |
| I15 | C |
| I16 | B |
| I17 | C |
| I18 | C |
| I19 | B |
| I20 | B |
| I21 | C |
| I22 | D |
| I23 | C |
| I24 | C |
| I25 | C |
| I26 | A |
| I27 | B |
| I28 | C |
| I29 | D |
| I30 | C |
| I31 | C |
| I32 | B |
| I33 | C |
| I34 | B |
| I35 | C |
| I36 | C |
| J1 | C |
| J2 | C |
| J3 | C |
| J4 | C |
| J5 | C |
| J6 | C |
| J7 | C |
| J8 | C |
| J9 | C |
| J10 | C |
| J11 | C |
| K1 | B |
| K2 | C |
| K3 | B |
| K4 | C |
| K5 | B |
| K6 | C |
| K7 | C |
| K8 | C |
| K9 | C |
| K10 | C |
| K11 | C |
| K12 | D |
| K13 | B |
| K14 | C |
| K15 | B |
| K16 | C |
| K17 | B |
| K18 | B |
| K19 | B |
| K20 | B |
| L1 | C |
| L2 | C |
| L3 | C |
| L4 | C |
| L5 | C |
| L6 | C |
| L7 | C |
| L8 | C |
| L9 | C |
| L10 | A |
| L11 | B |
| L12 | B |
| L13 | C |
| L14 | C |
| L15 | B |

| Example | α7 nAChR Potency |
|---|---|
| L16 | C |
| L17 | B |
| L18 | B |
| L19 | C |
| L20 | C |
| L21 | C |
| L22 | C |
| M1 | C |
| M2 | C |
| M3 | A |
| M4 | B |
| M5 | B |
| M6 | C |
| M7 | C |
| M8 | D |
| M9 | B |

*Potency defined as A (EC$_{50}$≤0.1 µM); B (0.1 µM<EC$_{50}$≤0.5 µM); C (0.5 µM<EC$_{50}$≤5 µM); D (5 µM<EC$_{50}$≤50 µM) Electrophysiology EC$_{50}$ values for selected compounds of the present invention in the automated patch-clamp electrophysiology functional assay (Assay A) are provided in the table below:

| Example | α7 nAChR EC$_{50}$ (nM) |
|---|---|
| 1 | 4100 |
| 2 | 380 |
| 3 | 83 |
| 4 | 230 |
| 5 | 180 |
| 6 | 1100 |
| 7 | 910 |
| 8 | 500 |
| 9 | 430 |
| 10 | 1200 |
| 11 | 460 |
| 12 | 910 |
| 13 | 340 |
| 14 | 200 |
| 15 | 71 |
| 16 | 98 |
| 17 | 2000 |
| 18 | 380 |
| 19 | 780 |
| 20 | 660 |
| 21 | 390 |
| 22 | 120 |
| 23 | 460 |
| 24 | 2400 |
| 25 | 980 |
| 26 | 1600 |
| 27 | 620 |
| 28 | 460 |
| 29 | 140 |
| 30 | 1400 |
| 31 | 2400 |
| 32 | 860 |
| 33 | 1100 |
| 34 | 160 |
| 35 | 4400 |
| 36 | 470 |
| 37 | 240 |
| 38 | 4300 |
| A1 | 2900 |
| A2 | 1700 |
| A4 | 4800 |
| A5 | 7300 |
| A7 | 1300 |
| A10 | 1100 |
| A11 | 960 |
| B1 | 1500 |
| B3 | 8700 |
| B6 | 7700 |
| B7 | 2800 |
| B9 | 1000 |
| B10 | 3000 |
| B11 | 5800 |
| B13 | 4100 |
| B14 | 1200 |
| B16 | 2200 |
| B17 | 850 |
| B18 | 1200 |
| B19 | 370 |
| C3 | 6100 |
| C4 | 370 |
| C5 | 120 |
| C7 | 960 |
| C8 | 500 |
| C13 | 160 |
| C14 | 93 |
| C15 | 340 |
| C16 | 160 |
| C19 | 510 |
| C21 | 83 |
| D1 | 120 |
| D3 | 150 |
| D4 | 6800 |
| D5 | 420 |
| D6 | 820 |
| D8 | 190 |
| D10 | 410 |
| D11 | 430 |
| D12 | 800 |
| D13 | 6000 |
| D16 | 1300 |
| D17 | 2300 |
| D18 | 95 |
| D20 | 69 |
| D21 | 130 |
| D23 | 2100 |
| D24 | 230 |
| D26 | 810 |
| D27 | 200 |
| D30 | 1200 |
| D33 | 210 |
| D35 | 410 |
| E3 | 6900 |
| E4 | 1700 |
| F3 | 4700 |
| F4 | 420 |
| F5 | 1000 |
| G1 | 1800 |
| G3 | 740 |
| G5 | 1300 |
| G6 | 1100 |
| G7 | 1800 |
| G8 | 820 |
| G10 | 630 |
| G11 | 4500 |
| G13 | 2200 |
| G14 | 920 |
| G17 | 950 |
| H1 | 260 |
| H2 | 510 |
| H3 | 130 |
| H5 | 1500 |
| H7 | 2400 |
| H8 | 110 |
| H9 | 1400 |
| H10 | 240 |
| H11 | 1900 |
| H12 | 1200 |
| H15 | 190 |
| I2 | 93 |
| I3 | 96 |
| I4 | 170 |
| I7 | 710 |
| I8 | 4400 |
| I9 | 1800 |
| I13 | 3100 |

-continued

| Example | α7 nAChR EC$_{50}$ (nM) |
|---|---|
| I16 | 350 |
| I18 | 1300 |
| I20 | 450 |
| I22 | 5400 |
| I24 | 4400 |
| I25 | 710 |
| I26 | 64 |
| I29 | 6800 |
| I30 | 3800 |
| I33 | 2100 |
| I35 | 690 |
| I36 | 1400 |
| J1 | 1200 |
| J2 | 730 |
| J4 | 3200 |
| J7 | 4900 |
| J10 | 1600 |
| J11 | 730 |
| K2 | 1600 |
| K3 | 380 |
| K5 | 350 |
| K7 | 620 |
| K8 | 540 |
| K9 | 670 |
| K10 | 3900 |
| K11 | 1100 |
| K13 | 390 |
| K17 | 130 |
| K19 | 160 |
| L2 | 4800 |
| L4 | 640 |
| L5 | 770 |
| L6 | 950 |
| L10 | 88 |
| L13 | 740 |
| L15 | 370 |
| L18 | 220 |
| L20 | 1300 |
| M2 | 1700 |
| M3 | 83 |
| M4 | 210 |
| M6 | 2900 |
| M9 | 140 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having the formula I:

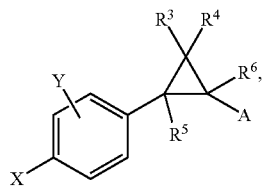

(I)

or a pharmaceutically acceptable salt thereof, wherein:
X is selected from

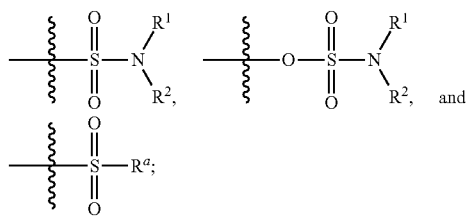

Y is 4 substituents, each independently selected from H, $(C_1-C_4)$alkyl, halogen, and OH, wherein said alkyl is optionally substituted with one or more halogen or OH;
A is a 5-membered heteroaryl ring which is substituted with 1 to 3 R groups each independently selected from OH, oxo, $NR^7R^8$, CN, alkoxy, halogen, aminoalkyl, hydroxyalkyl, alkyl, cycloalkyl, aryl, heteroaryl, and heterocyclyl, wherein said alkoxy, aminoalkyl, hydroxyalkyl, alkyl, cycloalkyl, aryl, heteroaryl and heterocyclyl are optionally substituted with one or more substituents independently selected from F, Cl, Br, OH, oxo, $CF_3$, $OCF_3$, CN, $(C_1-C_6)$alkyl, $O(C_1-C_4)$alkyl, $S(C_1-C_4)$alkyl, $C=O(C_1-C_4)$alkyl, $(C=O)NR^7R^8$, $(C=O)OR^7$, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, aryl, heteroaryl and heterocyclyl are optionally independently substituted with one or more halogen, $CF_3$, OH and oxo;
$R^1$ is H or $(C_1-C_4)$alkyl;
$R^2$ is H or $(C_1-C_4)$alkyl;
$R^3$ is H, halogen or $(C_1-C_4)$alkyl, wherein said alkyl is optionally substituted with one or more halogen;
$R^4$ is H, halogen or $(C_1-C_4)$alkyl, wherein said alkyl is optionally substituted with one or more halogen;
or, $R^3$ and $R^4$ optionally can come to together to form a cyclopropyl, cyclobutyl, cyclopentyl or cyclohexyl ring wherein said ring may be optionally substituted with one or more substituents independently selected from OH, halogen, or $(C_1-C_4)$alkyl;
$R^5$ is H or $(C_1-C_4)$alkyl;
$R^6$ is H or $(C_1-C_4)$alkyl;
$R^7$ is H or $(C_1-C_4)$alkyl;
$R^8$ is H or $(C_1-C_4)$alkyl; and
$R^a$ is H or $(C_1-C_4)$alkyl.

2. The compound of claim 1, or a pharmaceutically acceptable salt thereof, wherein X is

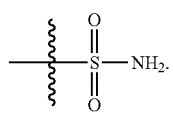 [SMILES: *S(N)(=O)=O]

3. The compound of claim 2, or a pharmaceutically acceptable salt thereof, wherein Y is H.

4. The compound of claim 3, or a pharmaceutically acceptable salt thereof, wherein A is selected from

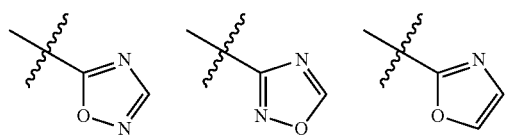

-continued

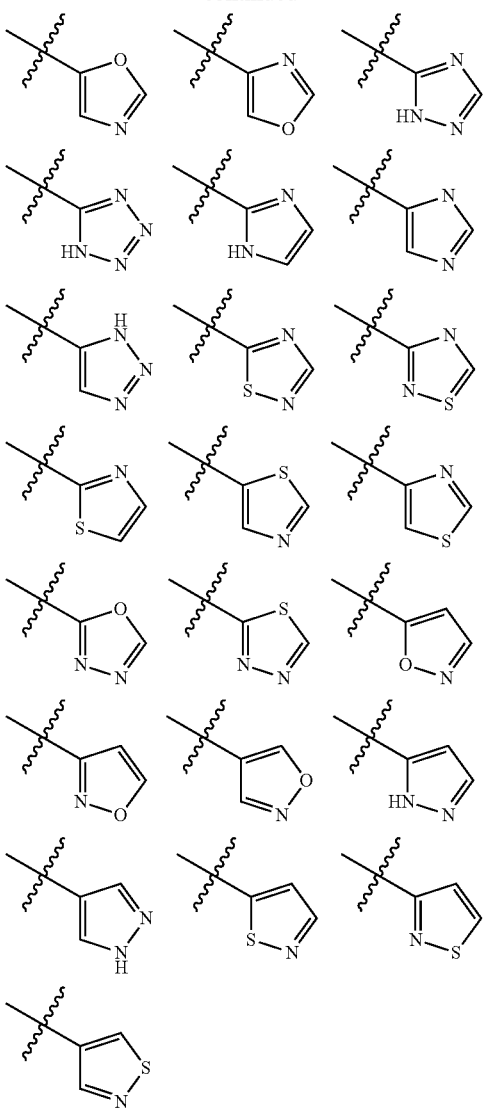

each substituted with 1 to 3 R groups independently selected from $(C_1-C_4)$alkyl, $(C_3-C_6)$cycloalkyl, aryl, heteroaryl and heterocyclyl, wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, aryl, heteroaryl and heterocyclyl are optionally independently substituted with one or more F, Cl, $CF_3$, OH and oxo.

5. The compound of claim 4, or a pharmaceutically acceptable salt thereof, wherein $R^5$ and $R^6$ are independently H or methyl.

6. The compound of claim 5, or a pharmaceutically acceptable salt thereof, wherein $R^3$ and $R^4$ are independently H, F or methyl.

7. The compound of claim 1, or a pharmaceutically acceptable salt thereof, having the formula:

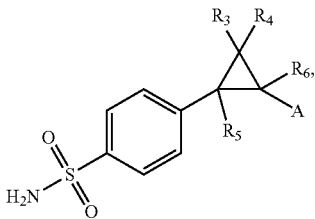

wherein;
A is selected from

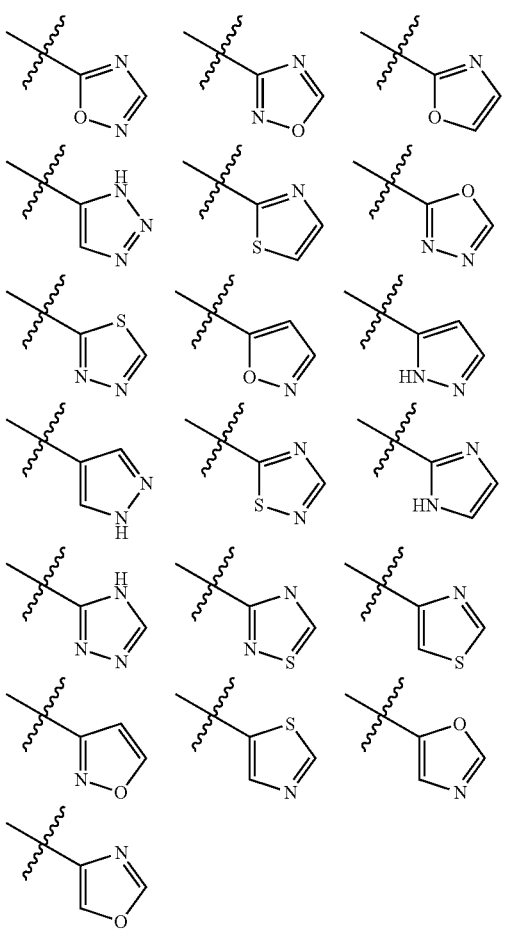

each substituted with 1 to 2 R groups independently selected from $(C_1-C_4)$alkyl, $(C_3-C_6)$cycloalkyl, aryl, heteroaryl and heterocyclyl, wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, $C=O(C_1-C_4)$alkyl, $(C_2-C_4)$alkynyl, $(C_3-C_6)$cycloalkyl, $O(C_3-C_6)$cycloalkyl, $C=O(C_3-C_6)$cycloalkyl, aryl, heteroaryl and heterocyclyl, wherein said alkyl, aryl, heteroaryl and heterocyclyl are optionally independently substituted with one or more F, Cl, $CF_3$, OH and oxo;

$R^3$ and $R^4$ are independently H, F or methyl; and $R^5$ and $R^6$ are independently H or methyl.

8. The compound of claim 7, or a pharmaceutically acceptable salt thereof, having the formula:

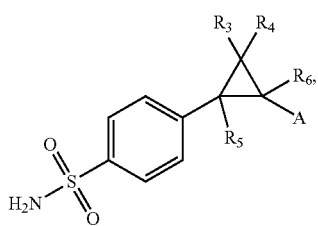

(Ia)

wherein;
A is selected from

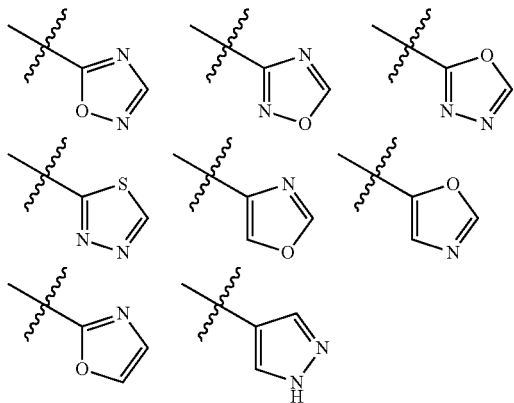

each substituted with 1 to 2 R groups independently selected from $(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, C=$O(C_1-C_4)$alkyl, $(C_2-C_4)$alkynyl, $(C_3-C_6)$cycloalkyl, $O(C_3-C_6)$cycloalkyl, C=$O(C_3-C_6)$cycloalkyl, phenyl, O-phenyl, imidazolyl, pyrazinyl, furanyl, oxazolidinyl, pyrrolidinyl, and benzoxazolyl, wherein said alkyl, phenyl, oxazolidinyl, pyrrolidinyl, and benzoxazolyl are optionally independently substituted with one or more F, Cl, $CF_3$ and oxo; and
$R^3$ and $R^4$ are independently H, F or methyl; and
$R^5$ and $R^6$ are independently H or methyl.

9. A compound having the formula:

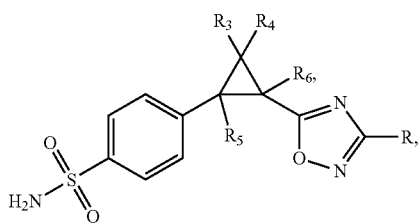

(Ib)

or a pharmaceutically acceptable salt thereof, wherein;
R is selected from $(C_1-C_4)$alkyl, $(C_3-C_6)$cycloalkyl, phenyl, indanyl, piperidinyl, pyridinyl, furanyl, oxazolyl, benzoxazinyl, cyclopentalpyrrolyl, thienopyrrolyl, thiazolyl, imidazolyl, azetidinyl, pyrrolyl, pyrazinyl, quinolinyl and benzothiazolyl wherein each are optionally substituted with one or more substituents independently selected from F, Cl, Br, OH, oxo, $CF_3$, $OCF_3$, CN, $(C_1-C_4)$alkyl, $O(C_1-C_4)$alkyl, $S(C_1-C_4)$alkyl, C=$O(C_1-C_4)$alkyl, $(C_2-C_4)$alkynyl, $(C_3-C_6)$cycloalkyl, $O(C_3-C_6)$cycloalkyl, C=$O(C_3-C_6)$cycloalkyl, phenyl, O-phenyl, imidazolyl, pyrazinyl, furanyl, oxazolidinyl, pyrrolidinyl, and benzoxazolyl, wherein said alkyl, phenyl, oxazolidinyl, pyrrolidinyl, and benzoxazolyl are optionally independently substituted with one or more F, Cl, $CF_3$ and oxo;
$R^3$ and $R^4$ are independently H, F or methyl; and
$R^5$ and $R^6$ are independently H or methyl.

10. The compound of claim 1 which is selected from the group consisting of
4-((1S,3S)-3-(3-(5-Fluoro-2-methylphenyl)-1,2,4-oxadiazol-5-yl)-2,2-dimethylcyclopropyl)-benzenesulfonamide;
4-((1S,3S)-3-(5-(2-Cyclopropylethyl)-1,2,4-oxadiazol-3-yl)-2,2-dimethylcyclopropyl)benzenesulfonamide;
4-((1S,3S)-2,2-Dimethyl-3-(5-(2,3,6-trifluorophenyl)-1,2,4-oxadiazol-3-yl)cyclopropyl) benzenesulfonamide;
4-((1R,2R)-2-(3-(3-Fluorophenyl)-1,2,4-oxadiazol-5-yl)cyclopropyl)benzenesulfonamide;
4-{(1R,3R)-3-[5-(2,4-Difluorophenyl)-1,3,4-thiadiazol-2-yl]-2,2-dimethylcyclopropyl}benzenesulfonamide;
4-{(1S,3S)-3-[5-(2,4-Difluorophenyl)-1,3,4-oxadiazol-2-yl]-2,2-dimethylcyclopropyl}benzenesulfonamide;
4-{(1S,3S)-2,2-Difluoro-3-[3-(propan-2-yl)-1,2,4-oxadiazol-5-yl]cyclopropyl}benzenesulfonamide;
4-[(1R,2R)-2-(5-Phenyl-1,3-oxazol-2-yl)cyclopropyl]benzenesulfonamide;
4-[(1R,2R)-2-(4-Phenyl-1,3-oxazol-2-yl)cyclopropyl]benzenesulfonamide;
4-[(1R,3R)-2,2-Dimethyl-3-(2-phenyl-1,3-oxazol-5-yl)cyclopropyl]benzenesulfonamide;
4-[(1R,3R)-2,2-Dimethyl-3-(3-phenylisoxazol-5-yl)cyclopropyl]benzenesulfonamide;
4-[(1R,3R)-2,2-Dimethyl-3-(1-phenyl-1H-1,2,3-triazol-4-yl)cyclopropyl]benzenesulfonamide;
4-{(1R,3R)-3-[1-(3-Fluorophenyl)-1H-pyrazol-4-yl]-2,2-dimethylcyclopropyl}benzene sulfonamide;
4-{(1R,2R)-2-[4-(3-Fluorophenyl)-1,3-thiazol-2-yl]cyclopropyl}benzene sulfonamide;
4-[(1R,2R)-2-(5-Methyl-4-phenyl-1,3-thiazol-2-yl)cyclopropyl]benzenesulfonamide;
4-[(1R,2R)-2-(4-Methyl-5-phenyl-1,3-thiazol-2-yl)cyclopropyl]benzenesulfonamide;
4-[(1S,3S)-2,2-Dimethyl-3-(5-phenyl-1,3-thiazol-2-yl)cyclopropyl]benzenesulfonamide;
4-{trans-2-[3-(Propan-2-yl)-1,2,4-thiadiazol-5-yl]cyclopropyl}benzenesulfonamide;
4-{(1R,2R)-2-[3-(5-Chloro-2-methoxyphenyl)-1,2,4-oxadiazol-5-yl]cyclopropyl}benzene sulfonamide;
4-((1R,3R)-3-(3-Cyclohexyl-1,2,4-oxadiazol-5-yl)-2,2-dimethylcyclopropyl)benzene sulfonamide;
4-{(1S,3S)-2,2-Dimethyl-3-[5-(propan-2-yl)-1,3-thiazol-2-yl]cyclopropyl}benzenesulfonamide;
4-(2-Methyl-3-(3-phenyl-1,2,4-oxadiazol-5-yl)cyclopropyl)benzenesulfonamide;
4-{(1R,2R)-2-[1-(3-Fluorobenzyl)-1H-pyrazol-3-yl]cyclopropyl}benzenesulfonamide;
4-[trans-2-(2-Phenyl-1,3-oxazol-4-yl)cyclopropyl]benzenesulfonamide;
4-[(1R,2R)-2-(2-Phenyl-1,3-thiazol-4-yl)cyclopropyl]benzenesulfonamide;

4-{(1R,2R)-2-[1-(3-Fluorophenyl)-1H-1,2,3-triazol-4-yl]cyclopropyl}benzenesulfonamide;
4-[(1R,2R)-2-(2-Phenyl-1,3-thiazol-5-yl)cyclopropyl]benzenesulfonamide;
4-[(1R,2R)-2-(2-Cyclohexyl-1,3-oxazol-5-yl)cyclopropyl]benzenesulfonamide;
4-{(1R,2R)-2-[5-(Piperidin-1-yl)-1,2,4-thiadiazol-3-yl]cyclopropyl}benzenesulfonamide;
4-[trans-2,2-Dimethyl-3-(3-phenyl-1,2,4-oxadiazol-5-yl)cyclopropyl]phenyl sulfamate;
4-[(1R,3R)-3-(4,5-Dicyclopropyl-1,3-oxazol-2-yl)-2,2-dimethylcyclopropyl]benzene sulfonamide;
4-[trans-2,2-Dimethyl-3-(3-phenyl-1,2,4-oxadiazol-5-yl)cyclopropyl]-2-fluorobenzenesulfonamide;
5-{trans-2,2-Dimethyl-3-[4-(methylsulfonyl)phenyl]cyclopropyl}-3-phenyl-1,2,4-oxadiazole;
4-[trans-3-(5-Cyclopentylisoxazol-3-yl)-2,2-dimethylcyclopropyl]benzenesulfonamide;
4-{(1S,3S)-3-[2-(3-Fluorophenyl)-1-methyl-1H-imidazol-4-yl]-2,2-dimethylcyclopropyl}benzene sulfonamide;
4-{trans-2,2-Dichloro-3-[3-(3-fluorophenyl)-1,2,4-oxadiazol-5-yl]cyclopropyl}benzene sulfonamide;
4-{(1R,2R)-2-[5-(Piperidin-1-yl)-1,2,4-oxadiazol-3-yl]cyclopropyl}benzenesulfonamide
4-[trans-2,2-Dimethyl-3-(3-phenyl-1,2,4-oxadiazol-5-yl)cyclopropyl]-3-methylbenzenesulfonamide
4-{(1R,3R)-3-[3-(5-Chloro-2-methoxyphenyl)-1,2,4-oxadiazol-5-yl]-2,2-dimethylcyclopropyl}benzenesulfonamide;
4-[(1R,3R)-3-{3-[4-Fluoro-2-(trifluoromethyl)phenyl]-1,2,4-oxadiazol-5-yl}-2,2-dimethyl cyclopropyl]benzene sulfonamide;
4-[(1R,3R)-2,2-Dimethyl-3-(3-phenyl-1,2,4-oxadiazol-5-yl)cyclopropyl]benzenesulfonamide;
4-[(1R,3R)-3-{3-[5-Chloro-2-(propan-2-yloxy)phenyl]-1,2,4-oxadiazol-5-yl}-2,2-dimethyl cyclopropyl]benzene sulfonamide;
4-[(1S,2S)-2-(3-Phenyl-1,2,4-oxadiazol-5-yl)cyclopropyl]benzenesulfonamide;
4-{(1R,3R)-3-[3-(5-Fluoro-2-methylphenyl)-1,2,4-oxadiazol-5-yl]-2,2-dimethylcyclopropyl}benzenesulfonamide;
4-{(1R,3R)-3-[3-(2,4-Difluorophenyl)-1,2,4-oxadiazol-5-yl]-2,2-dimethylcyclopropyl}benzenesulfonamide;
4-{(1S,2S)-2-[3-(2,4-Difluorophenyl)-1,2,4-oxadiazol-5-yl]cyclopropyl}benzenesulfonamide;
4-[(1S,3S)-2,2-Difluoro-3-(3-phenyl-1,2,4-oxadiazol-5-yl)cyclopropyl]benzenesulfonamide;
4-{(1R,3R)-3-[3-(3-Fluorophenyl)-1,2,4-oxadiazol-5-yl]-2,2-dimethylcyclopropyl}benzenesulfonamide;
4-{(1R,3R)-3-[3-(2,6-Difluorophenyl)-1,2,4-oxadiazol-5-yl]-2,2-dimethylcyclopropyl}benzenesulfonamide;
4-{(1R,3R)-3-[3-(2-Fluorophenyl)-1,2,4-oxadiazol-5-yl]-2,2-dimethylcyclopropyl}benzenesulfonamide;
4-[(1R,3R)-2,2-Dimethyl-3-{3-[2-(trifluoromethyl)phenyl]-1,2,4-oxadiazol-5-yl}cyclopropyl]benzenesulfonamide;
4-{(1R,3R)-3-[3-(3-Bromophenyl)-1,2,4-oxadiazol-5-yl]-2,2-dimethylcyclopropyl}benzenesulfonamide;
4-{(1S,2S)-2-[3-(5-Chloro-2-methoxyphenyl)-1,2,4-oxadiazol-5-yl]cyclopropyl}benzenesulfonamide;
4-{(1R,3R)-2,2-Dimethyl-3-[3-(propan-2-yl)-1,2,4-oxadiazol-5-yl]cyclopropyl}benzenesulfonamide;
4-{(1R,3R)-3-[3-(5-Fluoropyridin-3-yl)-1,2,4-oxadiazol-5-yl]-2,2-dimethylcyclopropyl}benzenesulfonamide;
4-[(1R,3R)-3-(3-Cyclobutyl-1,2,4-oxadiazol-5-yl)-2,2-dimethylcyclopropyl]benzenesulfonamide;
4-[(1S,2S)-2-(3-Cyclohexyl-1,2,4-oxadiazol-5-yl)cyclopropyl]benzenesulfonamide;
4-{(1S,2S)-2-[3-(5-Fluoropyridin-3-yl)-1,2,4-oxadiazol-5-yl]cyclopropyl}benzenesulfonamide;
4-{(1S,2S)-2-[3-(2-Methylpyridin-3-yl)-1,2,4-oxadiazol-5-yl]cyclopropyl}benzenesulfonamide;
4-[(1R,3R)-2,2-Dimethyl-3-{3-[5-(trifluoromethyl)pyridin-3-yl]-1,2,4-oxadiazol-5-yl}cyclopropyl]benzenesulfonamide;
4-{(1R,3R)-3-[3-(3,3-Difluorocyclobutyl)-1,2,4-oxadiazol-5-yl]-2,2-dimethylcyclopropyl}benzenesulfonamide;
4-[(1R,3R)-3-(3-Cyclopentyl-1,2,4-oxadiazol-5-yl)-2,2-dimethylcyclopropyl]benzene sulfonamide;
4-{(1R,3R)-3-[3-(Cyclopropylmethyl)-1,2,4-oxadiazol-5-yl]-2,2-dimethylcyclopropyl}benzenesulfonamide;
4-{(1R,3R)-2,2-Dimethyl-3-[3-(tetrahydrofuran-3-yl)-1,2,4-oxadiazol-5-yl]cyclopropyl}benzenesulfonamide;
4-{(1R,3R)-2,2-Dimethyl-3-[3-(tetrahydrofuran-2-yl)-1,2,4-oxadiazol-5-yl]cyclopropyl}benzenesulfonamide;
4-{(1R,3R)-2,2-Dimethyl-3-[3-(1-phenylcyclopropyl)-1,2,4-oxadiazol-5-yl]cyclopropyl}benzenesulfonamide;
4-{(1R,3R)-3-[3-(5-Fluoro-2,3-dihydro-1H-inden-1-yl)-1,2,4-oxadiazol-5-yl]-2,2-dimethyl cyclopropyl}benzenesulfonamide;
4-{(1R,3R)-2,2-Dimethyl-3-[3-(spiro[3.3]hept-2-yl)-1,2,4-oxadiazol-5-yl]cyclopropyl}benzenesulfonamide;
4-{(1R,3R)-3-[3-(1-Acetylpiperidin-4-yl)-1,2,4-oxadiazol-5-yl]-2,2-dimethylcyclopropyl}benzene sulfonamide;
4-[(1S,3S)-3-(3-tert-Butyl-1,2,4-oxadiazol-5-yl)-2,2-difluorocyclopropyl]benzenesulfonamide;
4-[(1S,3S)-2,2-Dimethyl-3-{3-[1-(trifluoromethyl)cyclopropyl]-1,2,4-oxadiazol-5-yl}cyclopropyl]benzenesulfonamide;
4-[(1S,3S)-3-(3-Cyclopentyl-1,2,4-oxadiazol-5-yl)-2,2-difluorocyclopropyl]benzenesulfonamide;
4-{(1S,3S)-3-[3-(5-Chloro-2-methoxyphenyl)-1,2,4-oxadiazol-5-yl]-2,2-dimethylcyclopropyl}benzenesulfonamide;
4-[(1S,3S)-3-{3-[4-Fluoro-2-(trifluoromethyl)phenyl]-1,2,4-oxadiazol-5-yl}-2,2-dimethyl cyclopropyl]benzene sulfonamide;
4-[(1S,3S)-3-{3-[5-Chloro-2-(propan-2-yloxy)phenyl]-1,2,4-oxadiazol-5-yl}-2,2-dimethyl cyclopropyl]benzene sulfonamide;
4-[(1S,3S)-2,2-Dimethyl-3-(3-phenyl-1,2,4-oxadiazol-5-yl)cyclopropyl]benzenesulfonamide;
4-[(1R,2R)-2-(3-Phenyl-1,2,4-oxadiazol-5-yl)cyclopropyl]benzenesulfonamide;
4-[(1R,2R)-2-{3-[2-(Trifluoromethyl)phenyl]-1,2,4-oxadiazol-5-yl}cyclopropyl]benzenesulfonamide;
4-[(1R,2R)-2-{3-[4-Fluoro-2-(trifluoromethyl)phenyl]-1,2,4-oxadiazol-5-yl}cyclopropyl]benzenesulfonamide;
4-[(1R,2R)-2-{3-[5-Fluoro-2-(trifluoromethyl)phenyl]-1,2,4-oxadiazol-5-yl}cyclopropyl]benzenesulfonamide;
4-{(1R,2R)-2-[3-(2,6-Difluorophenyl)-1,2,4-oxadiazol-5-yl]cyclopropyl}benzenesulfonamide;
4-{(1R,2R)-2-[3-(3-Bromophenyl)-1,2,4-oxadiazol-5-yl]cyclopropyl}benzenesulfonamide;
4-{(1R,2R)-2-[3-(2-Fluoro-6-methylphenyl)-1,2,4-oxadiazol-5-yl]cyclopropyl}benzenesulfonamide;
4-{(1S,3S)-3-[3-(2,4-Difluorophenyl)-1,2,4-oxadiazol-5-yl]-2,2-dimethylcyclopropyl}benzenesulfonamide;

4-{(1R,2R)-2-[3-(2,4-Difluorophenyl)-1,2,4-oxadiazol-5-yl]cyclopropyl}benzenesulfonamide;
4-{(1R,2R)-2-[3-(4-Fluorophenyl)-1,2,4-oxadiazol-5-yl]cyclopropyl}benzenesulfonamide;
4-{(1R,2R)-2-[3-(2,3-Difluorophenyl)-1,2,4-oxadiazol-5-yl]cyclopropyl}benzenesulfonamide;
4-{(1R,2R)-2-[3-(2,5-Difluorophenyl)-1,2,4-oxadiazol-5-yl]cyclopropyl}benzenesulfonamide;
4-{(1R,2R)-2-[3-(2-Methylphenyl)-1,2,4-oxadiazol-5-yl]cyclopropyl}benzenesulfonamide;
4-{(1R,2R)-2-[3-(3-Methylphenyl)-1,2,4-oxadiazol-5-yl]cyclopropyl}benzene sulfonamide;
4-{(1R,2R)-2-[3-(4-Methylphenyl)-1,2,4-oxadiazol-5-yl]cyclopropyl}benzenesulfonamide;
4-{(1R,2R)-2-[3-(2-Fluorophenyl)-1,2,4-oxadiazol-5-yl]cyclopropyl}benzenesulfonamide;
4-[(1R,3R)-2,2-Difluoro-3-(3-phenyl-1,2,4-oxadiazol-5-yl)cyclopropyl]benzenesulfonamide;
4-{(1R,3R)-2,2-Difluoro-3-[3-(propan-2-yl)-1,2,4-oxadiazol-5-yl]cyclopropyl}benzenesulfonamide;
4-[(1S,3S)-2,2-Dimethyl-3-{3-[4-(trifluoromethyl)pyridin-3-yl]-1,2,4-oxadiazol-5-yl}cyclopropyl]benzene sulfonamide;
4-[(1S,3S)-3-(3-Cyclohexyl-1,2,4-oxadiazol-5-yl)-2,2-dimethylcyclopropyl]benzenesulfonamide;
4-{(1S,3S)-2,2-Dimethyl-3-[3-(pyridin-2-yl)-1,2,4-oxadiazol-5-yl]cyclopropyl}benzenesulfonamide;
4-{(1S,3S)-2,2-Dimethyl-3-[3-(propan-2-yl)-1,2,4-oxadiazol-5-yl]cyclopropyl}benzenesulfonamide;
4-{(1S,3S)-3-[3-(5-Fluoropyridin-3-yl)-1,2,4-oxadiazol-5-yl]-2,2-dimethylcyclopropyl}benzenesulfonamide;
4-[(1S,3S)-3-(3-Cyclobutyl-1,2,4-oxadiazol-5-yl)-2,2-dimethylcyclopropyl]benzenesulfonamide;
4-[(1R,2R)-2-(3-Cyclohexyl-1,2,4-oxadiazol-5-yl)cyclopropyl]benzenesulfonamide;
4-[(1S,3S)-3-(3-Cyclopropyl-1,2,4-oxadiazol-5-yl)-2,2-dimethylcyclopropyl]benzene sulfonamide;
4-[(1S,3S)-3-(3-tert-Butyl-1,2,4-oxadiazol-5-yl)-2,2-dimethylcyclopropyl]benzenesulfonamide;
4-{(1R,2R)-2-[3-(Propan-2-yl)-1,2,4-oxadiazol-5-yl]cyclopropyl}benzenesulfonamide;
4-{(1R,2R)-2-[3-(5-Fluoropyridin-3-yl)-1,2,4-oxadiazol-5-yl]cyclopropyl}benzenesulfonamide;
4-[(1S,3S)-2,2-Dimethyl-3-(3-methyl-1,2,4-oxadiazol-5-yl)cyclopropyl]benzenesulfonamide;
4-{(1S,3S)-2,2-Dimethyl-3-[3-(2,2,2-trifluoroethyl)-1,2,4-oxadiazol-5-yl]cyclopropyl}benzenesulfonamide;
4-{(1S,3S)-2,2-Dimethyl-3-[3-(2-methylpyridin-3-yl)-1,2,4-oxadiazol-5-yl]cyclopropyl}benzenesulfonamide;
4-{(1R,2R)-2-[3-(2-Methylpyridin-3-yl)-1,2,4-oxadiazol-5-yl]cyclopropyl}benzenesulfonamide;
4-[(1S,3S)-2,2-Dimethyl-3-{3-[5-(trifluoromethyl)pyridin-3-yl]-1,2,4-oxadiazol-5-yl}cyclopropyl]benzene sulfonamide;
4-{(1S,3S)-3-[3-(3,3-Difluorocyclobutyl)-1,2,4-oxadiazol-5-yl]-2,2-dimethylcyclopropyl}benzenesulfonamide;
4-{(1R,2R)-2-[3-(3,3-Difluorocyclobutyl)-1,2,4-oxadiazol-5-yl]cyclopropyl}benzenesulfonamide;
4-[(1S,3S)-3-(3-Cyclopentyl-1,2,4-oxadiazol-5-yl)-2,2-dimethylcyclopropyl]benzene sulfonamide;
4-[(1R,2R)-2-(3-Cyclopentyl-1,2,4-oxadiazol-5-yl)cyclopropyl]benzenesulfonamide;
4-[(1R,2R)-2-{3-[5-(Trifluoromethyl)pyridin-3-yl]-1,2,4-oxadiazol-5-yl}cyclopropyl]benzenesulfonamide;
4-{(1R,2R)-2-[3-(1-Phenylcyclopropyl)-1,2,4-oxadiazol-5-yl]cyclopropyl}benzenesulfonamide;
4-{(1R,2R)-2-[3-(2-Cyclopropylpyridin-3-yl)-1,2,4-oxadiazol-5-yl]cyclopropyl}benzenesulfonamide;
4-[(1R,2R)-2-{3-[4-(Trifluoromethyl)pyridin-3-yl]-1,2,4-oxadiazol-5-yl}cyclopropyl]benzenesulfonamide;
4-{(1R,2R)-2-[3-(2,4-Difluorobenzyl)-1,2,4-oxadiazol-5-yl]cyclopropyl}benzenesulfonamide;
4-{(1S,3S)-3-[3-(Cyclopropylmethyl)-1,2,4-oxadiazol-5-yl]-2,2-dimethylcyclopropyl}benzenesulfonamide;
4-{(1R,2R)-2-[3-(Cyclopropylmethyl)-1,2,4-oxadiazol-5-yl]cyclopropyl}benzenesulfonamide;
4-[(1S,3S)-2,2-Dimethyl-3-{3-[6-(trifluoromethyl)pyridin-3-yl]-1,2,4-oxadiazol-5-yl}cyclopropyl]benzene sulfonamide;
4-[(1S,3S)-2,2-Dimethyl-3-{3-[2-(trifluoromethyl)pyridin-3-yl]-1,2,4-oxadiazol-5-yl}cyclopropyl]benzene sulfonamide;
4-{(1R,2R)-2-[3-(4-Methyl-1,3-oxazol-5-yl)-1,2,4-oxadiazol-5-yl]cyclopropyl}benzenesulfonamide;
4-{(1S,3S)-3-[3-(2-Hydroxycyclohexyl)-1,2,4-oxadiazol-5-yl]-2,2-dimethylcyclopropyl}benzene sulfonamide;
4-[(1S,3S)-2,2-Dimethyl-3-{3-[1-(trifluoromethyl)cyclopropyl]-1,2,4-oxadiazol-5-yl}cyclopropyl]benzenesulfonamide;
4-{(1S,3S)-2,2-Dimethyl-3-[3-(1-methylcyclohexyl)-1,2,4-oxadiazol-5-yl]cyclopropyl}benzenesulfonamide;
4-{(1R,3R)-2,2-Difluoro-3-[3-(2-fluoropropan-2-yl)-1,2,4-oxadiazol-5-yl]cyclopropyl}benzenesulfonamide;
4-{trans-2-[3-(5-Chloro-2-methoxyphenyl)-1,2,4-oxadiazol-5-yl]cyclopropyl}benzenesulfonamide;
4-{trans-3-[3-(5-Chloro-2-methoxyphenyl)-1,2,4-oxadiazol-5-yl]-2,2-difluorocyclopropyl}benzenesulfonamide;
4-{2-[3-(2,4-Difluorophenyl)-1,2,4-oxadiazol-5-yl]-2-methylcyclopropyl}benzenesulfonamide;
4-{2-[3-(2,4-Difluorophenyl)-1,2,4-oxadiazol-5-yl]-1-methylcyclopropyl}benzenesulfonamide;
4-{(1R,3R)-3-[5-(2,6-Difluorophenyl)-1,3,4-oxadiazol-2-yl]-2,2-dimethylcyclopropyl}benzenesulfonamide;
4-[(1R,3R)-3-{5-[5-Fluoro-2-(trifluoromethyl)phenyl]-1,3,4-oxadiazol-2-yl}-2,2-dimethylcyclopropyl]benzene sulfonamide;
4-[(1R,3R)-3-{5-[2-Fluoro-6-(trifluoromethyl)phenyl]-1,3,4-oxadiazol-2-yl}-2,2-dimethylcyclopropyl]benzene sulfonamide;
4-[(1R,3R)-2,2-Dimethyl-3-(5-phenyl-1,3,4-thiadiazol-2-yl)cyclopropyl]benzenesulfonamide;
4-[(1R,3R)-2,2-Dimethyl-3-(5-phenyl-1H-1,2,4-triazol-3-yl)cyclopropyl]benzenesulfonamide;
4-{(1R,3R)-3-[5-(2-Cyclopropylpyridin-3-yl)-1,3,4-oxadiazol-2-yl]-2,2-dimethylcyclopropyl}benzenesulfonamide;
4-[(1R,3R)-3-(5-Cyclohexyl-1,3,4-thiadiazol-2-yl)-2,2-dimethylcyclopropyl]benzene sulfonamide;
4-[(1S,3S)-2,2-Dimethyl-3-(5-phenyl-1,3,4-oxadiazol-2-yl)cyclopropyl]benzenesulfonamide;
4-[(1S,3S)-2,2-Dimethyl-3-{5-[3-(trifluoromethyl)phenyl]-1,3,4-oxadiazol-2-yl}cyclopropyl]benzenesulfonamide;
4-{(1S,3S)-3-[5-(3-Fluorophenyl)-1,3,4-oxadiazol-2-yl]-2,2-dimethylcyclopropyl}benzenesulfonamide;
4-[(1S,3S)-2,2-Dimethyl-3-{5-[2-(trifluoromethyl)phenyl]-1,3,4-oxadiazol-2-yl}cyclopropyl]benzenesulfonamide;
4-{(1S,3S)-3-[5-(2,6-Difluorophenyl)-1,3,4-oxadiazol-2-yl]-2,2-dimethylcyclopropyl}benzenesulfonamide;

4-[(1S,3S)-3-{5-[5-Fluoro-2-(trifluoromethyl)phenyl]-1,3,4-oxadiazol-2-yl}-2,2-dimethyl cyclopropyl]benzene sulfonamide;

4-[(1S,3S)-2,2-Dimethyl-3-(5-phenyl-1,3,4-thiadiazol-2-yl)cyclopropyl]benzenesulfonamide;

4-{(1S,3S)-3-[5-(2,4-Difluorophenyl)-1,3,4-thiadiazol-2-yl]-2,2-dimethylcyclopropyl}benzenesulfonamide;

4-{(1S,3S)-2,2-Dimethyl-3-[5-(propan-2-yl)-1,3,4-oxadiazol-2-yl]cyclopropyl}benzenesulfonamide;

4-[(1S,3S)-3-(5-Cyclopentyl-1,3,4-oxadiazol-2-yl)-2,2-dimethylcyclopropyl]benzene sulfonamide;

4-{(1S,3S)-3-[5-(Cyclopropylmethyl)-1,3,4-oxadiazol-2-yl]-2,2-dimethylcyclopropyl}benzenesulfonamide;

4-{(1S,3S)-3-[5-(2-Cyclopropylpyridin-3-yl)-1,3,4-oxadiazol-2-yl]-2,2-dimethylcyclopropyl}benzenesulfonamide;

4-[(1S,3S)-3-(5-Cyclohexyl-1,3,4-thiadiazol-2-yl)-2,2-dimethylcyclopropyl]benzenesulfonamide;

4-[(1S,3S)-3-(5-Cyclopentyl-1,3,4-thiadiazol-2-yl)-2,2-dimethylcyclopropyl]benzene sulfonamide;

4-[(1S,3S)-3-(5-Cyclopropyl-1,3,4-thiadiazol-2-yl)-2,2-dimethylcyclopropyl]benzene sulfonamide;

4-[(1R,2R)-2-(5-Cyclopentyl-1,3,4-thiadiazol-2-yl)cyclopropyl]benzenesulfonamide;

4-[(1S,3S)-3-{5-[2-Fluoro-6-(trifluoromethyl)phenyl]-1,3,4-oxadiazol-2-yl}-2,2-dimethyl cyclopropyl]benzene sulfonamide;

4-[(1S,3S)-2,2-Dimethyl-3-(5-phenyl-1,2,4-oxadiazol-3-yl)cyclopropyl]benzenesulfonamide;

4-{(1S,3S)-3-[5-(2-Chloro-4-fluorophenyl)-1,2,4-oxadiazol-3-yl]-2,2-dimethylcyclopropyl}benzenesulfonamide;

4-{(1S,3S)-2,2-Dimethyl-3-[5-(2,4,6-trifluorophenyl)-1,2,4-oxadiazol-3-yl]cyclopropyl}benzenesulfonamide;

4-[(1S,3S)-3-{5-[4-Fluoro-3-(trifluoromethoxy)phenyl]-1,2,4-oxadiazol-3-yl}-2,2-dimethyl cyclopropyl]benzene sulfonamide;

4-{(1S,3S)-3-[5-(3-Fluorophenyl)-1,2,4-oxadiazol-3-yl]-2,2-dimethylcyclopropyl}benzenesulfonamide;

4-{(1S,3S)-3-[5-(2-Fluoro-6-methylphenyl)-1,2,4-oxadiazol-3-yl]-2,2-dimethylcyclopropyl}benzenesulfonamide;

4-[(1S,3S)-3-{5-[2-Fluoro-5-(2-oxo-1,3-oxazolidin-3-yl)phenyl]-1,2,4-oxadiazol-3-yl}-2,2-dimethylcyclopropyl]benzenesulfonamide;

4-{(1S,3S)-3-[5-(2,6-Difluorophenyl)-1,2,4-oxadiazol-3-yl]-2,2-dimethylcyclopropyl}benzenesulfonamide;

4-{(1S,3S)-3-[5-(3-Cyclopropylphenyl)-1,2,4-oxadiazol-3-yl]-2,2-dimethylcyclopropyl}benzenesulfonamide;

4-{(1S,3S)-2,2-Dimethyl-3-[5-(2,3,5-trifluorophenyl)-1,2,4-oxadiazol-3-yl]cyclopropyl}benzenesulfonamide;

4-{(1S,3S)-3-[5-(4-Ethynylphenyl)-1,2,4-oxadiazol-3-yl]-2,2-dimethylcyclopropyl}benzenesulfonamide;

4-{(1S,3S)-3-[5-(4-Cyanophenyl)-1,2,4-oxadiazol-3-yl]-2,2-dimethylcyclopropyl}benzenesulfonamide;

4-[(1S,3S)-2,2-Dimethyl-3-{5-[4-(trifluoromethoxy)phenyl]-1,2,4-oxadiazol-3-yl}cyclopropyl]benzenesulfonamide;

4-[(1S,3S)-2,2-Dimethyl-3-{5-[3-(1,1,2,2-tetrafluoroethoxy)phenyl]-1,2,4-oxadiazol-3-yl}cyclopropyl]benzenesulfonamide;

4-{(1R,2R)-2-[5-(3-Fluorophenyl)-1,2,4-oxadiazol-3-yl]cyclopropyl}benzenesulfonamide;

4-{(1S,3S)-3-[5-(2,4-Difluorobenzyl)-1,2,4-oxadiazol-3-yl]-2,2-dimethylcyclopropyl}benzenesulfonamide;

4-[(1S,3S)-3-{5-[1-(3-Chlorophenoxy)ethyl]-1,2,4-oxadiazol-3-yl}-2,2-dimethylcyclopropyl]benzenesulfonamide;

4-{(1S,3S)-3-[5-(5-Fluoro-2,3-dihydro-1H-inden-1-yl)-1,2,4-oxadiazol-3-yl]-2,2-dimethyl cyclopropyl}benzenesulfonamide;

4-[(1S,3S)-3-{5-[1-(2,5-Difluorophenyl)cyclobutyl]-1,2,4-oxadiazol-3-yl}-2,2-dimethyl cyclopropyl]benzene sulfonamide;

4-[(1S,3S)-3-{5-[(5-Chloro-2-oxo-1,3-benzoxazol-3(2H)-yl)methyl]-1,2,4-oxadiazol-3-yl}-2,2-dimethylcyclopropyl]benzenesulfonamide;

4-{(1S,3S)-2,2-Dimethyl-3-[5-(1,3-thiazol-4-yl)-1,2,4-oxadiazol-3-yl]cyclopropyl}benzenesulfonamide;

4-{(1S,3S)-2,2-Dimethyl-3-[5-(4-methyl-1,3-oxazol-5-yl)-1,2,4-oxadiazol-3-yl]cyclopropyl}benzenesulfonamide;

4-{(1S,3S)-3-[5-(2-Cyclopropyl-1H-imidazol-4-yl)-1,2,4-oxadiazol-3-yl]-2,2-dimethyl cyclopropyl}benzenesulfonamide;

4-{(1S,3S)-3-[5-(1-Cyclopropylpiperidin-4-yl)-1,2,4-oxadiazol-3-yl]-2,2-dimethylcyclopropyl}benzenesulfonamide;

4-{(1S,3S)-2,2-Dimethyl-3-[5-(1-methyl-H-pyrrol-3-yl)-1,2,4-oxadiazol-3-yl]cyclopropyl}benzenesulfonamide;

4-[(1S,3S)-3-{5-[1-(1H-Imidazol-1-yl)ethyl]-1,2,4-oxadiazol-3-yl}-2,2-dimethylcyclopropyl]benzenesulfonamide;

4-[(1S,3S)-2,2-Dimethyl-3-{5-[1-(pyrazin-2-yl)cyclopropyl]-1,2,4-oxadiazol-3-yl}cyclopropyl]benzenesulfonamide;

4-[(1S,3S)-2,2-Dimethyl-3-{5-[4-(trifluoromethyl)quinolin-2-yl]-1,2,4-oxadiazol-3-yl}cyclopropyl]benzene sulfonamide;

4-[(1S,3S)-3-{5-[6-(2-Fluoroethoxy)pyridin-3-yl]-1,2,4-oxadiazol-3-yl}-2,2-dimethyl cyclopropyl]benzene sulfonamide;

4-{(1S,3S)-2,2-Dimethyl-3-[5-(tetrahydrofuran-2-ylmethyl)-1,2,4-oxadiazol-3-yl]cyclopropyl}benzenesulfonamide;

4-{(1S,3S)-3-[5-(1,1-Difluoroethyl)-1,2,4-oxadiazol-3-yl]-2,2-dimethylcyclopropyl}benzenesulfonamide;

4-[(1S,3S)-3-{5-[4-(4-Fluorophenyl)-1H-imidazol-2-yl]-1,2,4-oxadiazol-3-yl}-2,2-dimethyl cyclopropyl]benzene sulfonamide;

4-[(1S,3S)-2,2-Dimethyl-3-(5-{2-[(2,2,2-trifluoroethyl)sulfanyl]-1,3-oxazol-5-yl}-1,2,4-oxadiazol-3-yl)cyclopropyl]benzenesulfonamide;

4-[(1S,3S)-2,2-Dimethyl-3-{5-[3-(trifluoromethyl)pyridin-4-yl]-1,2,4-oxadiazol-3-yl}cyclopropyl]benzene sulfonamide;

4-[(1S,3S)-2,2-Dimethyl-3-{5-[4-(trifluoromethyl)pyridin-3-yl]-1,2,4-oxadiazol-3-yl}cyclopropyl]benzene sulfonamide;

4-[(1S,3S)-2,2-Dimethyl-3-{5-[2-(trifluoromethyl)pyridin-3-yl]-1,2,4-oxadiazol-3-yl}cyclopropyl]benzene sulfonamide;

4-{(1S,3S)-2,2-Dimethyl-3-[5-(4H-thieno[3,2-b]pyrrol-5-yl)-1,2,4-oxadiazol-3-yl]cyclopropyl}benzenesulfonamide;

4-[(1S,3S)-3-{5-[1-(Cyclopropylcarbonyl)azetidin-3-yl]-1,2,4-oxadiazol-3-yl}-2,2-dimethyl cyclopropyl]benzene sulfonamide;

4-{(1S,3S)-3-[5-(2-Cyclopentyl-1-oxooctahydrocyclopenta[c]pyrrol-5-yl)-1,2,4-oxadiazol-3-yl]-2,2-dimethylcyclopropyl}benzene sulfonamide;

4-[(1S,3S)-3-(5-Cyclopropyl-1,2,4-oxadiazol-3-yl)-2,2-dimethylcyclopropyl]benzenesulfonamide;
4-[(1S,3S)-3-(5-Cyclopentyl-1,2,4-oxadiazol-3-yl)-2,2-dimethylcyclopropyl]benzene sulfonamide;
4-{(1S,3S)-2,2-Dimethyl-3-[5-(spiro[2.5]oct-4-yl)-1,2,4-oxadiazol-3-yl]cyclopropyl}benzenesulfonamide;
4-{(1S,3S)-2,2-Dimethyl-3-[5-(2,2,2-trifluoro-1-hydroxyethyl)-1,2,4-oxadiazol-3-yl]cyclopropyl}benzenesulfonamide;
4-{(1S,3S)-3-[5-(4-Hydroxycyclohexyl)-1,2,4-oxadiazol-3-yl]-2,2-dimethylcyclopropyl}benzenesulfonamide;
4-{(1S,3S)-3-[5-(3-Hydroxycyclobutyl)-1,2,4-oxadiazol-3-yl]-2,2-dimethylcyclopropyl}benzenesulfonamide;
4-{(1S,3S)-2,2-Dimethyl-3-[5-(3-oxo-3,4-dihydro-2H-1,4-benzoxazin-8-yl)-1,2,4-oxadiazol-3-yl]cyclopropyl}benzenesulfonamide;
4-{(1S,3S)-3-[5-(2-Hydroxy-1,3-benzothiazol-6-yl)-1,2,4-oxadiazol-3-yl]-2,2-dimethyl cyclopropyl}benzenesulfonamide;
4-{(1R,3R)-3-[5-(2-Cyclopropylethyl)-1,2,4-oxadiazol-3-yl]-2,2-dimethylcyclopropyl}benzenesulfonamide;
4-[(1R,2R)-2-(5-Cyclohexyl-1,2,4-oxadiazol-3-yl)cyclopropyl]benzenesulfonamide;
4-[(1R,2R)-2-{5-[1-(Trifluoromethyl)cyclopropyl]-1,2,4-oxadiazol-3-yl}cyclopropyl]benzenesulfonamide;
4-{(1R,2R)-2-[5-(5-Fluoropyridin-3-yl)-1,2,4-oxadiazol-3-yl]cyclopropyl}benzenesulfonamide;
4-{(1R,3R)-3-[4-(2-Fluorophenyl)-1,3-oxazol-2-yl]-2,2-dimethylcyclopropyl}benzenesulfonamide;
4-{(1R,3R)-3-[4-(2,4-Difluorophenyl)-1,3-oxazol-2-yl]-2,2-dimethylcyclopropyl}benzenesulfonamide;
4-{(1R,3R)-3-[4-(2,5-Difluorophenyl)-1,3-oxazol-2-yl]-2,2-dimethylcyclopropyl}benzenesulfonamide;
4-[(1R,3R)-3-(4-tert-Butyl-1,3-oxazol-2-yl)-2,2-dimethylcyclopropyl]benzenesulfonamide;
4-[(1R,3R)-3-(4-Cyclopropyl-1,3-oxazol-2-yl)-2,2-dimethylcyclopropyl]benzenesulfonamide;
4-[(1S,2S)-2-(4-Phenyl-1,3-oxazol-2-yl)cyclopropyl]benzenesulfonamide;
4-{(1S,2S)-2-[4-(3-Fluorophenyl)-1,3-thiazol-2-yl]cyclopropyl}benzenesulfonamide;
4-[(1R,3R)-3-(4-Cyclopentyl-1,3-oxazol-2-yl)-2,2-dimethylcyclopropyl]benzenesulfonamide;
4-[(1R,3R)-3-(5-Cyclopentyl-1,3-thiazol-2-yl)-2,2-dimethylcyclopropyl]benzenesulfonamide;
4-{(1S,2S)-2-[5-(3-Fluorophenyl)-1,3-thiazol-2-yl]cyclopropyl}benzenesulfonamide;
4-[(1S,3S)-3-(5-Cyclopentyl-1,3-oxazol-2-yl)-2,2-difluorocyclopropyl]benzenesulfonamide; 4-{(1S,3S)-3-[4-(2-Fluorophenyl)-1,3-oxazol-2-yl]-2,2-dimethylcyclopropyl}benzenesulfonamide;
4-{(1S,3S)-3-[4-(2,5-Difluorophenyl)-1,3-oxazol-2-yl]-2,2-dimethylcyclopropyl}benzenesulfonamide;
4-{(1S,3S)-3-[4-(2,4-Difluorophenyl)-1,3-oxazol-2-yl]-2,2-dimethylcyclopropyl}benzenesulfonamide;
4-[(1R,2R)-2-(5-tert-Butyl-1,3-oxazol-2-yl)cyclopropyl]benzenesulfonamide;
4-[(1R,2R)-2-(5-Cyclopropyl-1,3-oxazol-2-yl)cyclopropyl]benzenesulfonamide;
4-[(1R,2R)-2-(4-Ethyl-1,3-oxazol-2-yl)cyclopropyl]benzenesulfonamide;
4-[(1S,3S)-3-(4-tert-Butyl-1,3-oxazol-2-yl)-2,2-dimethylcyclopropyl]benzenesulfonamide;
4-[(1S,3S)-3-(4-Ethyl-1,3-oxazol-2-yl)-2,2-dimethylcyclopropyl]benzenesulfonamide;
4-[(1R,2R)-2-(4-Phenyl-1,3-thiazol-2-yl)cyclopropyl]benzenesulfonamide;
4-{(1S,3S)-3-[4-(3-Fluorophenyl)-1,3-thiazol-2-yl]-2,2-dimethylcyclopropyl}benzenesulfonamide;
4-{(1S,3S)-2,2-Dimethyl-3-[4-(propan-2-yl)-1,3-thiazol-2-yl]cyclopropyl}benzenesulfonamide;
4-[(1R,2R)-2-(4-Phenyl-1H-imidazol-2-yl)cyclopropyl]benzenesulfonamide;
4-[(1R,3R)-3-(5-Cyclopentyl-1,3-oxazol-2-yl)-2,2-difluorocyclopropyl]benzenesulfonamide;
4-[(1S,3S)-3-(5-Cyclopentyl-1,3-oxazol-2-yl)-2,2-dimethylcyclopropyl]benzenesulfonamide;
4-[(1R,2R)-2-(5-Cyclopentyl-1,3-thiazol-2-yl)cyclopropyl]benzenesulfonamide;
4-[(1S,3S)-3-(5-Cyclopentyl-1,3-thiazol-2-yl)-2,2-dimethylcyclopropyl]benzenesulfonamide;
4-[(1S,3S)-3-(4-Cyclopentyl-1,3-oxazol-2-yl)-2,2-dimethylcyclopropyl]benzenesulfonamide;
4-{(1R,2R)-2-[5-(3-Fluorophenyl)-1,3-thiazol-2-yl]cyclopropyl}benzenesulfonamide;
4-[(1R,2R)-2-(4-Cyclopentyl-1,3-oxazol-2-yl)cyclopropyl]benzenesulfonamide;
4-[(1R,3S)-3-(4-Cyclohexyl-1,3-thiazol-2-yl)-2,2-difluorocyclopropyl]benzenesulfonamide;
4-[(1S,3S)-2,2-Dimethyl-3-(2-phenyl-1,3-oxazol-5-yl)cyclopropyl]benzenesulfonamide;
4-[(1S,2S)-2-(2-Phenyl-1,3-oxazol-5-yl)cyclopropyl]benzenesulfonamide;
4-[(1R,2R)-2-(2-Phenyl-1,3-oxazol-5-yl)cyclopropyl]benzenesulfonamide;
4-[(1S,3S)-2,2-Dimethyl-3-(3-phenylisoxazol-5-yl)cyclopropyl]benzenesulfonamide;
4-{(1R,3R)-3-[1-(3-Fluorophenyl)-1H-1,2,3-triazol-4-yl]-2,2-dimethylcyclopropyl}benzenesulfonamide;
4-{(1S,3S)-3-[1-(3-Fluorophenyl)-1H-1,2,3-triazol-4-yl]-2,2-dimethylcyclopropyl}benzenesulfonamide;
4-[(1S,3S)-2,2-Dimethyl-3-(1-phenyl-1H-1,2,3-triazol-4-yl)cyclopropyl]benzenesulfonamide;
4-[(1R,3R)-3-(1-Cyclopentyl-1H-pyrazol-4-yl)-2,2-dimethylcyclopropyl]benzenesulfonamide;
4-[(1R,3R)-3-(5-Ethoxy-1,2,4-thiadiazol-3-yl)-2,2-dimethylcyclopropyl]benzenesulfonamide;
4-{(1R,2R)-2-[5-(3-Fluorophenyl)-1,2,4-thiadiazol-3-yl]cyclopropyl}benzenesulfonamide;
4-[(1R,2R)-2-(5-Cyclohexyl-1,2,4-thiadiazol-3-yl)cyclopropyl]benzenesulfonamide;
4-{(1S,3S)-2,2-Difluoro-3-[5-(piperidin-1-yl)-1,2,4-thiadiazol-3-yl]cyclopropyl}benzenesulfonamide;
4-[(1S,3S)-2,2-Difluoro-3-(5-phenyl-1,2,4-thiadiazol-3-yl)cyclopropyl]benzenesulfonamide;
4-[(1R,2R)-2-(2-Cyclopentyl-1,3-thiazol-4-yl)cyclopropyl]benzenesulfonamide;
4-[(1S,3S)-3-(2-Cyclopentyl-1,3-thiazol-4-yl)-2,2-dimethylcyclopropyl]benzenesulfonamide;
4-[(1R,3R)-3-(5-Cyclohexyl-1,2,4-oxadiazol-3-yl)-2,2-dimethylcyclopropyl]benzenesulfonamide;
4-[(1R,3R)-2,2-Dimethyl-3-(5-phenyl-1,2,4-oxadiazol-3-yl)cyclopropyl]benzenesulfonamide;
4-{(1R,3R)-3-[5-(3-Fluorophenyl)-1,2,4-oxadiazol-3-yl]-2,2-dimethylcyclopropyl}benzenesulfonamide;
4-[(1R,3R)-2,2-Dimethyl-3-{5-[1-(trifluoromethyl)cyclopropyl]-1,2,4-oxadiazol-3-yl}cyclopropyl]benzenesulfonamide;
4-{(1R,3R)-2,2-Dimethyl-3-[5-(piperidin-1-yl)-1,2,4-oxadiazol-3-yl]cyclopropyl}benzenesulfonamide;
4-[(1R,2R)-2-(2-Cyclopentyl-1,3-oxazol-5-yl)cyclopropyl]benzenesulfonamide;
4-[(1S,2S)-2-(2-Phenyl-1,3-thiazol-5-yl)cyclopropyl]benzenesulfonamide;

4-[trans-2,2-Difluoro-3-(5-phenyl-1,3-oxazol-2-yl)cyclopropyl]benzenesulfonamide;
4-[2-Methyl-3-(3-phenyl-1,2,4-oxadiazol-5-yl)cyclopropyl]benzenesulfonamide;
4-[trans-2-(3-Phenyl-1,2,4-oxadiazol-5-yl)spiro[2.4]hept-1-yl]benzenesulfonamide;
4-{trans-2-[3-(3-Fluorophenyl)-1,2,4-thiadiazol-5-yl]cyclopropyl}benzenesulfonamide;
4-[trans-2,2-Dichloro-3-(3-cyclopentyl-1,2,4-oxadiazol-5-yl)cyclopropyl]benzenesulfonamide;
4-{trans-3-[5-(3-Fluorophenyl)isoxazol-3-yl]-2,2-dimethylcyclopropyl}benzenesulfonamide;
4-[trans-2,2-Dimethyl-3-(3-phenyl-1,2,4-oxadiazol-5-yl)cyclopropyl]-3-fluorobenzenesulfonamide;
4-[trans-2,2-Dimethyl-3-(3-phenyl-1,2,4-oxadiazol-5-yl)cyclopropyl]-2-methylbenzenesulfonamide; and
4-[trans-2,2-Dichloro-3-(3-phenyl-1,2,4-oxadiazol-5-yl)cyclopropyl]benzenesulfonamide;
or a pharmaceutically acceptable salt thereof.

11. A pharmaceutical composition comprising (i) a pharmaceutically acceptable carrier and (ii) a compound of claim 1, or a pharmaceutically acceptable salt thereof.

12. The pharmaceutical composition of claim 11, further comprising a second therapeutic agent selected from the group consisting of acetylcholinesterase inhibitors; NMDA receptor antagonists; antipsychotics; MAO-B inhibitors; and levodopa.

13. A method of treating a patient with cognitive impairments associated with Alzheimer's disease, Parkinson's disease, and schizophrenia, the method comprising administering to the patient the compound of claim 1, or a pharmaceutically acceptable salt thereof, in an amount effective to treat the patient.

14. A compound which is

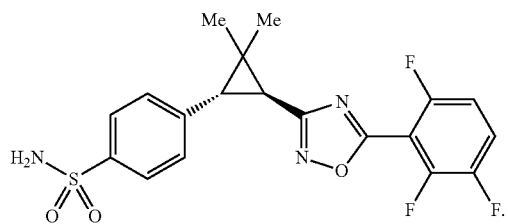 [SMILES: CC1(C)[C@@H](c2ccc(S(N)(=O)=O)cc2)[C@@H]1c1noc(-c2c(F)ccc(F)c2F)n1]

15. A pharmaceutically acceptable salt of a compound which is

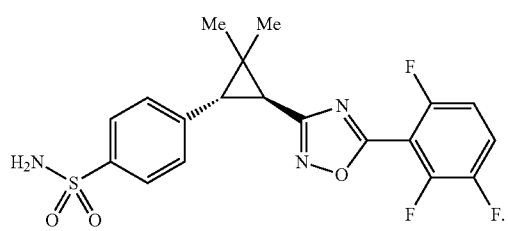 [SMILES: CC1(C)[C@@H](c2ccc(S(N)(=O)=O)cc2)[C@@H]1c1noc(-c2c(F)ccc(F)c2F)n1]

16. A pharmaceutical composition comprising (i) a pharmaceutically acceptable carrier and (ii) the compound of claim 14.

17. A pharmaceutical composition comprising (i) a pharmaceutically acceptable carrier and (ii) the pharmaceutically acceptable salt of claim 15.

18. A method of treating a patient with mild to moderate dementia of the Alzheimer's type, the method comprising administering to the patient the compound of claim 14 in an amount effective to treat the patient.

19. A compound which is

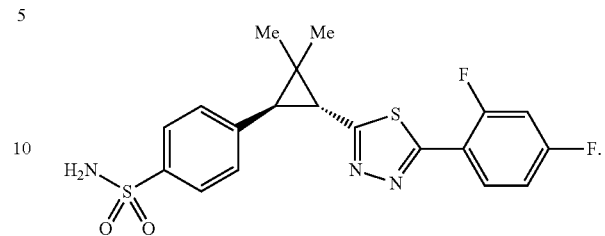

20. A pharmaceutically acceptable salt of a compound which is

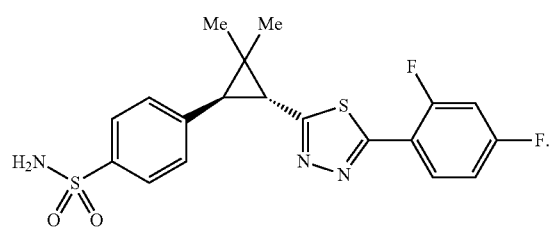

21. A pharmaceutical composition comprising (i) a pharmaceutically acceptable carrier and (ii) the compound of claim 19.

22. A pharmaceutical composition comprising (i) a pharmaceutically acceptable carrier and (ii) the pharmaceutically acceptable salt of claim 20.

23. A method of treating a patient with mild to moderate dementia of the Alzheimer's type, the method comprising administering to the patient the compound of claim 19 in an amount effective to treat the patient.

24. A compound which is

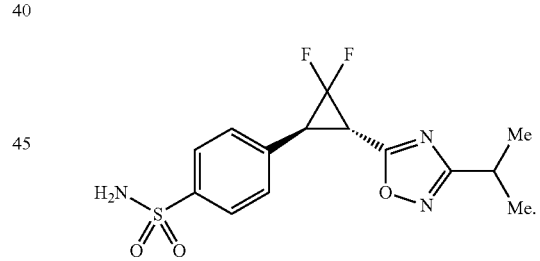

25. A pharmaceutically acceptable salt of a compound which is

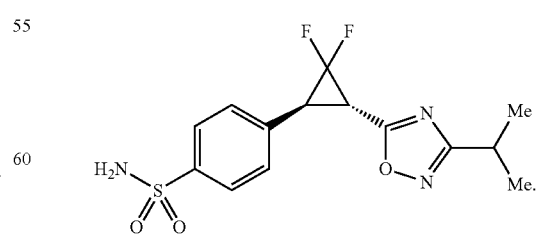

26. A pharmaceutical composition comprising (i) a pharmaceutically acceptable carrier and (ii) the compound of claim 24.

27. A pharmaceutical composition comprising (i) a pharmaceutically acceptable carrier and (ii) the pharmaceutically acceptable salt of claim 25.

28. A method of treating a patient with mild to moderate dementia of the Alzheimer's type, the method comprising administering to the patient the compound of claim 24 in an amount effective to treat the patient.

29. A compound which is

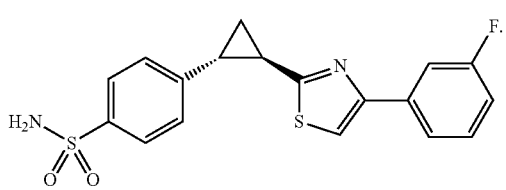 [SMILES: NS(=O)(=O)c1ccc([C@@H]2C[C@H]2c2nc(-c3cccc(F)c3)cs2)cc1]

30. A pharmaceutically acceptable salt of a compound which is

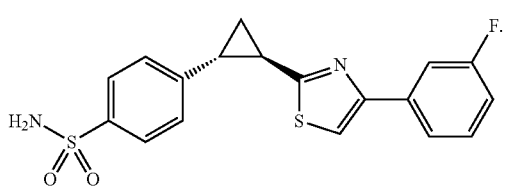 [SMILES: NS(=O)(=O)c1ccc([C@@H]2C[C@H]2c2nc(-c3cccc(F)c3)cs2)cc1]

31. A pharmaceutical composition comprising (i) a pharmaceutically acceptable carrier and (ii) the compound of claim 29.

32. A pharmaceutical composition comprising (i) a pharmaceutically acceptable carrier and (ii) the pharmaceutically acceptable salt of claim 30.

33. A method of treating a patient with mild to moderate dementia of the Alzheimer's type, the method comprising administering to the patient the compound of claim 29 in an amount effective to treat the patient.

34. A compound which is

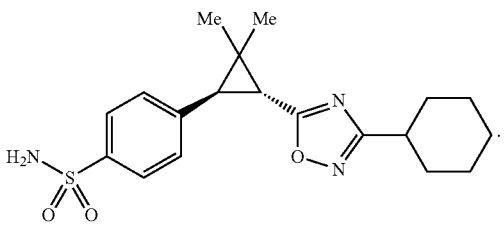 [SMILES: CC1(C)[C@H](c2ccc(S(N)(=O)=O)cc2)[C@H]1c1nc(C2CCCCC2)no1]

35. A pharmaceutically acceptable salt of a compound which is

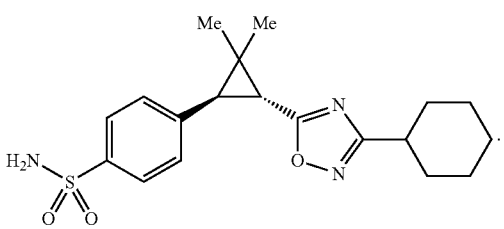 [SMILES: CC1(C)[C@H](c2ccc(S(N)(=O)=O)cc2)[C@H]1c1nc(C2CCCCC2)no1]

36. A pharmaceutical composition comprising (i) a pharmaceutically acceptable carrier and (ii) the compound of claim 34.

37. A pharmaceutical composition comprising (i) a pharmaceutically acceptable carrier and (ii) the pharmaceutically acceptable salt of claim 35.

38. A method of treating a patient with mild to moderate dementia of the Alzheimer's type, the method comprising administering to the patient the compound of claim 34 in an amount effective to treat the patient.

* * * * *